US008071543B2

(12) United States Patent
Schaebitz et al.

(10) Patent No.: US 8,071,543 B2
(45) Date of Patent: Dec. 6, 2011

(54) METHODS OF TREATING NEUROLOGICAL CONDITIONS WITH HEMATOPOEITIC GROWTH FACTORS

(75) Inventors: Wolf-Ruediger Schaebitz, Dossenheim (DE); Armin Schneider, Heidelberg (DE); Carola Krueger, Neustadt/Wstr. (DE); Clemens Sommer, Guenzburg (DE); Stefan Schwab, Heidelberg (DE); Rainer Kollmar, Heidelberg (DE); Martin Maurer, Heidelberg (DE); Daniela Weber, Mannheim (DE); Nikolaus Gassler, Heidelberg (DE)

(73) Assignee: Sygnis Bioscience GmbH & Co. KG, Heidelberg (DE)

( * ) Notice: Subject to any disclaimer, the term of this patent is extended or adjusted under 35 U.S.C. 154(b) by 87 days.

(21) Appl. No.: 11/931,295

(22) Filed: Oct. 31, 2007

(65) Prior Publication Data

US 2009/0087481 A1 Apr. 2, 2009

Related U.S. Application Data

(63) Continuation of application No. 10/880,101, filed on Jun. 30, 2004, which is a continuation-in-part of application No. PCT/IB03/06446, filed on Dec. 31, 2003, which is a continuation-in-part of application No. 10/659,295, filed on Sep. 11, 2003, which is a continuation of application No. 10/331,755, filed on Dec. 31, 2002, now abandoned.

(51) Int. Cl.
*A61K 38/00* (2006.01)
*A61K 38/18* (2006.01)
*C07K 14/53* (2006.01)

(52) U.S. Cl. ............ 514/7.6; 514/7.7; 514/7.9; 530/350
(58) Field of Classification Search .................. None
See application file for complete search history.

(56) References Cited

U.S. PATENT DOCUMENTS

| 4,810,643 | A | 3/1989 | Souza |
| 5,599,690 | A | 2/1997 | Fenton et al. |
| 2002/0151488 | A1 | 10/2002 | Lauffenburger et al. |
| 2002/0198150 | A1 | 12/2002 | Chajut |
| 2004/0120925 | A1 | 6/2004 | Toda et al. |
| 2004/0141946 | A1 | 7/2004 | Schaebitz et al. |
| 2005/0003453 | A1 | 1/2005 | Sarkar et al. |
| 2005/0142102 | A1 | 6/2005 | Schaebitz et al. |
| 2007/0243160 | A1 | 10/2007 | Toda et al. |
| 2009/0087481 | A1 | 4/2009 | Schaebitz et al. |
| 2010/0284926 | A1 | 11/2010 | Schneider et al. |

FOREIGN PATENT DOCUMENTS

| CA | 2213906 | | 3/1998 |
| DE | 100 33 219 A1 | | 1/2002 |
| EP | 231819 | * | 8/1987 |
| EP | 0 327 545 B2 | | 9/1987 |
| EP | 272703 | * | 6/1988 |
| EP | 0661057 | * | 5/1995 |
| EP | 1 374 898 | | 1/2002 |
| EP | 1 327 449 | | 7/2003 |
| JP | 3-503418 | | 8/1991 |
| JP | 1992000357539 | | 9/1991 |
| JP | 4-198134 | | 7/1992 |
| JP | 05246885 | | 9/1993 |
| JP | 2002-530068 | | 9/2002 |
| JP | 2002-281962 | | 10/2002 |
| WO | WO 87/01132 | | 2/1987 |
| WO | WO 89/09060 | | 10/1989 |
| WO | WO 97/14307 | | 4/1997 |
| WO | WO 99/17798 | | 4/1999 |
| WO | WO 99/61445 | | 12/1999 |
| WO | WO 99/61446 | | 12/1999 |
| WO | WO 00/04926 | | 2/2000 |
| WO | WO 00/44785 | | 8/2000 |
| WO | WO 02/22163 A1 | | 3/2002 |
| WO | WO 02/072144 A1 | | 9/2002 |
| WO | 02/099081 | | 12/2002 |
| WO | WO 02/099081 | | 12/2002 |
| WO | 03/061685 | | 7/2003 |
| WO | WO 2004/011632 A2 | | 2/2004 |

OTHER PUBLICATIONS

Bederson et al., Stroke. 1986; 17: 472-6.*
Tan et al., J Interv Cardiol. Aug. 2001; 14: 465-74.*
Matchett et al., Brain Research, 2007; 1136: 200-207.*
Whalen et al., Crit Care Med. 1999, 27: 1014-1018—HTML version only available; downloaded Feb. 9, 2010; 9 pages total.*
Lawrence et al., Journal of Vascular Surgery, 1998, 27: 329-337.*
Sevimli et al., Experimental Neurology, 2009; 217: 328-335.*
Strecker et al., Experimental Neurology; 2010, 222: 108-113.*
U.S. Appl. No. 10/331,755, filed Dec. 31, 2002, Schaebitz, et al.
U.S. Appl. No. 11/846,699, filed Aug. 29, 2007, Schaebitz, et al.
U.S. Appl. No. 11/930,758, filed Oct. 31, 2007, Schaebitz, et al.
U.S. Appl. No. 11/931,128, filed Oct. 31, 2007, Schaebitz, et al.
U.S. Appl. No. 11/931,326, filed Oct. 31, 2007, Schaebitz, et al.
U.S. Appl. No. 11/931,618, filed Oct. 31, 2007, Schaebitz, et al.
U.S. Appl. No. 11/932,383, filed Oct. 31, 2007, Schaebitz, et al.
Tarkowski, et al, "Local and systemic GM-CSF increase in Alzheimer's disease and vascular dementia", Acta Neurol Scand, 2001:103: 166-174.
Tarkowski, et al., "Intrathecal release of pro- and anti-inflammatory cytokines during stroke", Clin Exp Immunol, 1997;110:492-499.
Tarkowski, et al., "Intrathecal Expression of Proteins Regulating Apoptisis in Acute Stroke", Apoptosis During Stroke, Feb. 1999.
Heard, et al., "Effect of prophylactic administration of recombinant human granulocyte colony-stimulating factor (filgrastim) on the frequency of nosocomial infections in patients with acute traumatic brain injury or cerebral hemorrhage", Crit Care Med, 1998, vol. 26, No. 4, pp. 748-754.

(Continued)

*Primary Examiner* — Bridget E Bunner
*Assistant Examiner* — Christina Borgeest
(74) *Attorney, Agent, or Firm* — Oblon, Spivak, McClelland, Maier & Neustadt, L.L.P.

(57) ABSTRACT

The present invention relates to a method of treating a neurological condition in a mammal by administering at least one hematopoietic growth factor.

8 Claims, 74 Drawing Sheets

OTHER PUBLICATIONS

Patterson, The emerging neuropoietic cytokine family: first CDF/LIF, CNTF and IL-6; next ONC, MGF, GCSF?, Current Biology, Ltd. vol. 2, No. 1, (1992).

Konishi, et al., "Trophic effect of erythropoietin and other hematopoietic factors on central cholinergic neurons in vitro and in vivo", Brain Research, 609, (1993), pp. 29-35.

Zavala, et al., "G-CSF Therapy of Ongoing Experimental Allergic Encephalomyelitis Via Chemokine- and Cytokine-Based Immune Deviation", Article by the American Association of Immunologists (2002), pp. 2011-2019.

Suzumara, et al., "Selective induction of interleukin-6 in mouse microglia by granulocyte-macrophage colony-stimulating factor", Brain Research, 713 (1996), pp. 192-198.

Lee, et al., "GM-CSF Promotes Proliferation of Human Fetal and Adult Microglia in Primary Cultures", GLIA 12:309-318 (1994).

Guillemin, et al., "Granulocyte Macrophage Colony Stimulating Factor Stimulates In Vitro Proliferation of Astrocytes Derived From Simian Mature Brains", GLIA, 16:71-80 (1996).

Dame, et al., "The Distribution of Granulocyte-Macrophage Colony-Stimulating Factor and its Receptor in the Developing Human Fetus", Pediatric Research, vol. 46, No. 4, (1999), pp. 358-366.

Dame, et al., "The effect of interleukin-1β (IL-1β) and tumor necrosis factor-α (TNF-α) on granulocyte macrophage-colony stimulating factor (GM-CSF) production by neuronal precursor cells", Eur. Cytokine Netw, vol. 13, No. 1, Mar. 2002, pp. 128-133.

Baldwin, et al., "Identification and Characterization of a High-Affinity Granulocyte-Macrophage Colony-Stimulating Factor Receptor on Primary Rat Oligodendrocytes", Blood, vol. 82, No. 11, Dec. 1, 1993, pp. 3279-3282.

Konishi, et al., "Trophic effect of erythropoietin and other hematopoietic factors on central cholinergic neurons in vitro and in vivo", Brain Research, 609 (1993) 29-35.

Schaebitz W. R. et al: "Recombinant Granulocyte-Colony Stimulating Factor (RG-CSF) is Neuroprotective Following Focal Transient Cerebral Ischemia and Excitotoxity" Society for Neuroscience Abstracts,Society for Neuroscience, US, vol. 27, No. Part 2, Nov. 10, 2001, p. 2027, AN76411, XP008009334, ISSN: 0190-5295 the whole document.

Konishi Y, et al.: "Trophic Effect of Erythropoietin and Other Hematopoietic Factors on Central Cholinergic Neurons in Vitro an in Vivo.", Brain Research, Apr. 23, 1993, vol. 609, Nos. 1-2, pp. 29-35, XP001183386 ISSN: 0006-8993, Abstract, Introduction, p. 29, Discussion pp. 32-34.

Hierholzer, et al., "Activation of Stat Proteins Following Ischemia Reperfusion Injury Demonstrates a Distinct IL-6 and G-CSF Mediated Profile.", Transplantation Proceedings, Sep. 1998, vol. 30, No. 6, p. 2647, XP001182894, ISSN: 0041-1345 the whole document.

Tian Shin-Shay, et al.: "Multiple Signaling Pathways Induced by Granulocyte Colony-Stimulating Factor Involving Activation of JAKs, STAT5, and/or STAT3 Are Required for Regulation of Three Distinct Classes of Immediate Early Genes" Blood, vol. 88, No. 12, 1996, pp. 4435-4444 XP001183387 ISSN: 0006-4971 the whole document.

Ward Alister, et al., "Tyrosine-Dependent and—Independent Mechanisms of STAT3 Activation by the Human Granulocyte Colony-Stimulating Factor (G-CSF) Receptor Are Differentially Utilized Depending on G-CSF Concentration", Blood, vol. 93, No. 1, Jan. 1, 1999 pp. 113-124 XP001183113, ISSN: 0006-4971 the whole document.

Schaebitz, et al. "Neuroprotective Effect of Granulocyte Colony-Stimulating Factor After Focal Cerebral Ischemia.", Stroke, vol. 34, No. 3, Mar. 2003, pp. 745-751, XP002294803, ISSN: 0039-2399 the whole document.

Iverson et al., Proc Nat. Acad. Sci. 1996; 93: 2785-2789.

Tavernier et al., Proc. Nat. Acad. Sci. 1995; 92:5194-5198.

International Preliminary Examination Report as received in corresponding PCT/IB 03/06446 filed Dec. 31, 2003.

Wells, 1990, Biochemistry 29:8509-8517; Ngo et al., 1994. The Protein Folding Problem and Tertiary Structure Prediction, pp. 492-495.

Bork, 2000, Genome Research 10:398-400.

Skolnick, et al., 2000. Trends in Biotech. 18(1):34-39.

Doerks, et al., 1998, Trends in Genetics 14:248-250.

Smith et al., 1997, Nature Biotechnology 15:1222-1223.

Brenner, 1999, Trends in Genetics 15:132-133.

Bork, et al., 1996, Trends in Genetics 12:425-427.

Lee, et al., NeuroImmunoModulation, 2004; 11:279-292.

Emerich, et al., Clin Pharmacokinet. 2001; 40: 105-23.

Klein, et al. BMC Neurosci. 2007; 8-61.

Kreyden, et al. Hautarzt. 2001. 52:327-330.

Farese, et al. Stern Cells. 2001; 19:522-533.

Information sheet on Filgrastim; downloaded from Zenotechlabs.com/htmlfiles/nugraf.pdf, Nov. 7, 2007; 6 pages.

Office Action issued Oct. 28, 2010 in Australia Application No. 2009201467.

Office Action issued Jul. 26, 2010 in Korea Application No. 2005-7012226 (English Translation).

Office Action issued Nov. 2, 2010 in Japan Application No. 2007-518715.

Mark F. Mehler, et al., "Cytokines Regulate the Cellular Phenotype of Developing Neural Lineage Species", Int. J. Devl. Neuroscience, vol. 13, No. 3/4, 1995, pp. 213-240.

Thomas E. Smithgall, et al., "Control of Myeloid differentitation and survival by Stats", Oncogene, vol. 19, 2000, pp. 2612-2618.

Rolf P. De Groot, et al., "Regulation of Proliferation, Differentiation and Survival by the IL-3/IL-5/GM-CSF Receptor Family", Cell. Signal, vol. 10, 1998, pp. 619-628.

Sudesh S. Kothari, et al., "Expression of Granulocyte Colony Stimulating Factor (G-CSF) and Granulocyte/Macrophage Colony Stimulating Factor (GM-CSF) mRNA upon Stimulation with Phorbol Ester", Blood Cells, Molecules, and Diseases, vol. 21, 1995, pp. 192-200.

David M. Brown, et al., "Platelet-derived growth factor BB induces functional vascular anastomoses in vivo", Proc. Natl. Acad. Sci. USA, vol. 92, Jun. 1995, pp. 5920-5924.

Mark F. Mehler, et al., "Cytokine regulation of neuronal differentiation of hippocampal progenitor cells", Nature, vol. 362, No. 6415, 1993, pp. 62-65.

H. Awatsuji, et al., "Interleukin-4 and -5 as Modulators of Nerve Growth Factor Synthesis/Secretion in Astrocytes", J. Neurosci. Res., vol. 34, No. 5, 1993, pp. 539-545.

Rachelle Franzen, et al., "Nervous system injury: focus on the inflammatory cytokine 'granulocyte-macrophage colony stimulating factor'", Neurosci Lett., vol. 361, No. 1-3, 2004, pp. 76-78.

K. Takahashi, et al., "Granulocyte Macrophage Colony-Stimulating Factor (GM-CSF) Promotes Locomotor Recovery After Spinal Cord Injury in Adult Mice", Society for neuroscience abstract viewer and itinerary planner, vol. 2002, Abstract No. 203.5, 2002, 2 pages.

By Tong-Chun Wen, et al., "Interleukin 3 Prevents Delayed Neuronal Death in the Hippocampal CA1 Field", J. Exp. Med., vol. 188, No. 4, 1998, pp. 635-649.

Yasuo Iwasaki, et al., "Protective effect of interleukin-3 and erythropoietin on motor neuron death after neonatal axotomy", Neurological Res., vol. 24, No. 7, 2002, pp. 643-646.

Yasumitsu Ichikawa, "Neurite Outgrowth Promoting Effect of Cytokines on Cultured Rat Embryonic Ventral Spinal Cord Neurons". Journal of the Medical Society of Toho University, vol. 29, No. 4, 5, 2002, pp. 258-263 (With English Abstract).

T. Tabira, et al., "Neurotrophic effect of Hematopoietic Cytokines on Cholinergic and Other Neurons in vitro", Int. J. Devl. Neuroscience, vol. 13, No. 3/4, 1995, pp. 241-252.

Yukiko Kannan, et al., "Neurotrophic Action of Interleukin 3 and Granulocyte-Macrophage Colony-Stimulating Factor on Murine Sympathetic Neurons", NeuroImmunoModulation, vol. 8, No. 3, 2000, pp. 132-141.

Masahiro Kamegai, et al., "Interleukin 3 as a Trophic Factor for Central Cholinergic Neurons in Vitro and in Vivo", Neuron, vol. 4, No. 3, 1990, pp. 429-436.

Eric Caldenhoven, et al., "Activation of the STAT3/Acute Phase Response Factor Transcription Factor by Interleukin-5", Journal of Biological Chemistry, vol. 270, No. 43, 1995, pp. 25778-25784.

Eric Caldenhoven, et al., "Activation of a Functionally Distinct 80-kDa STAT5 Isoform by IL-5 and GM-CSF in Human Eosinophils and Neutrophils", Molecular Cell Biology Research Communications, vol. 1, No. 2, 1999, pp. 95-101.

Mark W. Sleeman, et al., "The ciliary neurotrophic factor and its receptor, CNTFRα", Pharm. Acta Helvetiae, vol. 74, No. 2-3, 2000, pp. 265-272.

Extended Search Report issued Jan. 12, 2011 in Europe Application No. 09011942.1.

Office Action issued Mar. 29, 2011 in Japan Application No. 2007-518715 (With English Translation).

Atsushi Saito, et al., "Neuroprotective Role of a Proline-Rich Akt Substrate in Apoptotic Neuronal Cell Death after Stroke: Relationships with Nerve Growth Factor", The Journal of Neuroscience, vol. 24, No. 7, 2004, pp. 1584-1593.

Koji Shimoke, et al., "Nerve Growth Factor Prevents 1-Methyl-4-Phenyl-1,2,3,6-Tetrahydropyridine -Induced Cell Death Via the Akt Pathway by Suppressing Caspase-3-Like Activity Using PC12 Cells: Relevance to Therapeutical Application for Parkinson's Disease", J. Neurosci. Res., vol. 63, No. 5, 2001, pp. 402-409.

Rosario Garrido, et al., "Nicotine upregulates nerve growth factor expression and prevents apoptosis of cultured spinal cord neurons", Neuroscience Research, vol. 47, No. 3, 2003, pp. 349-355.

* cited by examiner

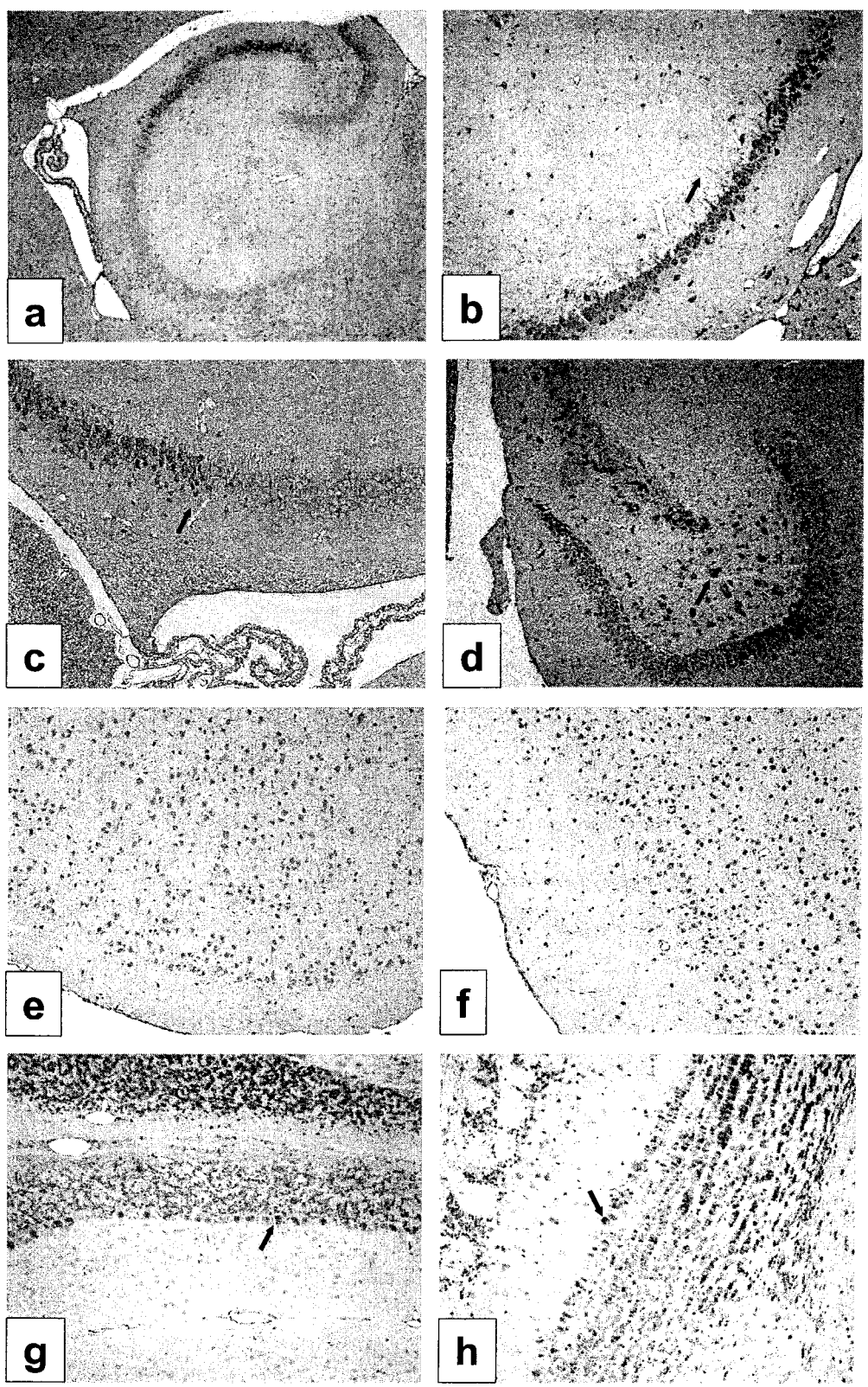
Figure 4, part I

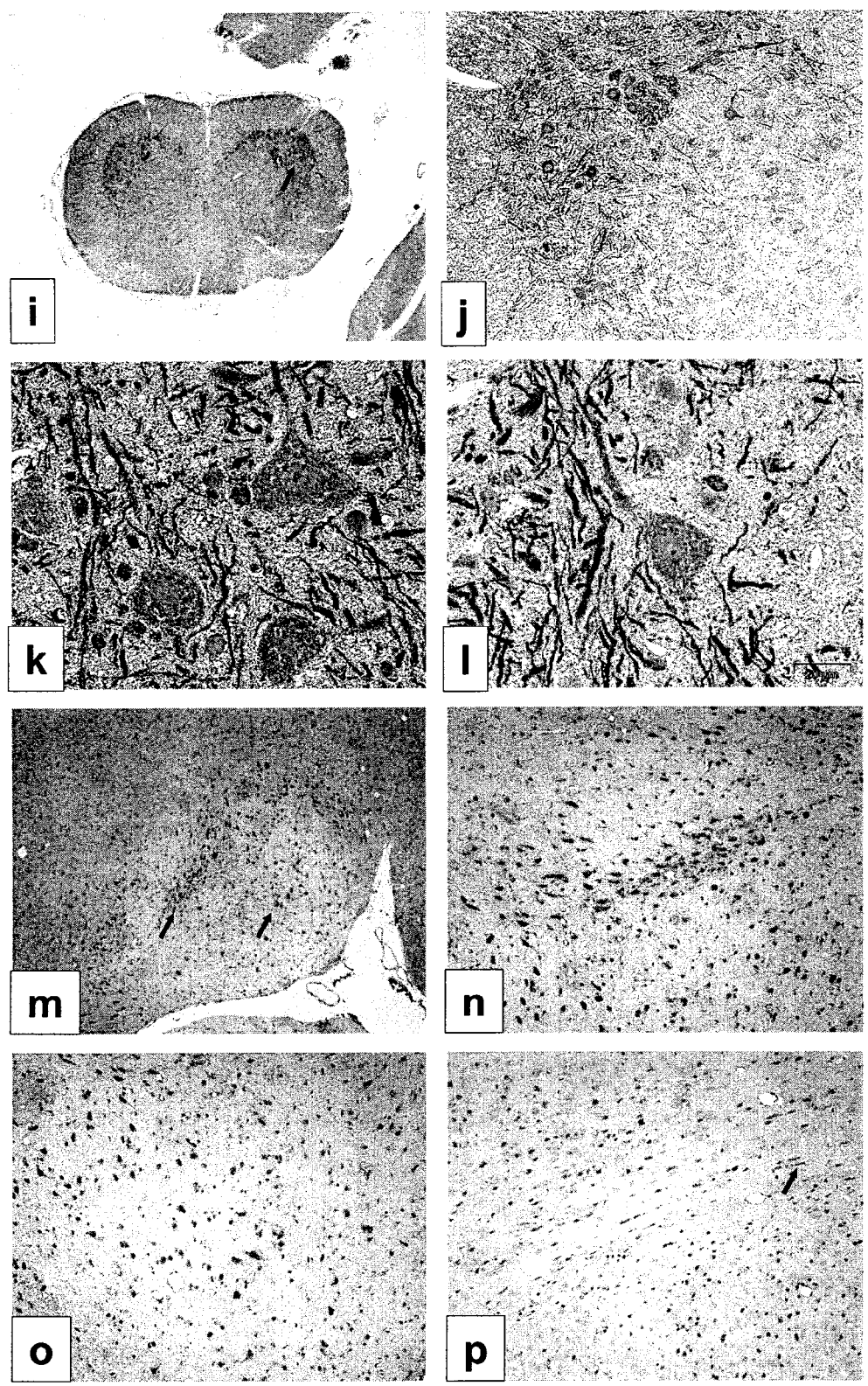
Figure 4, part II

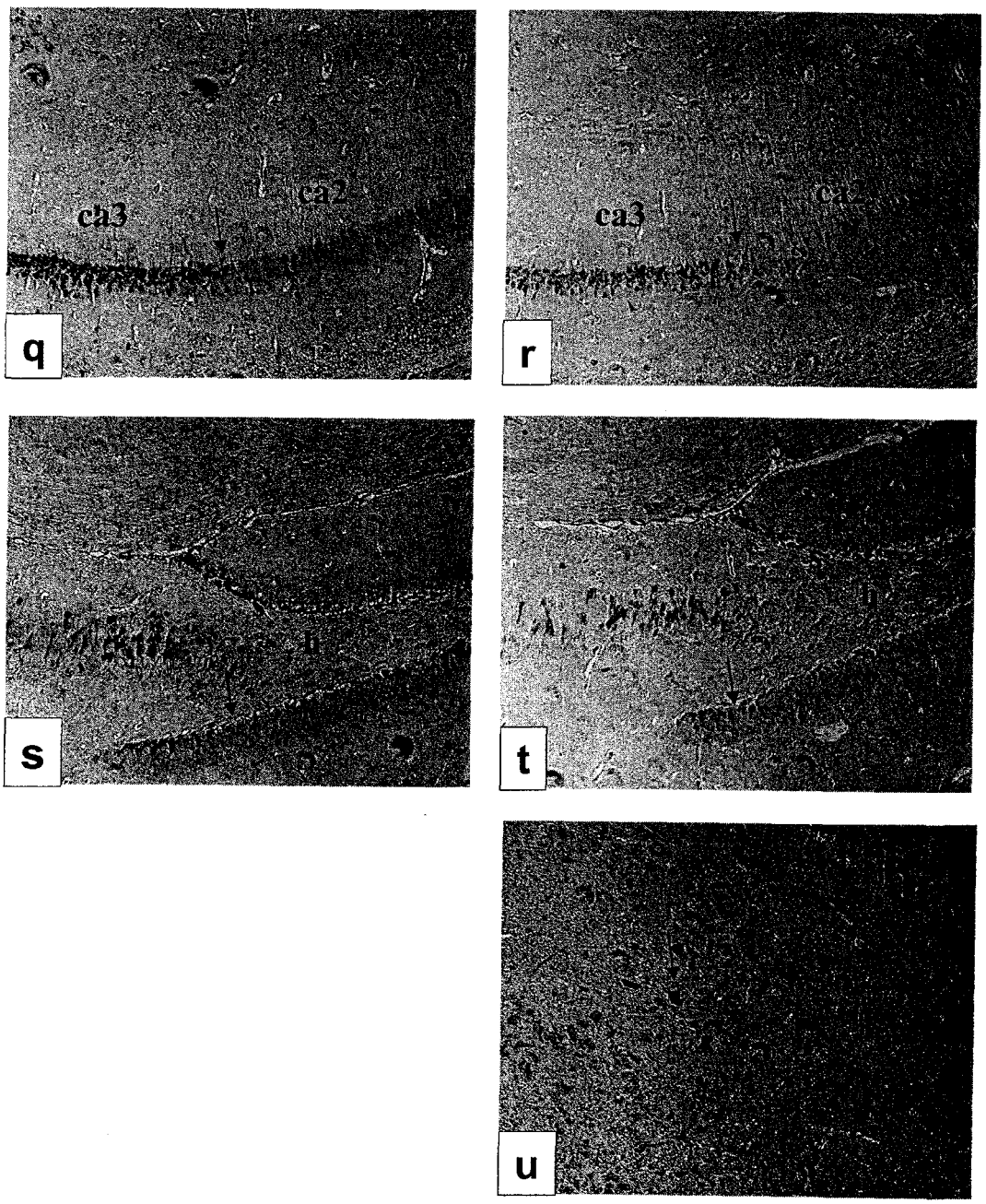
Figure 4, part III

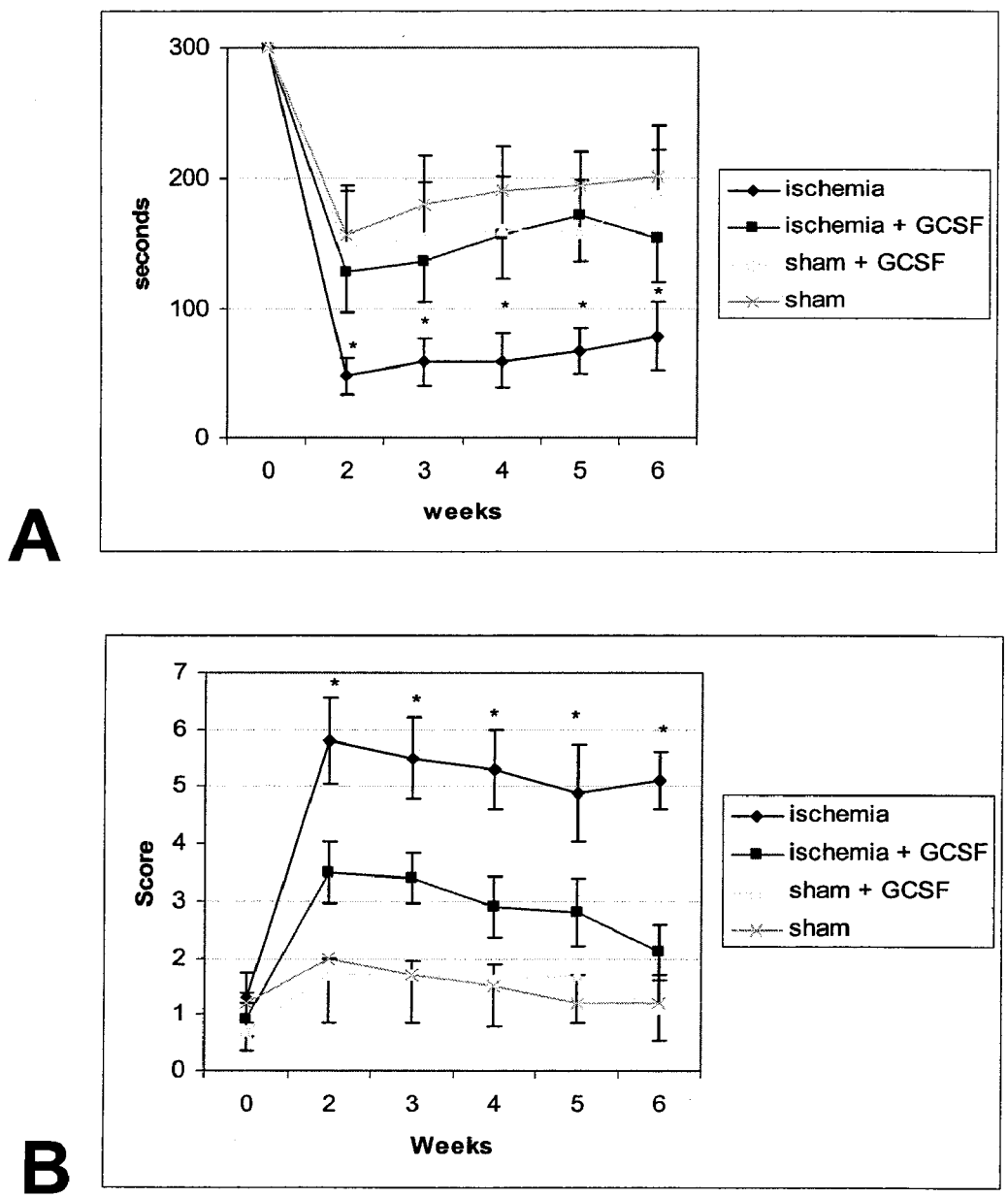
Figure 8, part I

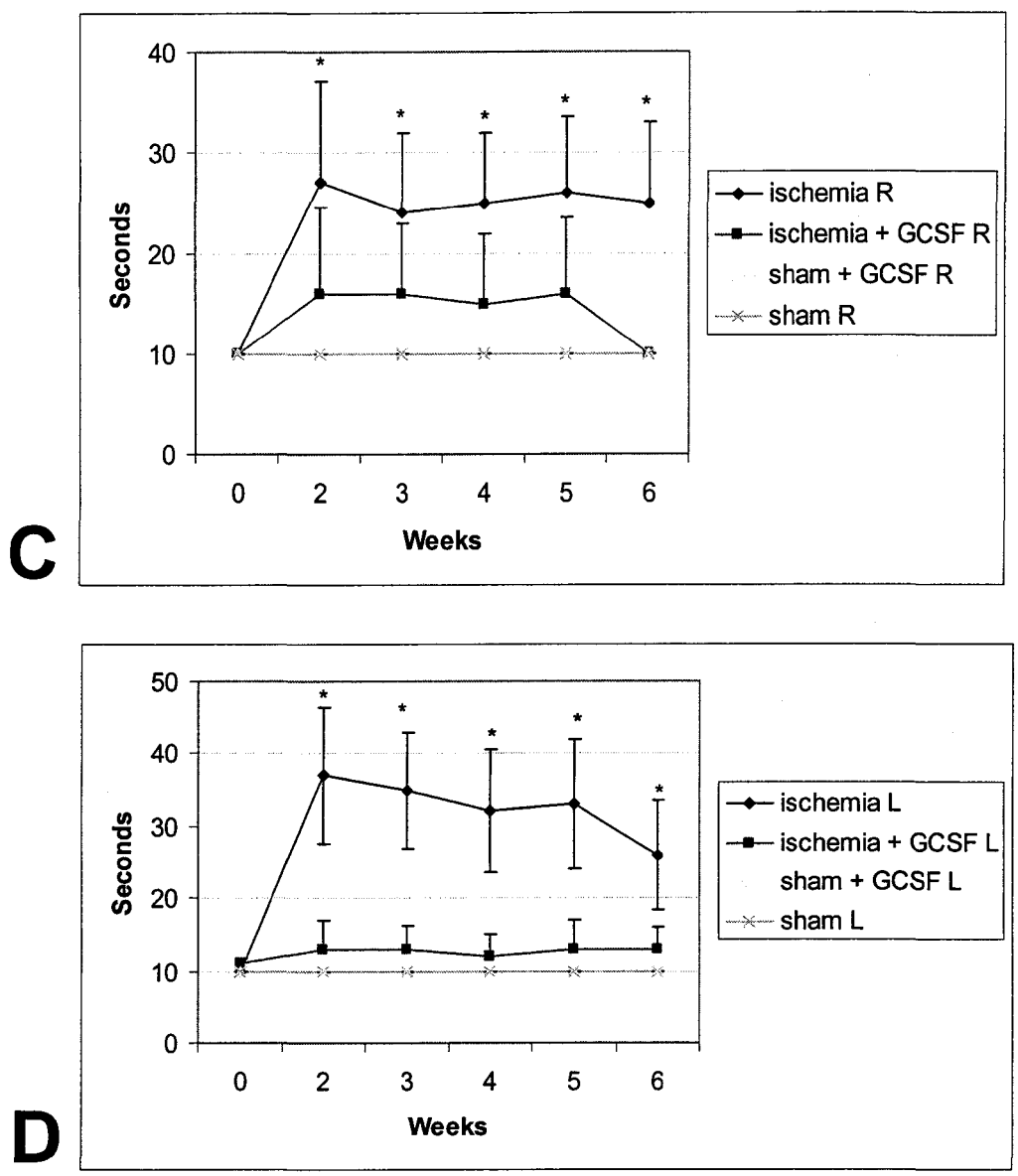
Figure 8, part II

```
  1  M A G P A T Q S P M K L M A L Q L L L W H S A L W T V Q E A  hum G-CSF
  1  M A Q L S A Q R R M K L M A L Q L L L W Q S A L W S G R E A  mouse G-CSF
  1  - - - - - - - - - M K L M A L Q L L L W H S A L W S G Q E A  rat G-CSF
  1  - - - - - - - - - - K L M A L Q L L L W H S A L W M V Q E A  feline G-C
  1  - - - - - - - - - M K L M V L Q L L L W H S A L W T V H E A  bovine G-C
  1  - - - - - - - - - M K L M A L Q L L L W H I A L W M V P E A  pig G-CSF 31  T P L G P A S S L P - - - - - - Q S F L L K C L E Q V R K I  hum G-CSF
 31  V P L V T V S A L P P S L P L P R S F L L K S L E Q V R K I  mouse G-CSF
 22  I P L L T V S S L P P S L P L P R S F L L K S L E Q V R K I  rat G-CSF
 21  T P L G P T S S L P - - - - - - Q S F L L K C L E Q V R K V  feline G-C
 22  T P L G P A R S L P - - - - - - Q S F L L K C L E Q V R K I  bovine G-C
 22  A P L S P A S S L P - - - - - - Q S F L L K C L E Q V R K I  pig G-CSF 55  Q G D G A A L Q E K L V S E C A T Y K L C H P E E L V L L G  hum G-CSF
 61  Q A S G S V L L E Q L - - - C A T Y K L C H P E E L V L L G  mouse G-CSF
 52  Q A R N T E L L E Q L - - - C A T Y K L C H P E E L V L F G  rat G-CSF
 45  Q A D G T A L Q E R L - - - C A A H K L C H P E E L V L L G  feline G-C
 46  Q A D G A E L Q E R L - - - C A A H K L C H P E E L M L L R  bovine G-C
 46  Q A D G A E L Q E R L - - - C A T H K L C H P Q E L V L L G  pig G-CSF 85  H S L G I P W A P L S S C P S Q A L Q L A G C L S Q L H S G  hum G-CSF
 88  H S L G I P K A S L S G C S S Q A L Q Q T Q C L S Q L H S G  mouse G-CSF
 79  H S L G I P K A S L S S C S S Q A L Q Q T K C L S Q L H S G  rat G-CSF
 72  H A L G I P Q A P L S S C S S Q A L Q L T G C L R Q L H S G  feline G-C
 73  H S L G I P Q A P L S S C S S Q S L Q L T S C L N Q L H G G  bovine G-C
 73  H S L G L P Q A S L S S C S S Q A L Q L T G C L N Q L H G G  pig G-CSF 115  L F L Y Q G L L Q A L E G I S P E L G P T L D T L Q L D V A  hum G-CSF
118  L C L Y Q G L L Q A L S G I S P A L A P T L D L L Q L D V A  mouse G-CSF
109  L F L Y Q G L L Q A L A G I S S E L A P T L D M L H L D V D  rat G-CSF
102  L F L Y Q G L L Q A L A G I S P E L A P T L D M L Q L D I T  feline G-C
103  L F L Y Q G L L Q A L A G I S P E L A P T L D T L Q L D V T  bovine G-C
103  L V L Y Q G L L Q A L A G I S P E L A P A L D I L Q L D V T  pig G-CSF 145  D F A T T I W Q Q M E E L G M A P A L Q P T Q G A M P A F A  hum G-CSF
148  N F A T T I W Q Q M E N L G V A P T V Q P T Q S A M P A F T  mouse G-CSF
139  N F A T T I W Q Q M E S L G V A P T V Q P T Q S T M P I F T  rat G-CSF
132  D F A I N I W Q Q M E D V G M A P A V P P T Q G T M P T F T  feline G-C
133  D F A T N I W L Q M E D L G A A P A V Q P T Q G A M P T F T  bovine G-C
133  D L A T N I W L Q M E D L R M A P A S L P T Q G T V P T F T  pig G-CSF 175  S A F Q R R A G G V L V A S H L Q S F L E V S Y R V L R H L  hum G-CSF
178  S A F Q R R A G G V L A I S Y L Q G F L E T A R L A L H H L  mouse G-CSF
169  S A F Q R R A G G V L V T S Y L Q S F L E T A H H A L H H L  rat G-CSF
162  S A F Q R R A G G T L V A S N L Q S F L E V A Y R A L R H F  feline G-C
163  S A F Q R R A G G V L V A S Q L H R F L E L A Y R G L R Y L  bovine G-C
163  S A F Q R R A G G V L V V S Q L Q S F L E L A Y R V L R Y L  pig G-CSF 205  A Q P                                                       hum G-CSF
208  A .                                                         mouse G-CSF
199  P R P A Q K H F P E S L F I S I .                           rat G-CSF
192  T K P                                                       feline G-C
193  A E P                                                       bovine G-C
193  A E P                                                       pig G-CSF
```

Figure 10

```
MARLGNCSLTWAALI I LLLLPGSLEECGHI SVSAPI VHLGDPI TASCI I KQNCSHLDPEPQ    h gcsfr
MVGLGACTLTGVTLI FLLLPRSLESCGHI EI SPPVVRLGDPVLASCTI SPNCSKLDQQAK       m gcsfr
- - - - - - - - - - - - - - - - - - - - LEGCGQI RI SPPI VHLGDPVLASCTI SPNCSKLDRQPK    r gcsfr (frag)

I LWRLGAE- LQPGGRQQRLSDGTQESI I TLPHLNHTQAFLSCCLNWGNSLQI LDQVELRA       h gcsfr
I LWRLQDEPI QPGDRQHHLPDGTQESLI TLPHLNYTQAFLFCLVPWEDSVQLLDQAELHA        m gcsfr
I LWRLQDEPNQPGDRQHHLPDGSQESI I TLPHLNYTQAFLFCLVPWNNSFQVLDQAELRA        r gcsfr (frag)

GYPPAI PHNLSCLMNLTTSSLI CQWEPGPETHLPTSFTLKSFKSRGNCQTQGDSI LDCVP         h gcsfr
GYPPASPSNLSCLMHLTTNSLVCQWEPGPETHLPTSFI LKSFRSRADCQYQGDTI PDCVA          m gcsfr
GCKSLQPP- - - - - - - - - THLLQC                                        r gcsfr (frag)

KDGQSHCCI PRKHLLLYQNMGI WVQAENALGTSMSPQLCLDPMDVVKLEPPMLRTMDPSP          h gcsfr
KKRQNNCSI PRKNLLLYQYMAI WVQAENMLGSSESPKLCLDPMDVVKLEPPMLQALDI GP         m gcsfr
                                                                        r gcsfr (frag)

EAAPPQAGCLQLCWEPWQPGLHI NQKCELRHKPQRGEASWALVGPLPLEALQYELCGLLP           h gcsfr
DVVSHQPGCLWLSWKPWKPSEYMEQECELRYQPQLKGANWTLVFHLPSSKDQFELCGLHQ            m gcsfr
                                                                        r gcsfr (frag)

ATAYTLQI RCI RWPLPGHWSDWSPSLELRTTERAPTVRLDTWWRQRQLDP- - RTVQLFWK        h gcsfr
APVYTLQMRCI RSSLPGFWSPWSPGLQLRPTMKAPTI RLDTWCQKKQLDPGTVSVQLFWK          m gcsfr
                                                                        r gcsfr (frag)

PVPLEEDSGRI QGYVVSWRPSGQAGAI LPLCNTTELSCTFHLPSEAQEVALVAYNSAGTS          h gcsfr
PTPLQEDSGQI QGYLLSWNSPDHQGQDI HLCNTTQLSCI FLLPSEAQNVTLVAYNKAGTS         m gcsfr
                                                                        r gcsfr (frag)

RPTPVVFSESRGPALTRLHAMARDPHSLWGWEPPNPWPQGYVI EWGLGPPSASNSNKTW            h gcsfr
SPTTVVFLENEGPAVTGLHAMAQDLNTI WDWEAPSLLPQGYLI EWEMSSPSYNNSYKSW           m gcsfr
                                                                        r gcsfr (frag)

RMEQNGRATGFLLKENI RPFQLYEI I VTPLYQDTMGPSQHVYAYSQEMAPSHAPELHLKH         h gcsfr
MI EPNGNI TGI LLKDNI NPFQLYRI TVAPLYPGI VGPPVNVYTFAGERAPPHAPALHLKH      m gcsfr
                                                                        r gcsfr (frag)

I GKTWAQLEWPEPPELGKSPLTHYTI FWTNAQNQSFSAI LNASSRGFVLHGLEPASLYH          h gcsfr
VGTTWAQLEWPEAPRLGMI PLTHYTI FWADAGDHSFSVTLNI SLHDFVLKHLEPASLYH          m gcsfr
                                                                        r gcsfr (frag)

I HLMAASQAGATNSTVLTLMTLTPEGSELHI I LGLFGLLLLLTCLCGTAWLCCSPNRKNP          h gcsfr
VYLMATSRAGSTNSTGLTLRTLDP- - SDLNI FLGI L- CLVLLSTTCVVTWLCCKRRGKTS        m gcsfr
                                                                        r gcsfr (frag)

LWPSVPDPAHSSLGSWVPTI MEEDAFQLPGLG- - - TPPI TKLTVLEEDEKKPVPWESHNS        h gcsfr
FWSDVPDPAHSSLSSWLPTI MTEETFQLPSFWDSSVPSI TKI TELEED- KKPTHWDSE- S        m gcsfr
                                                                        r gcsfr (frag)

SETCGLPTLVQTYVLQGDPRAVSTQPQSQSGTSDQVLYGQLLGSPTSPGPGHYLRCDSTQ           h gcsfr
SGNGSLPALVQAYVLQGDPREI SNQSQPPSRTGDQVLYGQVLESPTSPGVMQYI RSDSTQ          m gcsfr
                                                                        r gcsfr (frag)

PLLAGLTPSPKSYENLWFQASPLGTLVTPAPSQEDDCVFGPLLNFPLLQGI RVHGMEALG           h gcsfr
PLLGGPTPSPKSYENI WFHSRPQETFVPQPPNQEDDCVFGPPFDFPLFQGLQVHGVEEQG           m gcsfr
                                                                        r gcsfr (frag)

SF                                                                      h gcsfr
GF                                                                      m gcsfr
                                                                        r gcsfr (frag)
```

Figure 11

Biotinylated G-CSF detected on blot
via Streptavidin-HRP
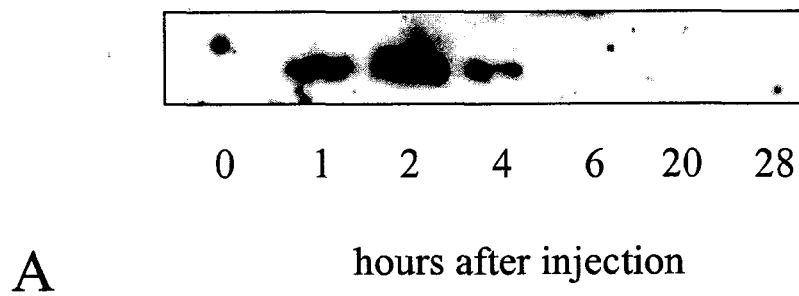
0   1   2   4   6   20   28
A                hours after injection
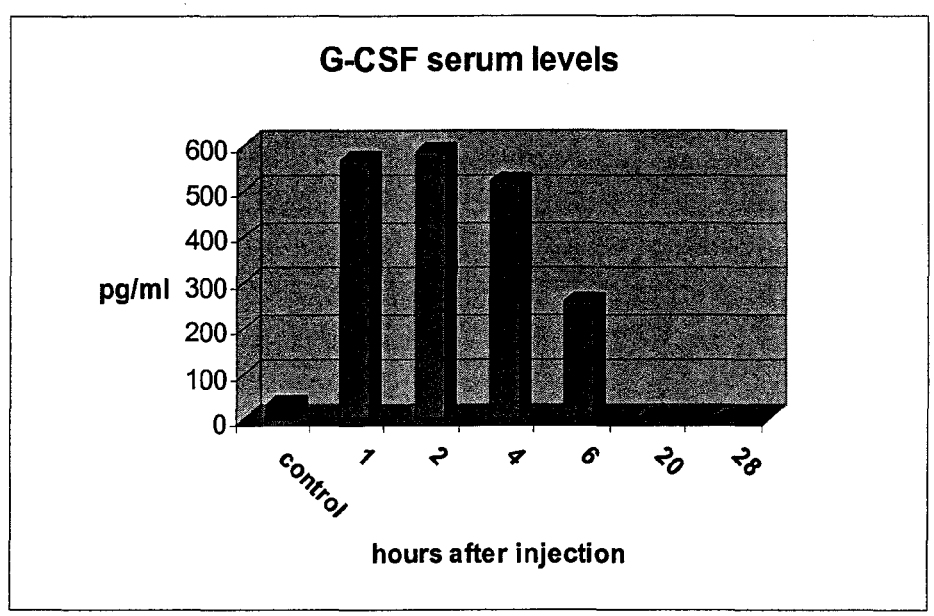
B
Figure 14

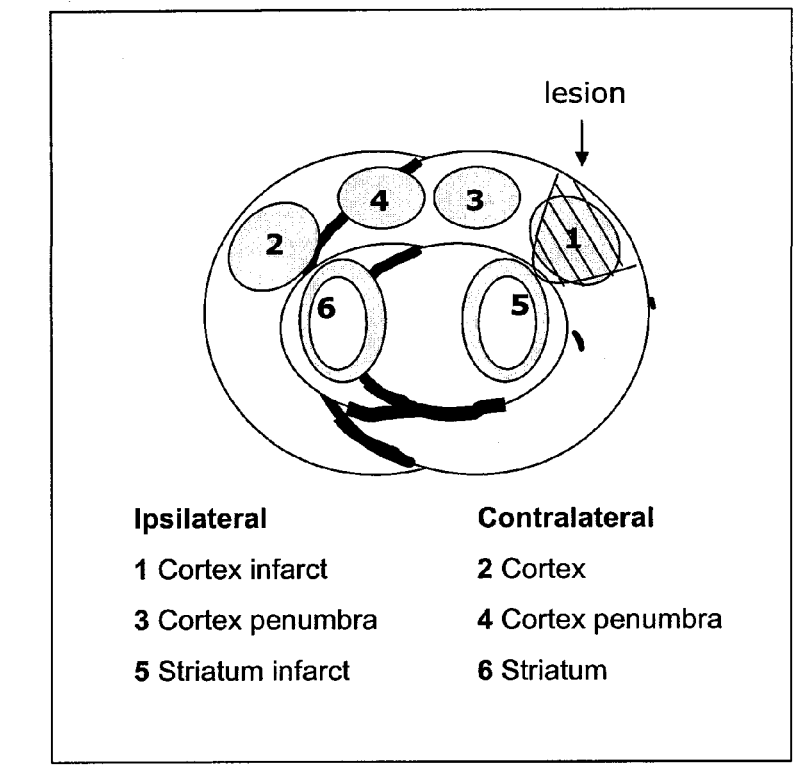
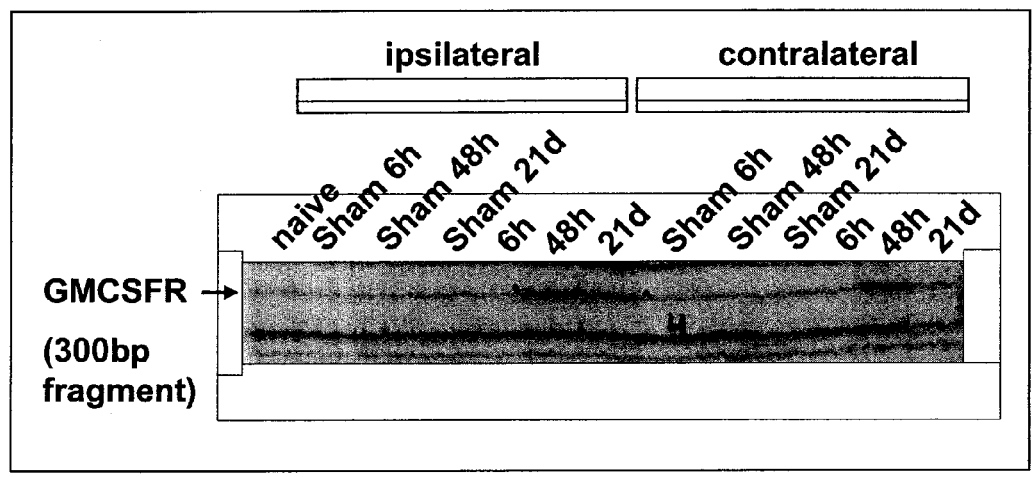
Figure 15

```
              10              20              30              40
- - - - - - - - M L L L V T - - S   L   E   P H P A F L L I P E K   D L R T V   hum gmcsfr
M T S S H A M N   T P L A C -         F S T       L P G T Q A L L A P T T P - - -   mouse csf
- - - - - - M S   I P   P Q L   A L L C C C G   A A A T Q G P T D     T P P N L   rat gmcsfr 50              60              70              80
A P A S S   N V R   D S R   M N   S W D C Q E N T - - -   F S K C F L T D K K N   hum gmcsfr
D A G S A   N L T   D   W   R T L T W A C D T A A G N V   V T S C T V T S R E A   mouse csf
G L A H F H N   T   D P G T W T   S W A C G G H D C - - A   M S C T V   D Q E A   rat gmcsfr 90             100             110             120
R V V E P   L S N N E C S C T     - E I C L H E G V T F E V H V N T S Q R G F Q   hum gmcsfr
    H R - R V S P F G C R C W   R R M M A L H G V   L D   N G T V G   A A A H   mouse csf
    I R R - R V R S R G C R C R   Q - P M E L H R G V D L E V A G D K G H A Q V H   rat gmcsfr 130             140             150             160
Q K   L Y P   S G R E G T A A Q N F S C F   Y N A D L M N C T W A R G   T A   R   hum gmcsfr
W R D S   V N   S A A G S G A E N L T C     R   A R P L S C A W R E G P A A P A   mouse csf
Q T   R F E N   G A P G S G A E N L T C F L   A H   L C C Y W A V G P A A P D   rat gmcsfr 170             180             190             200
D V Q Y F   Y I R N S K R R R E I R C P Y Y I Q D S G T H V G C H L D N   S G     hum gmcsfr
D V   Y S L R V   N S T G H D V A R C M A D P G D - D V I T Q C I A N D L S L L   mouse csf
D I R Y S L R V L N A T G H E V A S C S A A P C - - T P P T R C Q A D D L T H L   rat gmcsfr 210             220             230             240
T S R N Y F L W N G T S R E I G I Q F F D S L L D T K K L   R F N P P S N V T V   hum gmcsfr
G S E A Y L V V T G R S G A G P V R F L D D V V A T K A L E R L G P P R D V T A   mouse csf
P R L A   I V V T G Q S R T G L V R F L D A V V N F K G T E R L G P P D N V S A   rat gmcsfr 250             260             270             280
R C N T T H C L V R W K Q P R T Y Q K T S Y L D F C Y Q L D V H R K N T Q   G T   hum gmcsfr
S C N S S   H C T V S W A P P S T W A S L T A R D P Q - - T E T Q W Q S A P G S   mouse csf
S C N F S H C T   T W A P P P T W A P M E Q D E R - - F E I E W K K A P P S S   rat gmcsfr 290             300             310             320
E N L L I N V S C D L E N R Y N F S S E P R A K H S V K I R A A D V R I L N W   hum gmcsfr
T P R K V L V V - -   E T R L A   P S P A P H G G   K V K V R A G D T R M K H W   mouse csf
I A Q K V V I A G R E D N A F A   P S P A P R G R L W V R V R A G D T R S D R W   rat gmcsfr 330             340             350             360
S S W S E A I E F G S D D G N L G S V Y I   V L L I V G T   V C G I V   G F L F   hum gmcsfr
G E W S   A H P L E A   D T R V   G A L L Y A V T A C A V L L C A L A L G V T C   mouse csf
S D W S P A L E L G S E A T P   R A L V L A A S S C A A L L C A L A L G A A C   rat gmcsfr 370             380             390             400
K   L R I Q     F       V   Q   K D   L N   N H E   E D   I I W E E F T P E E G   hum gmcsfr
        E V T                         G           K V S D D V     N P E                 Q     mouse csf
        L A L S                       L           P D R V S D D E   V N S                 R     rat gmcsfr 410
K G Y R E E V L T V K E I T .                                                     hum gmcsfr
                                                                                  mouse csf
                                                                                  rat gmcsfr
```

Fig. 17

```
                10                  20                  30                  40
- - - - - - - - - - - - - - A P T R S P N P V T R P W K H V D A I K E A L   rat gmc
M W L Q N L L F L G I V V Y S L S A P T R S P I T V T R P W K H V E A I K E A L   mouse g
M W L Q S L L L L G T V A C S I S A P A R S P S P S T Q P W E H V N A I Q E A R   hum gmc 50                  60                  70                  80
S L L N D M R A L E N E K N E D V D I I S N E F S I Q R P T C V Q T R L K L Y K   rat gmc
N L L D D M P V T L N - - - E E V E V V S N E F S F K K L T C V Q T R L K I F E   mouse g
R L L N L S R D T A A E M N E T V E V I S E M F D L Q E P T C L Q T R L E L Y K   hum gmc 90                  100                 110                 120
Q G L R G N L T K L N G A L T M I A S H Y Q T N C P P T P E T D C E I E V T T F   rat gmc
Q G L R G N F T K L K G A L N M T A S Y Y Q T Y C P P T P E T D C E T Q V T T Y   mouse g
Q G L R G S L T K L K G P L T M M A S H Y K Q H C P P T P E T S C A T Q I I T F   hum gmc 130                 140
E D F I K N L K G F L F D I P F D C W K P V Q K                                   rat gmc
A D F I D S L K T F L T D I P F E C K K P G Q K                                   mouse g
E S F K E N L K D F L L V I P F D C W E P V Q E                                   hum gmc
```

Figure 18

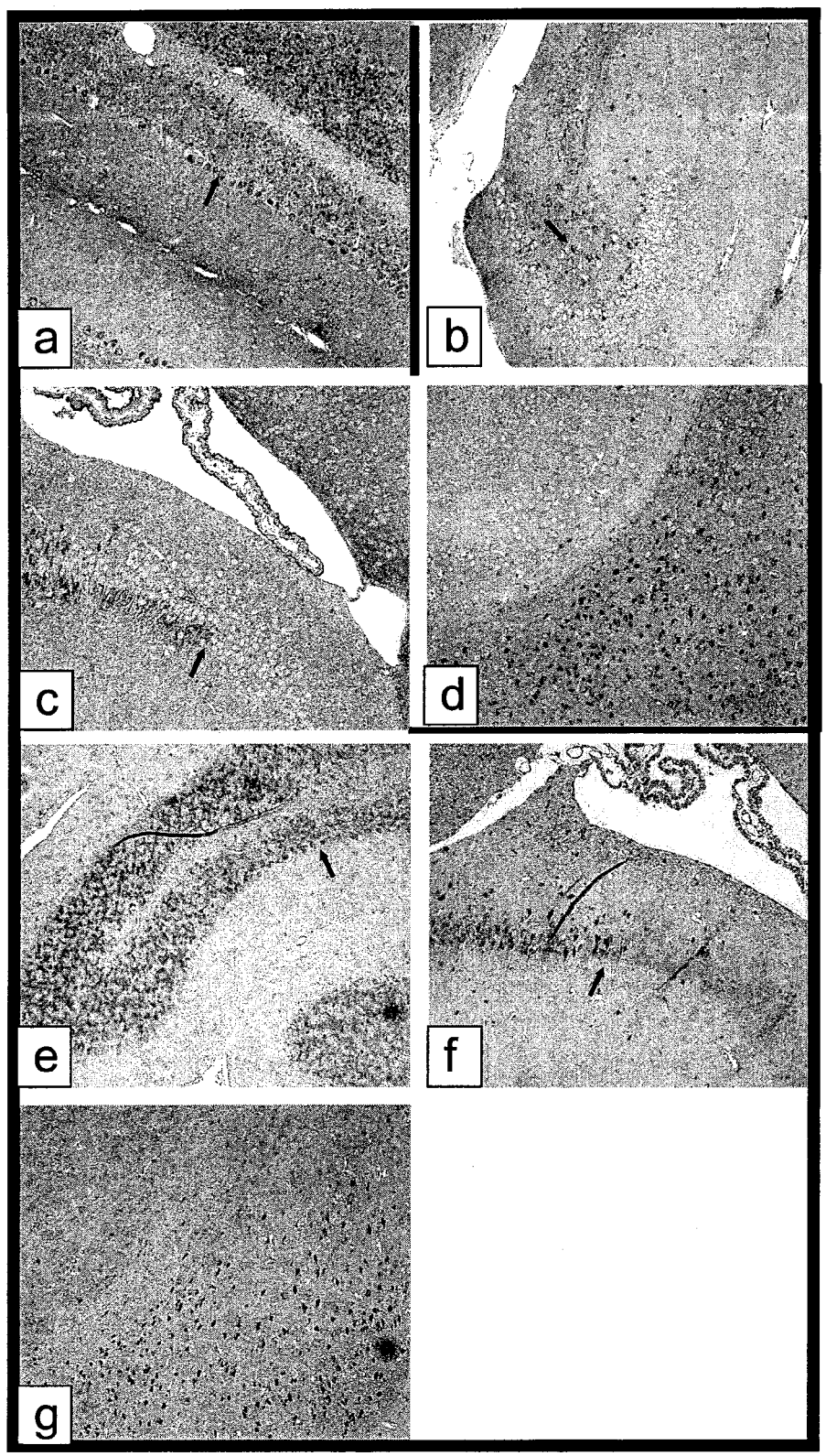
Figure 19, part I

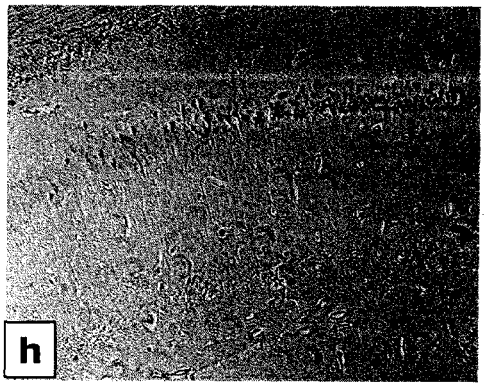 
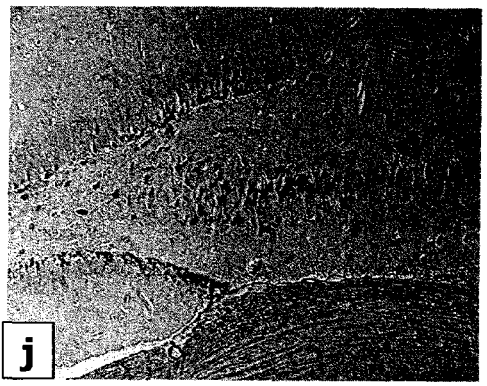 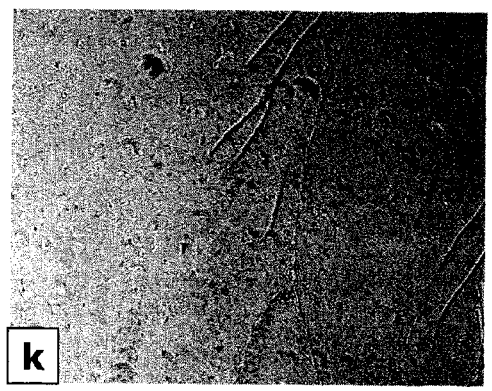
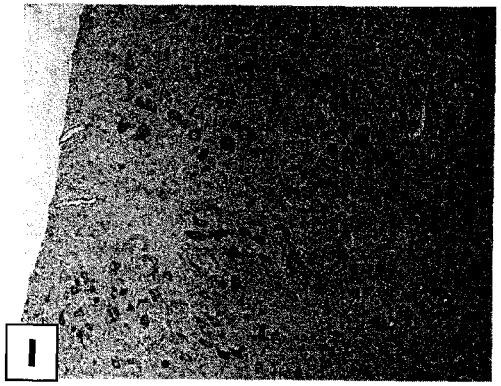 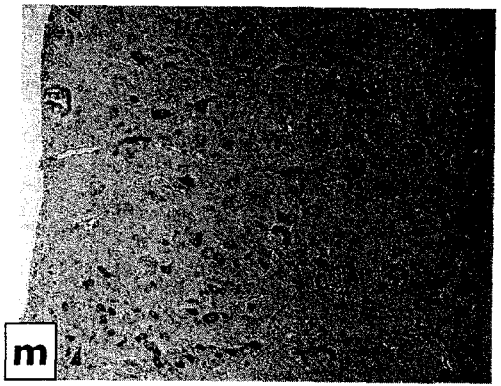
Figure 19, part II

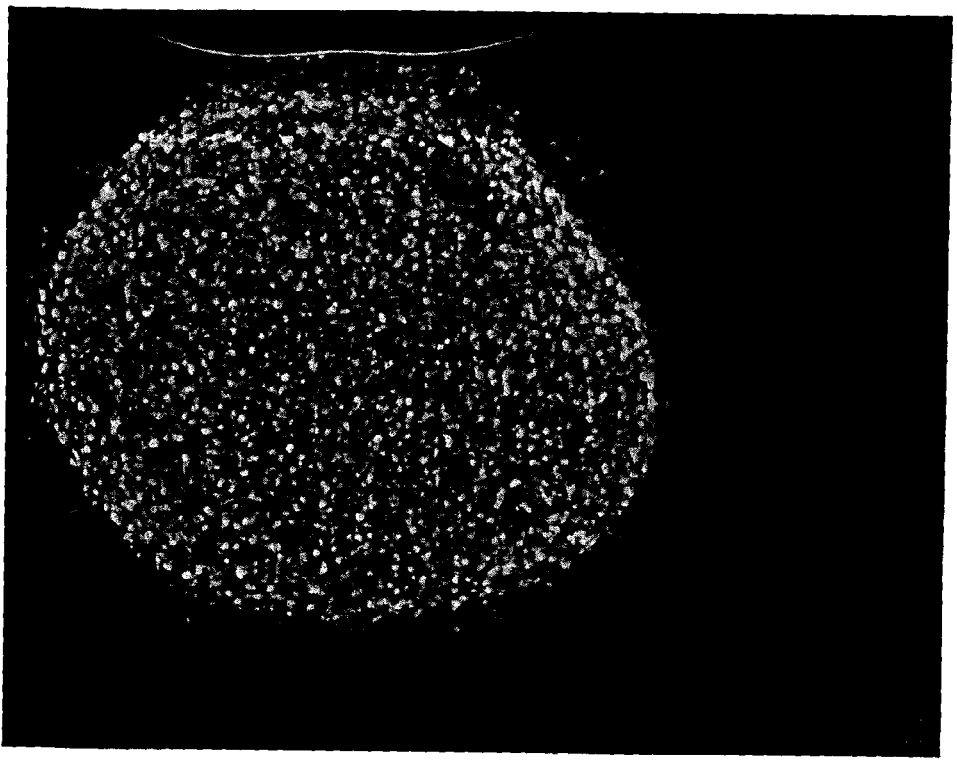
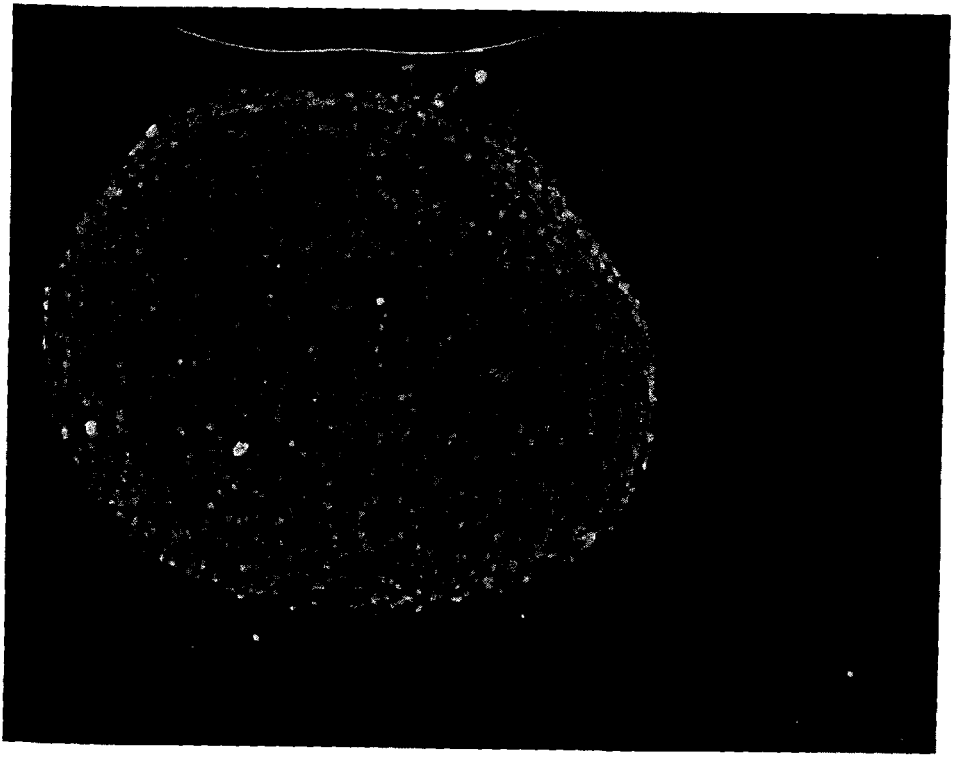
Figure 22

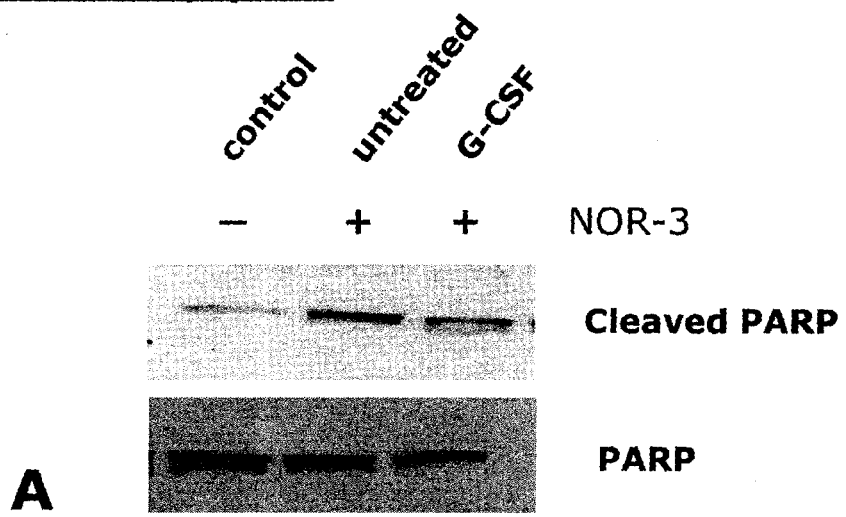
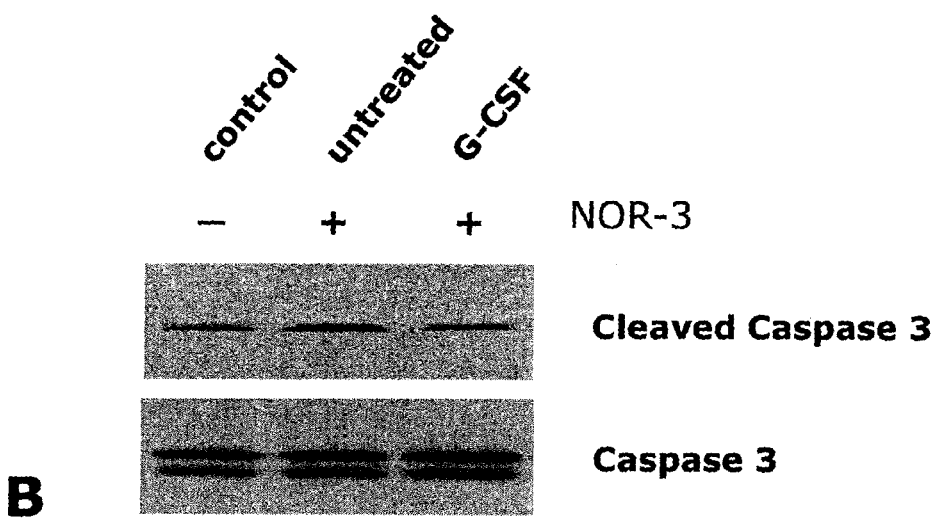
Figure 27, part I

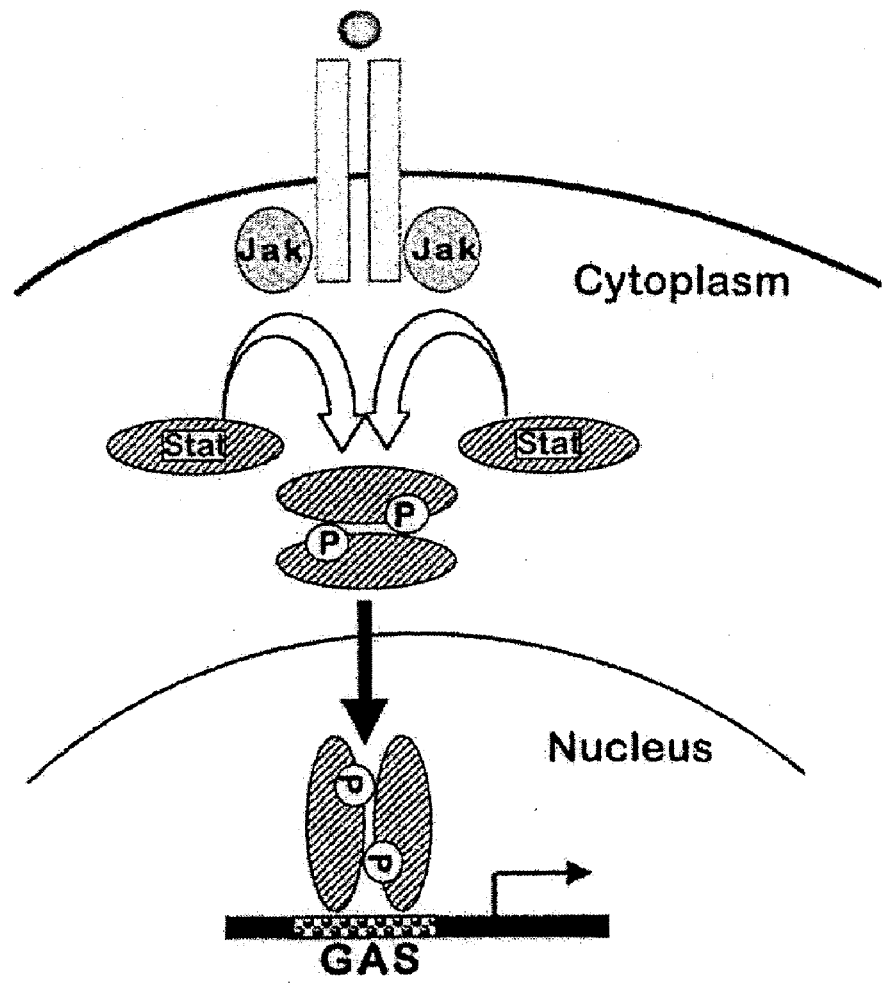
Figure 27, part II

GCSF
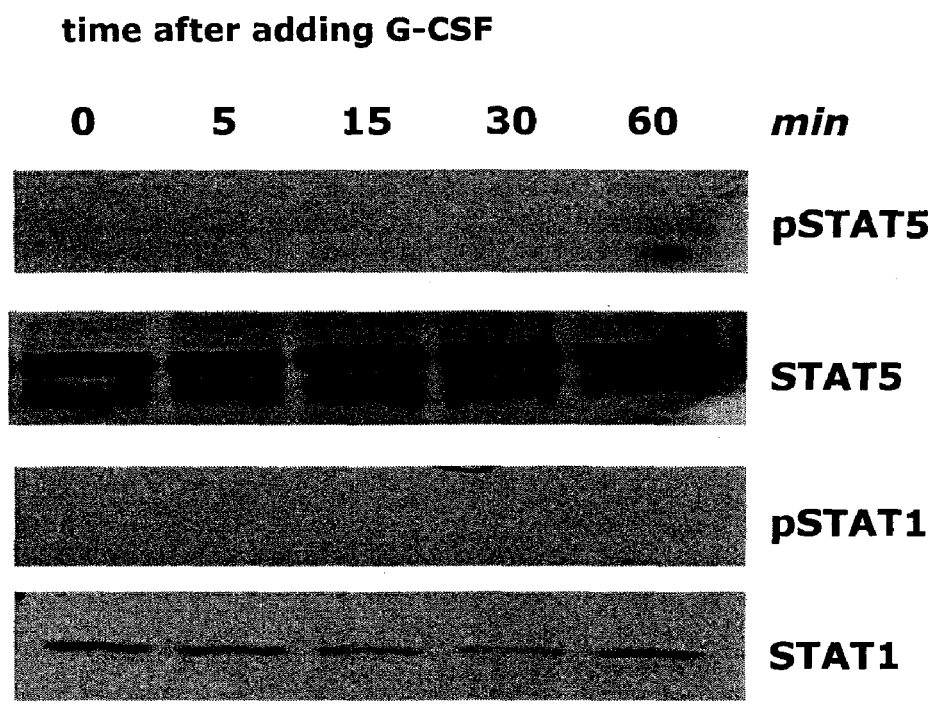
Figure 27, part III

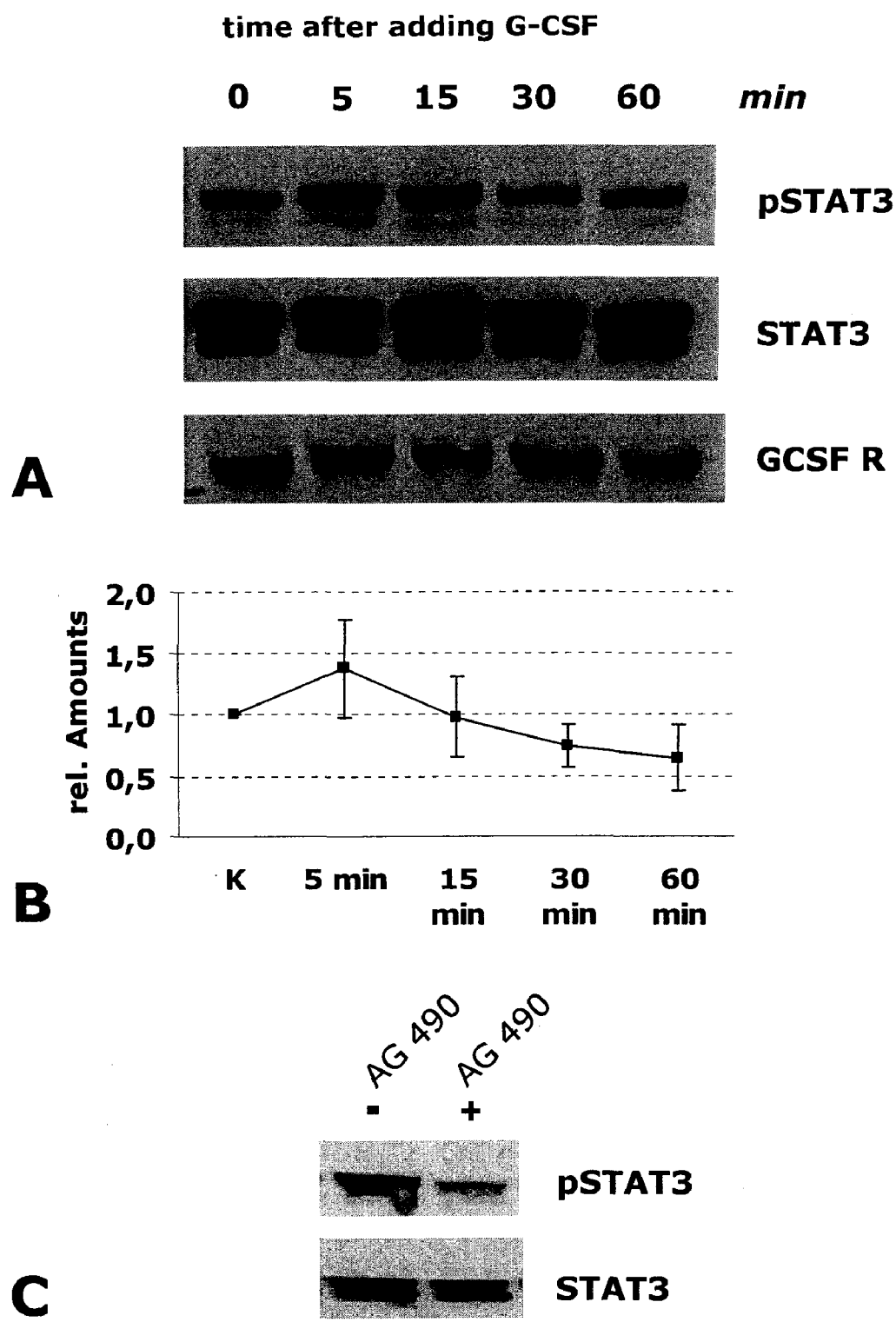
Figure 27, part IV

Transient phosphorylation of STAT3 within other systems
GM-CSF / G-CSF on Neutrophils
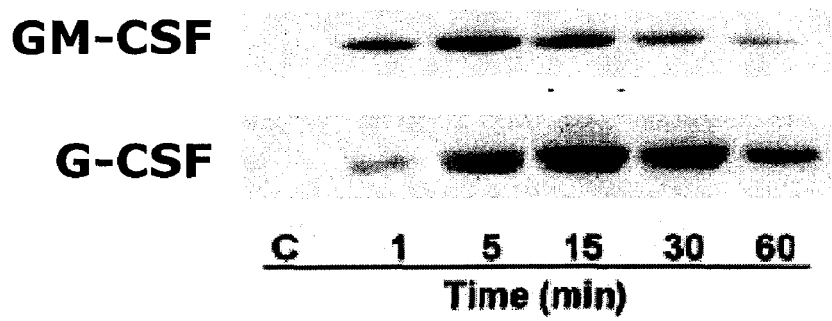
*taken and adapted from : Kuroki, M. & O'Flaherty, J. T. Extracellular signal-regulated protein kinase (ERK)-dependent and ERK-independent pathways target STAT3 on serine-727 in human neutrophils stimulated by chemotactic factors and cytokines. *Biochem J* 341 ( Pt 3), 691-6 (1999)
Figure 27, part V

GCSF activates STAT3 target genes
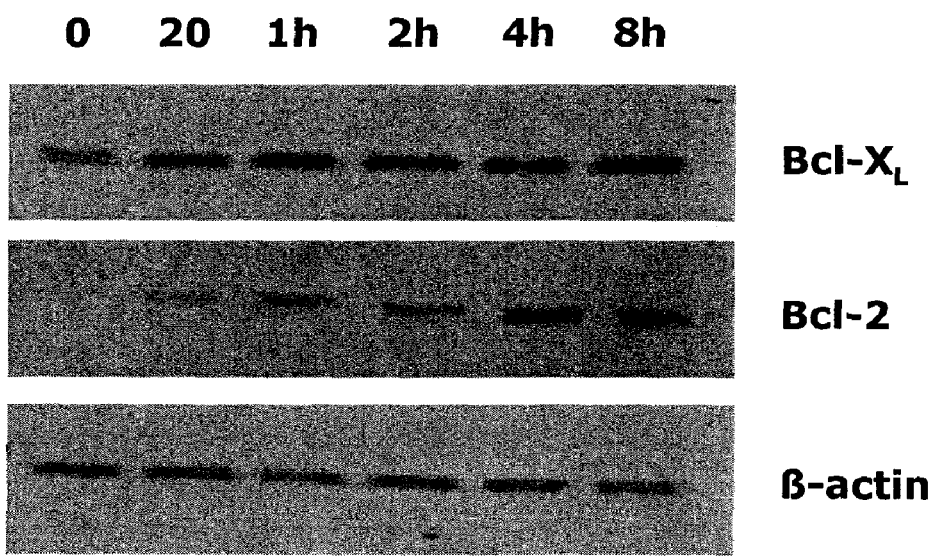
Figure 27, part VI

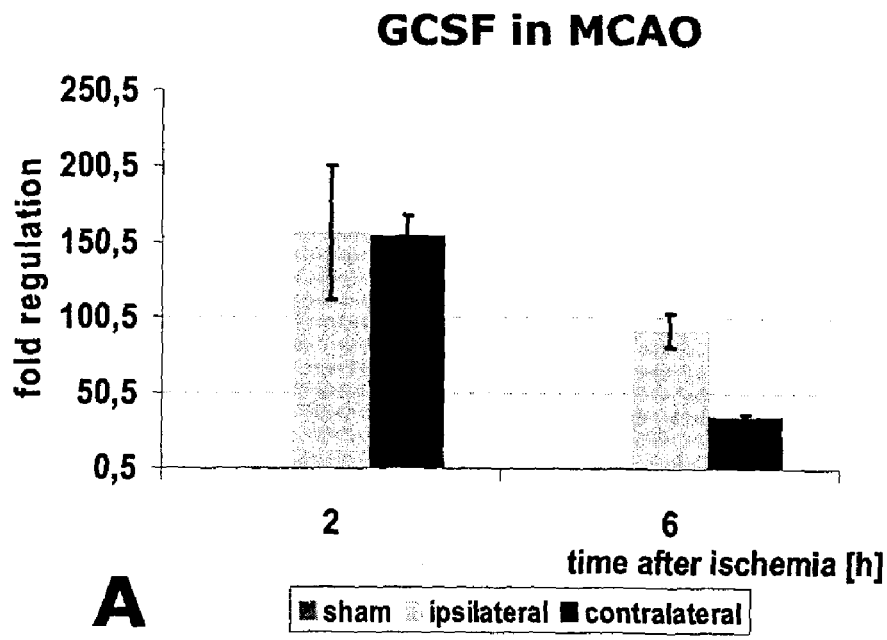
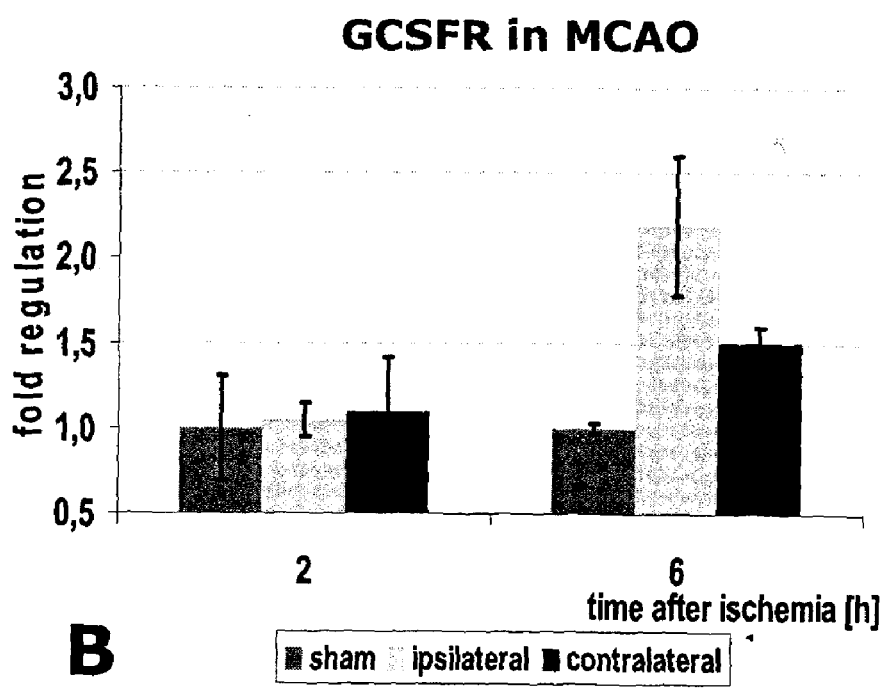
Figure 28, part I

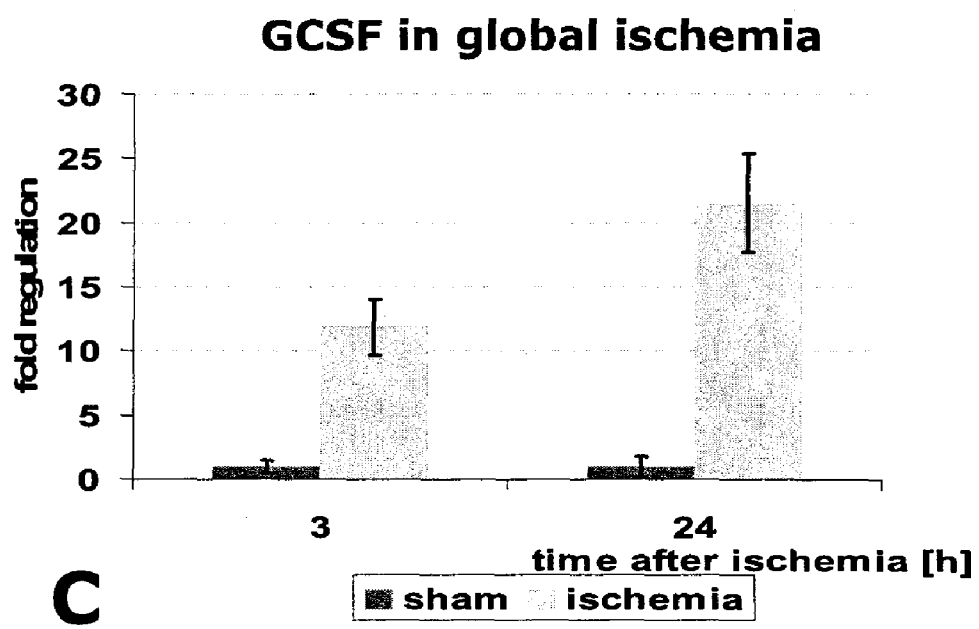
Figure 28, part II

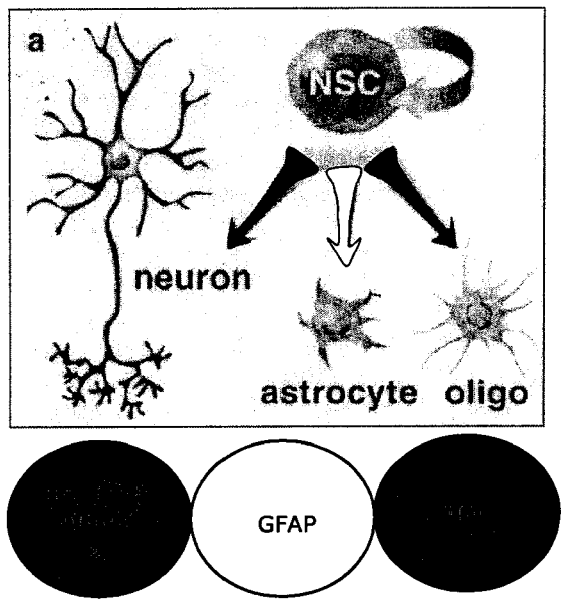
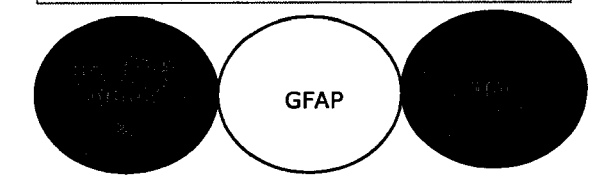
A
Neural stem cells treated with GMCSF 10ng/ml for 3d
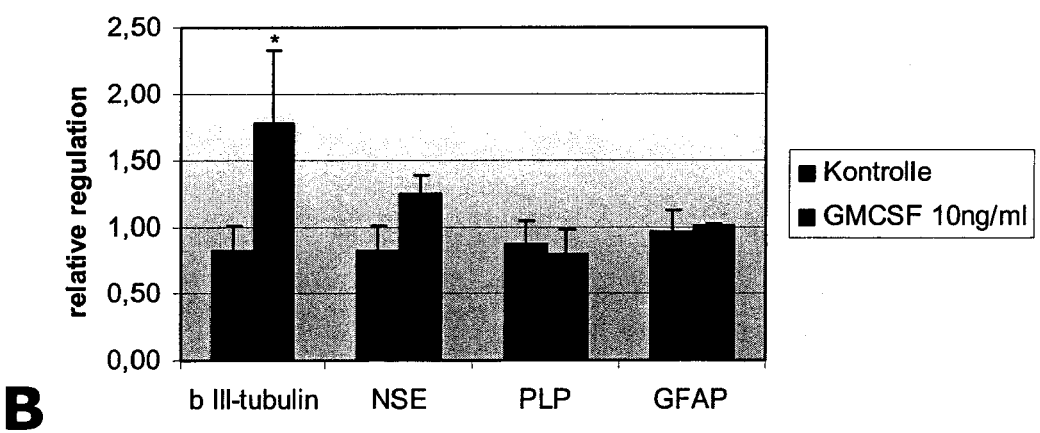
B
Figure 35

ALS
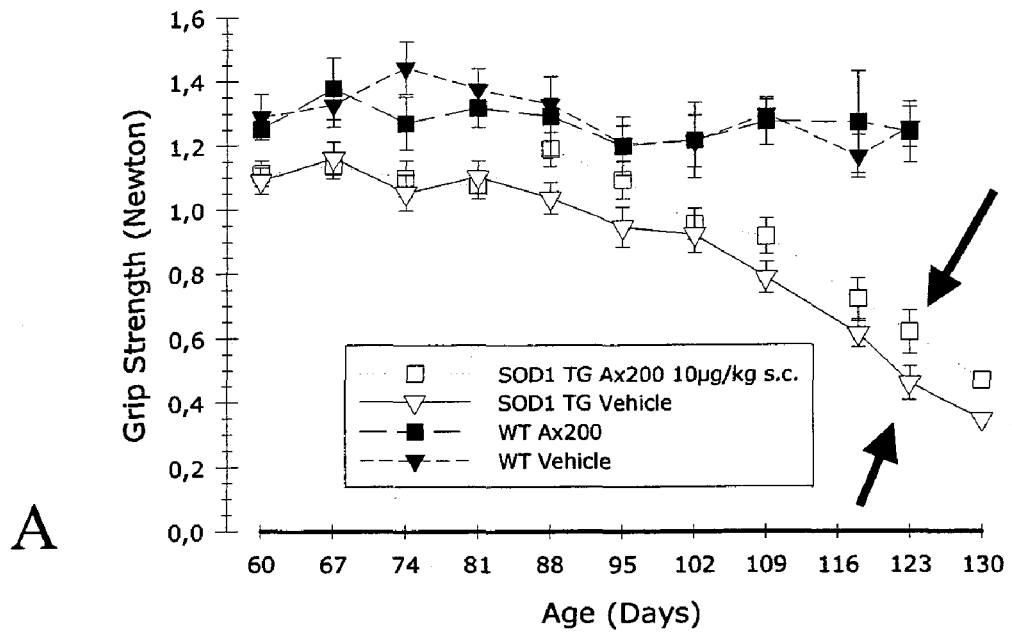
A
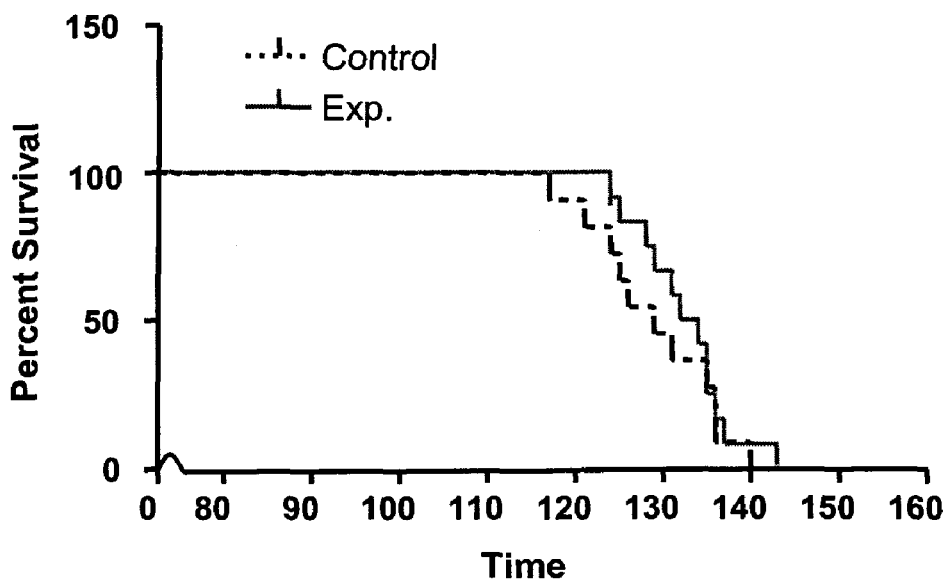
B
Figure 38

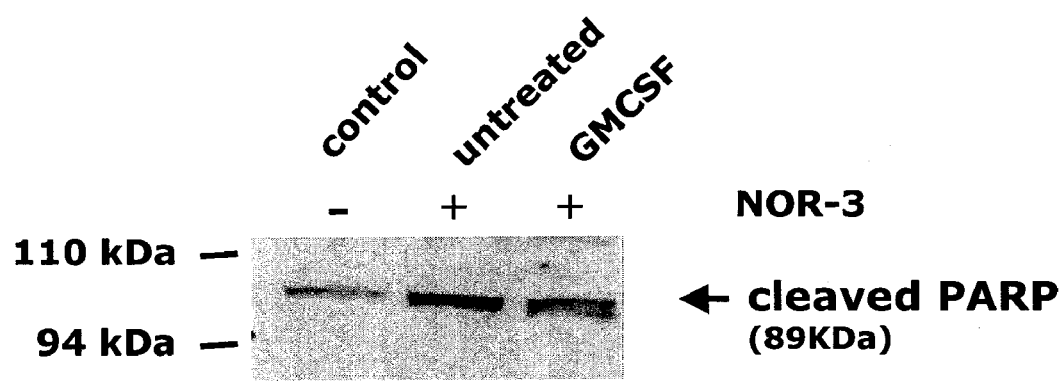
Figure 40, part I

GMCSF
time after adding GMCSF
0  5  15  30  60  *min*
pSTAT5
STAT5
pSTAT1
STAT1
A
Figure 40, part II

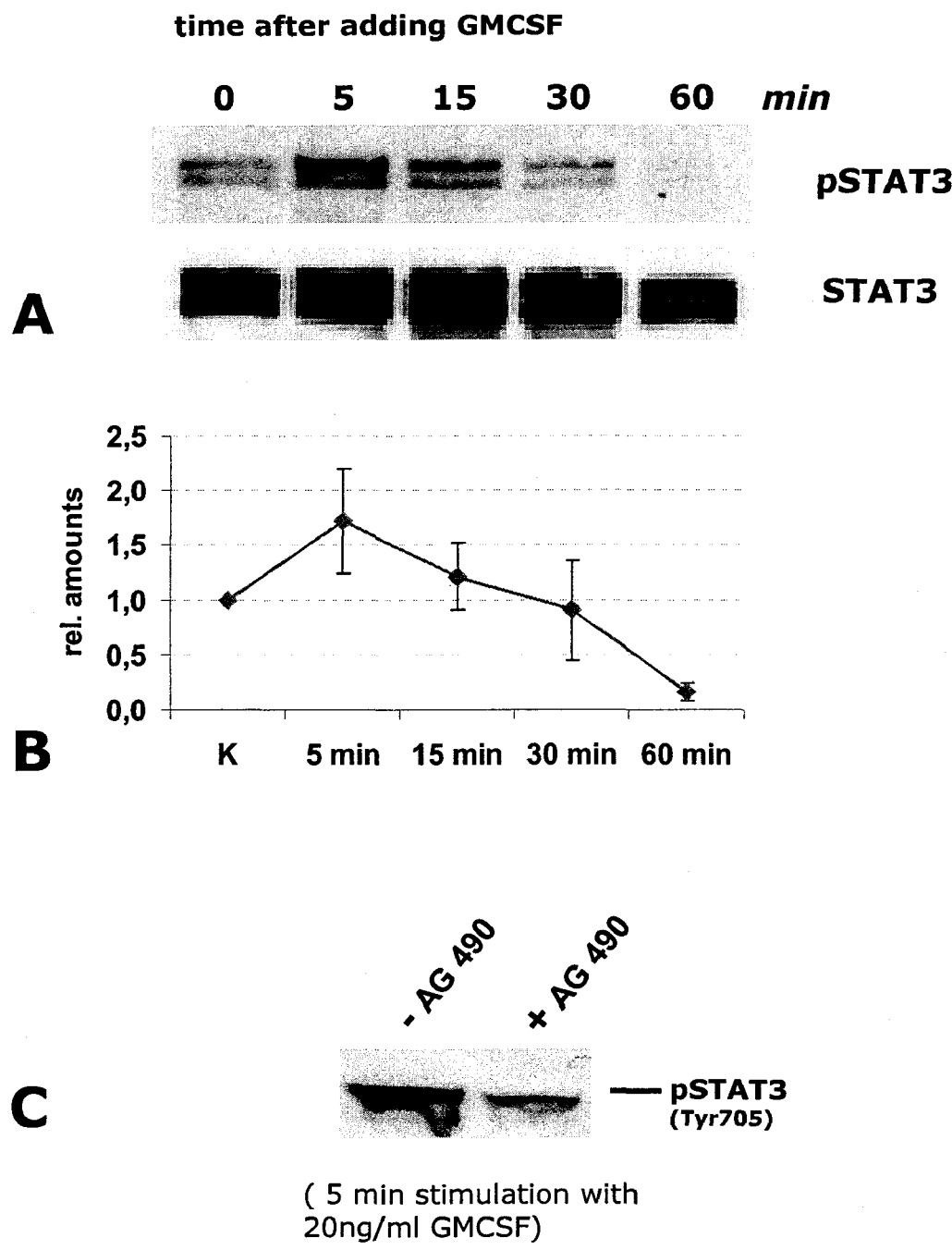
Figure 40, part III

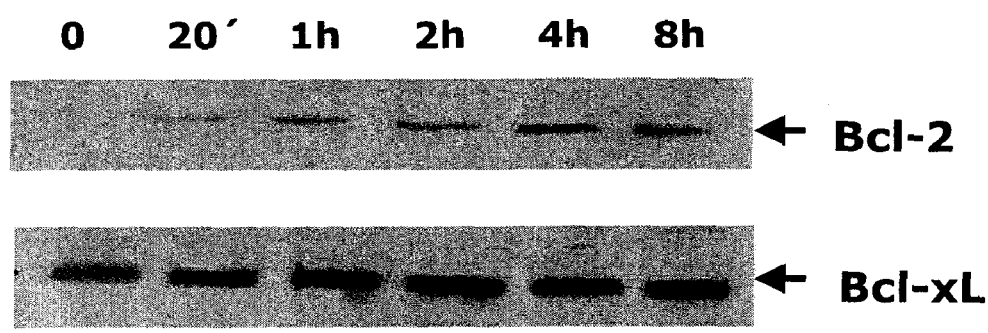
Figure 40, part IV

GMCSF reduces significantly infarct volumes

30 min (mean ?SEM; N = 19 (vehicle) and 20 (GMCSF); $p < 0.05$; dose: GMCSF 250 µg/kg body weight; treatment 30 min after MCA occlusion)

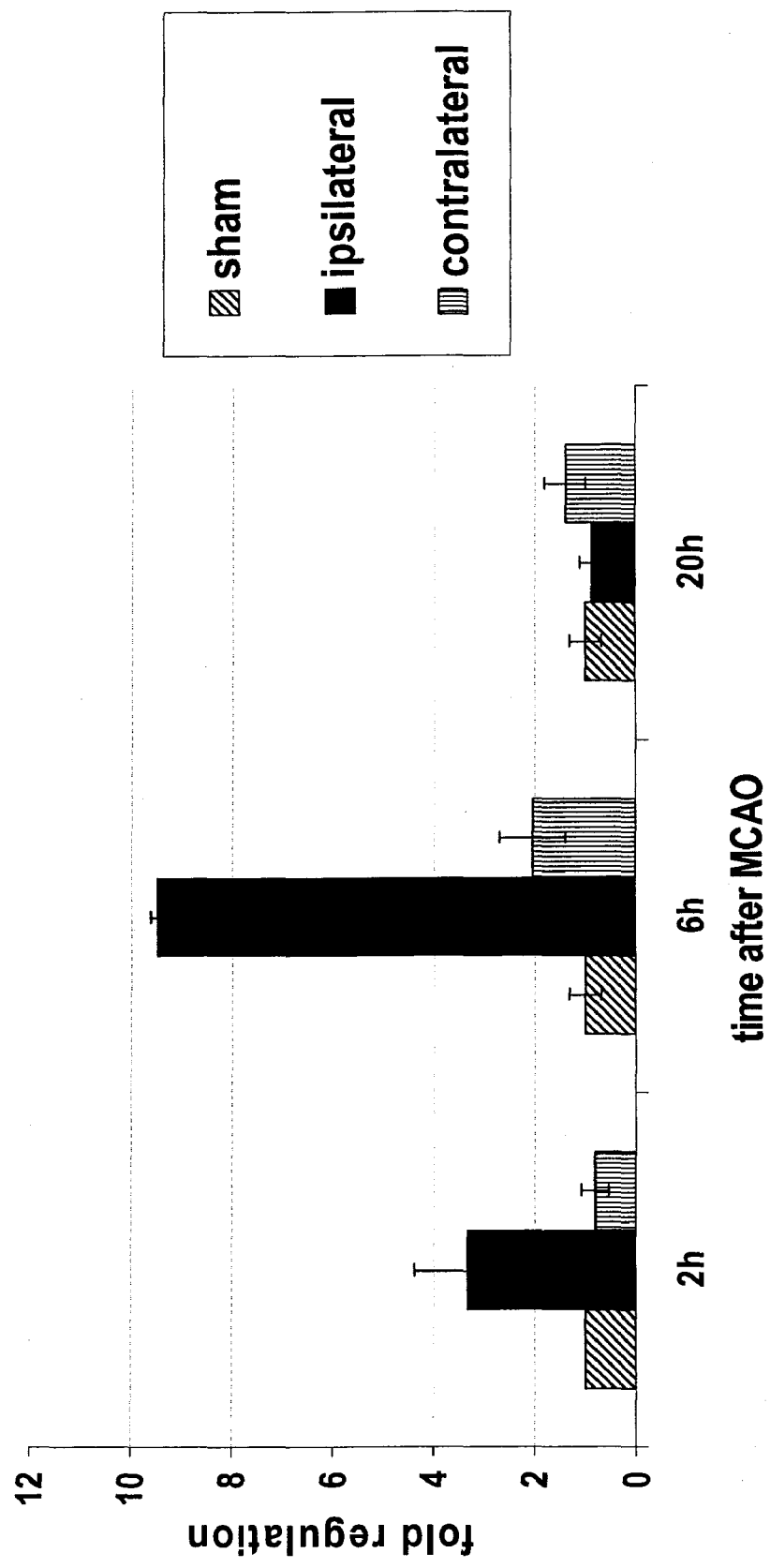
Figure 42  Regulation of IL-5 after focal ischemia

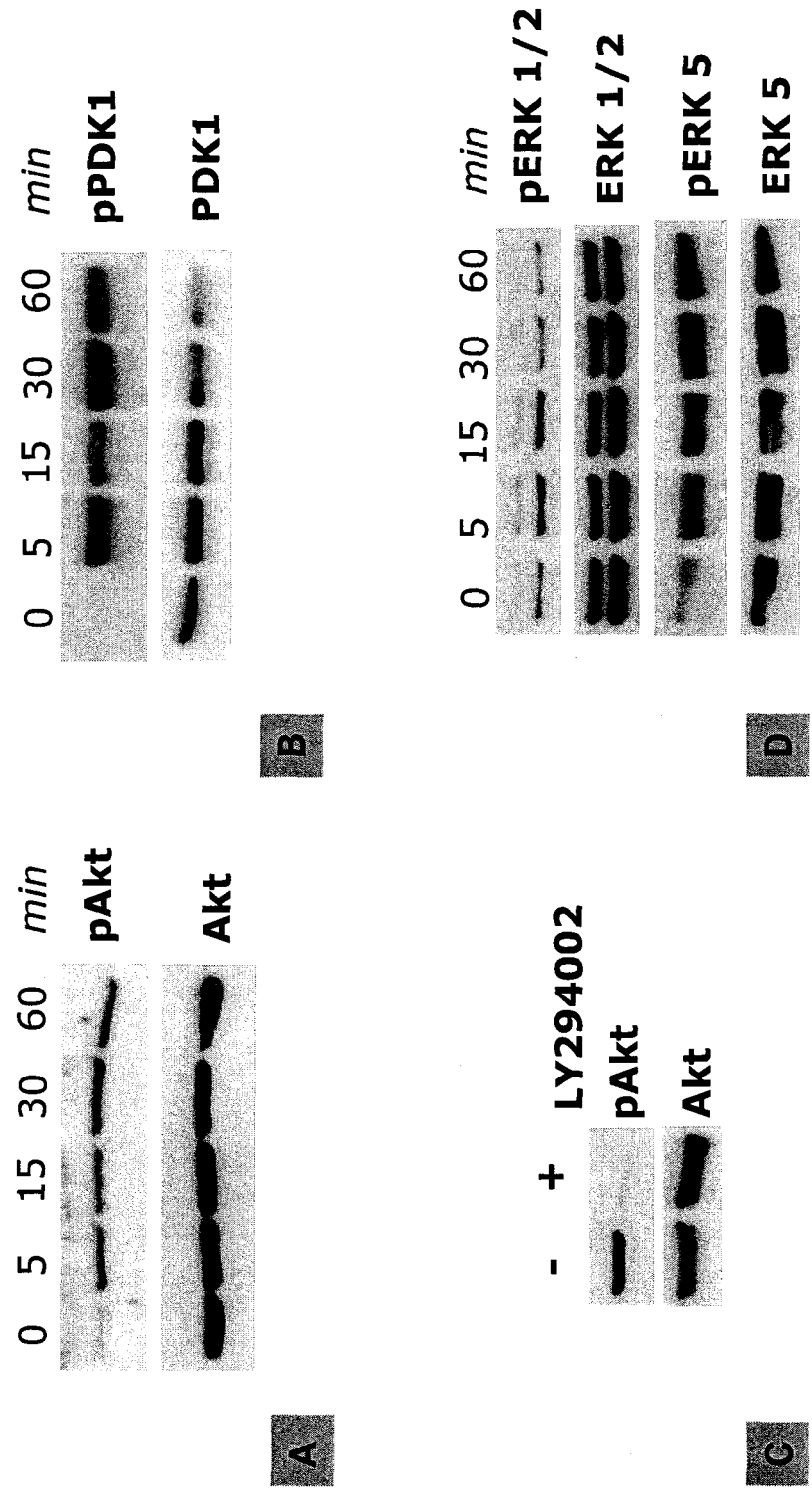
Figure 43 G-CSF induces anti-apoptotic pathways

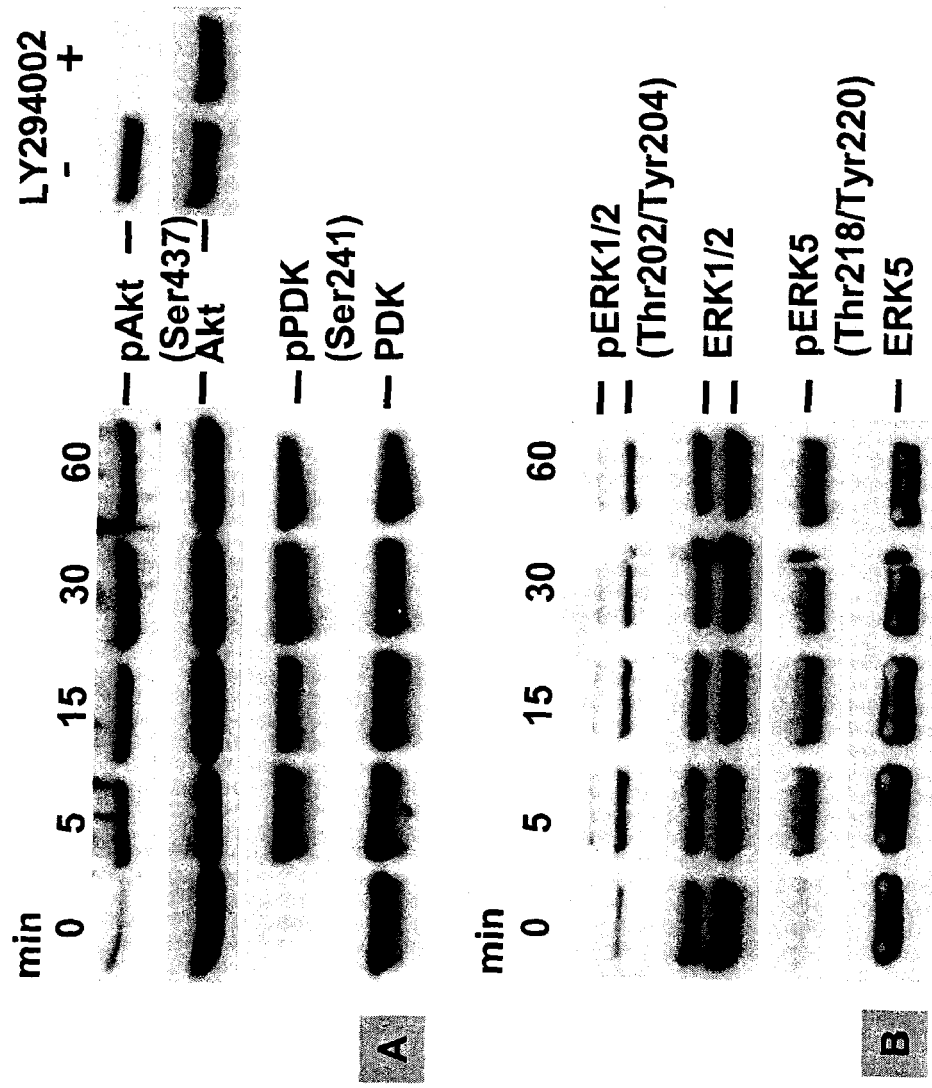
Figure 44   GM-CSF induces anti-apoptotic pathways

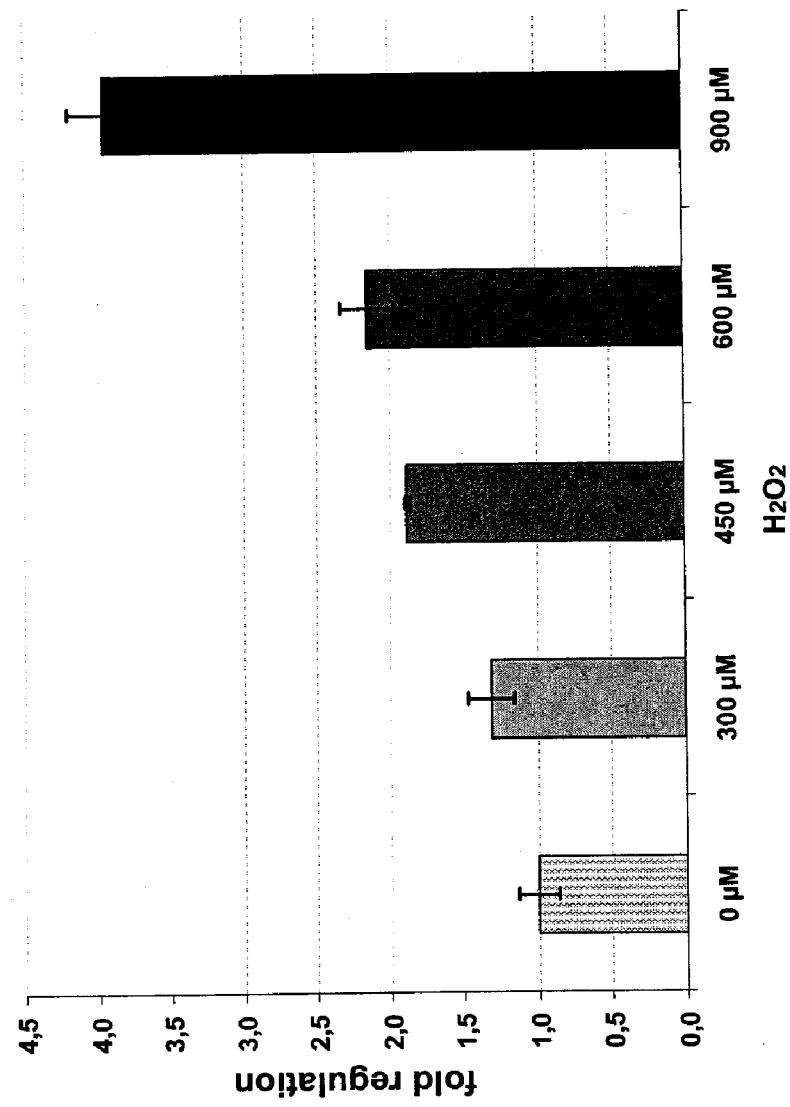
Figure 45  Upregulation of GM-CSF after cell death in vitro

Figure 46a IL-3 has an anti-apoptotic activity in neuronal cells and SHSY5-Y
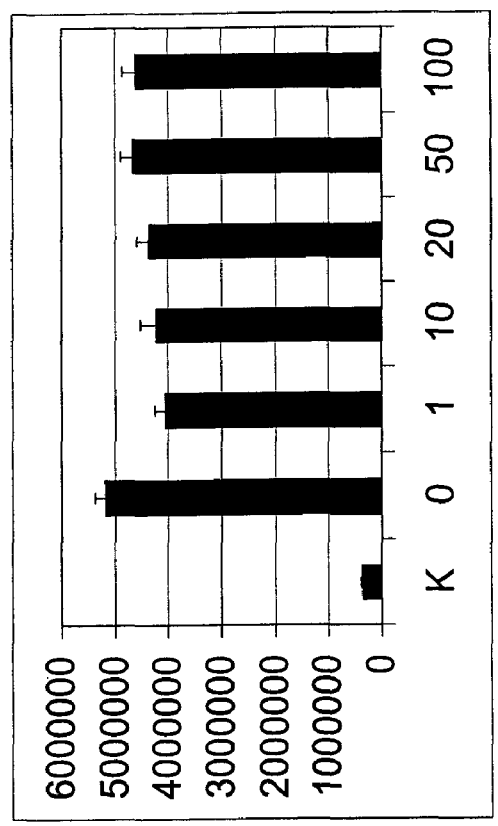
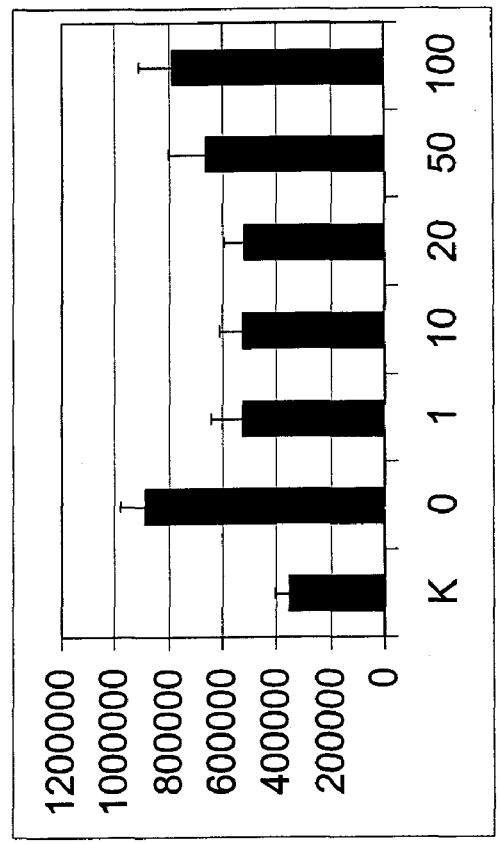

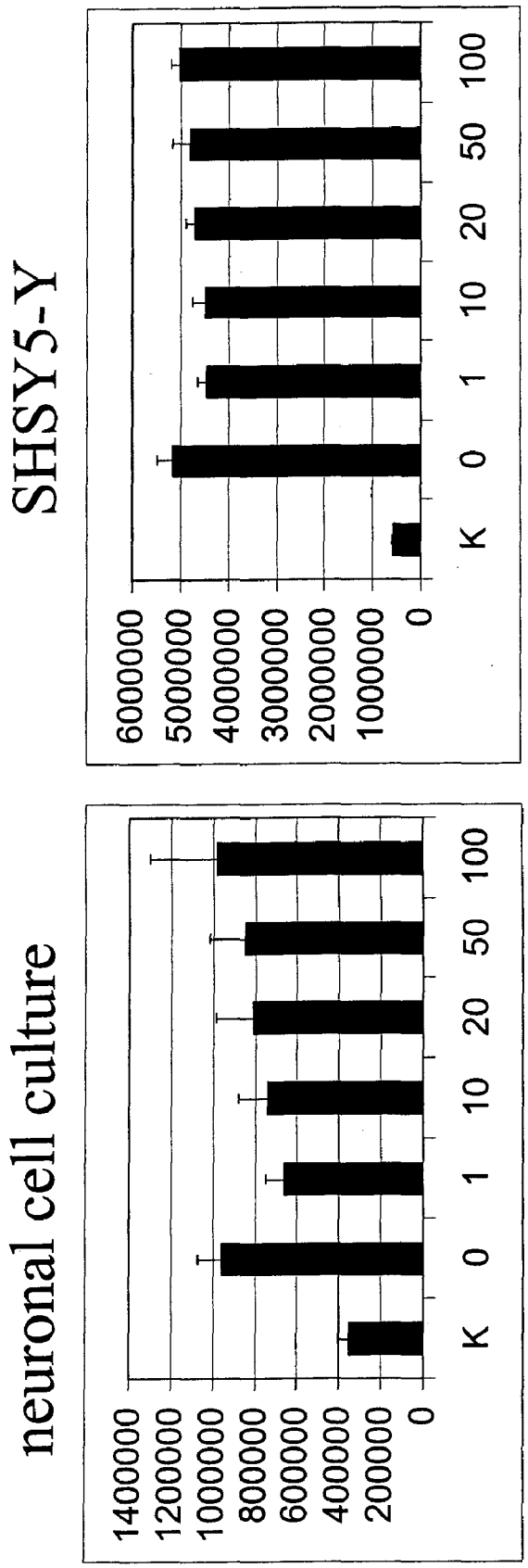
Figure 46b IL-5 has an anti-apoptotic activity in neuronal cells and SHSY5-Y

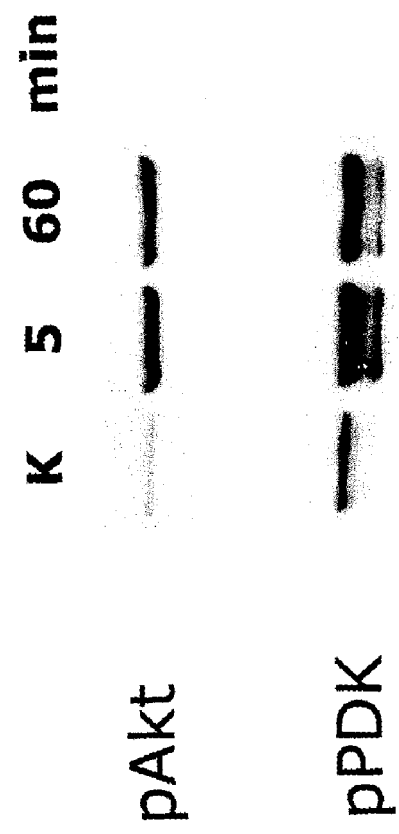
Figure 47 IL-3 induce anti-apoptotic pathways

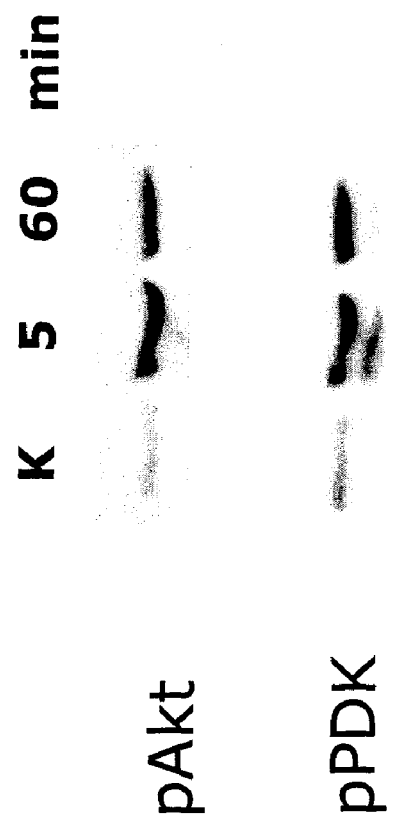
Figure 48 IL-5 induces anti-apoptotic pathways

Figure 49  G-CSF is neuroprotective in a model of cortical ischemia
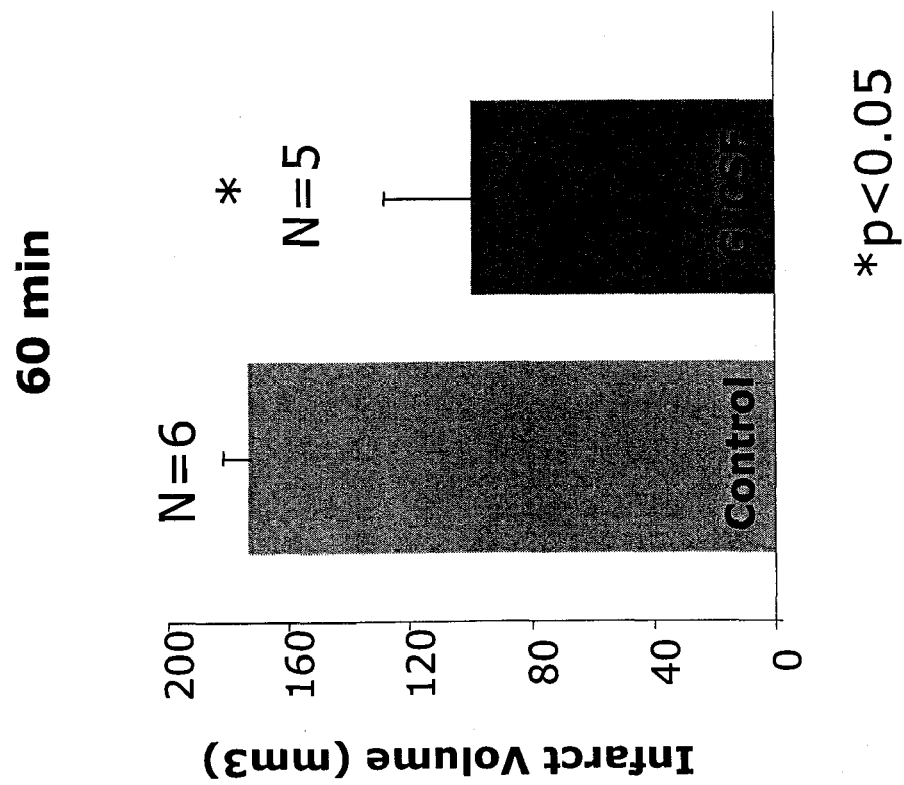

Figure 52  GM-CSF stimulates neurogenesis

Figure 53 Colocalisation of GM-CSF and its receptor in human brain

Figure 54 Expression of the G-CSF receptor in the human Cortex

Figure 55  Upregulation of G-CSF after cell death in vitro

Figure 56  Expression of the IL-5 receptor in the rat brain

SEQUENCE LISTING

```
<160> NUMBER OF SEQ ID NOS: 94

<210> SEQ ID NO 1
<211> LENGTH: 70
<212> TYPE: PRT
<213> ORGANISM: Artificial Sequence
<220> FEATURE:
<223> OTHER INFORMATION: computer generated consensus sequence
<220> FEATURE:
<221> NAME/KEY: misc_feature
<222> LOCATION: (2)..(5)
<223> OTHER INFORMATION: Xaa is any amino acid
<220> FEATURE:
<221> NAME/KEY: misc_feature
<222> LOCATION: (7)..(41)
<223> OTHER INFORMATION: Xaa is any amino acid
<220> FEATURE:
<221> NAME/KEY: misc_feature
<222> LOCATION: (33)..(41)
<223> OTHER INFORMATION: may be present or absent
<220> FEATURE:
<221> NAME/KEY: misc_feature
<222> LOCATION: (46)..(46)
<223> OTHER INFORMATION: Xaa is any amino acid
<220> FEATURE:
<221> NAME/KEY: misc_feature
<222> LOCATION: (48)..(50)
<223> OTHER INFORMATION: Xaa is any amino acid
<220> FEATURE:
<221> NAME/KEY: misc_feature
<222> LOCATION: (48)..(50)
<223> OTHER INFORMATION: amino acids may be present or absent
<220> FEATURE:
<221> NAME/KEY: misc_feature
<222> LOCATION: (52)..(60)
<223> OTHER INFORMATION: Xaa is any amino acid
<220> FEATURE:
<221> NAME/KEY: misc_feature
<222> LOCATION: (57)..(60)
<223> OTHER INFORMATION: may  be present or absent
```

```
<220> FEATURE:
<221> NAME/KEY: misc_feature
<222> LOCATION: (63)..(64)
<223> OTHER INFORMATION: Xaa is any amino acid
<220> FEATURE:
<221> NAME/KEY: misc_feature
<222> LOCATION: (64)..(64)
<223> OTHER INFORMATION: may be present or absent
<220> FEATURE:
<221> NAME/KEY: misc_feature
<222> LOCATION: (69)..(69)
<223> OTHER INFORMATION: Xaa is any amino acid

<400> SEQUENCE: 1

Asn Xaa Xaa Xaa Xaa Ser Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Leu Val Ile Met Xaa Trp Xaa
        35                  40                  45

Xaa Xaa Pro Xaa Xaa Xaa Xaa Xaa Xaa Xaa Xaa Tyr Phe Xaa Xaa
    50                  55                  60

Val Ile Leu Met Xaa Trp
65                  70

<210> SEQ ID NO 2
<211> LENGTH: 21
<212> TYPE: DNA
<213> ORGANISM: Artificial Sequence
<220> FEATURE:
<223> OTHER INFORMATION: synthetic DNA

<400> SEQUENCE: 2
gcgggcaaat caggatctca c                                         21

<210> SEQ ID NO 3
<211> LENGTH: 21
<212> TYPE: DNA
<213> ORGANISM: Artificial Sequence
<220> FEATURE:
<223> OTHER INFORMATION: synthetic DNA

<400> SEQUENCE: 3
cgaagctcag cttgatccag g                                         21

<210> SEQ ID NO 4
<211> LENGTH: 280
<212> TYPE: DNA
<213> ORGANISM: Rattus rattus

<400> SEQUENCE: 4
gcgggcaaat caggatctca ccccccattg tccatcttgg ggatcctgtc ctggcctcct    60
gcaccatcag cccaaactgc agcaaactgg accgacagcc aaagatccta tggagactgc   120
aagatgaacc aaaccagcct ggggacagac agcatcacct gcctgacggg tcccaggagt   180
ccatcatcac tctgcctcat ctgaactaca ctcaggcctt cctcttctgc ttggtgccat   240
ggaacaacag cttccaggtc ctggatcaag ctgagcttcg                         280

<210> SEQ ID NO 5
<211> LENGTH: 22
<212> TYPE: DNA
<213> ORGANISM: Artificial Sequence
<220> FEATURE:
<223> OTHER INFORMATION: synthetic DNA
```

-continued

```
<400> SEQUENCE: 5
cccctcaaac ctatcctgcc tc                                              22

<210> SEQ ID NO 6
<211> LENGTH: 22
<212> TYPE: DNA
<213> ORGANISM: Artificial Sequence
<220> FEATURE:
<223> OTHER INFORMATION: synthetic DNA

<400> SEQUENCE: 6
tccaggcaga gatcagcgaa tg                                              22

<210> SEQ ID NO 7
<211> LENGTH: 21
<212> TYPE: DNA
<213> ORGANISM: Artificial Sequence
<220> FEATURE:
<223> OTHER INFORMATION: synthetic DNA

<400> SEQUENCE: 7
ccattgtcca tcttggggat c                                               21

<210> SEQ ID NO 8
<211> LENGTH: 21
<212> TYPE: DNA
<213> ORGANISM: Artificial Sequence
<220> FEATURE:
<223> OTHER INFORMATION: synthetic DNA

<400> SEQUENCE: 8
cctggaagct gttgttccat g                                               21

<210> SEQ ID NO 9
<211> LENGTH: 20
<212> TYPE: DNA
<213> ORGANISM: Artificial Sequence
<220> FEATURE:
<223> OTHER INFORMATION: synthetic DNA

<400> SEQUENCE: 9
accccaccgt gttcttcgac                                                 20

<210> SEQ ID NO 10
<211> LENGTH: 20
<212> TYPE: DNA
<213> ORGANISM: Artificial Sequence
<220> FEATURE:
<223> OTHER INFORMATION: synthetic DNA

<400> SEQUENCE: 10
catttgccat ggacaagatg                                                 20

<210> SEQ ID NO 11
<211> LENGTH: 7
<212> TYPE: PRT
<213> ORGANISM: Artificial Sequence
<220> FEATURE:
<223> OTHER INFORMATION: synthetic peptide sequence

<400> SEQUENCE: 11

Leu Gly His Ser Leu Gly Ile
1               5

<210> SEQ ID NO 12
<211> LENGTH: 39
```

<212> TYPE: DNA
<213> ORGANISM: Artificial Sequence
<220> FEATURE:
<223> OTHER INFORMATION: synthetic DNA

<400> SEQUENCE: 12
cgggatccgg gaccgcgtat ctgatgacga gcgtgtcaa                    39

<210> SEQ ID NO 13
<211> LENGTH: 25
<212> TYPE: DNA
<213> ORGANISM: Artificial Sequence
<220> FEATURE:
<223> OTHER INFORMATION: synthetic DNA

<400> SEQUENCE: 13
ctcggagacg ctgaggaagg acctg                                   25

<210> SEQ ID NO 14
<211> LENGTH: 40
<212> TYPE: DNA
<213> ORGANISM: Artificial Sequence
<220> FEATURE:
<223> OTHER INFORMATION: synthetic DNA

<400> SEQUENCE: 14
ctgcggccct agaccacgcc caccgctccc cgtgacgtcg                   40

<210> SEQ ID NO 15
<211> LENGTH: 22
<212> TYPE: DNA
<213> ORGANISM: Artificial Sequence
<220> FEATURE:
<223> OTHER INFORMATION: synthetic DNA

<400> SEQUENCE: 15
acgtcgttgg ctcagttatg tc                                      22

<210> SEQ ID NO 16
<211> LENGTH: 24
<212> TYPE: DNA
<213> ORGANISM: Artificial Sequence
<220> FEATURE:
<223> OTHER INFORMATION: synthetic DNA

<400> SEQUENCE: 16
atttatgtca gagatggagg atgg                                    24

<210> SEQ ID NO 17
<211> LENGTH: 20
<212> TYPE: DNA
<213> ORGANISM: Artificial Sequence
<220> FEATURE:
<223> OTHER INFORMATION: synthetic DNA

<400> SEQUENCE: 17
accccaccgt gttcttcgac                                         20

<210> SEQ ID NO 18
<211> LENGTH: 20
<212> TYPE: DNA
<213> ORGANISM: Artificial Sequence
<220> FEATURE:
<223> OTHER INFORMATION: synthetic DNA

<400> SEQUENCE: 18
catttgccat ggacaagatg                                         20

```
<210> SEQ ID NO 19
<211> LENGTH: 22
<212> TYPE: DNA
<213> ORGANISM: Artificial Sequence
<220> FEATURE:
<223> OTHER INFORMATION: synthetic DNA

<400> SEQUENCE: 19
acgtcgttgg ctcagttatg tc                                              22

<210> SEQ ID NO 20
<211> LENGTH: 24
<212> TYPE: DNA
<213> ORGANISM: Artificial Sequence
<220> FEATURE:
<223> OTHER INFORMATION: synthetic DNA

<400> SEQUENCE: 20
atttatgtca gagatggagg atgg                                            24

<210> SEQ ID NO 21
<211> LENGTH: 177
<212> TYPE: DNA
<213> ORGANISM: Rattus rattus

<400> SEQUENCE: 21
acgtcgttgg ctcagttatg tcagacagga aatctcacca tcccacaatg attgacagct     60
ctcacaggga atcccgcctc cgctgggacc aattgacatc acggacagga atacccgccc    120
ctgtggccct gatgggcagg tcctgcctgg ctcccatcct ccatctctga cataaat       177

<210> SEQ ID NO 22
<211> LENGTH: 400
<212> TYPE: PRT
<213> ORGANISM: Homo sapiens

<400> SEQUENCE: 22
```

Met Leu Leu Leu Val Thr Ser Leu Leu Leu Cys Glu Leu Pro His Pro
1               5                   10                  15

Ala Phe Leu Leu Ile Pro Glu Lys Ser Asp Leu Arg Thr Val Ala Pro
            20                  25                  30

Ala Ser Ser Leu Asn Val Arg Phe Asp Ser Arg Thr Met Asn Leu Ser
        35                  40                  45

Trp Asp Cys Gln Glu Asn Thr Thr Phe Ser Lys Cys Phe Leu Thr Asp
    50                  55                  60

Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
            100                 105                 110

Asn Ser Gly Arg Glu Gly Thr Ala Ala Gln Asn Phe Ser Cys Phe Ile
        115                 120                 125

Tyr Asn Ala Asp Leu Met Asn Cys Thr Trp Ala Arg Gly Pro Thr Ala
    130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

```
Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
        195                 200                 205

Leu Leu Asp Thr Lys Lys Ile Glu Arg Phe Asn Pro Pro Ser Asn Val
210                 215                 220

Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
                245                 250                 255

Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
        275                 280                 285

Arg Ala Lys His Ser Val Lys Ile Arg Ala Ala Asp Val Arg Ile Leu
290                 295                 300

Asn Trp Ser Ser Trp Ser Glu Ala Ile Glu Phe Gly Ser Asp Asp Gly
305                 310                 315                 320

Asn Leu Gly Ser Val Tyr Ile Tyr Val Leu Leu Ile Val Gly Thr Leu
                325                 330                 335

Val Cys Gly Ile Val Leu Gly Phe Leu Phe Lys Arg Phe Leu Arg Ile
            340                 345                 350

Gln Arg Leu Phe Pro Pro Val Pro Gln Ile Lys Asp Lys Leu Asn Asp
        355                 360                 365

Asn His Glu Val Glu Asp Glu Ile Ile Trp Glu Glu Phe Thr Pro Glu
370                 375                 380

Glu Gly Lys Gly Tyr Arg Glu Glu Val Leu Ile Val Lys Glu Ile Thr
385                 390                 395                 400

<210> SEQ ID NO 23
<211> LENGTH: 388
<212> TYPE: PRT
<213> ORGANISM: Mus musculus

<400> SEQUENCE: 23

Met Thr Ser Ser His Ala Met Asn Ile Thr Pro Leu Ala Gln Leu Ala
1               5                   10                  15

Leu Leu Phe Ser Thr Leu Leu Leu Pro Gly Thr Gln Ala Leu Leu Ala
            20                  25                  30

Pro Thr Pro Asp Ala Gly Ser Ala Leu Asn Leu Thr Phe Asp Pro
        35                  40                  45

Trp Thr Arg Thr Leu Thr Trp Ala Cys Asp Thr Ala Ala Gly Asn Val
    50                  55                  60

Thr Val Thr Ser Cys Thr Val Thr Ser Arg Glu Ala Gly Ile His Arg
65                  70                  75                  80

Arg Val Ser Pro Phe Gly Cys Arg Cys Trp Phe Arg Arg Met Met Ala
                85                  90                  95

Leu His His Gly Val Thr Leu Asp Val Asn Gly Thr Val Gly Gly Ala
            100                 105                 110

Ala Ala His Trp Arg Leu Ser Phe Val Asn Glu Ser Ala Ala Gly Ser
        115                 120                 125

Gly Ala Glu Asn Leu Thr Cys Glu Ile Arg Ala Ala Arg Phe Leu Ser
    130                 135                 140

Cys Ala Trp Arg Glu Gly Pro Ala Ala Pro Ala Asp Val Arg Tyr Ser
145                 150                 155                 160
```

```
Leu Arg Val Leu Asn Ser Thr Gly His Asp Val Ala Arg Cys Met Ala
                165                 170                 175

Asp Pro Gly Asp Val Ile Thr Gln Cys Ile Ala Asn Asp Leu Ser
            180                 185                 190

Leu Leu Gly Ser Glu Ala Tyr Leu Val Val Thr Gly Arg Ser Gly Ala
            195                 200                 205

Gly Pro Val Arg Phe Leu Asp Asp Val Ala Thr Lys Ala Leu Glu
            210                 215                 220

Arg Leu Gly Pro Pro Arg Asp Val Thr Ala Ser Cys Asn Ser Ser His
225                 230                 235                 240

Cys Thr Val Ser Trp Ala Pro Pro Ser Thr Trp Ala Ser Leu Thr Ala
                245                 250                 255

Arg Asp Phe Gln Phe Glu Val Gln Trp Gln Ser Ala Glu Pro Gly Ser
            260                 265                 270

Thr Pro Arg Lys Val Leu Val Glu Glu Thr Arg Leu Ala Phe Pro
            275                 280                 285

Ser Pro Ala Pro His Gly Gly His Lys Val Lys Val Arg Ala Gly Asp
            290                 295                 300

Thr Arg Met Lys His Trp Gly Glu Trp Ser Pro Ala His Pro Leu Glu
305                 310                 315                 320

Ala Glu Asp Thr Arg Val Pro Gly Ala Leu Leu Tyr Ala Val Thr Ala
                325                 330                 335

Cys Ala Val Leu Leu Cys Ala Leu Ala Leu Gly Val Thr Cys Arg Arg
                340                 345                 350

Phe Glu Val Thr Arg Arg Leu Phe Pro Pro Ile Pro Gly Ile Arg Asp
            355                 360                 365

Lys Val Ser Asp Asp Val Arg Val Asn Pro Glu Thr Leu Arg Lys Asp
            370                 375                 380

Leu Leu Gln Pro
385

<210> SEQ ID NO 24
<211> LENGTH: 9
<212> TYPE: PRT
<213> ORGANISM: Rattus rattus

<400> SEQUENCE: 24

Ile Asn Ser Glu Arg Thr Ser Glu Gln
1               5

<210> SEQ ID NO 25
<211> LENGTH: 127
<212> TYPE: PRT
<213> ORGANISM: Rattus rattus

<400> SEQUENCE: 25

Ala Pro Thr Arg Ser Pro Asn Pro Val Thr Arg Pro Trp Lys His Val
1               5                   10                  15

Asp Ala Ile Lys Glu Ala Leu Ser Leu Leu Asn Asp Met Arg Ala Leu
                20                  25                  30

Glu Asn Glu Lys Asn Glu Asp Val Asp Ile Ile Ser Asn Glu Phe Ser
                35                  40                  45

Ile Gln Arg Pro Thr Cys Val Gln Thr Arg Leu Lys Leu Tyr Lys Gln
            50                  55                  60

Gly Leu Arg Gly Asn Leu Thr Lys Leu Asn Gly Ala Leu Thr Met Ile
65                  70                  75                  80

Ala Ser His Tyr Gln Thr Asn Cys Pro Pro Thr Pro Glu Thr Asp Cys
```

```
                85                  90                  95
Glu Ile Asp Val Thr Thr Phe Glu Asp Phe Ile Lys Asn Leu Lys Gly
            100                 105                 110
Phe Leu Phe Asp Ile Pro Phe Asp Cys Trp Lys Pro Val Gln Lys
        115                 120                 125

<210> SEQ ID NO 26
<211> LENGTH: 141
<212> TYPE: PRT
<213> ORGANISM: Mus musculus

<400> SEQUENCE: 26

Met Trp Leu Gln Asn Leu Arg Leu Lys Ile Phe Glu Gln Gly Leu Arg
1               5                   10                  15
Gly Asn Phe Thr Lys Leu Lys Gly Ala Leu Asn Met Thr Ala Ser Tyr
            20                  25                  30
Tyr Gln Thr Tyr Cys Pro Pro Thr Pro Glu Thr Asp Cys Glu Thr Gln
        35                  40                  45
Val Thr Thr Tyr Ala Asp Phe Ile Asp Ser Leu Lys Thr Leu Phe Leu
    50                  55                  60
Gly Ile Val Val Tyr Ser Leu Ser Ala Pro Thr Arg Ser Pro Ile Phe
65                  70                  75                  80
Leu Thr Asp Ile Pro Phe Glu Cys Lys Lys Pro Gly Gln Lys Thr Val
                85                  90                  95
Thr Arg Pro Trp Lys His Val Glu Ala Ile Lys Glu Ala Leu Asn Leu
            100                 105                 110
Leu Asp Asp Met Pro Val Thr Leu Asn Glu Glu Val Glu Val Val Ser
        115                 120                 125
Asn Glu Phe Ser Phe Lys Lys Leu Thr Cys Val Gln Thr
    130                 135                 140

<210> SEQ ID NO 27
<211> LENGTH: 144
<212> TYPE: PRT
<213> ORGANISM: Homo sapiens

<400> SEQUENCE: 27

Met Trp Leu Gln Ser Leu Leu Leu Leu Gly Thr Val Ala Cys Ser Ile
1               5                   10                  15
Ser Ala Pro Ala Arg Ser Pro Ser Pro Ser Thr Gln Pro Trp Glu His
            20                  25                  30
Val Asn Ala Ile Gln Glu Ala Arg Arg Leu Leu Asn Leu Ser Arg Asp
        35                  40                  45
Thr Ala Ala Glu Met Asn Glu Thr Val Glu Val Ile Ser Glu Met Phe
    50                  55                  60
Asp Leu Gln Glu Pro Thr Cys Leu Gln Thr Arg Leu Glu Leu Tyr Lys
65                  70                  75                  80
Gln Gly Leu Arg Gly Ser Leu Thr Lys Leu Lys Gly Pro Leu Thr Met
                85                  90                  95
Met Ala Ser His Tyr Lys Gln His Cys Pro Pro Thr Pro Glu Thr Ser
            100                 105                 110
Cys Ala Thr Gln Ile Ile Thr Phe Glu Ser Phe Lys Glu Asn Leu Lys
        115                 120                 125
Asp Phe Leu Leu Val Ile Pro Phe Asp Cys Trp Glu Pro Val Gln Glu
    130                 135                 140

<210> SEQ ID NO 28
```

```
<211> LENGTH: 207
<212> TYPE: PRT
<213> ORGANISM: Homo sapiens

<400> SEQUENCE: 28

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 29
<211> LENGTH: 208
<212> TYPE: PRT
<213> ORGANISM: Mus musculus

<400> SEQUENCE: 29

Met Ala Gln Leu Ser Ala Gln Arg Arg Met Lys Leu Met Ala Leu Gln
1               5                   10                  15

Leu Leu Leu Trp Gln Ser Ala Leu Trp Ser Gly Arg Glu Ala Val Pro
            20                  25                  30

Leu Val Thr Val Ser Ala Leu Pro Pro Ser Leu Pro Leu Pro Arg Ser
        35                  40                  45

Phe Leu Leu Lys Ser Leu Glu Gln Val Arg Lys Ile Gln Ala Ser Gly
50                  55                  60

Ser Val Leu Leu Glu Gln Leu Cys Ala Thr Tyr Lys Leu Cys His Pro
65                  70                  75                  80

Glu Glu Leu Val Leu Leu Gly His Ser Leu Gly Ile Pro Lys Ala Ser
                85                  90                  95

Leu Ser Gly Cys Ser Ser Gln Ala Leu Gln Gln Thr Gln Cys Leu Ser
            100                 105                 110

Gln Leu His Ser Gly Leu Cys Leu Tyr Gln Gly Leu Leu Gln Ala Leu
        115                 120                 125

Ser Gly Ile Ser Pro Ala Leu Ala Pro Thr Leu Asp Leu Leu Gln Leu
130                 135                 140
```

Asp Val Ala Asn Phe Ala Thr Thr Ile Trp Gln Gln Met Glu Asn Leu
145                 150                 155                 160

Gly Val Ala Pro Thr Val Gln Pro Thr Gln Ser Ala Met Pro Ala Phe
                165                 170                 175

Thr Ser Ala Phe Gln Arg Arg Ala Gly Gly Val Leu Ala Ile Ser Tyr
            180                 185                 190

Leu Gln Gly Phe Leu Glu Thr Ala Arg Leu Ala Leu His His Leu Ala
        195                 200                 205

<210> SEQ ID NO 30
<211> LENGTH: 214
<212> TYPE: PRT
<213> ORGANISM: Rattus norvegicus

<400> SEQUENCE: 30

Met Lys Leu Met Ala Leu Gln Leu Leu Leu Trp His Ser Ala Leu Trp
1               5                   10                  15

Ser Gly Gln Glu Ala Ile Pro Leu Leu Thr Val Ser Ser Leu Pro Pro
                20                  25                  30

Ser Leu Pro Leu Pro Arg Ser Phe Leu Leu Lys Ser Leu Glu Gln Val
            35                  40                  45

Arg Lys Ile Gln Ala Arg Asn Thr Glu Leu Leu Glu Gln Leu Cys Ala
50                  55                  60

Thr Tyr Lys Leu Cys His Pro Glu Glu Leu Val Leu Phe Gly His Ser
65                  70                  75                  80

Leu Gly Ile Pro Lys Ala Ser Leu Ser Ser Cys Ser Ser Gln Ala Leu
                85                  90                  95

Gln Gln Thr Lys Cys Leu Ser Gln Leu His Ser Gly Leu Phe Leu Tyr
            100                 105                 110

Gln Gly Leu Leu Gln Ala Leu Ala Gly Ile Ser Ser Glu Leu Ala Pro
        115                 120                 125

Thr Leu Asp Met Leu His Leu Asp Val Asp Asn Phe Ala Thr Thr Ile
130                 135                 140

Trp Gln Gln Met Glu Ser Leu Gly Val Ala Pro Thr Val Gln Pro Thr
145                 150                 155                 160

Gln Ser Thr Met Pro Ile Phe Thr Ser Ala Phe Gln Arg Arg Ala Gly
                165                 170                 175

Gly Val Leu Val Thr Ser Tyr Leu Gln Ser Phe Leu Glu Thr Ala His
            180                 185                 190

His Ala Leu His His Leu Pro Arg Pro Ala Gln Lys His Phe Pro Glu
        195                 200                 205

Ser Leu Phe Ile Ser Ile
        210

<210> SEQ ID NO 31
<211> LENGTH: 195
<212> TYPE: PRT
<213> ORGANISM: Felis catus

<400> SEQUENCE: 31

Met Lys Leu Thr Ala Leu Gln Leu Leu Leu Trp His Ser Ala Leu Trp
1               5                   10                  15

Met Val Gln Glu Ala Thr Pro Leu Gly Pro Thr Ser Ser Leu Pro Gln
                20                  25                  30

Ser Phe Leu Leu Lys Cys Leu Glu Gln Val Arg Lys Val Gln Ala Asp
            35                  40                  45

Gly Thr Ala Leu Gln Glu Arg Leu Cys Ala Ala His Lys Leu Cys His

-continued

```
                50                  55                  60
Pro Glu Glu Leu Val Leu Leu Gly His Ala Leu Gly Ile Pro Gln Ala
 65                  70                  75                  80

Pro Leu Ser Ser Cys Ser Ser Gln Ala Leu Gln Leu Thr Gly Cys Leu
                 85                  90                  95

Arg Gln Leu His Ser Gly Leu Phe Leu Tyr Gln Gly Leu Leu Gln Ala
                100                 105                 110

Leu Ala Gly Ile Ser Pro Glu Leu Ala Pro Thr Leu Asp Met Leu Gln
                115                 120                 125

Leu Asp Ile Thr Asp Phe Ala Ile Asn Ile Trp Gln Gln Met Glu Asp
            130                 135                 140

Val Gly Met Ala Pro Ala Val Pro Pro Thr Gln Gly Thr Met Pro Thr
145                 150                 155                 160

Phe Thr Ser Ala Phe Gln Arg Arg Ala Gly Gly Thr Leu Val Ala Ser
                    165                 170                 175

Asn Leu Gln Ser Phe Leu Glu Val Ala Tyr Arg Ala Leu Arg His Phe
                180                 185                 190

Thr Lys Pro
        195
```

<210> SEQ ID NO 32
<211> LENGTH: 195
<212> TYPE: PRT
<213> ORGANISM: Bos taurus

<400> SEQUENCE: 32

```
Met Lys Leu Met Val Leu Gln Leu Leu Leu Trp His Ser Ala Leu Trp
  1               5                  10                  15

Thr Val His Glu Ala Thr Pro Leu Gly Pro Ala Arg Ser Leu Pro Gln
                 20                  25                  30

Ser Phe Leu Leu Lys Cys Leu Glu Gln Val Arg Lys Ile Gln Ala Asp
                 35                  40                  45

Gly Ala Glu Leu Gln Glu Arg Leu Cys Ala Ala His Lys Leu Cys His
             50                  55                  60

Pro Glu Glu Leu Met Leu Arg His Ser Leu Gly Ile Pro Gln Ala
 65                  70                  75                  80

Pro Leu Ser Ser Cys Ser Ser Gln Ser Leu Gln Leu Thr Ser Cys Leu
                 85                  90                  95

Asn Gln Leu His Gly Gly Leu Phe Leu Tyr Gln Gly Leu Leu Gln Ala
                100                 105                 110

Leu Ala Gly Ile Ser Pro Glu Leu Ala Pro Thr Leu Asp Thr Leu Gln
                115                 120                 125

Leu Asp Val Thr Asp Phe Ala Thr Asn Ile Trp Leu Gln Met Glu Asp
            130                 135                 140

Leu Gly Ala Ala Pro Ala Val Gln Pro Thr Gln Gly Ala Met Pro Thr
145                 150                 155                 160

Phe Thr Ser Ala Phe Gln Arg Arg Ala Gly Gly Val Leu Val Ala Ser
                    165                 170                 175

Gln Leu His Arg Phe Leu Glu Leu Ala Tyr Arg Gly Leu Arg Tyr Leu
                180                 185                 190

Ala Glu Pro
        195
```

<210> SEQ ID NO 33
<211> LENGTH: 195
<212> TYPE: PRT

<213> ORGANISM: Sus scrofa

<400> SEQUENCE: 33

Met Lys Leu Met Ala Leu Gln Leu Leu Leu Trp His Ile Ala Leu Trp
1               5                   10                  15

Met Val Pro Glu Ala Ala Pro Leu Ser Pro Ala Ser Ser Leu Pro Gln
            20                  25                  30

Ser Phe Leu Leu Lys Cys Leu Glu Gln Val Arg Lys Ile Gln Ala Asp
        35                  40                  45

Gly Ala Glu Leu Gln Glu Arg Leu Cys Ala Thr His Lys Leu Cys His
    50                  55                  60

Pro Gln Glu Leu Val Leu Leu Gly His Ser Leu Gly Leu Pro Gln Ala
65                  70                  75                  80

Ser Leu Ser Ser Cys Ser Ser Gln Ala Leu Gln Leu Thr Gly Cys Leu
                85                  90                  95

Asn Gln Leu His Gly Gly Leu Val Leu Tyr Gln Gly Leu Leu Gln Ala
            100                 105                 110

Leu Ala Gly Ile Ser Pro Glu Leu Ala Pro Ala Leu Asp Ile Leu Gln
        115                 120                 125

Leu Asp Val Thr Asp Leu Ala Thr Asn Ile Trp Leu Gln Met Glu Asp
130                 135                 140

Leu Arg Met Ala Pro Ala Ser Leu Pro Thr Gln Gly Thr Val Pro Thr
145                 150                 155                 160

Phe Thr Ser Ala Phe Gln Arg Arg Ala Gly Gly Val Leu Val Val Ser
                165                 170                 175

Gln Leu Gln Ser Phe Leu Glu Leu Ala Tyr Arg Val Leu Arg Tyr Leu
            180                 185                 190

Ala Glu Pro
        195

<210> SEQ ID NO 34
<211> LENGTH: 836
<212> TYPE: PRT
<213> ORGANISM: Homo sapiens

<400> SEQUENCE: 34

Met Ala Arg Leu Gly Asn Cys Ser Leu Thr Trp Ala Ala Leu Ile Ile
1               5                   10                  15

Leu Leu Leu Pro Gly Ser Leu Glu Glu Cys Gly His Ile Ser Val Ser
            20                  25                  30

Ala Pro Ile Val His Leu Gly Asp Pro Ile Thr Ala Ser Cys Ile Ile
        35                  40                  45

Lys Gln Asn Cys Ser His Leu Asp Pro Glu Pro Gln Ile Leu Trp Arg
    50                  55                  60

Leu Gly Ala Glu Leu Gln Pro Gly Gly Arg Gln Gln Arg Leu Ser Asp
65                  70                  75                  80

Gly Thr Gln Glu Ser Ile Ile Thr Leu Pro His Leu Asn His Thr Gln
                85                  90                  95

Ala Phe Leu Ser Cys Cys Leu Asn Trp Gly Asn Ser Leu Gln Ile Leu
            100                 105                 110

Asp Gln Val Glu Leu Arg Ala Gly Tyr Pro Pro Ala Ile Pro His Asn
        115                 120                 125

Leu Ser Cys Leu Met Asn Leu Thr Thr Ser Ser Leu Ile Cys Gln Trp
130                 135                 140

Glu Pro Gly Pro Glu Thr His Leu Pro Thr Ser Phe Thr Leu Lys Ser
145                 150                 155                 160

-continued

```
Phe Lys Ser Arg Gly Asn Cys Gln Thr Gln Gly Asp Ser Ile Leu Asp
                165                 170                 175
Cys Val Pro Lys Asp Gly Gln Ser His Cys Cys Ile Pro Arg Lys His
            180                 185                 190
Leu Leu Leu Tyr Gln Asn Met Gly Ile Trp Val Gln Ala Glu Asn Ala
                195                 200                 205
Leu Gly Thr Ser Met Ser Pro Gln Leu Cys Leu Asp Pro Met Asp Val
            210                 215                 220
Val Lys Leu Glu Pro Pro Met Leu Arg Thr Met Asp Pro Ser Pro Glu
225                 230                 235                 240
Ala Ala Pro Pro Gln Ala Gly Cys Leu Gln Leu Cys Trp Glu Pro Trp
                245                 250                 255
Gln Pro Gly Leu His Ile Asn Gln Lys Cys Glu Leu Arg His Lys Pro
                260                 265                 270
Gln Arg Gly Glu Ala Ser Trp Ala Leu Val Gly Pro Leu Pro Leu Glu
            275                 280                 285
Ala Leu Gln Tyr Glu Leu Cys Gly Leu Leu Pro Ala Thr Ala Tyr Thr
            290                 295                 300
Leu Gln Ile Arg Cys Ile Arg Trp Pro Leu Pro Gly His Trp Ser Asp
305                 310                 315                 320
Trp Ser Pro Ser Leu Glu Leu Arg Thr Thr Glu Arg Ala Pro Thr Val
                325                 330                 335
Arg Leu Asp Thr Trp Trp Arg Gln Arg Gln Leu Asp Pro Arg Thr Val
                340                 345                 350
Gln Leu Phe Trp Lys Pro Val Pro Leu Glu Glu Asp Ser Gly Arg Ile
            355                 360                 365
Gln Gly Tyr Val Val Ser Trp Arg Pro Ser Gly Gln Ala Gly Ala Ile
            370                 375                 380
Leu Pro Leu Cys Asn Thr Thr Glu Leu Ser Cys Thr Phe His Leu Pro
385                 390                 395                 400
Ser Glu Ala Gln Glu Val Ala Leu Val Ala Tyr Asn Ser Ala Gly Thr
                405                 410                 415
Ser Arg Pro Thr Pro Val Val Phe Ser Glu Ser Arg Gly Pro Ala Leu
                420                 425                 430
Thr Arg Leu His Ala Met Ala Arg Asp Pro His Ser Leu Trp Val Gly
            435                 440                 445
Trp Glu Pro Pro Asn Pro Trp Pro Gln Gly Tyr Val Ile Glu Trp Gly
450                 455                 460
Leu Gly Pro Pro Ser Ala Ser Asn Ser Asn Lys Thr Trp Arg Met Glu
465                 470                 475                 480
Gln Asn Gly Arg Ala Thr Gly Phe Leu Leu Lys Glu Asn Ile Arg Pro
            485                 490                 495
Phe Gln Leu Tyr Glu Ile Ile Val Thr Pro Leu Tyr Gln Asp Thr Met
            500                 505                 510
Gly Pro Ser Gln His Val Tyr Ala Tyr Ser Gln Glu Met Ala Pro Ser
            515                 520                 525
His Ala Pro Glu Leu His Leu Lys His Ile Gly Lys Thr Trp Ala Gln
            530                 535                 540
Leu Glu Trp Val Pro Glu Pro Pro Glu Leu Gly Lys Ser Pro Leu Thr
545                 550                 555                 560
His Tyr Thr Ile Phe Trp Thr Asn Ala Gln Asn Gln Ser Phe Ser Ala
                565                 570                 575
Ile Leu Asn Ala Ser Ser Arg Gly Phe Val Leu His Gly Leu Glu Pro
```

```
                    580                 585                 590
Ala Ser Leu Tyr His Ile His Leu Met Ala Ser Gln Ala Gly Ala
            595                 600                 605

Thr Asn Ser Thr Val Leu Thr Leu Met Thr Leu Thr Pro Glu Gly Ser
            610                 615                 620

Glu Leu His Ile Ile Leu Gly Leu Phe Gly Leu Leu Leu Leu Leu Thr
625                 630                 635                 640

Cys Leu Cys Gly Thr Ala Trp Leu Cys Cys Ser Pro Asn Arg Lys Asn
            645                 650                 655

Pro Leu Trp Pro Ser Val Pro Asp Pro Ala His Ser Ser Leu Gly Ser
            660                 665                 670

Trp Val Pro Thr Ile Met Glu Glu Asp Ala Phe Gln Leu Pro Gly Leu
            675                 680                 685

Gly Thr Pro Pro Ile Thr Lys Leu Thr Val Leu Glu Glu Asp Glu Lys
            690                 695                 700

Lys Pro Val Pro Trp Glu Ser His Asn Ser Ser Glu Thr Cys Gly Leu
705                 710                 715                 720

Pro Thr Leu Val Gln Thr Tyr Val Leu Gln Gly Asp Pro Arg Ala Val
            725                 730                 735

Ser Thr Gln Pro Gln Ser Gln Ser Gly Thr Ser Asp Gln Val Leu Tyr
            740                 745                 750

Gly Gln Leu Leu Gly Ser Pro Thr Ser Pro Gly Pro Gly His Tyr Leu
            755                 760                 765

Arg Cys Asp Ser Thr Gln Pro Leu Leu Ala Gly Leu Thr Pro Ser Pro
            770                 775                 780

Lys Ser Tyr Glu Asn Leu Trp Phe Gln Ala Ser Pro Leu Gly Thr Leu
785                 790                 795                 800

Val Thr Pro Ala Pro Ser Gln Glu Asp Asp Cys Val Phe Gly Pro Leu
            805                 810                 815

Leu Asn Phe Pro Leu Leu Gln Gly Ile Arg Val His Gly Met Glu Ala
            820                 825                 830

Leu Gly Ser Phe
        835

<210> SEQ ID NO 35
<211> LENGTH: 837
<212> TYPE: PRT
<213> ORGANISM: Mus musculus

<400> SEQUENCE: 35

Met Val Gly Leu Gly Ala Cys Thr Leu Thr Gly Val Thr Leu Ile Phe
1               5                   10                  15

Leu Leu Leu Pro Arg Ser Leu Glu Ser Cys Gly His Ile Glu Ile Ser
            20                  25                  30

Pro Pro Val Val Arg Leu Gly Asp Pro Val Leu Ala Ser Cys Thr Ile
            35                  40                  45

Ser Pro Asn Cys Ser Lys Leu Asp Gln Gln Ala Lys Ile Leu Trp Arg
        50                  55                  60

Leu Gln Asp Glu Pro Ile Gln Pro Gly Asp Arg Gln His His Leu Pro
65              70                  75                  80

Asp Gly Thr Gln Glu Ser Leu Ile Thr Leu Pro His Leu Asn Tyr Thr
            85                  90                  95

Gln Ala Phe Leu Phe Cys Leu Val Pro Trp Glu Asp Ser Val Gln Leu
            100                 105                 110

Leu Asp Gln Ala Glu Leu His Ala Gly Tyr Pro Pro Ala Ser Pro Ser
```

```
              115                 120                 125
Asn Leu Ser Cys Leu Met His Leu Thr Thr Asn Ser Leu Val Cys Gln
            130                 135                 140
Trp Glu Pro Gly Pro Glu Thr His Leu Pro Thr Ser Phe Ile Leu Lys
145                 150                 155                 160
Ser Phe Arg Ser Arg Ala Asp Cys Gln Tyr Gln Gly Asp Thr Ile Pro
                165                 170                 175
Asp Cys Val Ala Lys Lys Arg Gln Asn Asn Cys Ser Ile Pro Arg Lys
            180                 185                 190
Asn Leu Leu Leu Tyr Gln Tyr Met Ala Ile Trp Val Gln Ala Glu Asn
            195                 200                 205
Met Leu Gly Ser Ser Glu Ser Pro Lys Leu Cys Leu Asp Pro Met Asp
            210                 215                 220
Val Val Lys Leu Glu Pro Pro Met Leu Gln Ala Leu Asp Ile Gly Pro
225                 230                 235                 240
Asp Val Val Ser His Gln Pro Gly Cys Leu Trp Leu Ser Trp Lys Pro
                245                 250                 255
Trp Lys Pro Ser Glu Tyr Met Glu Gln Glu Cys Glu Leu Arg Tyr Gln
            260                 265                 270
Pro Gln Leu Lys Gly Ala Asn Trp Thr Leu Val Phe His Leu Pro Ser
            275                 280                 285
Ser Lys Asp Gln Phe Glu Leu Cys Gly Leu His Gln Ala Pro Val Tyr
            290                 295                 300
Thr Leu Gln Met Arg Cys Ile Arg Ser Ser Leu Pro Gly Phe Trp Ser
305                 310                 315                 320
Pro Trp Ser Pro Gly Leu Gln Leu Arg Pro Thr Met Lys Ala Pro Thr
                325                 330                 335
Ile Arg Leu Asp Thr Trp Cys Gln Lys Lys Gln Leu Asp Pro Gly Thr
                340                 345                 350
Val Ser Val Gln Leu Phe Trp Lys Pro Thr Pro Leu Gln Glu Asp Ser
            355                 360                 365
Gly Gln Ile Gln Gly Tyr Leu Leu Ser Trp Asn Ser Pro Asp His Gln
            370                 375                 380
Gly Gln Asp Ile His Leu Cys Asn Thr Thr Gln Leu Ser Cys Ile Phe
385                 390                 395                 400
Leu Leu Pro Ser Glu Ala Gln Asn Val Thr Leu Val Ala Tyr Asn Lys
                405                 410                 415
Ala Gly Thr Ser Ser Pro Thr Thr Val Val Phe Leu Glu Asn Glu Gly
                420                 425                 430
Pro Ala Val Thr Gly Leu His Ala Met Ala Gln Asp Leu Asn Thr Ile
            435                 440                 445
Trp Val Asp Trp Glu Ala Pro Ser Leu Leu Pro Gln Gly Tyr Leu Ile
            450                 455                 460
Glu Trp Glu Met Ser Ser Pro Ser Tyr Asn Asn Ser Tyr Lys Ser Trp
465                 470                 475                 480
Met Ile Glu Pro Asn Gly Asn Ile Thr Gly Ile Leu Leu Lys Asp Asn
                485                 490                 495
Ile Asn Pro Phe Gln Leu Tyr Arg Ile Thr Val Ala Pro Leu Tyr Pro
                500                 505                 510
Gly Ile Val Gly Pro Pro Val Asn Val Tyr Thr Phe Ala Gly Glu Arg
            515                 520                 525
Ala Pro Pro His Ala Pro Ala Leu His Leu Lys His Val Gly Thr Thr
            530                 535                 540
```

```
Trp Ala Gln Leu Glu Trp Val Pro Glu Ala Pro Arg Leu Gly Met Ile
545                 550                 555                 560

Pro Leu Thr His Tyr Thr Ile Phe Trp Asp Ala Gly Asp His Ser
            565                 570                 575

Phe Ser Val Thr Leu Asn Ile Ser Leu His Asp Phe Val Leu Lys His
            580                 585                 590

Leu Glu Pro Ala Ser Leu Tyr His Val Tyr Leu Met Ala Thr Ser Arg
            595                 600                 605

Ala Gly Ser Thr Asn Ser Thr Gly Leu Thr Leu Arg Thr Leu Asp Pro
            610                 615                 620

Ser Asp Leu Asn Ile Phe Leu Gly Ile Leu Cys Leu Val Leu Leu Ser
625                 630                 635                 640

Thr Thr Cys Val Val Thr Trp Leu Cys Cys Lys Arg Arg Gly Lys Thr
                645                 650                 655

Ser Phe Trp Ser Asp Val Pro Asp Pro Ala His Ser Ser Leu Ser Ser
            660                 665                 670

Trp Leu Pro Thr Ile Met Thr Glu Glu Thr Phe Gln Leu Pro Ser Phe
            675                 680                 685

Trp Asp Ser Ser Val Pro Ser Ile Thr Lys Ile Thr Glu Leu Glu Glu
690                 695                 700

Asp Lys Lys Pro Thr His Trp Asp Ser Glu Ser Ser Gly Asn Gly Ser
705                 710                 715                 720

Leu Pro Ala Leu Val Gln Ala Tyr Val Leu Gln Gly Asp Pro Arg Glu
            725                 730                 735

Ile Ser Asn Gln Ser Gln Pro Pro Ser Arg Thr Gly Asp Gln Val Leu
            740                 745                 750

Tyr Gly Gln Val Leu Glu Ser Pro Thr Ser Pro Gly Val Met Gln Tyr
            755                 760                 765

Ile Arg Ser Asp Ser Thr Gln Pro Leu Leu Gly Gly Pro Thr Pro Ser
            770                 775                 780

Pro Lys Ser Tyr Glu Asn Ile Trp Phe His Ser Arg Pro Gln Glu Thr
785                 790                 795                 800

Phe Val Pro Gln Pro Pro Asn Gln Glu Asp Asp Cys Val Phe Gly Pro
            805                 810                 815

Pro Phe Asp Phe Pro Leu Phe Gln Gly Leu Gln Val His Gly Val Glu
            820                 825                 830

Glu Gln Gly Gly Phe
            835

<210> SEQ ID NO 36
<211> LENGTH: 112
<212> TYPE: PRT
<213> ORGANISM: Rattus rattus

<400> SEQUENCE: 36

Leu Glu Gly Cys Gly Gln Ile Arg Ile Ser Pro Ile Val His Leu
1               5                   10                  15

Gly Asp Pro Val Leu Ala Ser Cys Thr Ile Ser Pro Asn Cys Ser Lys
            20                  25                  30

Leu Asp Arg Gln Pro Lys Ile Leu Trp Arg Leu Gln Asp Glu Pro Asn
            35                  40                  45

Gln Pro Gly Asp Arg Gln His His Leu Pro Asp Gly Ser Gln Glu Ser
            50                  55                  60

Ile Ile Thr Leu Pro His Leu Asn Tyr Thr Gln Ala Phe Leu Phe Cys
65                  70                  75                  80
```

```
Leu Val Pro Trp Asn Asn Ser Phe Gln Val Leu Asp Gln Ala Glu Leu
                85                  90                  95

Arg Ala Gly Cys Lys Ser Leu Gln Pro Pro Thr His Leu Leu Gln Cys
            100                 105                 110
```

<210> SEQ ID NO 37
<211> LENGTH: 174
<212> TYPE: PRT
<213> ORGANISM: Homo sapiens

<400> SEQUENCE: 37

```
Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

<210> SEQ ID NO 38
<211> LENGTH: 175
<212> TYPE: PRT
<213> ORGANISM: Homo sapiens

<400> SEQUENCE: 38

```
Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
```

```
               130                 135                 140
Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 39
<211> LENGTH: 177
<212> TYPE: PRT
<213> ORGANISM: Homo sapiens

<400> SEQUENCE: 39

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Val Ser Glu Cys Ala Thr Tyr Lys Leu Cys His Pro Glu
        35                  40                  45

Glu Leu Val Leu Leu Gly His Ser Leu Gly Ile Pro Trp Ala Pro Leu
    50                  55                  60

Ser Ser Cys Pro Ser Gln Ala Leu Gln Leu Ala Gly Cys Leu Ser Gln
65                  70                  75                  80

Leu His Ser Gly Leu Phe Leu Tyr Gln Gly Leu Leu Gln Ala Leu Glu
                85                  90                  95

Gly Ile Ser Pro Glu Leu Gly Pro Thr Leu Asp Thr Leu Gln Leu Asp
            100                 105                 110

Val Ala Asp Phe Ala Thr Thr Ile Trp Gln Gln Met Glu Glu Leu Gly
        115                 120                 125

Met Ala Pro Ala Leu Gln Pro Thr Gln Gly Ala Met Pro Ala Phe Ala
    130                 135                 140

Ser Ala Phe Gln Arg Arg Ala Gly Gly Val Leu Val Ala Ser His Leu
145                 150                 155                 160

Gln Ser Phe Leu Glu Val Ser Tyr Arg Val Leu Arg His Leu Ala Gln
                165                 170                 175

Pro

<210> SEQ ID NO 40
<211> LENGTH: 1155
<212> TYPE: DNA
<213> ORGANISM: Rattus rattus

<400> SEQUENCE: 40
atgagcatca ttcccctgcc tcagctcctc gccctgctct gctgctgcgg acttgctgct      60
gctactcagg gccccacaga cccgtccacg cccccctaac tgggcctcgc ccacttccac     120
aacctgacct tcgaccccgg gacctggaca ctgagctggg cctgtggcgg ccatgatggg     180
gcagtgatgt cgtgcacggt gattgaccag gaggcaggga tccggcgcag agtgcggtcc     240
cggggctgcc gctgccggtt tcagccaatg gagttacacc gcggggtcga cctggaggtt     300
gcgggggaca aaggccatgc ccaagtccat cagactctgc gcttcgagaa tgaaggtgcc     360
ccaggctccg gggcagagaa cctgacctgt gagatccttg ctgcccactt cctgtgctgt     420
tattgggcgt gggggccggc tgcacccgat gacatcagat actcactgcg cgtgctcaac     480
gccactggtc atgaggtcgc cagctgctcc gctgcccccg aaccccacca cacgcgttgc     540
caggctgatg atctcacaca tctgccccgc ctcgcataca tcgtcgtcac tgggcagagc     600
cggacggggc tggtgcggtt cctggatgcc gtggtcaaca ccaagggcat tgagcgcctg     660
```

-continued

```
ggtcccccag ataacgtctc tgcctcctgt aacttctccc actgcaccat cacctgggct    720 ccgccccta cctgggcgcc tatgacggaa caggatttcc gctttgagat cgagtggaag    780
aaggcggagc ccagcagcat tgcccagaag gtggttatcg cagggcgcga ggacaacgcc    840
ttcgccttcc ccagccccgc ccccgtggcc gcctctggg tcagagttcg tgcaggggac    900
acacgcagtg atcggtggag cgactggagc cccgccctgg agctcggctc ggaggccaca    960
accccgccgc gggccctggt gttggcggcg tcgagctgtg cagccctgct gtgtgcgctg   1020
gcactggggg cggcctgcag gagactcgcg ctctcacgcc gcctcctccc cccatcccc   1080 gggatccggg accgcgtatc tgatgacgag cgtgtcaact cggagacgct gaggaaggac   1140
ctgctgcggc cctag                                                    1155
```

<210> SEQ ID NO 41
<211> LENGTH: 384
<212> TYPE: PRT
<213> ORGANISM: Rattus rattus

<400> SEQUENCE: 41

```
Met Ser Ile Ile Pro Leu Pro Gln Leu Leu Ala Leu Leu Cys Cys Cys
1               5                   10                  15

Gly Leu Ala Ala Ala Thr Gln Gly Pro Thr Asp Pro Ser Thr Pro Pro
            20                  25                  30

Asn Leu Gly Leu Ala His Phe His Asn Leu Thr Phe Asp Pro Gly Thr
        35                  40                  45

Trp Thr Leu Ser Trp Ala Cys Gly Gly His Asp Gly Ala Val Met Ser
    50                  55                  60

Cys Thr Val Ile Asp Gln Glu Ala Gly Ile Arg Arg Arg Val Arg Ser
65                  70                  75                  80

Arg Gly Cys Arg Cys Arg Phe Gln Pro Met Glu Leu His Arg Gly Val
                85                  90                  95

Asp Leu Glu Val Ala Gly Asp Lys Gly His Ala Gln Val His Gln Thr
            100                 105                 110

Leu Arg Phe Glu Asn Glu Gly Ala Pro Gly Ser Gly Ala Glu Asn Leu
        115                 120                 125

Thr Cys Glu Ile Leu Ala Ala His Phe Leu Cys Cys Tyr Trp Ala Val
    130                 135                 140

Gly Pro Ala Ala Pro Asp Asp Ile Arg Tyr Ser Leu Arg Val Leu Asn
145                 150                 155                 160

Ala Thr Gly His Glu Val Ala Ser Cys Ser Ala Ala Pro Gly Thr Pro
                165                 170                 175

Pro Thr Arg Cys Gln Ala Asp Asp Leu Thr His Leu Pro Arg Leu Ala
            180                 185                 190

Tyr Ile Val Val Thr Gly Gln Ser Arg Thr Gly Leu Val Arg Phe Leu
        195                 200                 205

Asp Ala Val Val Asn Thr Lys Gly Ile Glu Arg Leu Gly Pro Pro Asp
    210                 215                 220

Asn Val Ser Ala Ser Cys Asn Phe Ser His Cys Thr Ile Thr Trp Ala
225                 230                 235                 240

Pro Pro Pro Thr Trp Ala Pro Met Thr Glu Gln Asp Phe Arg Phe Glu
                245                 250                 255

Ile Glu Trp Lys Lys Ala Glu Pro Ser Ser Ile Ala Gln Lys Val Val
            260                 265                 270

Ile Ala Gly Arg Glu Asp Asn Ala Phe Ala Phe Pro Ser Pro Ala Pro
        275                 280                 285
```

```
Arg Gly Arg Leu Trp Val Arg Val Arg Ala Gly Asp Thr Arg Ser Asp
    290                 295                 300

Arg Trp Ser Asp Trp Ser Pro Ala Leu Glu Leu Gly Ser Glu Ala Thr
305                 310                 315                 320

Thr Pro Pro Arg Ala Leu Val Leu Ala Ala Ser Ser Cys Ala Ala Leu
                325                 330                 335

Leu Cys Ala Leu Ala Leu Gly Ala Ala Cys Arg Arg Leu Ala Leu Ser
            340                 345                 350

Arg Arg Leu Leu Pro Pro Ile Pro Gly Ile Arg Asp Arg Val Ser Asp
        355                 360                 365

Asp Glu Arg Val Asn Ser Glu Thr Leu Arg Lys Asp Leu Leu Arg Pro
    370                 375                 380

<210> SEQ ID NO 42
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 42
ccattgtcca tcttggggat c                                         21

<210> SEQ ID NO 43
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 43
cctggaagct gttgttccat g                                         21

<210> SEQ ID NO 44
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 44
cacagcgggc tcttcctcta ccaa                                      24

<210> SEQ ID NO 45
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 45
agcagcggca ggaatcaata ctcg                                      24

<210> SEQ ID NO 46
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 46
accccaccgt gttcttcgac                                           20
```

```
<210> SEQ ID NO 47
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 47
catttgccat ggacaagatg                                                  20

<210> SEQ ID NO 48
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 48
aggaagaagc tgcagcagag                                                  20

<210> SEQ ID NO 49
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 49
ttcacctgct tgggctctat                                                  20

<210> SEQ ID NO 50
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 50
ggcaaggatg ccactaatgt                                                  20

<210> SEQ ID NO 51
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 51
agggtcagca ggagacttga                                                  20

<210> SEQ ID NO 52
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 52
ccacctacgg ggacctcaac cac                                              23

<210> SEQ ID NO 53
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 53
```

```
gacatgcgcc cacggaagac g                                              21

<210> SEQ ID NO 54
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 54
tcattctttg gagcgggtgt g                                              21

<210> SEQ ID NO 55
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 55
taaggacggc aaagttgtaa gtgg                                           24

<210> SEQ ID NO 56
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 56
cctttcttat gcatgtacgg ag                                             22

<210> SEQ ID NO 57
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 57
gtacactaat acgaaggcac tc                                             22

<210> SEQ ID NO 58
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 58
accccaccgt gttcttcgac                                                20

<210> SEQ ID NO 59
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 59
catttgccat ggacaagatg                                                20

<210> SEQ ID NO 60
<211> LENGTH: 22
<212> TYPE: DNA
<213> ORGANISM: Artificial Sequence
```

```
<220> FEATURE:
<223> OTHER INFORMATION: synthetic oligonucleotide

<400> SEQUENCE: 60
acgtcgttgg ctcagttatg tc                                              22

<210> SEQ ID NO 61
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 61
atttatgtca gagatggagg atgg                                            24

<210> SEQ ID NO 62
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 62
ggagctctaa gcttctagat c                                               21

<210> SEQ ID NO 63
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 63
ggctcaatgt gatttcttgg g                                               21

<210> SEQ ID NO 64
<211> LENGTH: 175
<212> TYPE: PRT
<213> ORGANISM: Homo sapiens

<400> SEQUENCE: 64

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160
```

```
Phe Leu Glu Val Ser Tyr Arg Val Leu Arg His Leu Ala Gln Pro
            165                 170                 175

<210> SEQ ID NO 65
<211> LENGTH: 174
<212> TYPE: PRT
<213> ORGANISM: Homo sapiens

<400> SEQUENCE: 65

Ala Pro Thr Thr Arg Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 66
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 66
gctgtgtctg ggccattgct at                                              22

<210> SEQ ID NO 67
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 67
ctcttcgcca cacttctctt tttg                                            24

<210> SEQ ID NO 68
<211> LENGTH: 551
<212> TYPE: DNA
<213> ORGANISM: Homo sapiens

<400> SEQUENCE: 68
ccacgaagga ccagaacaag acagagtgct tcctgccgat ccaaacatga gccgcctgcc     60
cgtcctgctc ctgctccaac tcctggtccg ccccggactc caagctccca tgacccagac    120
```

```
aacgtccttg aagacaagct gggttaactg ctctaacatg atcgatgaaa ttataacacg    180
cttaaagcag ccacctttgc ctttgctgga cttcaacaac ctcaatgggg aagaccaaga    240
cattctgatg gaaaataacc ttcgaaggcc aaacctggag gcattcaaca gggctgtcaa    300
gagtttacag aacgcatcag caattgagag cattcttaaa aatctcctgc catgtctgcc    360
cctggccacg gccgcaccca cgcgacatcc aatccatatc aaggacggtg actggaatga    420
attccggagg aaactgacgt tctatctgaa acccttgag aatgcgcagg ctcaacagac     480
gactttgagc ctcgcgatct tttgagtcca acgtccagct cgttctctgg gccttctcac    540
cacagagcct c                                                         551

<210> SEQ ID NO 69
<211> LENGTH: 152
<212> TYPE: PRT
<213> ORGANISM: Homo sapiens

<400> SEQUENCE: 69

Met Ser Arg Leu Pro Val Leu Leu Leu Gln Leu Leu Val Arg Pro
1               5                   10                  15

Gly Leu Gln Ala Pro Met Thr Gln Thr Thr Ser Leu Lys Thr Ser Trp
            20                  25                  30

Val Asn Cys Ser Asn Met Ile Asp Glu Ile Ile Thr Arg Leu Lys Gln
        35                  40                      45

Pro Pro Leu Pro Leu Leu Asp Phe Asn Asn Leu Asn Gly Glu Asp Gln
    50                  55                      60

Asp Ile Leu Met Glu Asn Asn Leu Arg Arg Pro Asn Leu Glu Ala Phe
65                  70                      75                  80

Asn Arg Ala Val Lys Ser Leu Gln Asn Ala Ser Ala Ile Glu Ser Ile
                85                      90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 70
<211> LENGTH: 551
<212> TYPE: DNA
<213> ORGANISM: Homo sapiens

<400> SEQUENCE: 70
ccacgaagga ccagaacaag acagagtgcc tcctgccgat ccaaacatga gccgcctgcc     60
cgtcctgctc ctgctccaac tcctggtccg ccccggactc caagctccca tgacccagac    120
aacgtccttg aagacaagct gggttaactg ctctaacatg atcgatgaaa ttataacaca    180
cttaaagcag ccacctttgc ctttgctgga cttcaacaac ctcaatgggg aagaccaaga    240
cattctgatg gaaaataacc ttcgaaggcc aaacctggag gcattcaaca gggctgtcaa    300
gagtttacag aacgcatcag caattgagag cattcttaaa aatctcctgc catgtctgcc    360
cctggccacg gccgcaccca cgcgacatcc aatccatatc aaggacggtg actggaatga    420
attccggagg aaactgacgt tctatctgaa acccttgag aatgcgcagg ctcaacagac     480
gactttgagc ctcgcgatct tttgagtcca acgtccagct cgttctctgg gccttctcac    540
```

```
cacagagcct c                                                                551
```

<210> SEQ ID NO 71
<211> LENGTH: 152
<212> TYPE: PRT
<213> ORGANISM: Homo sapiens

<400> SEQUENCE: 71

```
Met Ser Arg Leu Pro Val Leu Leu Leu Gln Leu Leu Val Arg Pro
1               5                   10                  15

Gly Leu Gln Ala Pro Met Thr Gln Thr Thr Ser Leu Lys Thr Ser Trp
            20                  25                  30

Val Asn Cys Ser Asn Met Ile Asp Glu Ile Ile Thr His Leu Lys Gln
            35                  40                  45

Pro Pro Leu Pro Leu Leu Asp Phe Asn Asn Leu Asn Gly Glu Asp Gln
        50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
        130                 135                 140

Thr Thr Leu Ser Leu Ala Ile Phe
145                 150
```

<210> SEQ ID NO 72
<211> LENGTH: 551
<212> TYPE: DNA
<213> ORGANISM: Homo sapiens

<400> SEQUENCE: 72

```
ccacgaagga ccagaacaag acagagtgcc tcctgccgat ccaaacatga gccgcctgcc    60
cgtcctgctc ctgctccaac tcctggtccg ccccggactc caagctccca tgacccagac   120
aacgtccttg aagacaagct gggttaactg ctctaacatg atcgatgaaa ttataacaca   180
cttaaagcag ccacctttgc ctttgctgga cttcaacaac ctcaatgggg aagaccaaga   240
cattctgatg gaaaataacc ttcgaaggcc aaacctggag gcattcaaca gggctgtcaa   300
gagtttacag aacgcatcag caattgagag cattcttaaa aatctcctgc catgtctgcc   360
cctggccacg gccgcaccca cgcgacatcc aatccatatc aaggacggtg actggaatga   420
attccggagg aaactgacgt tctatctgaa aaccttgag aatgcgcagg ctcaacagac   480
gactttgagc ctcgcgatct tttgagtcca acgtccagct cgttctctgg gccttctcac   540
cacagagcct c                                                       551
```

<210> SEQ ID NO 73
<211> LENGTH: 152
<212> TYPE: PRT
<213> ORGANISM: Homo sapiens

<400> SEQUENCE: 73

```
Met Ser Arg Leu Pro Val Leu Leu Leu Gln Leu Leu Val Arg Pro
1               5                   10                  15
```

```
Gly Leu Gln Ala Pro Met Thr Gln Thr Thr Ser Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 74
<211> LENGTH: 551
<212> TYPE: DNA
<213> ORGANISM: Homo sapiens

<400> SEQUENCE: 74
ccacgaagga ccagaacaag acagagtgcc tcctgccgat ccaaacatga gccgcctgcc      60
cgtcctgctc ctgctccaac tcctggtccg ccccggactc caagctccca tgacccagac     120
aacgtccttg aagacaagct gggttaactg ctctaacatg atcgatgaaa ttataacaca     180
cttaaagcag ccacctttgc ctttgctgga cttcaacaac ctcaatgggg aagaccaaga     240
cattctgatg gaaaataacc ttcgaaggcc aaacctggag gcattcaaca gggctgtcaa     300
gagtttacag aacgcatcag caattgagag cattcttaaa aatctcctgc catgtctgcc     360
cctggccacg gccgcacccc gcgacatcc aatccatatc aaggacggtg actggaatga     420
attccggagg aaactgacgt tctatctgaa acccttgag aatgcgcagg ctcaacagac     480
gactttgagc ctcgcgatct tttgagtcca acgtccagct cgttctctgg gccttctcac     540
cacagagcct c                                                          551

<210> SEQ ID NO 75
<211> LENGTH: 152
<212> TYPE: PRT
<213> ORGANISM: Homo sapiens

<400> SEQUENCE: 75

Met Ser Arg Leu Pro Val Leu Leu Leu Gln Leu Leu Val Arg Pro
1               5                   10                  15

Gly Leu Gln Ala Pro Met Thr Gln Thr Thr Ser Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95
```

```
Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 76
<211> LENGTH: 557
<212> TYPE: DNA
<213> ORGANISM: Homo sapiens

<400> SEQUENCE: 76
gccccacgaa ggaccagaac aagacagagt gcctcctgcc gatccaaaca tgagccgcct    60
gcccgtcctg ctcctgctcc aactcctggt ccgccccgga ctccaagctc ccatgaccca   120
gacaacgccc ttgaagacaa gctgggttaa ctgctctaac atgatcgatg aaattataac   180
acacttaaag cagccaccct tgcctttgct ggacttcaac aacctcaatg gggaagacca   240
agacattctg atggaaaata accttcgaag gccaaacctg gaggcattca acagggctgt   300
caagagttta cagaacgcat cagcaattga gagcattctt aaaaatctcc tgccatgtct   360
gccccctggcc acggccgcac ccacgcgaca tccaatccat atcaaggacg gtgactggaa   420
tgaattccgg aggaaactga cgttctatct gaaaaccctt gagaatgcgc aggctcaaca   480
gacgactttg agcctcgcga tcttttgagt ccaacgtcca gctcgttctc tgggccttct   540
caccacagag cctcggg                                                   557

<210> SEQ ID NO 77
<211> LENGTH: 152
<212> TYPE: PRT
<213> ORGANISM: Homo sapiens

<400> SEQUENCE: 77

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150
```

```
<210> SEQ ID NO 78
<211> LENGTH: 924
<212> TYPE: DNA
<213> ORGANISM: Homo sapiens

<400> SEQUENCE: 78
cagagcccca cgaaggacca gaacaagaca gagtgcctcc tgccgatcca acatgagcc      60 gcctgcccgt cctgctcctg ctccaactcc tggtccgccc cggactccaa gctcccatga    120
cccagacaac gcccttgaag acaagctggg ttaactgctc taacatgatc gatgaaatta    180
taacacactt aaagcagcca cctttgcctt tgctggactt caacaacctc aatggggaag    240
accaagacat tctgatggaa ataaccttc gaaggccaaa cctggaggca ttcaacaggg     300
ctgtcaagag tttacagaac gcatcagcaa ttgagagcat tcttaaaaat ctcctgccat    360
gtctgcccct ggccacggcc gcacccacgc gacatccaat ccatatcaag gacggtgact    420
ggaatgaatt ccggaggaaa ctgacgttct atctgaaaac ccttgagaat gcgcaggctc    480
aacagacgac tttgagcctc gcgatctttt gagtccaacg tccagctcgt tctctgggcc    540
ttctcaccac agagcctcgg gacatcaaaa acagcagaac ttctgaaacc tctgggtcat    600
ctctcacaca ttccaggacc agaagcattt caccttttcc tgcggcatca gatgaattgt    660
taattatcta atttctgaaa tgtgcagctc ccatttggcc ttgtgcggtt gtgttctcat    720
ttttatccca ttgagactat ttatttatgt atgtatgtat ttatttattt attgcctgga    780
gtgtgaactg tatttatttt agcagaggag ccatgtcctg ctgcttctgc aaaaaactca    840
gagtggggtg gggagcatgt tcatttgtac ctcgagtttt aaactggttc ctagggatgt    900
gtgagaataa actagactct gaac                                            924

<210> SEQ ID NO 79
<211> LENGTH: 152
<212> TYPE: PRT
<213> ORGANISM: Homo sapiens

<400> SEQUENCE: 79

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
                20                  25                  30

Val Asn Cys Ser Asn Met Ile Asp Glu Ile Ile Thr His Leu Lys Gln
            35                  40                  45

Pro Pro Leu Pro Leu Leu Asp Phe Asn Asn Leu Asn Gly Glu Asp Gln
        50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 80
<211> LENGTH: 923
```

```
<212> TYPE: DNA
<213> ORGANISM: Homo sapiens

<400> SEQUENCE: 80
cagagcccca cgaaggacca gaacaagaca gagtgcctcc tgccgatcca aacatgagcc      60
gcctgcccgt cctgctcctg ctccaactcc tggtccgccc cggactccaa gctcccatga     120
cccagacaac gcccttgaag acaagctggg ttaactgctc taacatgatc gatgaaatta     180
taacacactt aaagcagcca cctttgcctt tgctggactt caacaacctc aatggggaag     240
accaagacat tctgatggaa aataaccttc gaaggccaaa cctggaggca ttcaacaggg     300
ctgtcaagag tttacagaac gcatcagcaa ttgagagcat tcttaaaaat ctcctgccat     360
gtctgcccct ggccacggcc gcacccacgc gacatccaat ccatatcaag gacggtgact     420
ggaatgaatt ccggaggaaa ctgacgttct atctgaaaac ccttgagaat gcgcaggctc     480
aacagacgac tttgagcctc gcgatctttt agtccaacgt ccagctcgtt ctctgggcct     540
tctcaccaca gagcctcggg acatcaaaaa cagcagaact tctgaaacct ctgggtcatc     600
tctcacacat tccaggacca gaagcatttc acctttttcct gcggcatcag atgaattgtt     660
aattatctaa tttctgaaat gtgcagctcc catttggcct tgtgcggttg tgttctcatt     720
tttatcccat tgagactatt tatttatgta tgtatgtatt tatttattta ttgcctggag     780
tgtgaactgt atttatttta gcagaggagc catgtcctgc tgcttctgca aaaaactcag     840
agtggggtgg ggagcatgtt catttgtacc tcgagtttta aactggttcc tagggatgtg     900
tgagaataaa ctagactctg aac                                             923

<210> SEQ ID NO 81
<211> LENGTH: 152
<212> TYPE: PRT
<213> ORGANISM: Homo sapiens

<400> SEQUENCE: 81

Met Ser Arg Leu Pro Val Leu Leu Leu Gln Leu Leu Val Arg Pro
1               5                   10                  15

Gly Leu Gln Ala Pro Met Thr Gln Thr Thr Pro Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150

<210> SEQ ID NO 82
<211> LENGTH: 674
<212> TYPE: DNA
<213> ORGANISM: Homo sapiens
```

<400> SEQUENCE: 82

```
gatccaaaca tgagccgcct gcccgtcctg ctcctgctcc aactcctggt ccgcccggga    60
ctccaagctc ccatgaccca gacaacgtcc ttgaagacaa gctgggttaa ctgctctaac   120
atgatcgatg aaattataac acacttaaag cagccacctt tgcctttgct ggacttcaac   180
aacctcaatg gggaagacca agacattctg atggaaaata accttcgaag gccaaacctg   240
gaggcattca cagggctgt caagagttta cagaacgcat cagcaattga gagcattctt   300
aaaaatctcc tgccatgtct gcccctggcc acggccgcac ccacgcgaca tccaatccat   360
atcaaggacg gtgactggaa tgaattccgg aggaaactga cgttctatct gaaaacccttt  420
gagaatgcgc aggctcaaca gacgactttg agcctcgcga tcttttagtc caacgtccag   480
ctcgttctct gggccttctc accacagcgc ctcgggacat caaaaacagc agaacttctg   540
aaacctctgg gtcatctctc acacattcca ggaccagaag catttcacct tttcctgcgg   600
catcagatga attgttaatt atctaatttc tgaaatgtgc agctcccatt tggccttgtg   660
cggttgtgtt ctca                                                     674
```

<210> SEQ ID NO 83
<211> LENGTH: 152
<212> TYPE: PRT
<213> ORGANISM: Homo sapiens

<400> SEQUENCE: 83

```
Met Ser Arg Leu Pro Val Leu Leu Leu Gln Leu Leu Val Arg Pro
 1               5                  10                  15

Gly Leu Gln Ala Pro Met Thr Gln Thr Thr Ser Leu Lys Thr Ser Trp
                20                  25                  30

Val Asn Cys Ser Asn Met Ile Asp Glu Ile Ile Thr His Leu Lys Gln
            35                  40                  45

Pro Pro Leu Pro Leu Leu Asp Phe Asn Asn Leu Asn Gly Glu Asp Gln
        50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150
```

<210> SEQ ID NO 84
<211> LENGTH: 490
<212> TYPE: DNA
<213> ORGANISM: Homo sapiens

<400> SEQUENCE: 84

```
gatccaaaca tgagccgcct gcccgtcctg ctcctgctcc aactcctggt ccgcccggga    60
ctccaagcgc ccatgaccca gacaacgtcc ttgaagacaa gctgggttaa ctgctctaac   120
atgatcgatg aaattataac acacttaaag cagccacctt tgcctttgct ggacttcaac   180
aacctcaatg gggaagacca agacattctg atggaaaata accttcgaag gccaaacctg   240
```

```
gaggcattca acagggctgt caagagttta cagaacgcat cagcaattga gagcattctt      300
aaaaatctcc tgccatgtct gcccctcgcc acggccgcac ccacgcgaca tccaatccat      360
atcaaggacg gtgactggaa tgagttccgg aggaaactga cgttctatct gaaaacccct      420
gagaatgcgc aggctcaaca gacgactttg agcctcgcga tcttttagtc caacgtccag      480
ctcgagctcg                                                             490
```

<210> SEQ ID NO 85
<211> LENGTH: 459
<212> TYPE: DNA
<213> ORGANISM: Homo sapiens

<400> SEQUENCE: 85

```
caaacgcaga acgtttcaga gccatgagga tgcttctgca tttgagtttg ctagctcttg       60
gagctgccta cgtgtatgcc atccccacag aaattcccac aagtgcattg gtgaaagaga      120
ccttggcact gctttctact catcgaactc tgctgatagc caatgagact ctgaggattc      180
ctgttcctgt acataaaaat caccaactgt gcactgaaga atctttcag ggaataggca       240 cactggagag tcaaactgtg caaggggta ctgtggaaag actattcaaa aacttgtcct       300
taataaagaa atacattgac ggccaaaaaa aaagtgtgg agaagaaaga cggagagtaa       360
accaattcct agactacctg caagagtttc ttggtgtaat gaacaccgag tggataatag      420
aaagttgaga ctaaactggt tgttgcagcc aaagataac                             459
```

<210> SEQ ID NO 86
<211> LENGTH: 134
<212> TYPE: PRT
<213> ORGANISM: Homo sapiens

<400> SEQUENCE: 86

Met Arg Met Leu Leu His Leu Ser Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Cys Gly Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser
    130

<210> SEQ ID NO 87
<211> LENGTH: 816
<212> TYPE: DNA
<213> ORGANISM: Homo sapiens

<400> SEQUENCE: 87

```
atgcactttc tttgccaaag gcaaacgcag aacgtttcag agccatgagg atgcttctgc       60
```

-continued

```
atttgagttt gctagctctt ggagctgcct acgtgtatgc catccccaca gaaattccca      120
caagtgcatt ggtgaaagag accttggcac tgctttctac tcatcgaact ctgctgatag      180
ccaatgagac tctgaggatt cctgttcctg tacataaaaa tcaccaactg tgcactgaag      240
aaatctttca gggaataggc acactggaga gtcaaactgt gcaaggggt actgtggaaa       300 gactattcaa aaacttgtcc ttaataaaga aatacattga cggccaaaaa aaaaagtgtg      360
gagaagaaag acgagagta aaccaattcc tagactacct gcaagagttt cttggtgtaa       420
tgaacaccga gtggataata gaaagttgag actaaactgg tttgttgcag ccaaagatt       480 tggaggagaa ggacatttta ctgcagtgag aatgagggcc aagaaagagt caggccttaa      540
ttttcagtat aatttaactt cagagggaaa gtaaatattt caggcatact gacactttgc      600
cagaaagcat aaaattctta aaatatattt cagatatcag aatcattgaa gtattttcct      660
ccaggcaaaa ttgatatact tttttcttat ttaacttaac attctgtaaa atgtctgtta      720
acttaatagt atttatgaaa tggttaagaa tttggtaaat tagtatttat ttaatgttat      780
gttgtgttct aataaaacaa aaatagacaa ctgttc                                816
```

<210> SEQ ID NO 88
<211> LENGTH: 134
<212> TYPE: PRT
<213> ORGANISM: Homo sapiens

<400> SEQUENCE: 88

```
Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
                20                  25                  30

Thr Leu Ala Leu Leu Ser Thr His Arg Thr Leu Leu Ile Ala Asn Glu
            35                  40                  45

Thr Leu Arg Ile Pro Val Pro Val His Lys Asn His Gln Leu Cys Thr
        50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
                100                 105                 110

Asn Gln Phe Leu Asp Tyr Leu Gln Glu Phe Leu Gly Val Met Asn Thr
            115                 120                 125

Glu Trp Ile Ile Glu Ser
        130
```

<210> SEQ ID NO 89
<211> LENGTH: 3230
<212> TYPE: DNA
<213> ORGANISM: Homo sapiens

<400> SEQUENCE: 89

```
atcctaatca agaccccagt gaacagaact cgaccctgcc aaggcttggc atttccattt       60
caatcactgt cttcccacca gtattttcaa tttcttttaa gacagattaa tctagccaca      120
gtcatagtag aacatagccg atcttgaaaa aaaacattcc caatatttat gtattttagc      180
ataaaattct gtttagtggg ctaccttata ctttgttttg cacacatctt ttaagaggaa      240
gttaattttc tgatttttaag aaatgcaaat gtggggcaat gatgtattaa cccaaagatt      300
ccttccgtaa tagaaaatgt ttttaagggg gggaaacagg gatttttatt attaaaagat      360
```

```
aaaagtaaat ttatttttta agatataagg cattggaaac atttagtttc acgatatgcc    420
attattaggc attctctatc tgattgttag aaattattca tttcctcaaa gacagacaat    480
aaattgactg gggacgcagt cttgtactat gcactttctt tgccaaaggc aaacgcagaa    540
cgtttcagag ccatgaggat gcttctgcat ttgagtttgc tagctcttgg agctgcctac    600
gtgtatgcca tccccacaga aattcccaca agtgcattgg tgaaagagac cttggcactg    660 cttctactc atcgaactct gctgatagcc aatgaggtaa ttttctttat gattcctaca    720
gtctgtaaag tgcataggta atcatttgtg atggttcctt tactatatat agagatctgt    780
tataaataat aagattctga gcacattagt acatgggtga taactacatc accagcaaac    840
attctgttaa aagttatgaa tgctggtgtg ctgtaaaaat gattgtattt cctttcctct    900
ccagactctg aggattcctg ttcctgtaca taaaaatgta agttaaatta tgattcagta    960
aaatgatggc atgaataagt aaatttcctg ttttaagctg taaatcatta gttatcattg   1020
gaactattta attttctata ttttgttttc atatgggtgg ctgtgaatgt ctgtacttat   1080
aaatatgagg aatgacttt tatcaagtag aatcctttaa acaagtggat taggctcttt   1140
ggtgatgttg ttagtttgcc ttcccaaaga gcatcgtgtc aggattcttt ccagaaggat   1200
tccacactga gtgagaggtg cgtgctagtc tccgtgcagt tctgactctt tctcactcta   1260
acgtgtttct gaaagtatta gcaactcaga attatatttt tagaaccatg atcagtagac   1320
attaaaatat ataacaaatg ccctatatta ataattctgc atacttaaat aattatgact   1380
atatgatggt gtgtatgcat tgaatatgcc tggtcatatt aaaatgtaaa atatatagtt   1440
tattagtcta aatagaataa aactaccagc tagaactgta gaaacacatt gatatgagtt   1500
taatgtataa tgcattacac ttccaaaaca ttttttttcca gttacataat taagttatat   1560
cctttataaa actcctcagt aatcatataa gcttcatcta cttttttgaaa attttatctt   1620 aatatgtggt ggtttgttgc ctagaaaaca aacaaaaaac tctttggaga agggaactca   1680
tgtaaatacc acaaaacaaa gcctaacttt gtggaccaaa attgttttaa taattatttt   1740
ttaattgatg aattaaaaag tatatatatt tattgtgtac aatatgatgt tttgaagtat   1800
gtatacattg cagaatggac aatggaccaa atttttatac cttgtcttga ttatttgcat   1860
tttaaaaatt ttcctcattt agcaccaact gtgcactgaa gaaatctttc agggaatagg   1920
cacactggag agtcaaactg tgcaaggggg tactgtggaa agactattca aaaacttgtc   1980
cttaataaag aaatacattg acggccaaaa agtaagttac acacattcaa tggaagctat   2040
atttgtcctg gctgtgccta tttctatgga attgacagtt tcctgtaata cctattgtca   2100
tttttctttt ttcacagaaa aagtgtggag aagaaagacg gagagtaaac caattcctag   2160
actacctgca agagtttctt ggtgtaatga acaccgagtg gataatagaa agttgagact   2220
aaactggttt gttgcagcca agattttgg aggagaagga catttttactg cagtgagaat   2280 gagggccaag aaagagtcag gccttaattt tcaatataat ttaacttcag agggaaagta   2340
aatatttcag gcatactgac actttgccag aaagcataaa attcttaaaa tatatttcag   2400
atatcagaat cattgaagta ttttcctcca ggcaaaattg atatactttt ttcttattta   2460
acttaacatt ctgtaaaatg tctgttaact taatagtatt tatgaaatgg ttaagaattt   2520
ggtaaattag tatttattta atgttatgtt gtgttcctaat aaaacaaaaa tagacaactg   2580
ttcaatttgc tgctggcctc tgtccttagc aatttgaagt tagcacagtc cattgagtac   2640
atgcccagtt tggaggaagg gtctgagcac atgtggctga gcatcccat ttctctggag   2700 aagtctcaag gttgcaaggc acaccagagg tggaagtgat ctagcaggac ttagtgggga   2760
```

```
tgtggggagc agggacacag gcaggaggtg aacctggttt tctctctaca gtatatccag   2820
aacctgggat ggtcgaaggg taaatggtag ggaataaatg aatgaatgtc gtttccaaga   2880
tgattgtaga actaaaatga gttgtaagct cccctggaag aagggatgtg aacctgtaa    2940 ctaggttcct gcccagcctg tgagaagaat ttggcagatc atctcattgc cagtatagag   3000
aggaagccag aaaccctctc tgccaaggcc tgcaggggtt cttaccacct gaccctgcac   3060
cataacaaaa ggacagagag acatggtagg gcagtcccat tagaaagact gagttccgta   3120
ttcccggggc agggcagcac caggccgcac aacatccatt ctgcctgctt atggctatca   3180
gtagcatcac tagagattct tctgtttgag aaaacttctc tcaaggatcc               3230
```

<210> SEQ ID NO 90
<211> LENGTH: 134
<212> TYPE: PRT
<213> ORGANISM: Homo sapiens

<400> SEQUENCE: 90

```
Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser
    130
```

<210> SEQ ID NO 91
<211> LENGTH: 3241
<212> TYPE: DNA
<213> ORGANISM: Homo sapiens

<400> SEQUENCE: 91

```
ggatcctaat caagacccca gtgaacagaa ctcgaccctg ccaaggcttg gcagtttcca    60
tttcaatcac tgtcttccca ccagtatttt caatttcttt taagacagat taatctagcc   120
acagtcatag tagaacatag ccgatctgaa aaaacattc  ccaatatttta tgtattttag   180 cataaaattc tgtttagtgg tctaccttat actttgtttt gcacacatct tttaagagga   240
agttaatttt ctgattttaa gaaatgcaaa tgtggggcaa tgatgtatta acccaaagat   300
tcttcgtaat agaaaatgtt tttaaggggg ggaaacaggg attttattta ttaaaagata   360
aaagtaaatt tattttttaa gatataaggc attggaaaca tttagtttca cgatatgcca   420
ttattaggca ttctctatct gattgttaga aattattcat ttcctcaaag acagacaata   480
aattgactgg ggacgcagtc ttgtactatg cactttcttt gccaaaggca aacgcagaac   540
gtttcagagc catgaggatg cttctgcatt tgagtttgct agctcttgga gctgcctacg   600
```

```
tgtatgccat ccccacagaa attcccacaa gtgcattggt gaaagagacc ttggcactgc    660
tttctactca tcgaactctg ctgatagcca atgaggtaat tttctttatg attcctacag    720
tctgtaaagt gcataggtaa tcatttgtga tggttccttt actatatata gagatctgtt    780
ataaataata agattctgag cacattagta catgggtgat aactcatca ccagcaaaca     840 ttctgttaaa agttatgaat gctggtgtgc tgtaaaaatg attgtatttc ctttcctctc    900
cagactctga ggattcctgt tcctgtacat aaaaatgtaa gttaaattat gattcagtaa    960
aatgatggca tgaataagta aatttcctgt tttaagctgt aaatcattag ttatcattgg   1020
aactatttaa ttttctatat tttgttttca tatgggtggc tgtgaatgtc tgtacttata   1080
aatatgagga atgactttt atcaagtaga atcctttaaa caagtggatt aggctctttg   1140
gtgatgttgt tagtttgcct cccaaagagc atcgtgtcag ggattctttc cagaaggatt   1200
ccacactgag tgagaggtgc gtgctagtct ccgtgcagtt ctgactcttt ctcactctaa   1260
cgtgtttctg aaagtattag caactcagaa ttatattttt agaaccatga tcagtagaca   1320
ttaaaatata taacaaatgc cctatattaa taatttctgc atacttaaat aattatgact   1380
atatgatggt gttgtatgca tttgaatatg tcctggtcat attaaaatgt aaaatatata   1440
gttttattag tctaaataga ataaaactac cagctagaac tgtagaaaca cattgatatg   1500
agtttaatgt ataatgcatt acacttccaa aacattttt tccagttaca taattaagtt    1560
atatccttta taaaactcct cagtaatcat ataagcttca tctacttttt gaaaatttta   1620
tcttaatatg tggtggtttg ttgcctagaa acaaacaaa aaactctttg gagaagggaa    1680
ctcatgtaaa taccacaaaa caaagcctaa ctttgtggac caaaattgtt ttaataatta   1740
ttttttaatt gatgaattaa aaagtatata tatttattgt gtacaatatg atgttttgaa   1800
gtatgtatac attgcagaat ggacaatgga ccaaattttt ataccttgtc ttgattattt    1860
gcatttaaaa aattttcctc atttagcacc aactgtgcac tgaagaaatc tttcagggaa   1920
taggcacact ggagagtcaa actgtgcaag ggggtactgt ggaaagacta ttcaaaaact   1980
tgtccttaat aaagaaatac attgacggcc aaaaagtaag ttacacacat tcaatggaag   2040
ctatatttgt ctggctgtgc ctatttctat ggaattgaca gtttcctgta atacctattg   2100 tcattttct tttttcacag aaaaagtgtg gagaagaaag acggagagta aaccaattcc     2160
tagactacct gcaagagttt cttggtgtaa tgaacaccga gtggataata gaaagttgag   2220
actaaactgg tttgttgcag ccaaagattt tggaggagaa ggacatttta ctgcagtgag   2280
aatgagggcc aagaaagagt caggccttaa ttttcagtat aatttaactt cagagggaaa   2340
gtaaatattt caggcatact gacactttgc cagaaagcat aaaattctta aaatatattt   2400
cagatatcag aatcattgaa gtattttcct ccaggcaaaa ttgatatact tttttcttat   2460
ttaacttaac attctgtaaa atgtctgtta acttaatagt atttatgaaa tggttaagaa   2520
tttggtaaat tagtatttat ttaatgttat gttgtgttct aataaaacaa aaatagacaa   2580
ctgttcaatt tgctgctggc ctctgtctta gcaattgaag ttagcacagt ccattgagta   2640
catgcccagt ttggaggaag ggtctgagca catgtggctg agcatcccca tttctctgga   2700
gaagtctcaa ggttgcaagg cacaccagag gtggaagtga tctagcagga cttagtgggg   2760
atgtggggag cagggacaca ggcaggaggt gaacctggtt ttctctctac agtatatcca   2820
gaacctggga tggtgcaggg taaatggtag ggaataaatg aatgaatgtg ctttccaaga   2880
ctgattgtag aactaaaatg agttgtaagg cgtcccctgg aagaagggca gtgtgggaac   2940
ctgtaactag gttcctgccc agcctgtgag aagaatttgg cagatcaatc tcattgccag   3000
```

```
tatagagagg aagccagaaa ccctctctgc caaggcctgc aggggttctt accccacctg   3060
accctgcacc ataacaaaag gaacagagag acactggtag ggcagtccca ttagaaagac   3120
tgagttccgt attcccgggg gcagggcagc accaggccgc acaacactcc attctgcctg   3180
cttatggcta tcagtagcat cactagagat tcttctgttt gagaaaactt ctcaaggatc   3240
c                                                                  3241

<210> SEQ ID NO 92
<211> LENGTH: 134
<212> TYPE: PRT
<213> ORGANISM: Homo sapiens

<400> SEQUENCE: 92

Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser
    130

<210> SEQ ID NO 93
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 93
ctggagaacg aaaagaacga agac                                          24

<210> SEQ ID NO 94
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 94
tcaaaaggga tatcaaacag aaag                                          24
```

METHODS OF TREATING NEUROLOGICAL CONDITIONS WITH HEMATOPOEITIC GROWTH FACTORS

CROSS-REFERENCE TO RELATED APPLICATIONS

The present application is a continuation-in-part of PCT/IB03/006446 filed Dec. 31, 2003, pending, and is also a continuation-in-part of U.S. application Ser. No. 10/659,295 filed Sep. 11, 2003, pending, which is a continuation application of U.S. application Ser. No. 10/331,755 filed Dec. 31, 2002, abandoned.

BACKGROUND OF THE INVENTION

1. Field of the Invention

The present invention relates to a method of treating a neurological condition in a mammal by administering at least one hematopoietic growth factor.

2. Discussion of the Related Art

Growth factors are proteins that are essentially involved in regulating survival, proliferation, maturation, and outgrowth of developing neuronal cells. For example, the expression of a large number of growth factors increases in response to various brain insults. Many factors display endogenous neuroprotective and neurotrophic effects (see Arvidsson A et al., *Neuroscience* 2001; 106:27-41; Larsson E, et al., *J Cereb Blood Flow Metab* 1999; 19:1220-8; Mattson M P, et al., *J Neurotrauma* 1994; 11:3-33; Semkova I, et al., *Brain Res Brain Res Rev* 1999; 30:176-88). These effects were also reported after exogenous administration in vitro and in vivo after brain trauma and stroke (see Semkova I., et al., *Brain Res. Rev.* 1999; 30:176-88; Fisher M, et al., *J. Cereb. Blood Flow Metab.* 1995; 15:953-9; Schäbitz W R, et al., *Stroke* 2001; 32:1226-33: Schäbitz W R, et al., *Stroke* 2000; 31:2212-7). After binding to high-affinity membrane receptors the effects of growth factors are mediated by a cascade of intracellular signal-transduction events (Kernie S G, et al., *Arch Neurol* 2000; 57:654-7), which induces cells to grow and differentiate; or provides trophic support for cell survival.

Granulocyte-colony stimulating factor (GCSF), a 20 kDa protein, together with tumor necrosis factor-α (TNF-α) and the interleukins is a member of the cytokine family of growth factors. GCSF is the major growth factor involved in the production of neutrophilic granulocytes.

GCSF exerts its function via the activation of a membrane receptor (GCSF receptor) that belongs to the super-family of hematopoietin receptors, also being referred to as class I cytokine receptors (de Koning and Touw, *Curr. Opin. Hematol.*, 1996, 3, 180-4).

A number of receptors for lymphokines, hematopoietic growth factors, and growth hormone-related molecules have been found to share a common binding domain. These receptors are referred to as hematopoietin receptors and the corresponding ligands as hematopoietins. Further, hematopoietins have been subdivided into two major structural groups: Large/long and small/short hematopoietins. One subset of individual receptor chains that are part of receptor complexes for large hematopoietins contain common structural elements in their extracellular parts: an immunoglobin-like domain, a hematopoietin-receptor domain, and 3 fibronectin type-III domains (2 in the leptin receptor). This subgroup was designated the "gp130 family of receptors" (Mosley, et al. *J. Biol. Chem.* 1996, 271, 32635-43) and include Leptin receptor (LPTR), Granulocyte colony stimulating factor receptor (GCSFR), Interleukin-6/-11/LIF/OSM/CNTF common beta chain (GPI30), Leukemia inhibiting factor receptor (LIFR), Oncostatin-M receptor beta chain (OSMR), Interleukin-12 receptor beta-1 chain (IL12RB1), Interleukin-12 receptor beta-2 chain (IL12RB2). These receptor chains homodimerize (GCSFR, GPI30, LPTR) or heterodimerize (GPI30 with LIFR or OSMR, IL12RB1 with IL12RB2) upon binding the cognate cytokine. In addition, a prosite consensus pattern is characteristic of this receptor family, which is:

N-x(4)-S-x(28,35)-[LVIM]-x-W-x(0,3)-P-x(5,9)-[YF]-x(1,2)-[VILM]-x-W (SEQ ID NO:1)

GCSF stimulates proliferation, survival, and maturation of cells committed to the neutrophilic granulocyte lineage through binding to the specific GCSF receptor (GCSFR) (see Hartung T., et al., *Curr. Opin. Hematol.* 1998; 5:221-5). GCSFR mediated signaling activates the family of Signal Transducer and Activator of Transcription (STAT) proteins which translocate to the nucleus and regulate transcription (Darnell J E Jr., *Science* 1997; 277:1630-5). GCSF is typically used for the treatment of different kinds of neutropenia in humans. It is one of the few growth factors approved for clinical use. In particular, it is used to reduce chemotherapy (CT)-induced cytopenia (Viens et al., *J. of Clin. Oncology*, Vol. 20, No. 1, 2002:24-36). GCSF has also been implicated for therapeutic use in infectious diseases as potential adjunctive agent (Hübel et al., *J. of Infectious Diseases*, Vol. 185: 1490-501, 2002). GCSF has reportedly been crystallized to some extent (EP 344 796), and the overall structure of GCSF has been surmised, but only on a gross level (Bazan, *Immunology Today* 11: 350-354 (1990); Parry et al. *J. Molecular Recognition* 8: 107-110 (1988)).

In recent years a number of growth factors such as bFGF and pharmaceutically promising substances such as thrombocyte adhesion blockers like anti-GP IIb/IIa and Abcizimab have been tested for neuroprotective efficacy in clinical studies. Unfortunately, none of these prevailed to provide neuroprotective efficacy. In particular, NMDA antagonists, free radical scavengers and glutamate antagonists failed or demonstrated severe side-effects. The list of substances such as anti-ICAM or inhibitors of the glutamate-mediated NO-synthetase that have failed growing (De Keyser, et al. (1999), *Trends Neurosci*, 22, 535-40).

Most studies on cerebral ischemia and testing of pharmacological substances in vivo have only been concerned with the immediate effects of the drug or paradigm under investigation (i.e. infarct size 24 h after induction of the stroke). However, a more valid parameter of true efficacy of a particular substance is the long-term effect on functional recovery, which is also reflected in human stroke studies, where clinical scales (e.g., Scandinavian stroke scale, NIH scale, Barthel index) also reflect the ability to perform daily life activities. Recovery in the first few days after focal lesions may be due to resolution of edema or reperfusion of the ischemic penumbra. Much of the functional recovery after the acute phase is likely due to brain plasticity, with adjacent cortical areas of the brain taking over functions previously performed by the damaged regions (Chen R, Cohen L G, Hallett M. *Neuroscience* 2002; 111(4):761-73). The two main mechanisms proposed to explain reorganization are unmasking of previously present but functionally inactive connections and growth of new connections such as collateral sprouting (Chen R, Cohen L G, Hallett M. 2002 *Neuroscience* 2002; 111(4): 761-73). Short term plastic changes are mediated by removing inhibition to excitatory synapses, which is likely due to reduced GABAergic inhibition (Kaas J H. *Annu Rev Neurosci.* 1991; 14:137-67; Jones E G. *Cereb Cortex.* 1993 September-October; 3(5):361-72). Plasticity changes that occur over a longer time involve mechanisms in addition to the unmasking of latent synapses such as long-term potentiation (LTP), which requires NMDA receptor activation and increased intracellular calcium concentration (Hess and Donoghue, *J Neurophysiol.* 1994 71(6):2543-7). Long term changes also involve axonal regeneration and sprouting with alterations in synapse shape, number, size and type (Kaas J H. *Annu Rev Neurosci.* 1991; 14:137-67, 3).

Stroke is the third-leading cause of death, and the main cause of disability in the western world. It presents a large socioeconomic burden. The etiology can be either ischemic (in the majority of cases) or hemorraghic. The cause of ischemic stroke is often embolic, or thrombotic. So far, there is no effective treatment for the majority of stroke patients. The only clinically proven drugs so far are tissue plasminogen activator (TPA) and Aspirin. After massive cell death in the immediate infarct core due to lack of glucose and oxygen, the infarct area expands for days, owing to secondary mechanisms such as glutamate excitotoxicity, apoptotic mechanisms, and generation of free radicals.

Amyotrophic lateral sclerosis (ALS; Lou-Gehrig's disease; Charcot's disease) is a neurodegenerative disorder with an annual incidence of 0.4 to 1.76 per 100,000 population (Adams et al., Principles of Neurology, 6$^{th}$ ed., New York, pp 1090-1095). It is the most common form of motor neuron disease with typical manifestations of generalized fasciculations, progressive atrophy and weakness of the skeletal muscles, spasticity and pyramidal tract signs, dysarthria, dysphagia, and dyspnea. The pathology consists principally in loss of nerve cells in the anterior horn of the spinal cord and motor nuclei of the lower brainstem, but can also include the first order motor neurons in the cortex. Pathogenesis of this devastating disease is still largely unknown, although the role of superoxide-dismutase (SOD1) mutants in familial cases has been worked out quite well, which invokes an oxidative stress hypothesis. So far, more than 90 mutations in the SOD1 protein have been described, that can cause ALS (Cleveland and Rothstein (2001), *Nat Rev Neurosci*, 2, 806-19). Also, a role for neurofilaments in this disease was shown. Excitotoxicity, a mechanism evoked by an excess glutamate stimulation is also an important factor, exemplified by the beneficial role of Riluzole in human patients. Most convincingly shown in the SOD1 mutants, activation of caspases and apoptosis seems to be the common final pathway in ALS (Ishigaki, et al. (2002), *J Neurochem*, 82, 576-84, Li, et al. (2000), *Science*, 288, 335-9). Therefore, it seems that ALS also falls into the same general pathogenetic pattern that is also operative in other neurodegenerative diseases and stroke, e.g. glutamate involvement, oxidative stress, and programmed cell death.

Parkinson's disease is the most frequent movement disorder, with approximately 1 million patients in North America; about 1 percent of the population over the age of 65 years is affected. The core symptoms of the disease are rigor, tremor and akinesia (Adams et al., Principles of Neurology, 6$^{th}$ ed., New York, pp 1090-1095). The etiology of Parkinson's disease is not known. Nevertheless, a significant body of biochemical data from human brain autopsy studies and from animal models points to an ongoing process of oxidative stress in the substantia nigra, which could initiate dopaminergic neurodegeneration. Oxidative stress, as induced by the neurotoxins 6-hydroxydopamine and MPTP (N-methyl-4-phenyl-1,2,3,6-tetrahydropyridine), has been used in animal models to investigate the process of neurodegeneration. Although a symptomatic therapy exists (e.g. L-DOPA plus a decarboxylase inhibitor; bromocriptine, pergolide as dopamin agonists; and anticholinergic agents such as trihexyphenidyl (artane)), there is a clear need for a causative therapy, e.g. a neuroprotective therapy, that really halts the disease progress. These animal models have been used to test the efficacy of radical scavengers, iron chelators, dopamine agonists, nitric oxide synthase inhibitors and certain calcium channel antagonists. Apoptotic mechanisms are clearly operative in the animal models as well as in the patient (Mochizuki, et al. (2001), *Proc. Natl. Acad. Sci. USA,* 98, 10918-23, Xu et al. (2002), *Nat. Med.,* 8, 600-6, Viswanath, et al. (2001), *J. Neurosci.,* 21, 9519-28, Hartmann, et al. (2002), *Neurology,* 58, 308-10). This pathophysiology with involvement of oxidative stress and apoptosis also places Parkinson's disease amongst the other neurodegenerative disorders and stroke.

Cerebral ischemia may result from a variety of causes that impair cerebral blood flow (CBF) and lead to deprivation of both oxygen and glucose. Traumatic brain injury (TBI), on the other hand, involves a primary mechanical impact that usually causes skull fracture and abruptly disrupts the brain parenchyma with shearing and tearing of blood vessels and brain tissue. This, in turn, triggers a cascade of events characterized by activation of molecular and cellular responses that lead to secondary injury. The evolution of such secondary damage is an active process in which many biochemical pathways are involved (Leker and Shohami (2002), *Brain Res. Rev.,* 39, 55-73). Many similarities between the harmful pathways that lead to secondary cellular death in the penumbral ischemic zone and in the area exposed to secondary post-traumatic injury have been identified (e.g. excitotoxity by excess glutamate release, nitric oxide, reactive oxygen species, inflammation, and apoptosis (Leker and Shohami (2002), *Brain Res. Rev.,* 39, 55-73)). In addition, early ischemic episodes are reported to occur after traumatic brain injury, adding a component of ischemia to the primary mechanical damage.

Cardiovascular disease is the major cause of death in western industrialized nations. In the United States, there are approximately 1 million deaths each year with nearly 50% of them being sudden and occurring outside the hospital (Zheng, et al. (2001), *Circulation,* 104, 2158-63). Cardio-pulmonary resuscitation (CPR) is attempted in 40-90 of 100,000 inhabitants annually, and restoration of spontaneous circulation (ROSC) is achieved in 25-50% of these patients. However, the hospital discharge rate following successful ROSC is only 2-10% (Bottiger, et al. (1999), *Heart,* 82, 674-9). Therefore, the vast majority of the cardiac arrest victims annually in the United States is not treated successfully. The major reason for the low survival rates after successful CPR, i.e., for postarrest in-hospital mortality, is persistent brain damage. Brain damage following cardiocirculatory arrest is related both to the short period of tolerance to hypoxic stress and to specific reperfusion disorders (Safar (1986), *Circulation,* 74, IV138-53, Hossmann (1993), *Resuscitation,* 26, 225-35). Initially, a higher number of patients can be stabilized hemodynamically after cardiocirculatory arrest; many of them, however, die due to central nervous system injury. The personal, social, and economic consequences of brain damage following cardiac arrest are devastating. One of the most important issues in cardiac arrest and resuscitation ("whole body ischemia and reperfusion") research, therefore, is cerebral resuscitation and postarrest cerebral damage (Safar (1986), *Circulation,* 74, IV138-53, Safar, et al. (2002), *Crit Care Med,* 30, p. 140-4). Presently, it is not possible to decrease the primary damage to neurons that is caused by hypoxia during cardiac arrest by any post-arrest therapeutic measures. Major pathophysiological issues include hypoxia and subsequent necrosis, reperfusion injury with free radical formation and cellular calcium influx, release of excitatory amino acids, cerebral microcirculatory reperfusion disorders, and programmed neuronal death or apoptosis (Safar (1986), *Circulation,* 74, IV138-53, Safar et al. (2002), *Crit Care Med,* 30, 140-4).

Several clinical trials have attempted to improve neurological outcome after cardiac arrest without success. The therapeutic use of barbiturates (to enhance neuroprotection) or the use of calcium channel blockers (to reduce ischemia reperfusion damage) was tested (Group (1986), *Am. J. Emerg. Med.,* 4, 72-86, Group (1986), *N. Engl. J. Med.,* 314, 397-403, Group (1991), *Control Clin. Trials,* 12, 525-45, Group (1991), *N. Engl. J. Med.,* 324, 1225-31). To date no specific post-arrest treatment options are available to improve neurological outcome following cardiocirculatory arrest in the clinical setting (with the possible exception of mild hypothermia and thrombolysis where the results of large, randomized, and controlled clinical trials are eagerly awaited (Safar et al (2002), *Crit. Care Med.,* 30, 140-4)). Therefore, an innovative therapy to improve neurological outcome after cardiac arrest is crucial.

Multiple sclerosis is the prototype inflammatory autoimmune disorder of the central nervous system and, with a lifetime risk of one in 400, potentially the most common cause of neurological disability in young adults. Worldwide, there are about 2-5 million patients suffering from this disease (Compston and Coles (2002), *Lancet,* 359, 1221-31). As with all complex traits, the disorder results from interplay between as yet unidentified environmental factors and susceptibility genes. Together, these factors trigger a cascade of events, involving engagement of the immune system, acute inflammatory injury of axons and glia, recovery of function and structural repair, post-inflammatory gliosis, and neurodegeneration. The sequential involvement of these processes underlies the clinical course characterized by episodes with recovery, episodes leaving persistent deficits, and secondary progression. The aim of treatment is to reduce the frequency, and limit the lasting effects of relapses, relieve symptoms, prevent disability arising from disease progression, and promote tissue repair.

Depression is a common mental disorder characterized by sadness, loss of interest in activities and by decreased energy. Depression is differentiated from normal mood changes by the extent of its severity, the symptoms and the duration of the disorder. Suicide remains one of the common and often unavoidable outcomes of depression. If depressive episodes alternate with exaggerated elation or irritability they are known as bipolar disorder. Depressive disorders and schizophrenia are responsible for 60% of all suicides. The causes of depression can vary. Psychosocial factors, such as adverse living conditions, can influence the onset and persistence of depressive episodes. Genetic and biological factors can also play a part.

An estimated 121 million people currently suffer from depression. Depression is the leading cause of disability as measured by YLDs (Years Lived with Disability) and the 4th leading contributor to the global burden of disease (DALYs=Disability Adjusted Life Years; The sum of years of potential life lost due to premature mortality and the years of productive life lost due to disability) in 2000. An estimated 5.8% of men and 9.5% of women will experience a depressive episode in any given year. By the year 2020, depression is projected to reach second place of the ranking of DALYs calculated for all ages, both sexes. In the developed regions, depression will then be the highest ranking cause of burden of disease.

Today the first-line treatment for most people with depression consists of antidepressant medication, psychotherapy or a combination of both. Anti-depressants are effective across the full range of severity of major depressive episodes. Currently, effective antidepressive therapy is closely related to modulation or fine-tuning of serotonergic neurotransmission. Drugs that increase the levels of serotonin in the brain are the most potent known antidepressants (such as fluoxetine, Prozac® or Fluctin®). Treatments, which have antidepressive effects in patients, too, are e.g. pharmacological antidepressants such as lithium, electro-convulsive therapy and physical exercise. Other interventions include setting up supportive network systems for vulnerable individuals, families and groups. The evidence regarding prevention of depression is less conclusive, only a few isolated studies show that interventions proposed for the prevention of depression are effective. It is important to have in mind that the existing drugs are aimed at alleviating symptoms of the disease, but not primarily to address basic pathophysiological mechanisms causative to this disease. Therefore, a new treatment is needed that specifically addresses the newly discovered causal aspects in depression Schizophrenia is one of the most common mental illnesses. About 1 of every 100 people (1% of the population) is affected by schizophrenia. This disorder is found throughout the world and in all races and cultures. Schizophrenia affects men and women in equal numbers, although on average, men appear to develop schizophrenia earlier than women. Generally, men show the first signs of schizophrenia in their mid 20s and women show the first signs in their late 20s. Schizophrenia has a tremendous cost to society, estimated at $32.5 billion per year in the US. Schizophrenia is characterized by several of the following symptoms: delusions, hallucinations, disorganized thinking and speech, negative symptoms (social withdrawal, absence of emotion and expression, reduced energy, motivation and activity), catatonia. The main therapy for schizophrenia is based on neuropleptics, such as chlorpromazine, haloperidol, olanzapine, clozapine, thioridazine, and others. However, neuroleptic treatment often does not reduce all of the symptoms of schizophrenia. Moreover, antipsychotic treatment can have severe side effects, such as tardive dyskinesias. The etiology of schizophrenia is not clear, although there seems to be a strong genetic influence. Recently, it has become clear that schizophrenia has at least some aspects of a neurodegenerative disease. In particular, MR studies have revealed rapid cortical grey matter loss in schizophrenic patients (Thompson, et al. (2001), *Proc Natl Acad Sci USA,* 98, 11650-5; Cannon, et al. (2002), *Proc Natl Acad Sci USA,* 99, 3228-33). Therefore, treatment of schizophrenics with neuroprotective medication such as GCSF or GMCSF or other hematopoetic factors is warranted.

In humans there is a need for ways to increase cognitive capacities, and boost intelligence. "Intelligence" in modern understanding is not limited to purely logical or semantic capabilities. For example, the theory of multiple intelligences by Howard Gardner evaluates intelligence from evolutionary and anthropological perspectives and yields a broader view that includes athletic, musical, artistic, and empathetic capacities as well as the linguistic/logical abilities that are more commonly associated with intelligence and measured by IQ tests. This broader sense of intelligence also extends into the area of creativity. In addition, there is a non-pathological condition known in the human as ARML (age-related memory loss) or MCI (mild cognitive impairment) or ARCD (age-related cognitive decline) that usually commences at about age 40, and is different from early signs of Alzheimer's disease.

There is a physiological loss of nerve cells throughout adulthood, estimated to as many as 100,000 neurons a day. Throughout adulthood, there is a gradual reduction in the weight and volume of the brain. This decline is about 2% per decade. Contrary to previously held beliefs, the decline does not accelerate after the age of 50, but continues at about the same pace from early adulthood on. The accumulative effects of this are generally not noticed until older age.

While the brain does shrink in size, it does not do so uniformly. Certain structures are more prone to shrinkage. For example, the hippocampus and the frontal lobes, two structures involved in memory, often become smaller. This is partly due to a loss of neurons and partly due to the atrophy of some neurons. Many other brain structures suffer no loss in size. The slowing of mental processing may be caused by the deterioration of neurons, whether they are lost, shrink, or lose connections. This depletion of fully functioning neurons makes it necessary to recruit additional networks of neurons to manage mental tasks that would otherwise be simple or automatic. Thus, the process is slowed down.

A portion of the frontal lobe, called the prefrontal cortex, is involved in monitoring and controlling thoughts and actions. The atrophy that occurs in this brain region may account for the word finding difficulties many older adults experience. It may also account for forgetting where the car keys were put or general absentmindedness. The shrinkage of both the frontal lobe and the hippocampus are thought to be responsible for memory difficulties. Therefore, there also remains a need for improving or enhancing the cognitive ability of an individual.

In the past, neuroprotective therapies were mostly explored in neurodegenerative disorders like Parkinson's and Alzheimer's disease, and in ischaemic stroke. More recently, however, neuroprotection has been proclaimed an important goal for multiple sclerosis (MS) therapy. The basis for widening the scope of neuroprotection is evidence that neuronal and axonal injury are key features of MS lesions. Axon loss most likely determines the persistent neurological deficit in progressive MS. Recent studies pointed out that axon damage occurs early in the disease and during lesion development. Two different phases of axon degeneration were characterized, the first occurring during active myelin breakdown and the second in chronic demyelinated plaques in which the naked axon seems more susceptible to further damage. In contrast with degenerative and ischaemic central nervous system injury, however, neurodegeneration in MS appears to be caused by an inflammatory, presumably autoimmune, process. The challenge for neuroprotection in MS is therefore greater than in degenerative and ischaemic disorders, because MS requires the combination of neuroprotective therapy and effective immunomodulation. The exact mechanisms and effector molecules of axonal degeneration, however, are not yet defined, and an axon-protective therapy has not yet been established. (Bruck and Stadelmann (2003), Neurol Sci, 24 Suppl 5, S265-7) (Hohlfeld (2003), Int MS J, 10, 103-5)

One group of Neurodegenerative disorders is characterized by an expansion of trinucleotides. Those neurodegenerative trinucleotide repeat disorders are chronic and progressive characterised by selective and symmetric loss of neurons in motor, sensory, or cognitive systems. Symptoms are often ataxia, dementia or motor dysfunction. The best known trinucleotide repeat disorder is Huntingtons disease, others are Spinal and bulbar muscular atrophy (Kennedy's disease), Autosomal dominant spinocerebellar ataxia's: Type 1 SCA1, Type 2 SCA2, Type 3 (Machado-Joseph disease) SCA3/MJD, Type6 SCA6, Type 7 SCA7, Type 8 SCA8, Friedreich's Ataxia and Dentatorubral pallidoluysian atrophy DRPLA/Haw-River syndrome. (Hardy and Gwinn-Hardy (1998), Science, 282, 1075-9) (Martin (1999), N Engl J Med, 340, 1970-80) (Schols, et al. (1997), Ann Neurol, 42, 924-32)

Huntington's disease (HD) is an autosomal dominant, inherited, neuropsychiatric disease which gives rise to progressive motor, cognitive and behavioural symptoms. The course of Huntington's is characterized by jerking uncontrollable movement of the limbs, trunk, and face (chorea); progressive loss of mental abilities; and the development of psychiatric problems. Huntington's disease progresses without remission over 10 to 25 years and usually appears in middle age (30-50 years). Juvenile HD (also called Westphal variant or akinetic-rigid HD) develops before the age of 20, progresses rapidly, and produces muscle rigidity in which the patient moves little, if at all (akinesia). It is estimated that one in every 10,000 persons—nearly 30,000 in the United States—have Huntington's disease. Juvenile Huntington's occurs in approximately 16% of all cases. Its core pathology involves degeneration of the basal ganglia, in particular, the caudate and putamen, and is caused by an unstable expansion of the trinucleotide CAG, coding for glutamine, in a single autosomal gene IT-15 on chromosome 4, coding for a mutated form of the protein, huntingtin. How the mutation of gene IT-15 alters the function of the protein is not well understood.

Treatment of Huntington's disease focuses on reducing symptoms, preventing complications, and providing support and assistance to the patient. There are several substances available today for the treatment of chorea. Other neurological symptoms, such as dystonia, can be treated, but treatment is associated with a high risk of adverse events. Psychiatric symptoms, on the other hand, are often amenable to treatment and relief of these symptoms may provide significant improvement in quality of life. (Bonelli and Hofmann (2004), Expert Opin Pharmacother, 5, 767-76). Most drugs used to treat the symptoms of HD have side effects such as fatigue, restlessness, or hyperexcitability. Cystamine (=Decarboxycystine) alleviates tremors and prolongs life in mice with the gene mutation for Huntington's disease (HD). The drug appears to work by increasing the activity of proteins that protect nerve cells, or neurons, from degeneration. The study suggests that a similar treatment may one day be useful in humans with HD and related disorders. (Karpuj, et al. (2002), Nat Med, 8, 143-9)

Glaucoma is the number one cause of preventable blindness in the United States. Glaucoma is a group of conditions where the nerve of sight (the optic nerve) is damaged, usually as a result of increased pressure within the eye, but glaucoma can also occur with normal or even below-normal eye pressure. The lamina cribrosa (LC) region of the optic nerve head (ONH) is a major site of injury in glaucomatous optic neuropathy. It is a patchy loss of vision, which is permanent, but progress of the condition can be minimised if it is detected early enough and treatment is begun. However, if left untreated, glaucoma can eventually lead to blindness. Glaucoma is one of the most common eye disorders amongst older people. Worldwide, it is estimated that about 66.8 million people have visual impairment from glaucoma, with 6.7 million suffering from blindness.

There are a variety of different types of glaucoma. The most common forms are: Primary Open-Angle Glaucoma; Normal Tension Glaucoma; Angle-Closure Glaucoma; Acute Glaucoma; Pigmentary Glaucoma; Exfoliation Syndrome or Trauma-Related Glaucoma.

Glaucoma can be treated with eyedrops, pills, laser surgery, eye operations, or a combination of methods. The whole purpose of treatment is to prevent further loss of vision. This is imperative as loss of vision due to glaucoma is irreversible. Keeping the IOP under control is the key to preventing loss of vision from glaucoma.

Peripheral neuropathy is a pain initiated or caused by a primary lesion or dysfunction of the nervous system. Many classification systems exist but typically it is divided into central (i.e. thalamic, post-stroke pain) and peripheral defferent pain (i.e. meralgia paresthetica). Neuropathies may affect just one nerve (mononeuropathy) or several nerves (polyneuropathy). They are allodynia, hyperalgesia, and dysesthesias. Common symptoms include burning, stabbing, electric shock, or deep aching sensations. The causes of neuralgia include diabetic neuropathy, trigeminal neuralgia, complex regional pain syndrome and post-herpetic neuralgia, uremia, AIDS, or nutritional deficiencies. Other causes include mechanical pressure such as compression or entrapment, direct trauma, penetrating injuries, contusions, fracture or dislocated bones; pressure involving the superficial nerves (ulna, radial, or peroneal) which can result from prolonged use of crutches or staying in one position for too long, or from a tumor; intraneural hemorrhage; exposure to cold or radiation or, rarely, certain medicines or toxic substances; and vascular or collagen disorders such as atherosclerosis, systemic lupus erythematosus, scleroderma, sarcoidosis, rheumatoid arthritis, and polyarteritis nodosa. A common example of entrapment neuropathy is carpal tunnel syndrome, which has become more common because of the increasing use of computers. Although the causes of peripheral neuropathy are diverse, they produce common symptoms including weakness, numbness, paresthesia (abnormal sensations such as burning, tickling, pricking or tingling) and pain in the arms, hands, legs and/or feet. A large number of cases are of unknown cause.

Treating the underlying condition may relieve some cases of peripheral neuropathy. In other cases, treatment may focus on managing pain. Therapy for peripheral neuropathy differs depending on the cause. For example, therapy for peripheral neuropathy caused by diabetes involves control of the diabetes. In cases where a tumor or ruptured disc is the cause, therapy may involve surgery to remove the tumor or to repair the ruptured disc. In entrapment or compression neuropathy treatment may consist of splinting or surgical decompression of the ulnar or median nerves. Peroneal and radial compression neuropathies may require avoidance of pressure. Physical therapy and/or splints may be useful in preventing contractures. Peripheral nerves have a remarkable ability to regenerate themselves, and new treatments using nerve growth factors or gene therapy may offer even better chances for recovery in the future.

The lysosomal storage diseases are a group of about 40 different diseases, each characterised by a specific lysosomal enzyme deficiency in a variety of tissues. They occur in total in about 1 in 5,000 live births and display considerable clinical and biochemical heterogeneity. The majority are inherited as autosomal recessive conditions although two (Hunter disease and Fabry disease) are X-linked. They include Tay-Sachs disease, a gangliosidosis, and Gaucher's and Niemann-Pick's diseases, which are lipid storage disorders. Most of these diseases affect the brain and are fatal. (Brooks, et al. (2002), Proc Natl Acad Sci USA, 99, 6216-21)

There has been limited success in only treating the symptoms of these diseases. One way is to replace the enzyme to put a normal gene into the body that can make the enzyme by bone marrow or stem cell transplant or gene therapy. Bone marrow transplantation (BMT) has been successful in several LSDs and allowed long term survival with less severe symptoms. Enzyme replacement therapy (ERT) has been available for patients with Gaucher disease for over 10 years and has provided enormous benefit.

Spinal cord injury (SCI) occurs when a traumatic event results in damage to cells within the spinal cord or severs the nerve tracts that relay signals up and down the spinal cord. The most common types of SCI include contusion (bruising of the spinal cord) and compression (caused by pressure on the spinal cord). Other types of injuries include lacerations (severing or tearing of some nerve fibers, such as damage caused by a gun shot wound), and central cord syndrome (specific damage to the corticospinal tracts of the cervical region of the spinal cord). Severe SCI often causes paralysis (loss of control over voluntary movement and muscles of the body) and loss of sensation and reflex function below the point of injury, including autonomic activity such as breathing and other activities such as bowel and bladder control. Other symptoms such as pain or sensitivity to stimuli, muscle spasms, and sexual dysfunction may develop over time. SCI patients are also prone to develop secondary medical problems, such as bladder infections, lung infections, and bed sores. While recent advances in emergency care and rehabilitation allow many SCI patients to survive, methods for reducing the extent of injury and for restoring function are still limited. Immediate treatment for acute SCI includes techniques to relieve cord compression, prompt (within 8 hours of the injury) drug therapy with corticosteroids such as methylprednisolone to minimize cell damage, and stabilization of the vertebrae of the spine to prevent further injury. The types of disability associated with SCI vary greatly depending on the severity of the injury, the segment of the spinal cord at which the injury occurs, and which nerve fibers are damaged.

In view of the above, there is a need for treating neurological and/or psychiatric conditions, such as neurological diseases that relate to the enhancement of plasticity and functional recovery, or cell-death in the nervous system. In particular, there is a need for treating neurological diseases by providing neuroprotection to the neural cells involved or to induce neurogenesis to recover from neuronal loss.

SUMMARY OF THE INVENTION

Accordingly, one object of the present invention is to provide a method of treating a neurological or a psychiatric condition in a mammal by administering to the mammal a hematopoietic factor such as GCSF, GM-CSF, IL-3, IL-5, derivatives thereof, mimetics thereof and combinations thereof, or cells secreting these factors, to treat the condition.

Another object of the present invention is to provide a method of treating a neurological condition in a mammal, by conditioning a neural stem cell composition with a hematopoietic factor such as GCSF, GM-CSF, IL-3, IL-5, derivatives thereof, mimetics thereof and combinations thereof; and subsequently administering the neural stem cells to a mammal for the treatment of the condition.

Another object of the present invention is to provide a method of treating a neurological condition in a mammal by agonizing a GMCSF receptor, a GCSF receptor, IL-3 receptor, 11-5 receptor or combinations of these to treat the neurological condition. Another object of the present invention is to provide a method of enhancing the survival of a cell transplanted into a mammal, by introducing into the cell one or more polynucleotides which encode GCSF, GM-CSF, IL-3, IL-5, derivatives thereof, mimetics thereof and/or combinations thereof prior to transplanting the cell into the mammal, whereby the cell expresses the hematopoietic factor in an amount sufficient to enhance the survival of the cell relative to the cell survival prior to the introduction of the polynucleotides.

Another object of the present invention is to provide a method of enhancing the viability of a neural cell culture by providing GCSF, GMCSF, IL-3, IL-5, derivatives thereof, mimetics thereof and/or combinations thereof to enhance the viability of the neural cell culture relative to the culture prior to providing the hematopoietic factor. In such a method, the hematopoietic factors can be used to contact the cells of the culture or may be provided using polynucleotides that encode and express the hematopoietic factors.

An other object of the present invention is to provide a method to treat a neurological condition such as trinucleotide repeate disorder, a peripheral neuropathy, a lysosomal storage disease, a Parkinsonism or a Glaucoma with a hematopoietic factor such as GCSF, GMCSF, IL-3 or IL-5 combinations thereof or fusion proteins thereof.

BRIEF DESCRIPTION OF THE DRAWINGS

FIG. 4 Immunohistochemistry showing the distribution of GCSF-receptor in different brain regions in the mouse (paraffin sections, 2 μm). a-d: localization of GCSF-R in the hippocampus. Note that the antibody predominantly stains neurons in the CA3 area (a,b), with a sharp boundary between the CA3 and CA2 region (c, arrow). GCSF-R is distributed over the soma, as well as processes of neurons (b, arrow). Note the presence of the receptor in the hilus and the basal cell layers of the dentate gyrus (d, arrow). GCSF-Receptor was also detected in cortical areas: piriform cortex (e), and perirhinal cortex (f) as examples. In the cerebellum, Purkinje cells are labeled (g, arrow). Also, some of the large mitral cells in the olfactory bulb are GCSF-R positive (h, arrow). Strong staining is exhibited by the anterior columns in the spinal cord (i, j), and higher magnification identifies the large motoneurons as GCSF-R positive (k,l). Note that the neuronal processes are strongly labeled. In the midbrain, neurons in the substantia nigra show GCSF-R positivity (m). Especially, all neurons in the pars compacta (SNC) are labeled (arrow in m, and n). Also, in the pars reticulata, several neurons express GCSF-R(O). Apart from neurons, oligodendrocytes in white matter tracts are stained, for example, in the anterior commissure (*p, arrow). Surprisingly, the staining of the GCSF ligand (antibody sc13102, Santa Cruz) colocalizes with the expression of its receptor (antibody sc694, Santa Cruz) (FIGS. 4 *q-u*). This argues for a autocrine mechanism as a protective measure of neurons against noxious stimuli. In the hippocampus, the same subfield specificity is observed for the GCSF ligand (q: GCSFR, r: GCSF, arrows point to the border between subfields CA 2-3, ca3 and ca2 labels indicate the subfield). This specificity coincides with known differences in susceptibilities of these regions against ischemic damage, and argues again for a neuroprotective function of the GCSF system. Also, in the dentate gyrus, the same interesting pattern of expression in the hilus and the subgranular zone is observed (FIG. 4*s*, GCSF receptor; FIG. 4*t*, GCSF; arrows point to one neuron in the subgranular zone, labels: s: subgranular zone, h: hilus of the dentate gyrus), which underlines the importance of the GCSF system for neurogenesis, and nicely parallels the expression of receptor and ligand on neurospheres (see FIG. 13). Interestingly, GCSF is also expressed in the large motoneurons of the spinal cord (FIG. 4 *u*) where its receptor is also expressed (FIG. 4 *i-l*).

FIG. 6: STAT3 immunohistochemistry. Note, that numerous neuronal nuclei are positively stained in the cortical penumbra of GCSF treated rats (b, arrows) compared to the cortical periinfarct area of a placebo treated animal (a, arrows; left: infarct; right: penumbra; original magnification×200). FIG. 7: Cortical neurons in the unaffected contralateral side (CL) and ipsilateral in the vicinity of the infarction (IL) were quantified in GCSF treated animals and controls. There was a significant activation of STAT3 in neurons adjacent to the infarction in the GCSF-treated group as quantified by counting neurons with nuclear translocation of STAT3 (*$p<0.05$, t-test).

FIG. 8 shows the effect of GCSF treatment in the photothrombotic bengal rose model of cerebral ischemia. A, rotarod performance; B, neurological score, including beam balance; C, D: adhesive tape removal test, measured on the ipsi–(C), as well as contralateral side (D). Legend: ischemia: group of ischemic rats, non-treated; ischemia+GCSF: group of ischemic rats treated with GCSF; sham+GCSF: sham-operated animals, treated with GCSF; sham: sham-operated animals, untreated. L: tape-removal test on the left paw; R: tape-removal test on the right paw. Note that there is an effect on both sides in the tape-removal test (C,D), probably caused by a predominant motor deficit when the tape is on the ipsilateral side, and a predominant sensor deficit, when the tape is on the contralateral side.

FIG. 10 shows an alignment of the GCSF from different species using the ClustalW algorithm (SEQ ID NOS:28-33) (MEGALIGN™, Lasergene, Wis.).

FIG. 11 shows an alignment of GCSF receptors from mouse and human, and a fragment of rat using the ClustalW algorithm (SEQ ID NOS: 34-36) (MEGALIGN™, Lasergene, Wis.).

lane 2: PCR products from neuronal stem cells (nsc), visible is the rat GCSFR—specific band (279 bp); lane 3: negative control.

Figure 13:
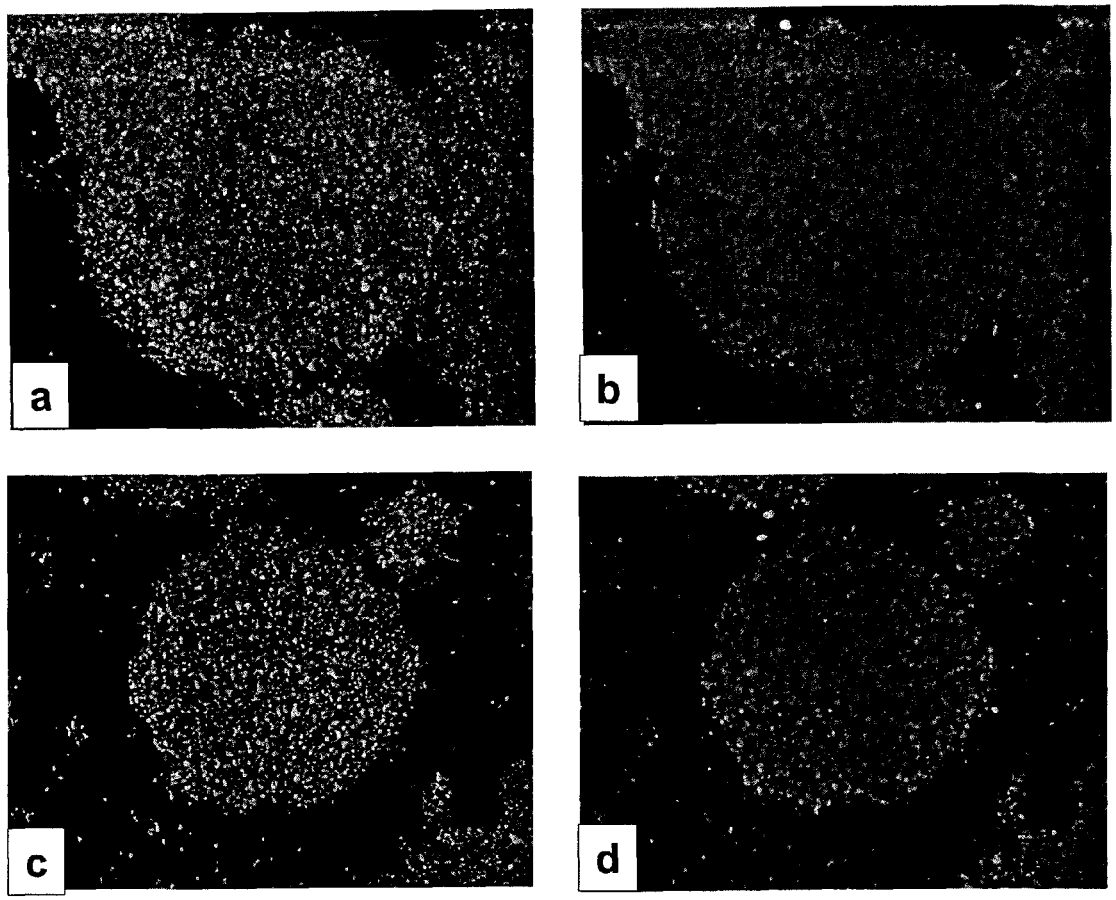

FIG. 13 demonstrates the presence of the GCSF-Receptor and GCSF on neural stem cells. A. DAPI stain of a neurosphere for visualization of all cells, B, the same neurosphere stained with an antibody directed against the GCSF receptor. C,D neurosphere stained with DAPI (C) and an antibody for GCSF (D).

FIG. 14 demonstrates the rapid uptake of biotinylated GCSF after intraperitoneal injection into mice. A, Western blot of serum from mice sacrificed at 1, 2, 4, 6, 20, 28 h post injection of 7.5 ug GCSF/mouse. B. ELISA of Serum GCSF after i.p. injection. There is rapid uptake of GCSF from the peritoneum with serum peak levels at 2 hrs., demonstrating applicability of this administration route.

FIG. 15 shows the identification of the GMCSF-Receptor as an upregulated mRNA after induction of photothrombosis (bengal rose model) on the ipsilateral and contralateral side to the ischemia. A shows a schematic coronal section of a mouse brain and areas of interest are marked in grey; B shows a section of an RMDD-Gel, on which the transcript of the GMCSF-Receptor was identified as being regulated. The lanes represent RT-PCR-products on RNA samples of mouse brain. Samples were taken from cortex penumbra at different timepoints after the stroke (3 and 4 in A, respectively).

Figure 16:
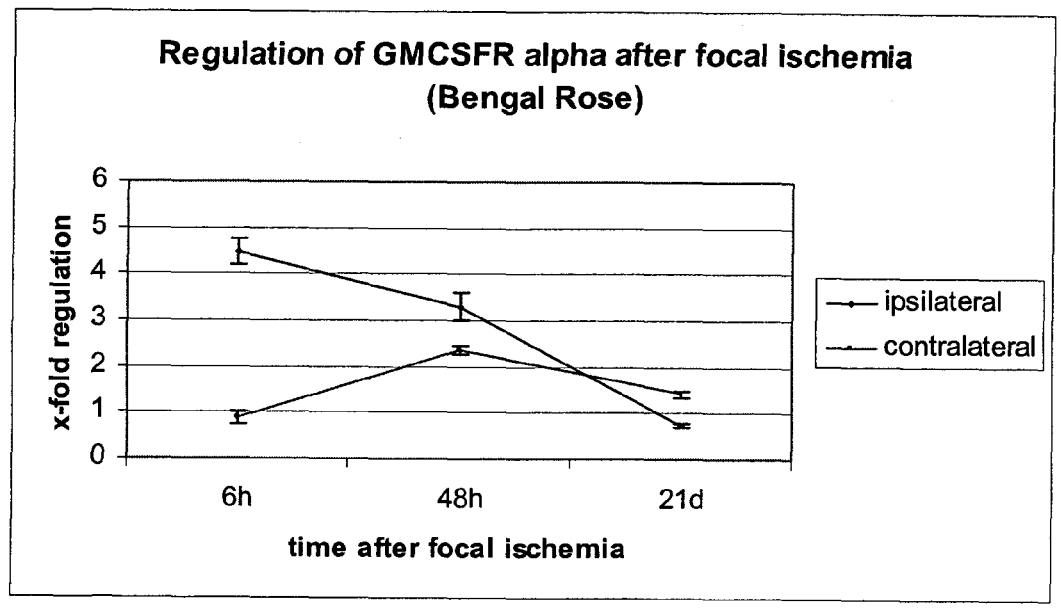

FIG. 16 shows the verification of the upregulation of the GMCSF-Receptor in the bengal-rose model at 48 h by quantitative RT-PCR by applying the LightCycler-System. Samples were taken at 6 h, 48 h and 21d after induction of photothrombosis and induction levels were compared to sham-operated animals. On the ipsilateral hemisphere the upregulation of the GMCSF receptor is maximal early after the cortical ischemia and drops steadily until day 21. On the corresponding contralateral cortex-sample, the upregulation is seen most clearly at 2 days after the infarct, and is still moderately upregulated at day 21. This regulation pattern on the contralateral side is reminiscent of the GCSF receptor (see above).

FIG. 17 shows an alignment of GMCSF receptors from human, mouse, and the sequence from rat identified as an upregulated transcript (SEQ ID NOS:22, 23 and 24) (ClustalW algorithm, MEGALIGN™, Lasergene, Wis.). It is concluded from this homology that the identified sequence is the rat GMCSF receptor.

FIG. 18 shows an alignment of GMCSF from human, mouse, and rat (SEQ ID NOS: 25, 26, and 27) (ClustalW algorithm, MEGALIGN™, Lasergene, Wis.).

FIG. 19 Immunohistochemistry showing the distribution of GMCSF-receptor alpha (a-d) and GMCSF (e-g) in different brain regions in the mouse (paraffin sections, 2 μm). a: In the cerebellum, Purkinje cells are labeled (arrow). b-d: localization of GMCSF-R alpha in the hippocampus. Note the presence of the receptor in the hilus of the dentate gyrus (b, arrow). The antibody predominantly stains neurons in the CA3 area (c) with a sharp boundary between the CA3 and CA2 region (c, arrow). GMCSF-R alpha is distributed over the soma (CA3), as well as processes of neurons (CA2). GMCSF-receptor was also detected in the entorhinal cortex (d). GMCSF shows similar distribution in comparison with GMCSF-receptor alpha. Note that the GMCSF antibody stains as well Purkinje cells (e, arrow), neurons in the CA3 area (f) with sharp boundary between CA3 and CA2 region (f, arrow), and neurons in the entorhinal cortex (g). FIGS. 19 h-m: Shown here is the surprising colocalization of the GMCSF receptor and its ligand in neurons. h, localization of the GMCSF receptor (antibody sc690, Santa Cruz) in neurons in hipocampal subfield CA3, arrow points to the sharp expression boundary to the adjacent CA2 region. i, the GMCSF ligand (antibody sc13101) shows the same subfield-specific expression, the arrow points to one neuron in the CA3 region. j, expression of the GMCSF receptor in the hilus and subgranular zone of the dentate gyrus. An arrow points to a neuron in the subgranular zone. k, expression of the GMCSF ligand in that region. Here, the ligand shows a slightly different expression compared to its receptor. There is clear expression in the CA3 region (arrow), but less in the dentate gyrus region. l,m: expression of the GMCSF receptor (l) and ligand (m) in the large motoneurons of the spinal cord. This surprising expression is a clear indication for the therapeutic applicability of the GMCSF system for motoneuron diseases, especially amyotrophic lateral sclerosis (ALS).

Figure 20:
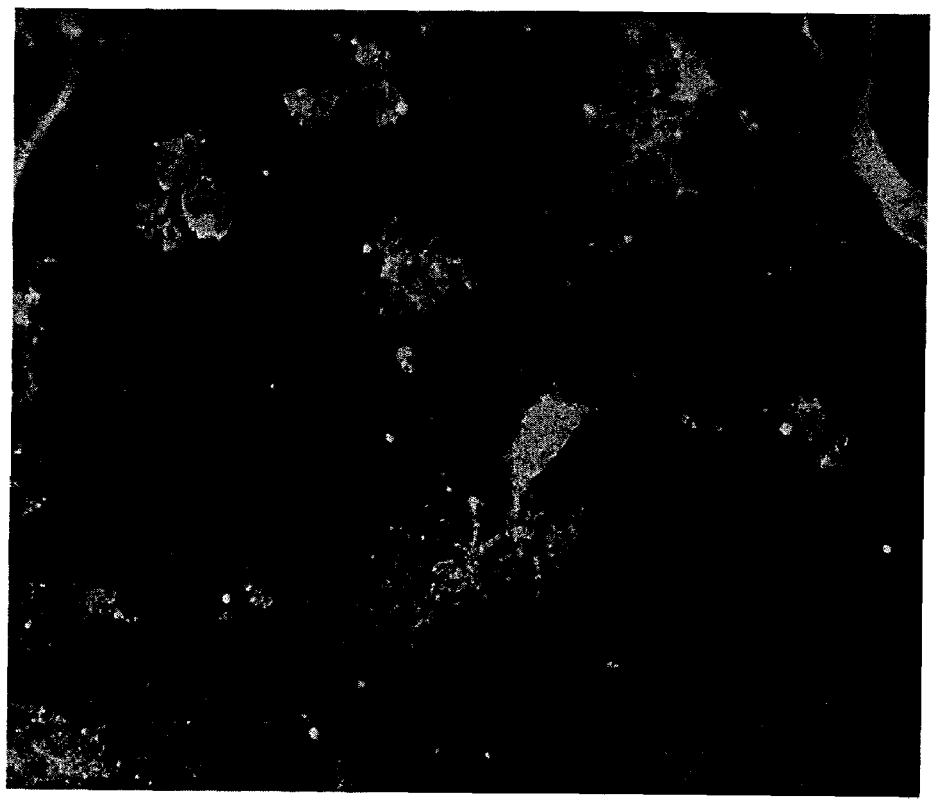

FIG. 20 shows a staining for the GMCSFR alpha on cortical neuronal cultures. The receptor is both present on the somata and processes of the neurons (verified by double labeling with an antibody directed against the nuclear epitope NeuN, and an antibody for synaptophysin, which is not included in the Figure). Preincubation of the antibody with the respective peptide, or omission of the primary antibody did not result in specific staining (not shown).

Figure 21:
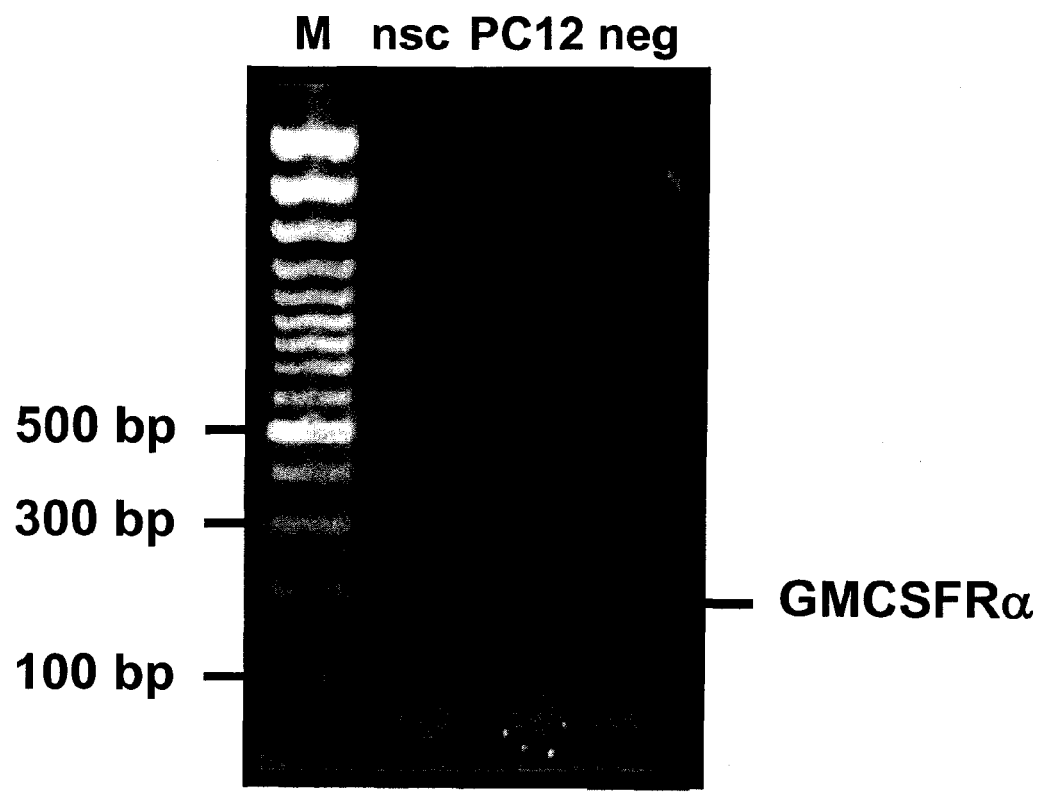

FIG. 21 demonstrates the presence of the GMCSF-receptor alpha on adult neuronal stem cells (nsc) and on PC12 cells (PC12) by RT-PCR. Shown is an agarose gel. Lane 1: size marker (M); lane 2: PCR on neuronal stem cells (nsc); lane 3: PCR on PC12 cells (PC12); lane 4: negative control (neg). The rat GM-CSFR alpha-specific band (176 bp) is visible in lanes 2 and 3.

FIG. 22 demonstrates the presence of the GMCSF-receptor alpha on adult neuronal stem cells (nsc) by immunocytochemistry. Shown is one neurosphere that is stained with DAPI (A, stains all cell nuclei), and an antibody specific for the GMCSF receptor (B) (magnification 10×).

Figure 23:
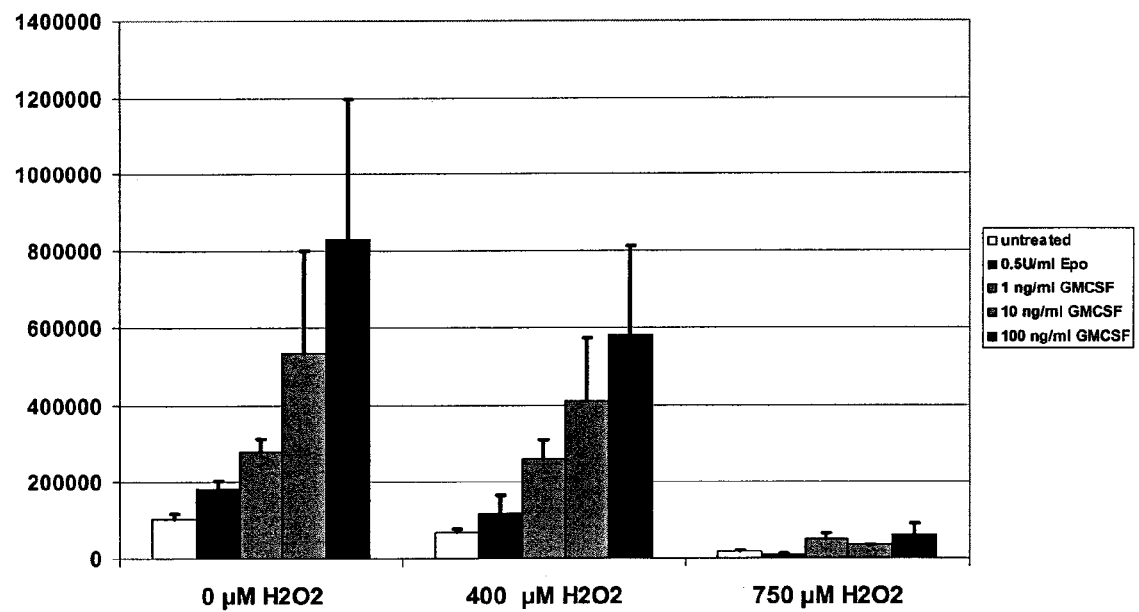

FIG. 23 demonstrates effective neuroprotection by GMCSF in vitro. Cell survival assay in NGF-treated PC12 cells under increasing oxidative stress by $H_2O_2$ (O uM, 400 uM, 750 uM). GMCSF treatment produces dramatic increases in cell survival. In comparison, cell survival after treatment of the cells with Erythropoetin (EPO; 0.5 U/ml), a known neuroprotective substance, is given. Y-axis: Rel. cell survival (light units of luciferase activity).

Figure 24:
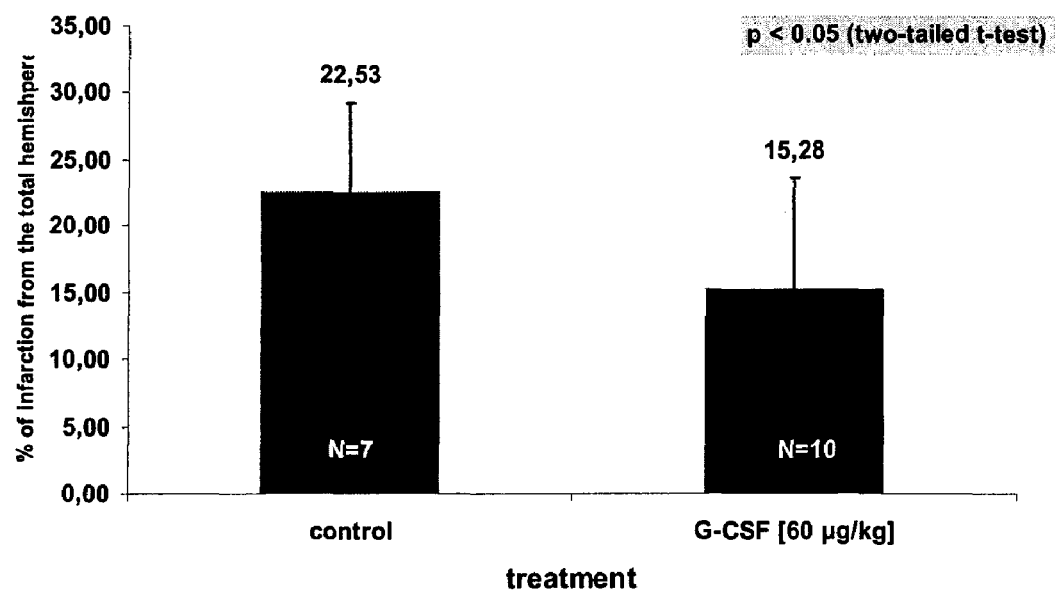

FIG. 24 shows the effect of intravenously applied G-CSF on infarct volume in the rat MCAO model when applied 120 min after onset of ischemia compared to no C-CSF administration (control).

Figure 25:
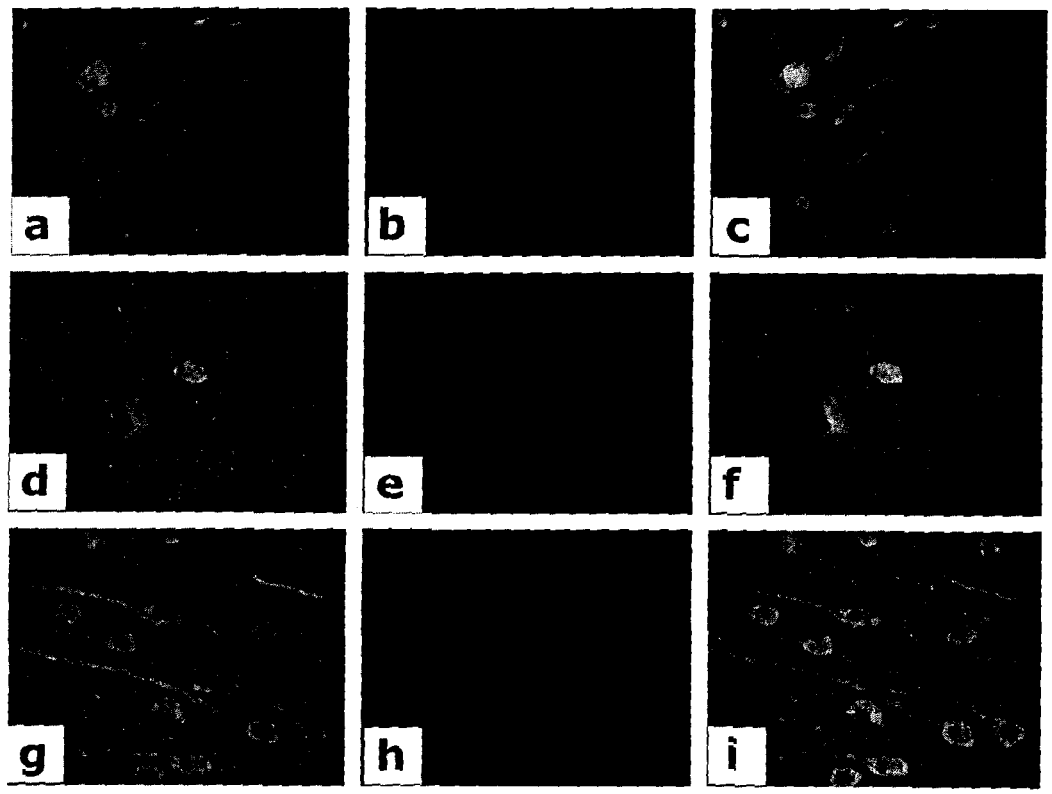

FIG. 25 shows TTC-staining in the hippocampus and cortex for the G-CSG receptor and G-CSF. The data shows that the GCSF receptor (a, d, g) shows a co-localization with its ligand (b, e, h) both in the hippocampus (a-c dentate gyrus, d-f hilus) and the cortex (g-i).

Figure 26:
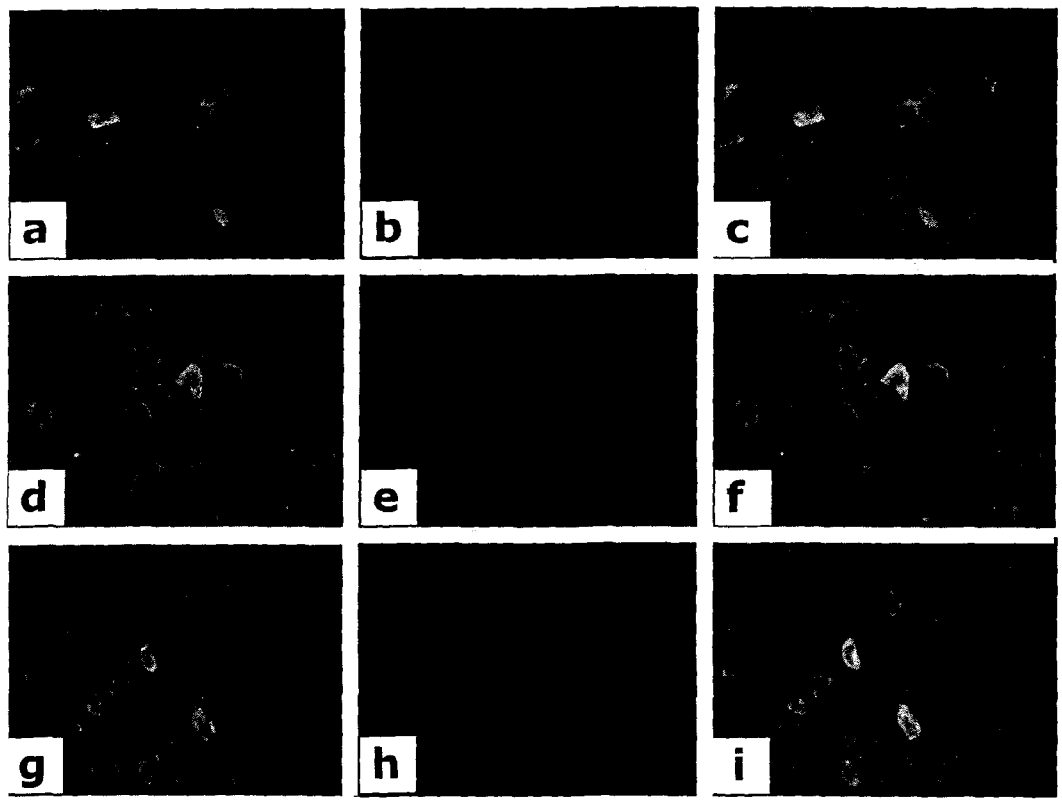

FIG. 26 shows coexpression of both the G-CSF and GM-CSF receptors on neurons in the dentate gyrus (a-c) and the hilus (d-f) of the hippocampus as well as in the cortex (g-i). The GCSF receptor (a, d, g) and the GMCSF receptor (b, e, h) are expressed on the same neurons in both the hippocampus and the cortex (c, f, i).

FIG. 27 shows that G-CSF acts anti-apoptotically by activiating stat3 in neurons.

FIG. 28 (parts I and II) A shows a very strong upregulation of GCSF 2 h and 6 h after focal ischemia on the ipsi- and contralateral side, whereas the receptor is moderately regulated (B) after 6 h. An induced expression of GCSF is not specific to the MCAO model, but could also be seen albeit to a lesser degree in global ischemia (C).

Figure 29:
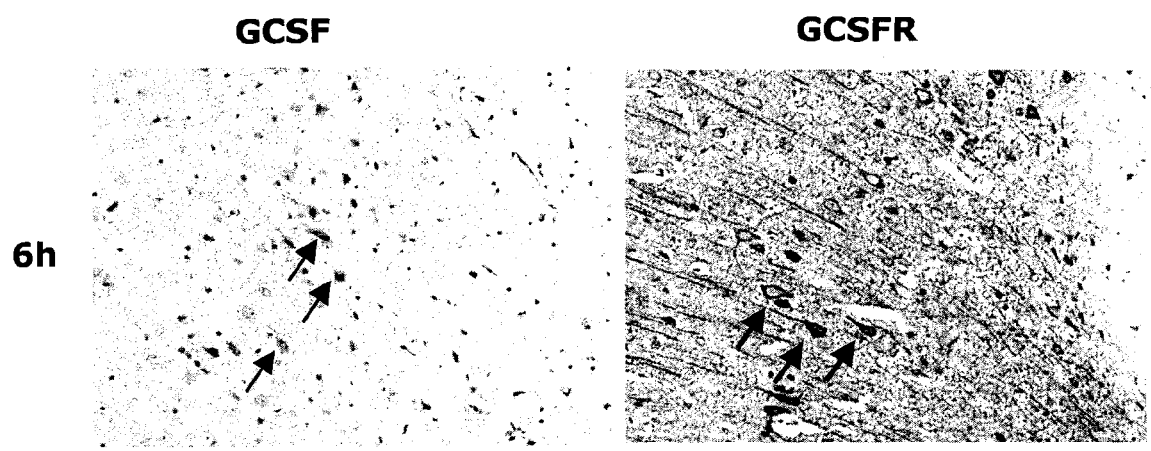

FIG. 29 shows G-CSF and its receptor in the penumbra of the infarct (Benegal Rose).

Figure 30:
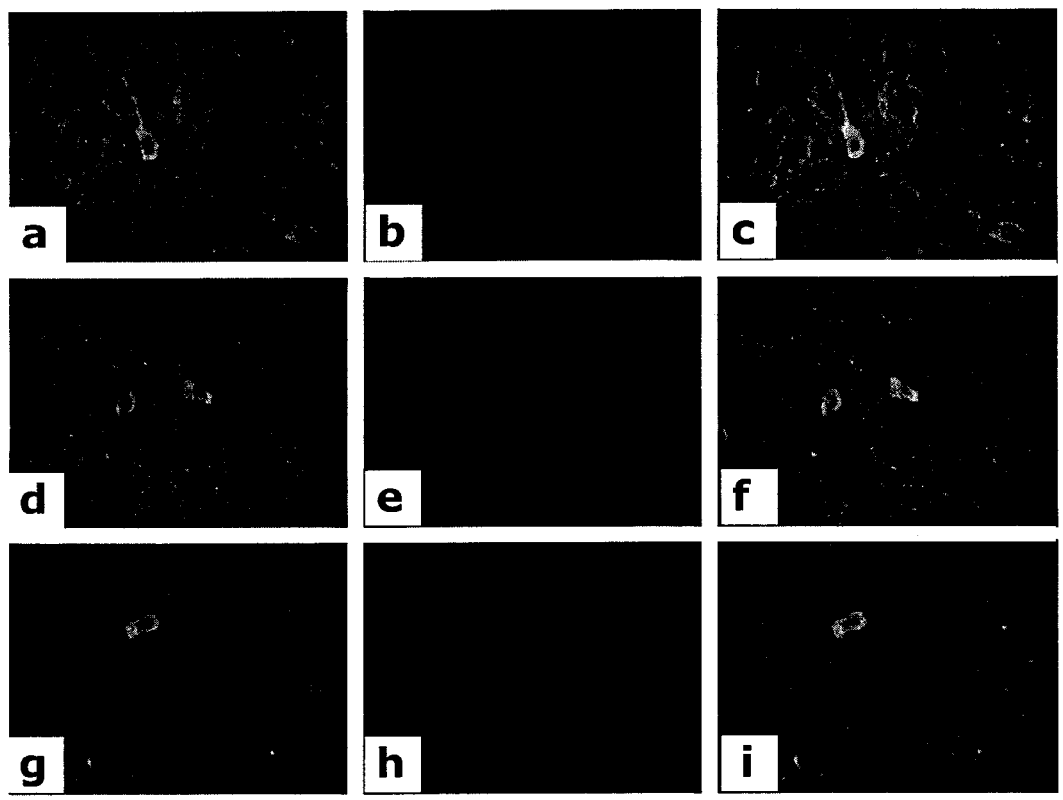

FIG. 30 shows the expression of GCSF receptors (a, d, g) and doublecortin (b, e, h) on neurons in the dentate gyrus (a-f) and the hilus (g-i) of the hippocampus.

Figure 31:
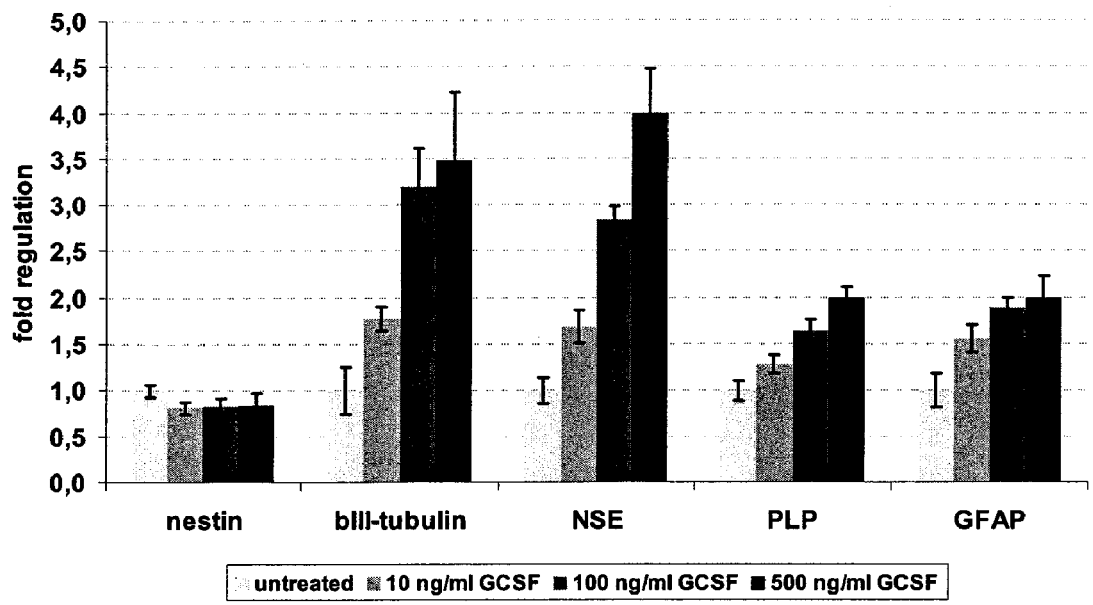

FIG. 31 shows a strong and concentration dependent upregulation of the neuronal markers NSE and beta III-tubulin 4d after GCSF treatment. PLP and GFAP are moderately regulated in depedency of the GCSF-concentration. Error bars indicate standard deviations, calculated from 3-fold serially diluted cDNA-samples, and reflect reliability of measurements.

Figure 32:
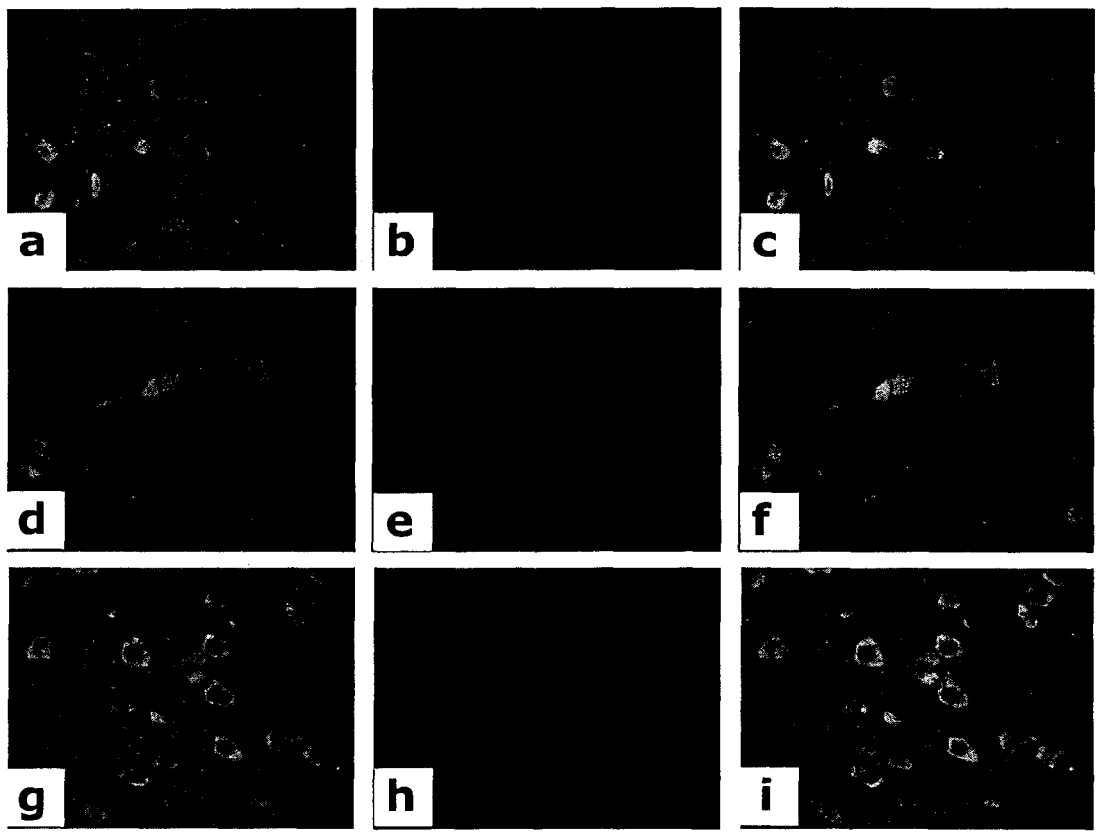

FIG. 32 shows co-localisation of GMCSF and its receptor in the brain. The GMCSF receptor (a, d, g) and GMCSF (b, e, h) are colocalised on neurons in the dentate gyrus (a-c), the hilus (d-f), and the cortex (g-i).

Figure 33A:
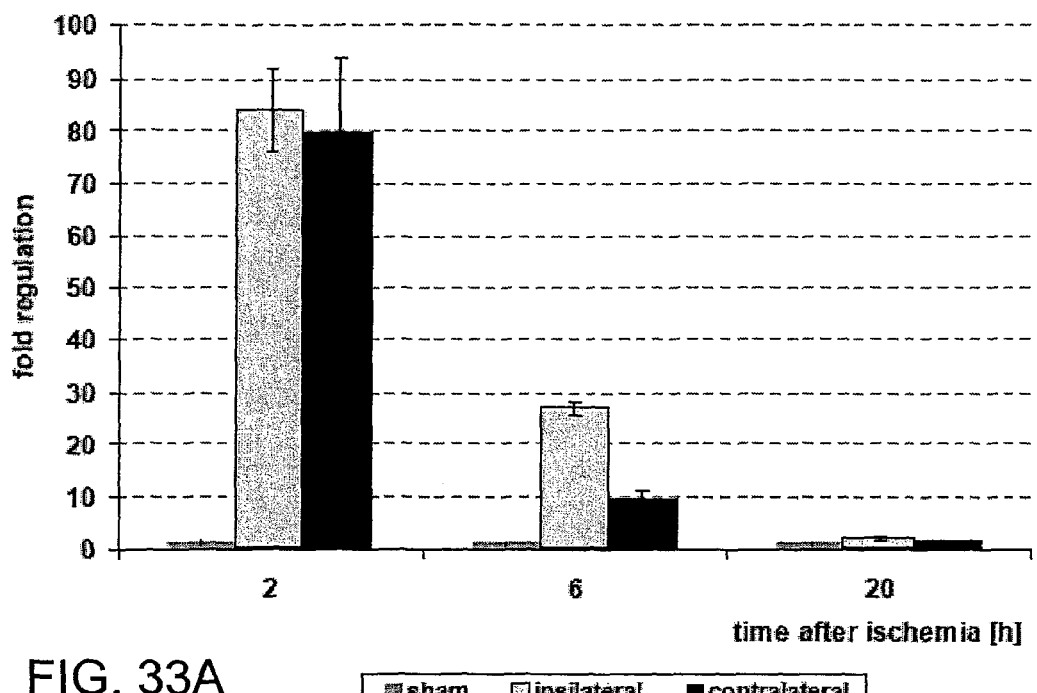
Figure 33B:
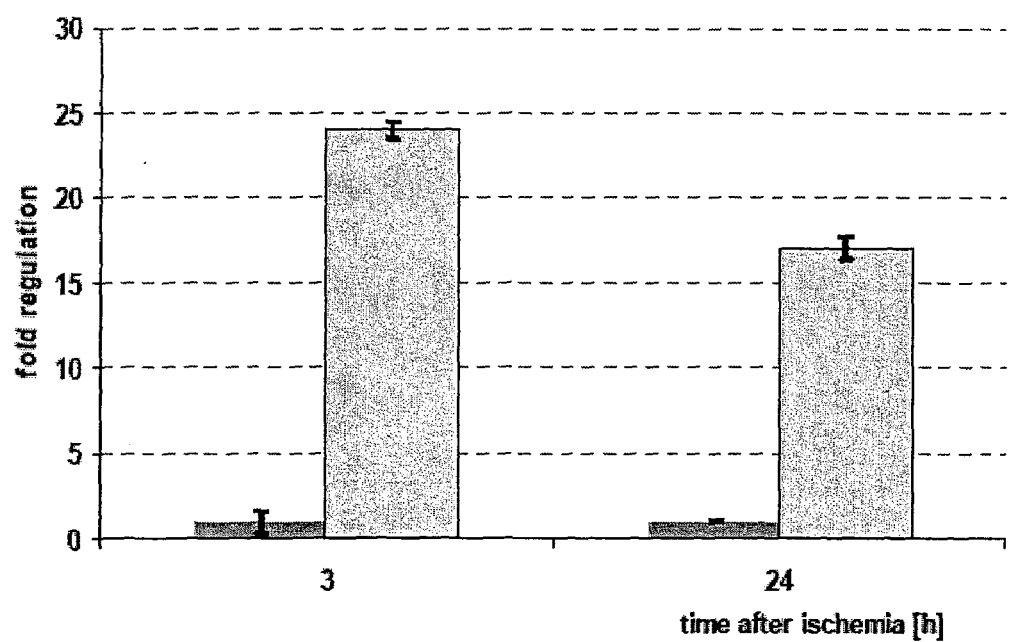
Figure 33C:
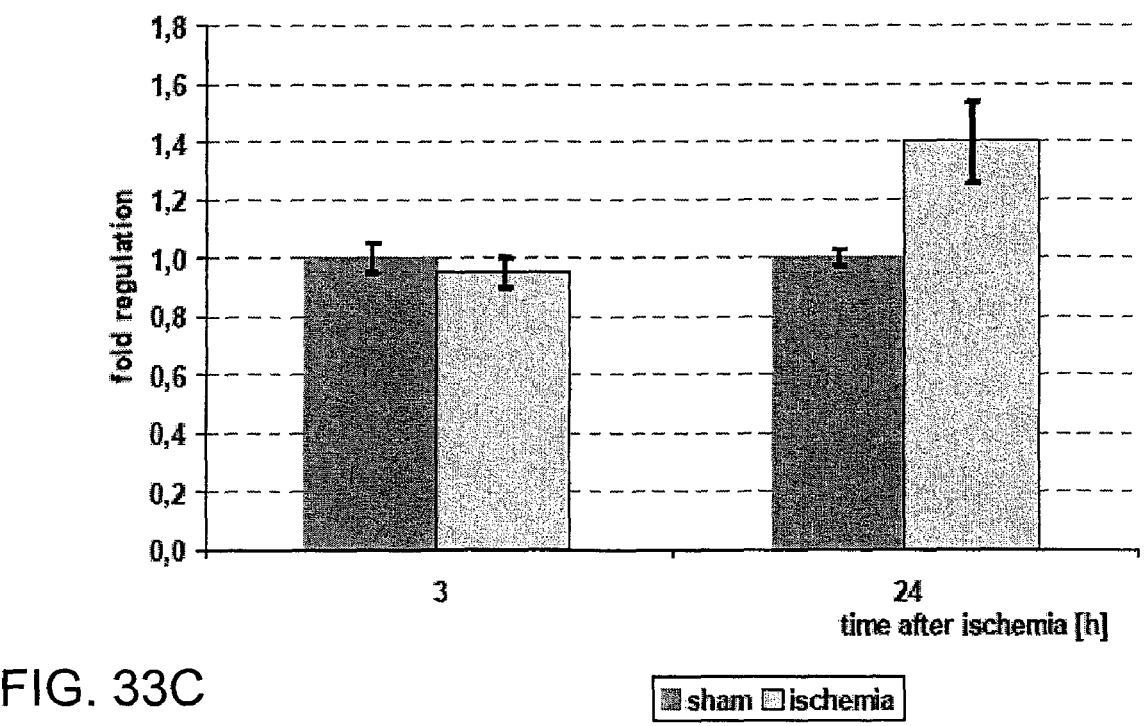

FIG. 33 shows that GCSF and its receptor are upregulated by cerebral ischemia.

Figure 34:
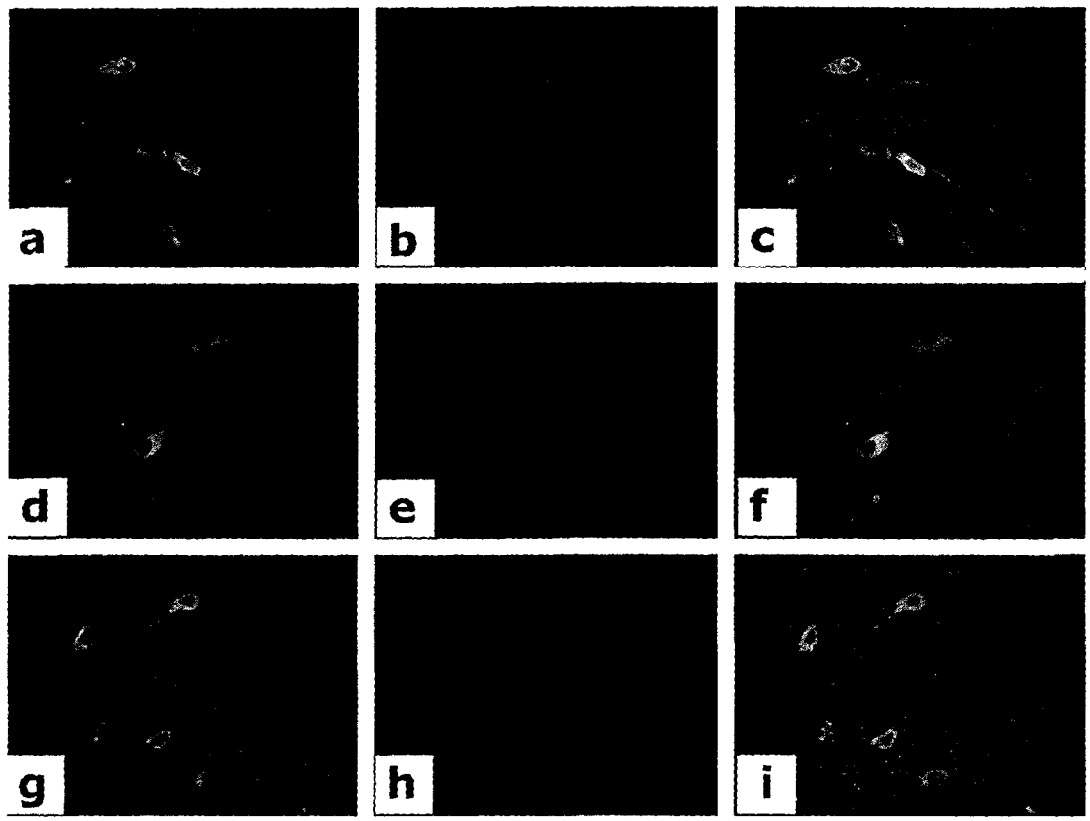

FIG. 34 shows the expression of the GMCSF receptor (a, d, g) and doublecortin (b, e, h) on neurons in the dentate gyrus (a-c) and the hilus (d-i) of the hippocampus.

FIG. 35 shows the differentiation potential of neural stem cells and the specific marker expressions of differentiated cells and that treatment of neural stem cells with 10 ng/ml GMCSF results in a significantly induced expression of beta III-tubulin (n=3; $p<0.05$, two-tailed t-test) and to a lesser extend of NSE, a marker for mature neurons (B).

Figure 36:
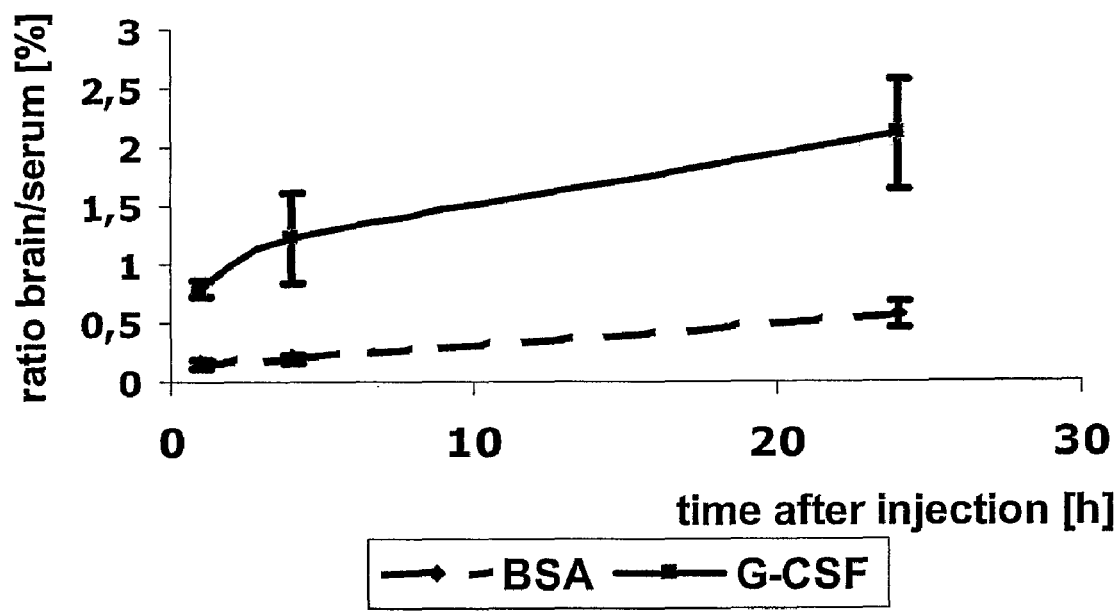

FIG. 36 shows that G-CSF passes the blood-brain-barrier (BBB).

Figure 37:
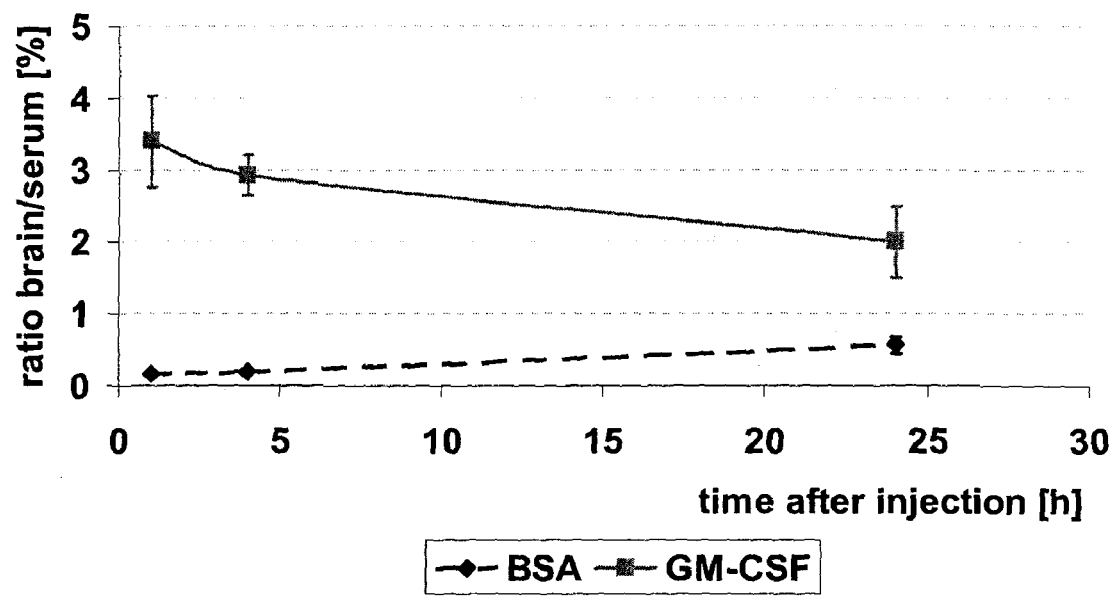

FIG. 37 shows that GM-CSF passes the blood-brain-barrier (BBB).

FIG. 38 shows the efficacy of G-CSF for the treatment of Amyotrophic Lateral Sclerosis (ALS).

Figure 39:
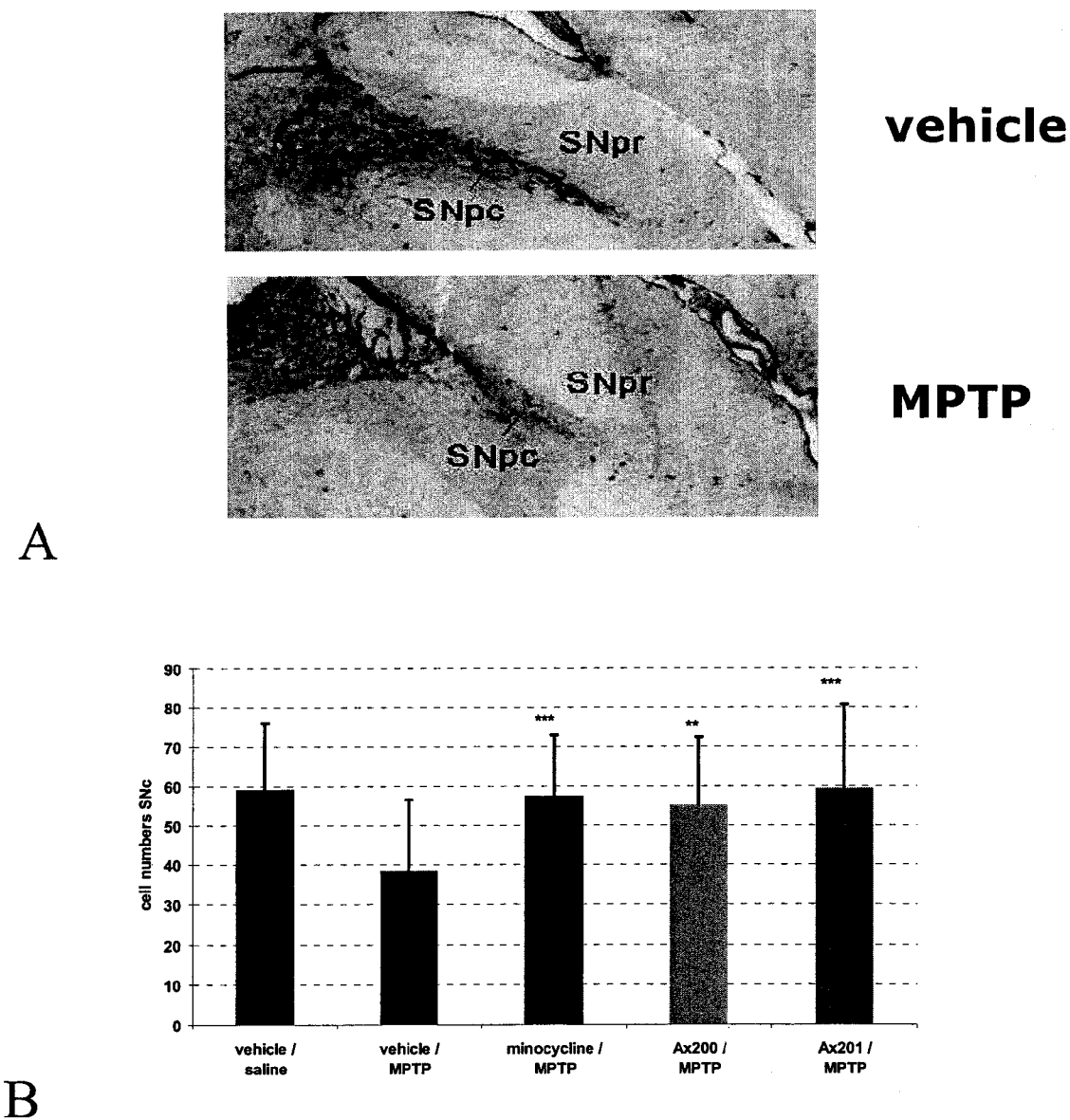

FIG. 39 shows the efficacy of GCSF in rodent models of Parkinson's disease (PD).

FIG. 40 shows that GMCSF acts anti-apoptotically in neurons by activating stat3 pathways, part I shows that GMCSF inhibits PARP cleavage, that is specifically occurring as a sign of apoptosis. Cell death was induced in primary neurons by using the NO-donor NOR-3. Part II shows that GMCSF does not lead to increased phosphorylation of STAT1 ("pSTAT1") or STAT5 ("pSTAT5"), although the proteins themselves are expressed in neurons. part III A shows that GMCSF leads to a time-dependent activation of STAT3, that is maximal at 5 min following the GMCSF stimulus. B, quantification of three independent experiments. C. Activation of STAT3 by phosphorylation can be inhibited by the JAK2 inhibitor AG490. part IV shows that GMCSF strongly induces the expression of the stat3 target genes Bcl2, and BclXI. These genes are known as being antiapoptotic.

Figure 41A:
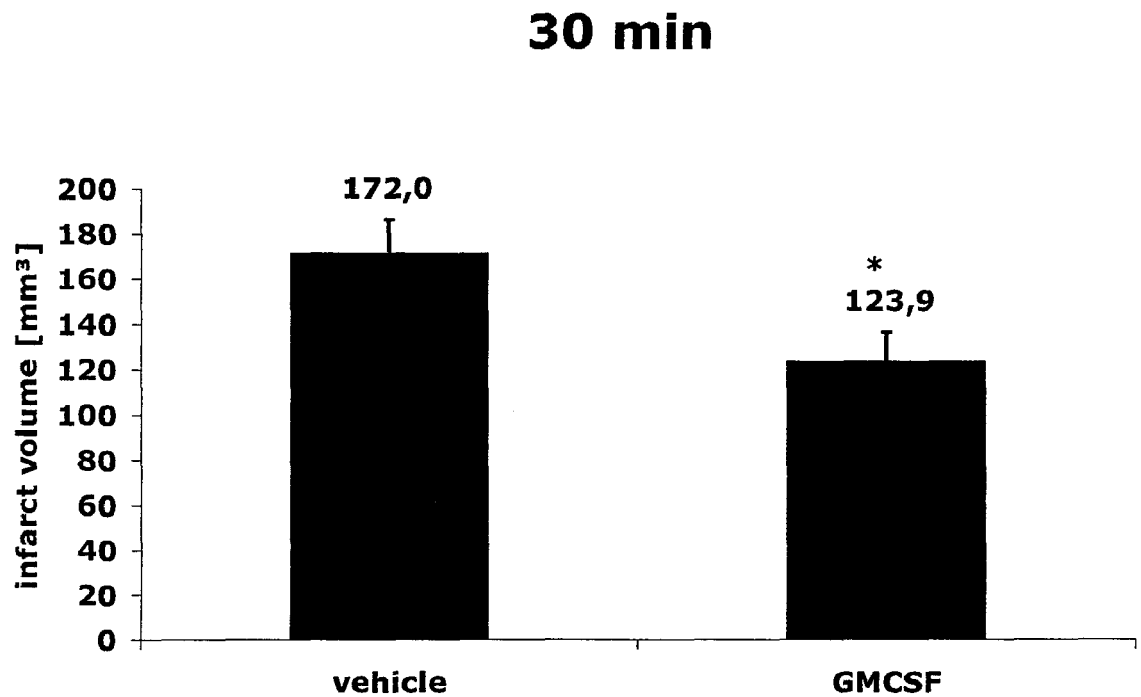
Figure 41B:
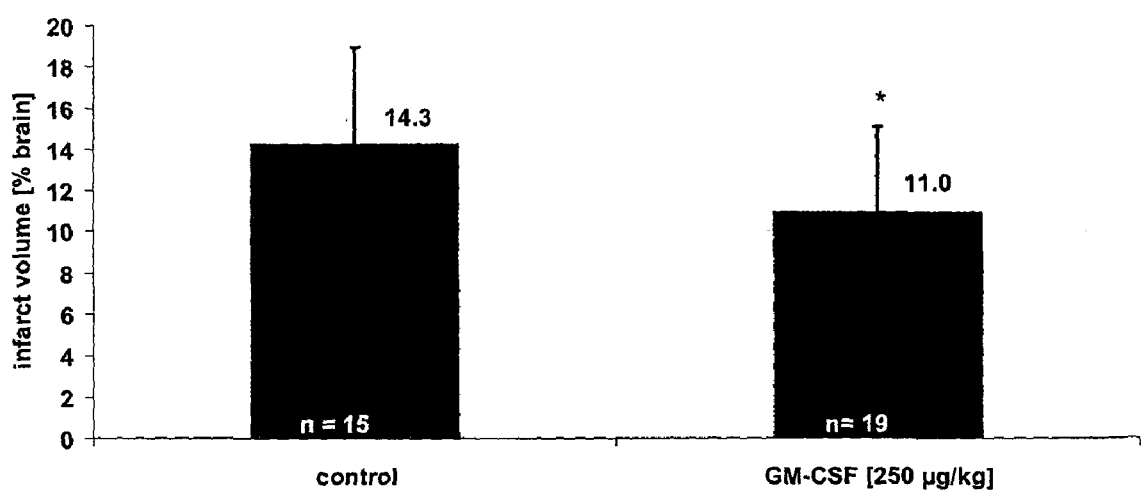

FIG. 41 demonstrates that there is a significant reduction of infarct volume in the GMCSF-treated animals, both at the early (part I), and at the late time window of 3 h (part II).

FIG. 42 shows the upregulation of IL-5 in focal ischemia at 2 h and 6 h by quantitative RT-PCR by applying the LightCycler-System. Samples were taken at 2 h, 6 h and 20 h after induction of MCAo in rats and induction levels were compared to sham-operated animals. On the ipsilateral hemisphere the upregulation of the IL-5 mRNA is rising early after the focal ischemia and reaches its maximum 6 h after the stroke. 20 h after onset normal IL-5 level is reached. On the corresponding contralateral cortex-sample, a slight upregulation is seen 6 h after the infarct.

FIG. 43 shows the induction of both, PI3K/Akt pathway and ERK-pathway, in neurons after G-CSF-treatment. In FIG. 43A, B and D the lanes show different timepoints after onset of G-CSF treatment. In FIG. 43A the phosphorylation of Akt (upper lane) compared to total Akt-Protein is shown. Akt was phosphorylated 5 min after GCSF addition. In FIG. 43B the amount of phosphorylation of PDK1 (upper lane) compared to total PDK1-Protein is shown. PDK1 was phosphorylated 5 min after G-CSF addition with a peak after 30 min of G-CSF exposure. FIG. 43C shows that the PI3-kinase inhibitor LY294002 completely blocked phosphorylation of Akt 5 min after G-CSF addition. FIG. 43D shows the phosphorylation of ERK1, 2 and 5 after G-CSF addition. The amount of phosphorylated ERK1/2 peaked at 5-15 min after G-CSF addition, while most ERK5 was phosphorylated at 30 min of exposure.

FIG. 44 shows the induction of both, PI3K/Akt pathway and ERK-pathway, in neurons after GM-CSF-treatment. In FIGS. 44A and B the lanes show different timepoints after onset of G-CSF treatment. In FIG. 44A the phosphorylation of Akt (upper lane) and phosphorylation of PDK1 (Third lane) compared to total Akt-(second lane) and PDK1-protein (fourth lane) is shown. Akt and PDK1 were phosphorylated 5 min after GCSF addition. The blot also shows that the PI3-kinase inhibitor LY294002 completely blocked phosphorylation of Akt 5 min after GM-CSF addition. FIG. 44B shows the phosphorylation of ERK1/2 and 5 after GM-CSF addition. The amount of phosphorylated ERK1/2 peaked 5 min after GM-CSF addition, while ERK5 was phosphorylated after 5 min of exposure and stayed constant.

FIG. 45 shows that GM-CSF is upregulated after cell death in vitro.

FIGS. 46a and b shows that IL-3 and IL-5 have an anti-apoptotic effect on cells after Camptothecin treatment at specific concentrations (rising from 1 to 100 ng/ml). Given are Luminiscence values of detected Caspase-3 and -7 activity as a detector for Apoptosis (Caspase Glow assay (Promega).

FIG. 46a shows that IL-3 is protective at concentrations of 1-20 ng/ml in rat neuronal cultures and human neuroblastoma cells (SHSY5-Y).

FIG. 46b shows that IL-5 has its highest protectivity at a concentration of 1 ng/ml in rat neuronal cultures and human SHSY5-Y.

FIG. 47 shows the induction of PI3K/Akt pathway after IL-3 treatment. Given are different timepoints after onset of IL-3 treatment (5 and 60 min after onset). The first lane in FIG. 47 shows the phosphorylation of Akt. Akt was phosphorylated 5 min after IL-3 addition and was still phosphorylated 1 h later. The second lane shows that PDK was phosphorylated after 5 min of IL-5 and was still phosphorylated 1 h later, too.

FIG. 48 shows the induction of PI3K/Akt pathway after IL-5 treatment. Given are different timepoints after onset of IL-5 treatment (5 and 60 min after onset). The first lane in FIG. 48 shows the phosphorylation of Akt. Akt was phosphorylated 5 min after IL-5 addition and was still phosphorylated 1 h later. The second lane shows that PDK was phosphorylated after 5 min of IL-5 and was still phosphorylated 1 h later, too.

FIG. 49 shows that the infarct volume in an additional model of cortical ischemia was reduced after GCSF treatment. Given is the average value of the measured infarct volume of 6 respectively 5 animals. The infarct volume is significantly reduced if GCSF is given 1 h after onset of ischemia.

Figure 50:
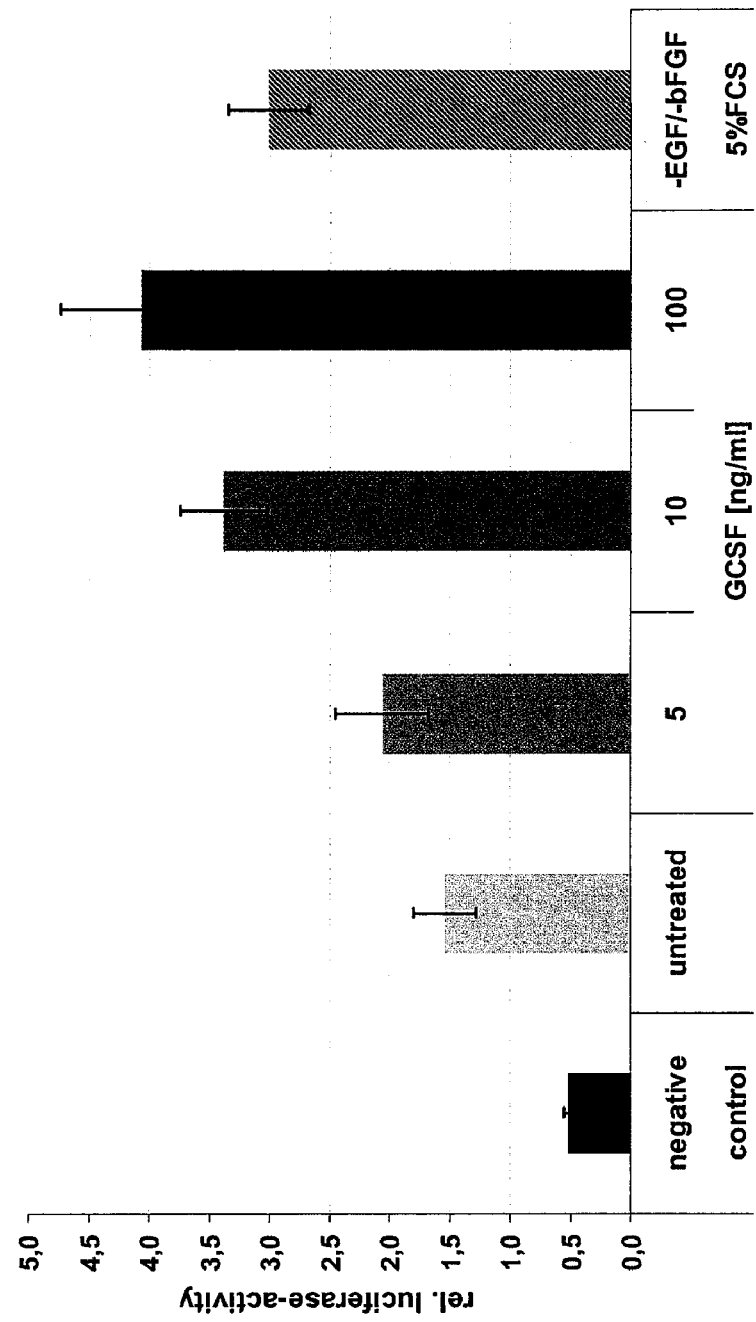

FIG. 50 shows that GCSF stimulated the differentiation of neuronal stem cells toward a neuronal phenotype. Cells were transfected with a Luciferase under the control of β-Tubulin-Promotor. Given are relative luciferase signals after stimulation with different concentrations of GCSF. The more GCSF is added to the culture medium, the more Luciferasesignal can be detected. This shows that GCSF triggers the differentiation towards a neuronal phenotype.

Figure 51:
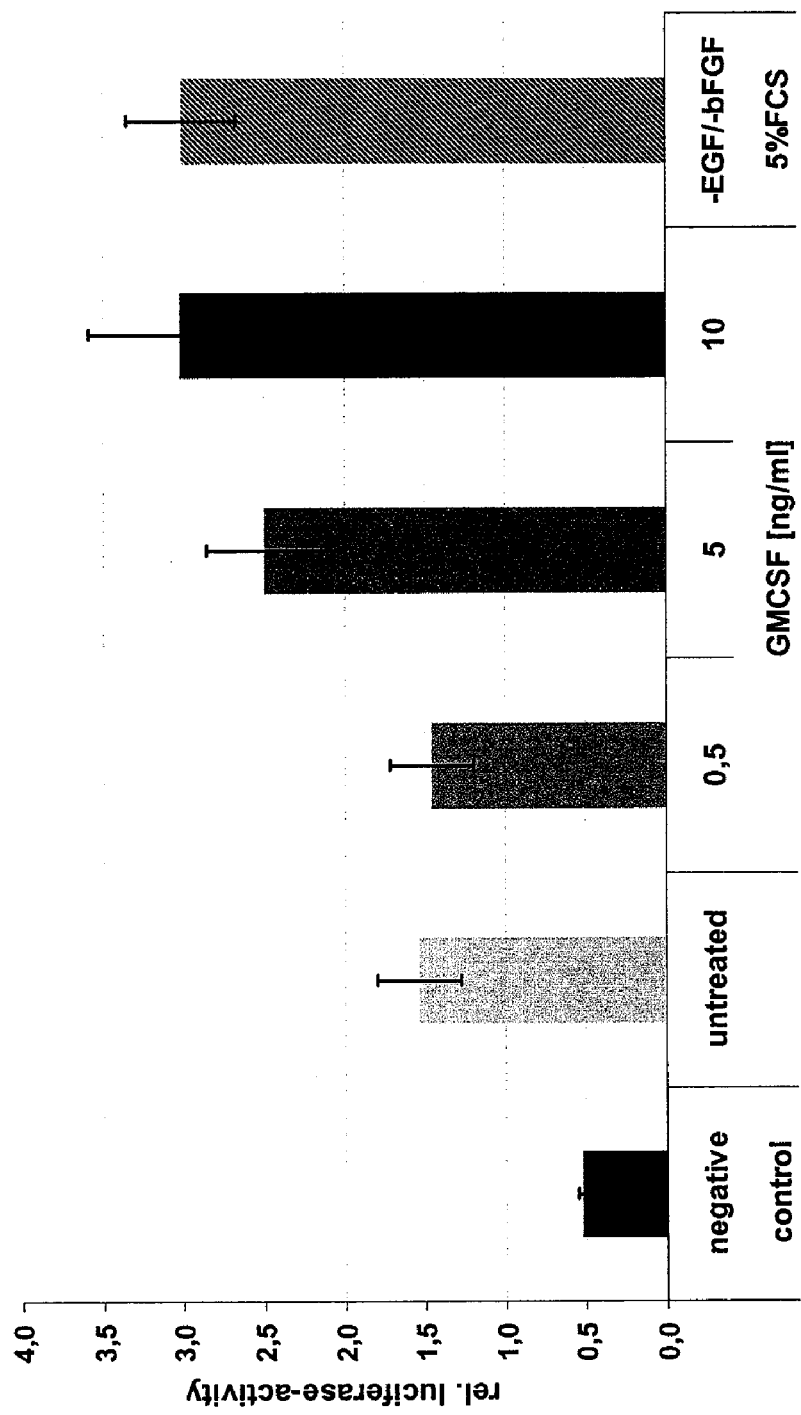

FIG. 51 shows that GMCSF stimulated the differentiation of neuronal stem cells toward a neuronal phenotype. Cells were transfected with a Luciferase under the control of β-Tubulin-Promotor. Given are relative luciferase signals after stimulation with different concentrations of GMCSF. The more GMCSF is added to the culture medium, the more Luciferasesignal can be detected. This shows that GMCSF triggers the differentiation towards a neuronal phenotype.

Figure 52:
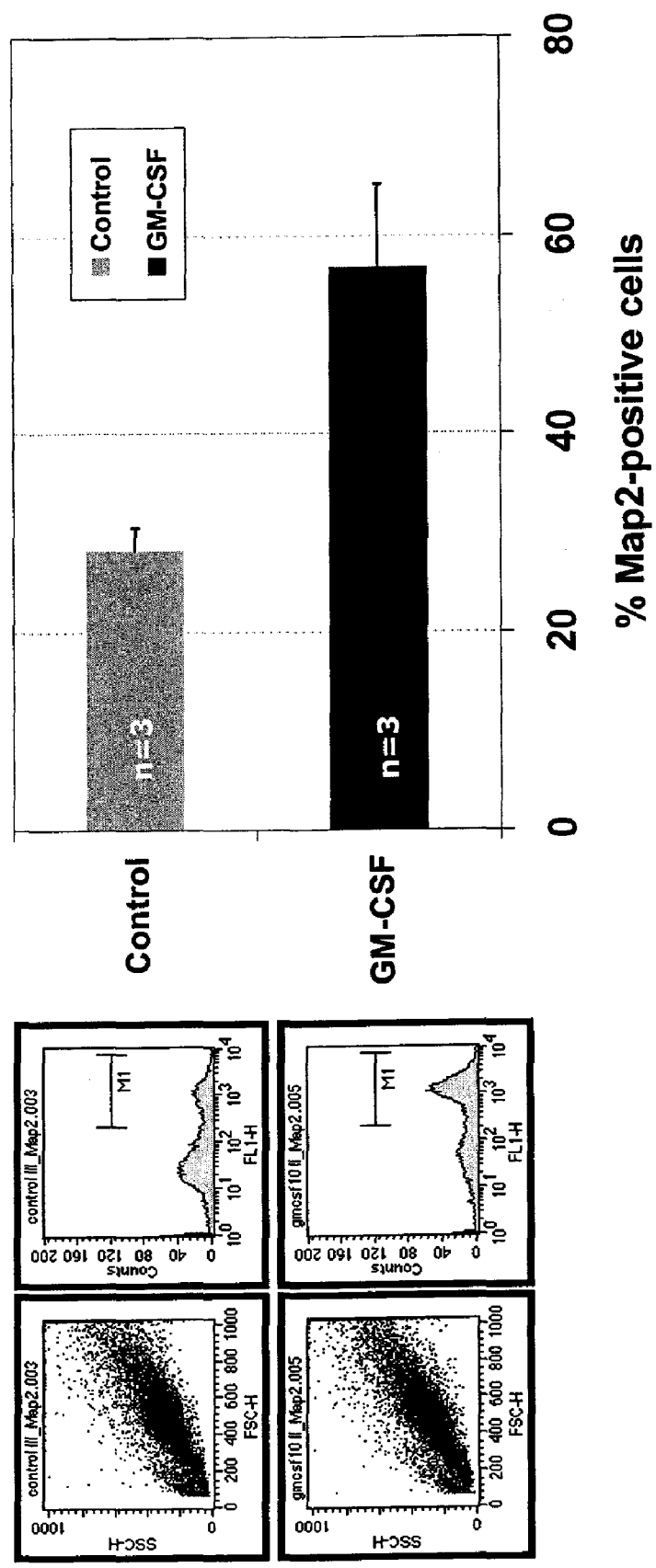

FIG. 52 demonstrates that GMCSF triggers the differentiation towards a neuronal phenotype. Given are the results of a FACS analysis of NSC after GMCSF treatment. MAP-2 as a neuronal marker protein is detected by a fluorescent labeled antibody. The bars give the percentage of MAP-2-positive cells in the sample analyzed. This showed that GMCSF induced the expression of a typically neuronal protein.

Figure 53:
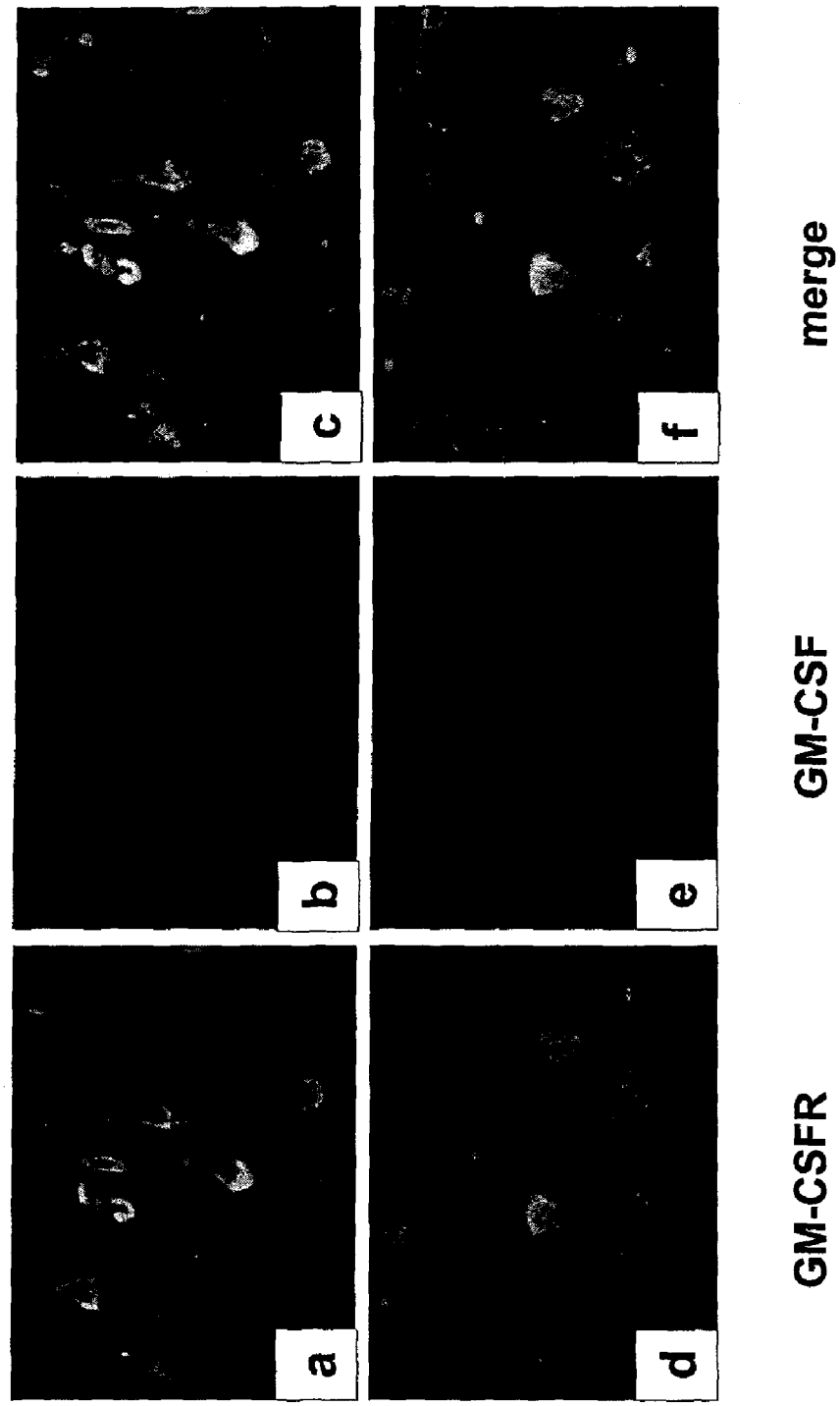

FIG. 53 shows the detection of GMCSF receptor (GMCSFR) and GMCSF in human brain slices. 53a and d show the detection of GMCSFR, b and e show GMCSF and c and f reflect an overlay of a and b and d and e, respectively. The merged pictures show that in human brain GMCSF and its receptor are expressed in the same cell.

Figure 54:
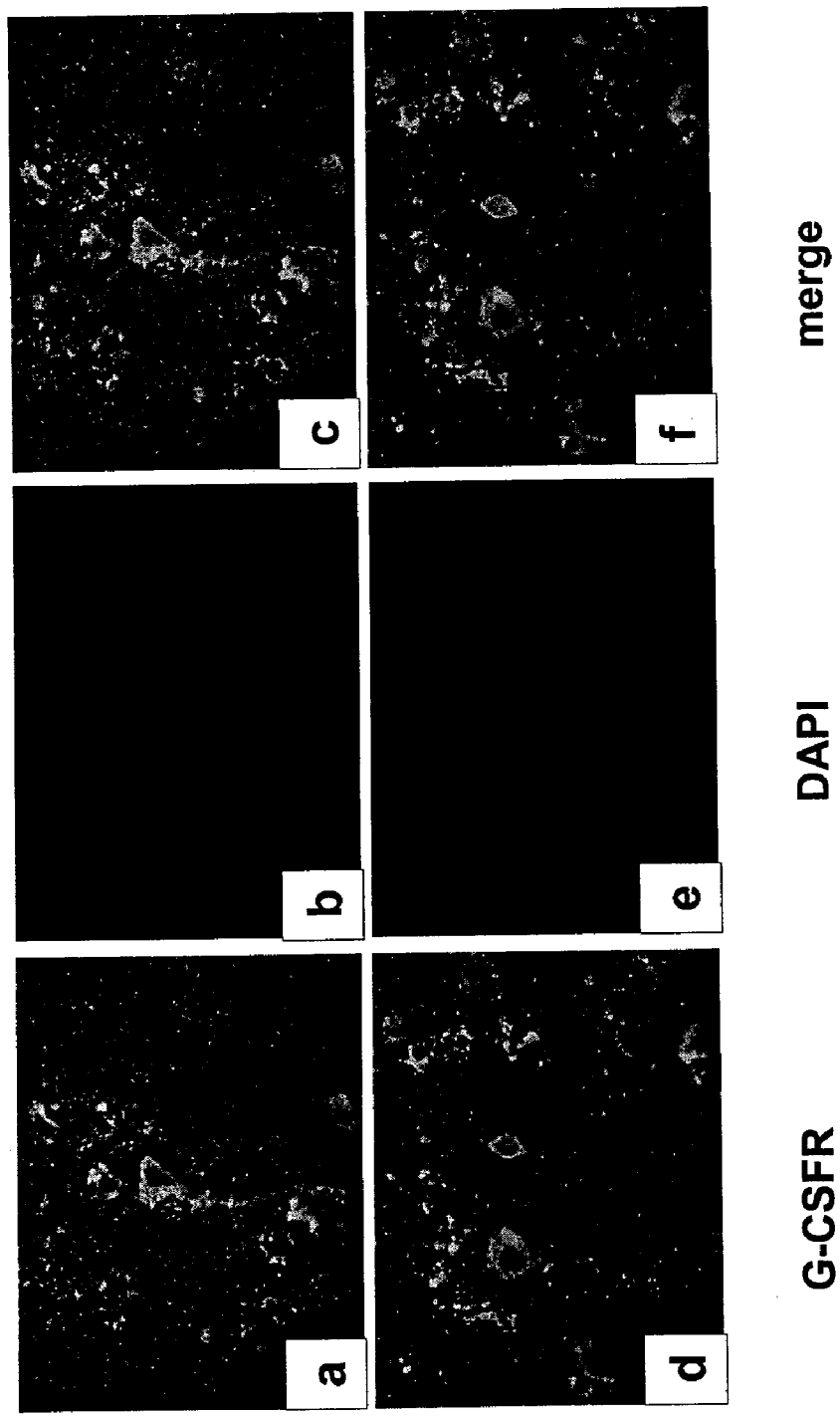

FIG. 54 shows the detection of GCSF receptor (GCSFR) in human brain slices from cortex. 54a and d show the detection of GCSFR, b and e show a DAPI-staining of the cell nuclei and c and f reflect an overlay of the a and b and d and e, respectively. The pictures show that GMCSF is expressed in human Cortex.

Figure 55:
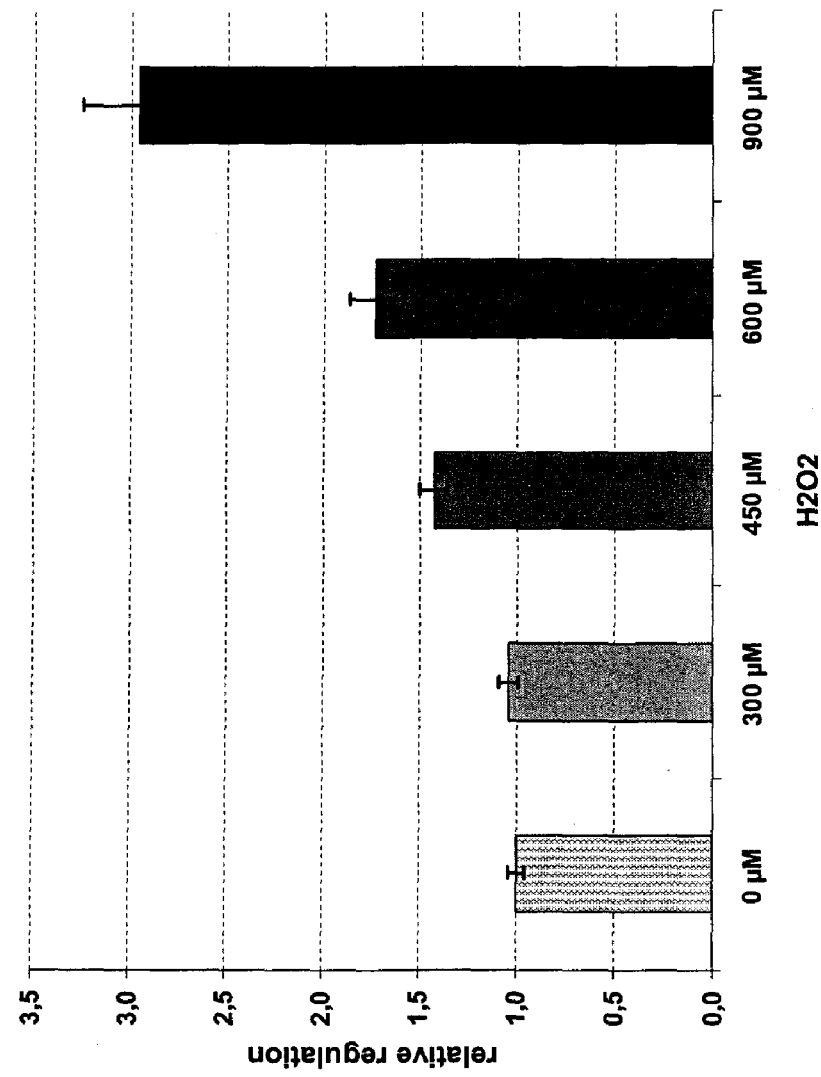

FIG. 55 shows that GCSF was upregulated after cell death induction. Given are the relative values of GCSF-mRNA expression in neuronal cell culture after $H_2O_2$ treatment. Stimulation with rising concentrations of $H_2O_2$ lead to an increasing amount of GCSF-mRNA Synthesis in these stressed cells; GCSF-mRNA was upregulated up to 3 fold.

Figure 56:
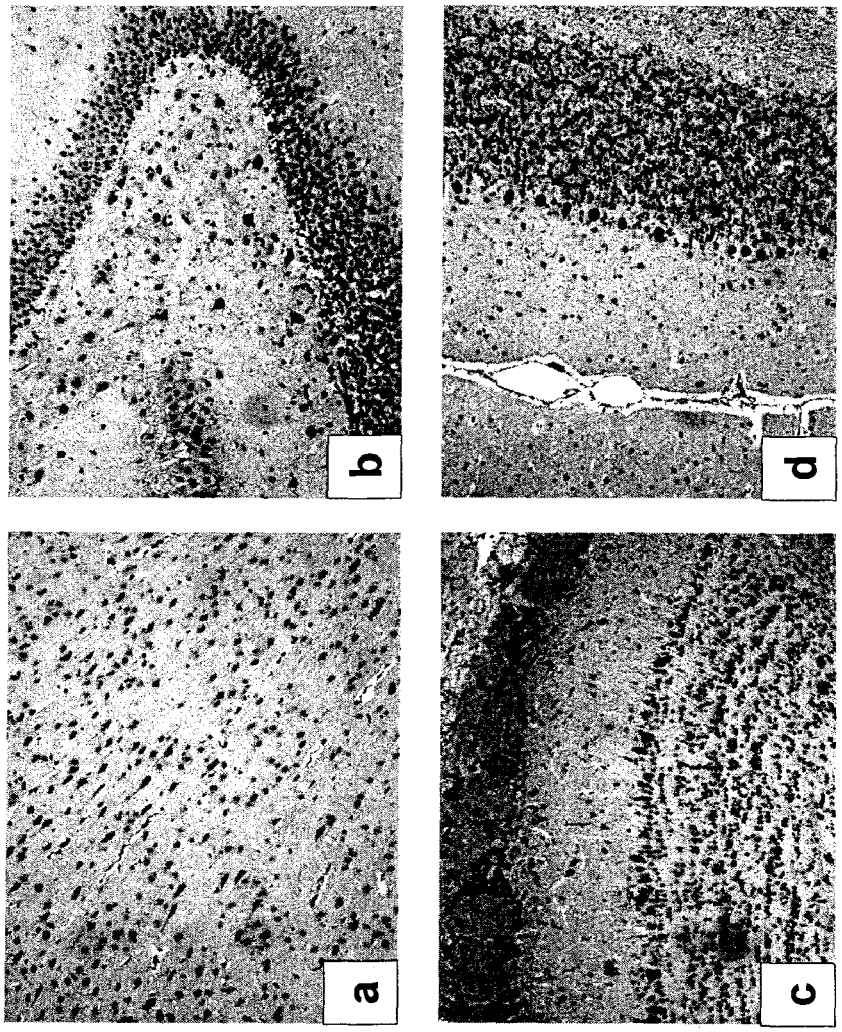

FIG. 56 shows the detection of IL-5 receptor alpha (IL5Ra) by immunohistochemistry in slices of the rat brain. The expression of the IL-5 receptor alpha was detected in the frontal Cortex (FIG. 56 a), in the dentate gyrus (FIG. 56 b), in the mitral cells of the olfactory bulb (FIG. 56 c), and in Purkinje cells of the cerebellum (FIG. 56 d). This reflects the widespread expression of IL5Ra in the rat brain.

Figure 57:
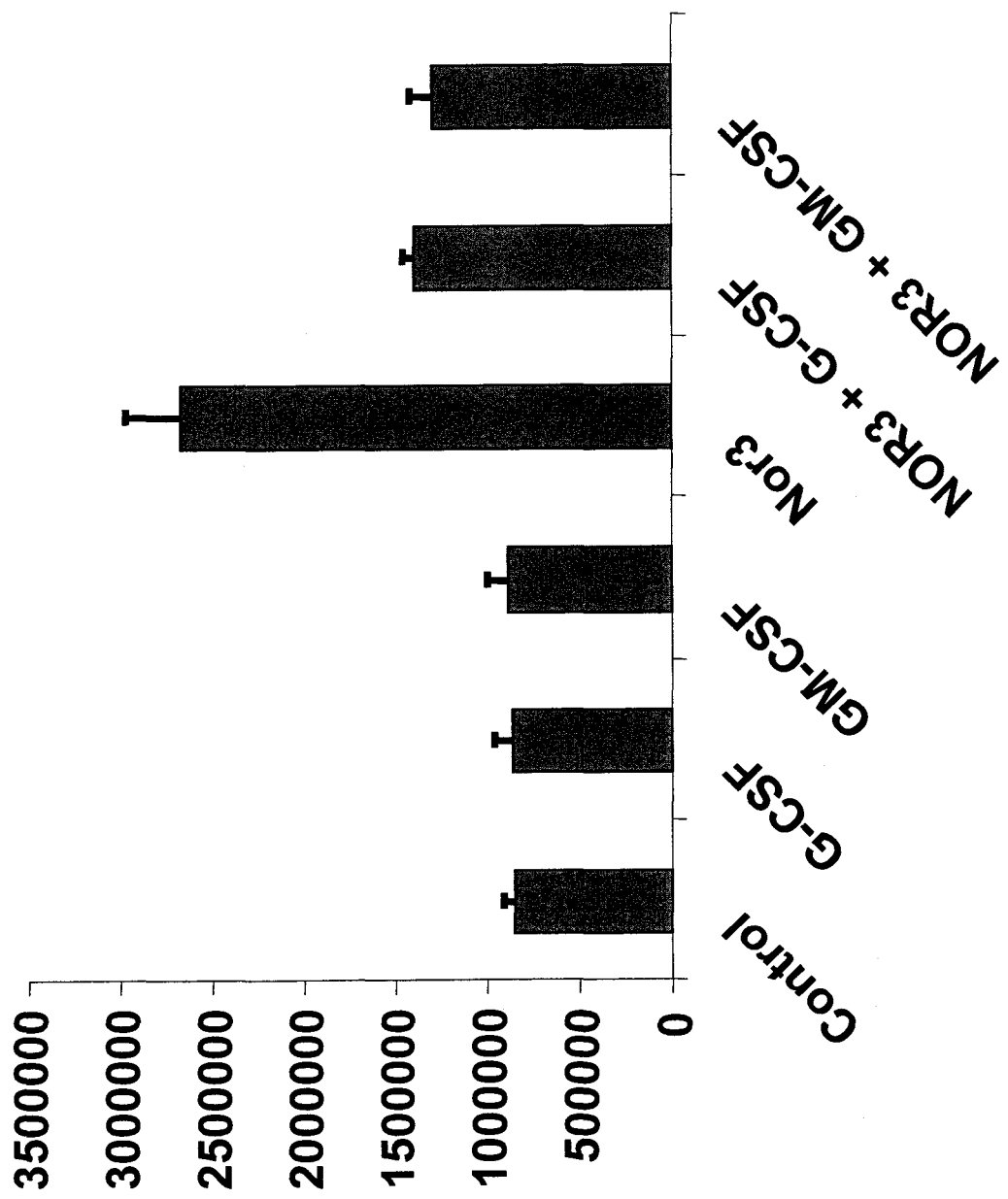

FIG. 57: G-CSF and GM-CSF protect human neuroblastoma cells from Nor3 induced apoptosis. Caspase 3/7 activity of SHSY5Y cells after treatment with 150 µM Nor3 for 5 h in the presence or absence of 60 ng/ml G-CSF or 20 ng/ml GM-CSF, as determined with Caspase Glow assay (Promega).

Figure 58:
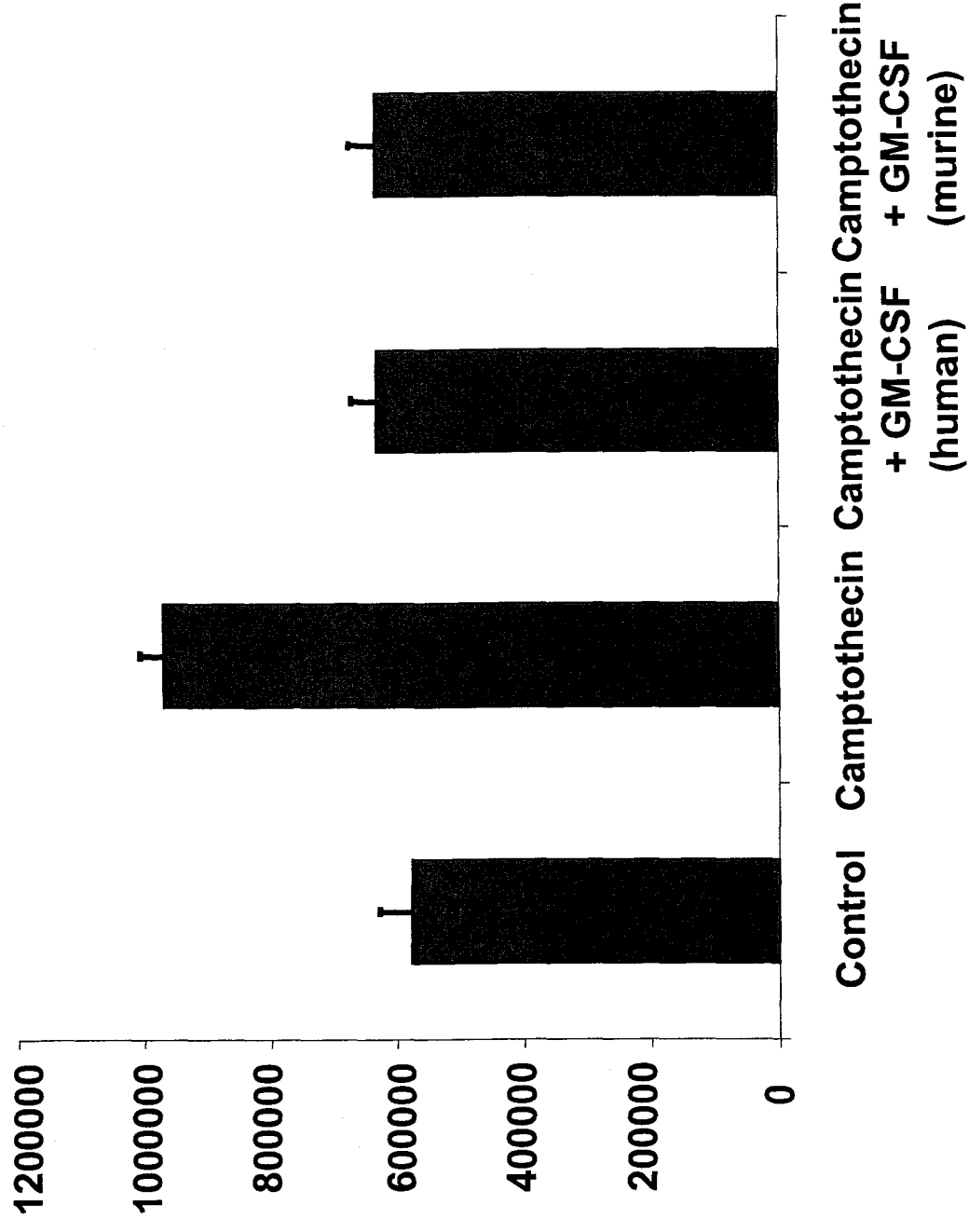

FIG. 58: Human and murine GM-CSF both reduce camptothecxin induced cell death in human neuroblastoma cells (SHSY5Y). Caspase 3/7 activity of SHSY5Y cells after treatment with Camptothecin for 5 h in the presence or absence of human or murine GM-CSF (20 ng/ml), as determined with Caspase Glow assay (Promega).

DETAILED DESCRIPTION OF THE INVENTION

The receptors for human IL-3, IL-5, and GM-CSF are members of the hematopoietin receptor superfamily. Multisubunit receptors may consist of two subunit types such as the receptors for granulocyte-macrophage CSF (GM-CSF), interleukin-3 (IL-3), and IL-5 where an α subunit is specific for each ligand and a β subunit is common to all three $β_c$, with both chains participating in signalling. In the GM-CSF, IL-3, IL-5 receptor subfamily, intriguing differences are beginning to emerge that may have implications for the role of these receptors in hematopoietic cell function. The major difference lies in the absolute requirement for IL-3 and IL-5 for dimerization of IL-3Rχ with $β_c$, and IL-5Rχ with $β_c$ whereas, in contrast, at least some of the GM-CSFR probably exists as a preformed complex. (Guthridge, et al. (2004), Blood, 103, 820-7) This shows that although IL-3, IL-5 and GM-CSF even share a Receptor-Subunit; they still differ in their specific function.

IL-3

Interleukin 3 (IL-3) is a well known hematopoietic factor. The IL-3 that can be employed in the inventive methods described herein are those full length coding sequences, protein sequences, and the various functional variants, chimeric proteins, muteins, and mimetics that are known and available. The structure of both the coding DNA and protein are known. For example, DNA encoding IL-3 and IL-3 protein sequences comprise the sequences of SEQ ID NOS: 68-84.

Human IL3 is a protein of 15-17 kDa (133 amino acids). It is synthesized as a precursor containing a hydrophobic secretory signal sequence of 19 amino acids. IL-3 contains two putative glycosylation sites at positions 15 and 70 and contains a single disulfide bond (Cys16/84). The analysis of bacterial-derived recombinant IL-3 shows that glycosylation is not required for the activity of IL-3.

IL-3 is produced mainly by T-cells following cell activation by antigens and mitogens, but also by keratinocytes, NK-cells, mast cells, endothelial cells, and monocytes. IL-3 may be associated with the extracellular matrix in the form of complexes with heparin sulfate/proteoglycan. It can thus be stored in a biologically inactive form but it may exert juxtacrine activities also. The molecular mechanisms underlying the release from extracellular matrix stores are still unknown.

IL-3 is a growth factor that establishes the link between the immune system and the hematopoietic system. It supports the proliferation and development of almost all types of hematopoietic progenitor cells. In rhesus monkeys IL-3 causes the expansion of all types of circulating hematopoietic progenitor cells. IL-3 also supports the differentiation of early non-lineage-committed hematopoietic progenitor cells into granulocytes, macrophages, erythroid cells, megakaryocytes, and mast cell colonies. IL-3 also stimulates clonal growth of non-hematopoietic stromal cells in bone marrow cultures. IL3 is one of the priming factors for hematopoietic stem cells in vitro and in vivo that makes the cells responsive to later-acting factors such as Erythropoietin, GM-CSF and IL6. IL3 also induces the increased expression of receptors for colony stimulating factors.

IL-3 also specifically induces the production of enzymes involved in cellular metabolism, differentiation and DNA/RNA metabolism. Among other things IL3 induces the expression of 20-alpha-steroid dehydrogenase and of histidine and Ornithine decarboxylase.

In another embodiment, the IL-3 that can be used are those that are encoded by polynucleotide sequence with at least 70%, preferably 80%, more preferably at least 90% identity to the wildtype full-length human IL-3 coding sequence, these polynucleotides will hybridize under stringent conditions to the coding polynucleotide sequence of the wild-type full length human IL-3. The terms "stringent conditions" or "stringent hybridization conditions" includes reference to conditions under which a polynucleotide will hybridize to its target sequence, to a detectably greater degree than other sequences (e.g., at least 2-fold over background). Stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides), for example, high stringency conditions include hybridization in 50% formamide, 1 M NaCl, 1% SDS at 37° C., and a wash in 0.1×SSC at 60 to 65° C. (see Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995)). Amino acid and polynucleotide identity, homology and/or similarity can be determined using the ClustalW algorithm, MEGALIGN™, Lasergene, Wis.)

Examples of the various IL-3 functional variants, muteins, and mimetics include functional fragments and variants (e.g., structurally and biologically similar to the wild-type protein and having at least one biologically equivalent domain), chemical derivatives of IL-3 (e.g., containing additional chemical moieties, such as polyethyleneglycol and polyethyleneglycol derivatives thereof, and/or glycosylated forms), and peptidomimetics of IL-3 (e.g., a low molecular weight compound that mimics a peptide in structure and/or function (see, e.g., Abell, *Advances in Amino Acid Mimetics and Peptidomimetics*, London: JAI Press (1997); Gante, *Peptidmimetica—massgeschneiderte Enzyminhibitoren Angew. Chem.* 106: 1780-1802 (1994); and Olson et al., *J. Med. Chem.* 36: 3039-3049 (1993)).

The various functional derivatives, variants, muteins and/or mimetics of IL-3 preferably retain at least 20%, preferably 50%, more preferably at least 75% and/or most preferably at least 90% of the biological activity of wild-type mammalian IL-3 activity—the amount of biological activity include 25%, 30%, 35%, 40%, 45%, 55%, 60%, 65%, 70%, 75%, 80%, 85%, 95%; and all values and subranges there between. Furthermore, the functional derivatives, variants, muteins and/or mimetics of IL-3 can also have 100% or more of the biological activity relative to wild-type mammalian IL-3 activity—the amount of biological activity including at least 105%, at least 110%, at least 125%, at least 150%, and at least 200%.

One example of a functional variant is the human recombinant interleukin-3 (IL-3; SDZ ILE-964; Sandoz A G, Basel, Switzerland/Novartis) (Lokker, et al. (1991), J Biol Chem, 266, 10624-31).

To measure the biological activity of IL-3, several known assays can be employed singularly or in combination. Those IL-3 functions include its known immunomodulatory functions and to one or more functions relating to its role in neuroprotection. IL-3 can be detected in Bioassays employing cell lines that respond to this factor (e.g., cell lines: AML-193; 32D; B6SUt-A; B13; Da; Ea3.17; FDCP1; GF-D8; IC-2; KMT-2; L138.8A; LyD9; MO7E; NFS-60; PT-18; TALL-103; TF-1; TMD2; UT-7).

These and other assays are described in (Aglietta, et al. (1993), Blood, 82, 2054-61); (Cohen, et al. (1991), Immunol Lett, 28, 121-6) (Kobayashi, et al. (1989), Blood, 73, 1836-41) (Lemoli, et al. (1993), Exp Hematol, 21, 1668-72); (Warring a, et al. (1991), Blood, 77, 2694-700))

In other embodiments of the present invention combinations of IL-3 with other hematopoietic factors preparations to support their therapeutic actions, preferably by its neuroprotective action can be used. The effect exerted by these combinations can be cumulative or superadditive/synergistic. In one embodiment, various IL-3 and/or IL-3 derivatives are used in combination with each other. Likewise, IL-3 can be used in combination with one or more additional hematopoietic growth factors such as Erythropoietin, and derivatives thereof, which has recently been shown to mediate strong neuroprotective properties (e.g., Brines et al (2000) *Proc Natl Acad Sci USA* 97:10526-10531; Cerami et al (2002) *Nephrol Dial Transplant* 17:8-12; Siren A L, Ehrenreich H (2001) *Eur Arch Psychiatry Clin Neurosci* 251:179-184). In addition, IL-3 can be used in combination with, for example, various colony stimulating factors (such as G-CSF, GM-CSF or M-CSF), SCF (stem cell factor), SCPF (stem cell proliferation factor), various Interleukins (IL1, IL4, IL5, IL6, IL11, IL12), LIF, TGF-β, MIP-1-α, TNF-α, and also many other low molecular weight factors.

In one embodiment the biological activity of IL-3 is enhanced by fusion to another hematopoietic factor. Examples for such fusion proteins are the IL-3/GMCSF-fusion protein PIXY321, Immunex (Vadhan-Raj (1994), Stem Cells, 12, 253-61) (Anderson and Appelbaum (1994), Curr Opin Hematol, 1, 203-9) (Buescher, McIlheran, Banks and Vadhan-Raj (1993), Exp Hematol, 21, 1467-72); or Promegapoietin; IL-3/thrombopoietin, Pharmacia (Farese, Smith, Giri, Siegel, McKeam and MacVittie (2001), Stem Cells, 19, 329-38). The enhanced activity can be measured in a biological activity assay as described above. In one embodiment, the IL-3 is modified or formulated, or is present as a IL-3 mimetic that increases its ability to cross the blood-brain barrier, or shift its distribution coefficient towards brain tissue. An example of such a modification is the addition of PTD or TAT sequences (Cao et al. (2002) *J. Neurosci.* 22:5423-5431; Mi et al. (2000) *Mol. Ther.* 2:339-347; Morris et al. (2001) *Nat Biotechnol* 19:1173-1176; Park et al. (2002) *J Gen Virol* 83:1173-1181). These sequences can also be used in mutated forms, and added with additional amino acids at the amino- or carboxy-terminus of proteins. Also, adding bradykinin, or analogous substances to an intravenous application of any IL-3 preparation will support its delivery to the brain, or spinal cord (Emerich et al. (2001) *Clin Pharmacokinet* 40:105-123; Siegal et al (2002) *Clin Pharmacokinet* 41:171-186).

IL-3 and IL-3Ralpha show a widespread expression in the brain. Its mRNA was detected in Neurons and Astrocytes (Farrar, et al. (1989), Blood, 73, 137-40) and is localized in discrete areas of the brain e.g. in hippocampal neurons but not in glia (Konishi, et al. (1994), Neurosci Lett, 182, 271-4). IL-3R was shown to be expressed by Microglia and Oligodendrocytes and septal cholinergic neurons. IL-3R alpha-positive cells are mainly present in the medial septal and basal forebrain region. Tabira et al. have demonstrated that interleukin 3 (IL-3) has a neurotrophic effect on central cholinergic neurons and have demonstrated the presence of IL-3 receptor (IL-3R)beta subunits in septal cholinergic neurons. Functional IL-3 receptors were expressed in the central cholinergic neurons and contribute to some physiological roles such as the differentiation and maintenance of these neurons. (Tabira, et al. (1998), Ann N Y Acad Sci, 840, 107-16)

Several members of hematopoietic factors are known to have neuroprotective effects against axotomized motor neuron death. Iwasaki et al. have shown that IL-3 and EPO significantly prevented the loss of motor neurons. Protective potentials is the same between them. These results suggest that IL-3 and EPO play a role for motor neuron survival in vivo and suggest the potential use of these hematopoietic factors in treating diseases that involve degeneration and death of motor neurons, such as motor neuropathy and amyotrophic lateral sclerosis. (Iwasaki, et al. (2002), Neurol Res, 24, 643-6).

In the central nervous system, interleukin (IL)-3 has been shown to exert a trophic action only on septal cholinergic neurons in vitro and in vivo, but a widespread distribution of IL-3 receptor (IL-3R) in the brain does not conform to such a selective central action of the ligand. Moreover, the mechanism(s) underlying the neurotrophic action of IL-3 has not been elucidated. Wen et al. have shown that IL-3 prevents delayed neuronal death in the hippocampal CA1 field through a receptor-mediated expression of Bcl-xL protein, which is known to facilitate neuron survival. Since IL-3Ralpha in the hippocampal CA1 region, even though upregulated in response to ischemic insult, is much less intensely expressed than that in the CA3 region tolerant to ischemia, the paucity of IL-3R interacting with the ligand may account for the vulnerability of CA1 neurons to ischemia. (Wen, et al. (1998), J Exp Med, 188, 635-49).

Bright et al, in contrast suggest a role of IL-3 in inflammatory responses by activating Microglia. Microglia, the resident macrophage of the brain, mediates immune and inflammatory responses in the central nervous system (CNS). Activation of microglia and secretion of inflammatory cytokines associate with the pathogenesis of CNS diseases, including multiple sclerosis (MS), Alzheimer's disease (AD), Parkinson's disease, prion disease, and AIDS dementia. IL-3 induces the activation of JAK-STAT and MAP kinase pathways in microglial cells and leads to a IL3-induced activation of microglia. (Bright, et al. (2004), Glia, 45, 188-96). Thus, there is evidence for the presence of the IL-3 receptor and ligand in the nervous system.

For IL-3 it was shown that it has a neuroprotective activity on rat cortical cells in culture. IL-3 had a neuroprotective activity in an Caspase-3/7 activity-assay in camptothecin treated primary cortical cultures (FIG. 46a). This shows that IL-3 has the potential to reduce cell death in neuronal cells. We also have shown that IL-3 induces Akt-Pathway in these cells, which demonstrates that a typically anti-apoptotic pathway is activated by the treatment of neuronal cells with IL-3 (FIG. 47).

Additionally we could show that IL-3 is effective on human neuroblastoma cells. Camptothecin treated SHSY5-Y cells had shown a reduced Caspase 3/7 activity when IL-3 was added (FIG. 46a). In summary the results show the neuroprotective effect of IL-3 in rat and human cell culture.

IL-5

Interleukin 5 (IL-5) is a well known hematopoietic factor. The IL-5 that can be employed in the inventive methods described herein are those full length coding sequences, protein sequences, and the various functional variants, chimeric proteins, muteins, and mimetics that are known and available. The structure of both the coding DNA and protein are known. For example, DNA encoding IL-5 and IL-5 proteins comprise the sequences of SEQ ID NOS:85-92.

The human IL5 cDNA encodes a protein of 115 amino acids. Interleukin-5 (IL-5) is produced by lymphocytes as a N-glycosylated, disulfide-linked antiparallel homodimer. Monomeric forms are biologically inactive. Variable molecular masses of the native protein are caused by heterogeneous glycosylation. Non-glycosylated IL5 is also biologically active. The genes encoding IL-4 and IL-5 are tightly linked and the proteins are frequently co-expressed although they are under the control of unrelated promoters. IL-5 belongs to a family of structurally related cytokines including IL-2, IL-4, GM-CSF and Growth Hormone.

While initially identified by a number of groups based on different biochemical aspects, IL-5 is now known to be the predominant cytokine in eosinophilia. IL5 is a specific hematopoietic growth factor that is responsible for the growth and differentiation of eosinophils. IL5 promotes the growth of immature hematopoietic progenitor cells BFU-E while it causes differentiation of CFU-E the proliferation of which is inhibited by IL5. IL5 strongly stimulates the proliferation, cell activation, and differentiation of eosinophilic granulocytes.

IL5 also promotes the generation of cytotoxic T-cells from thymocytes. In thymocytes IL5 induces the expression of high affinity IL2 receptors.

In one embodiment, the proteins that are at least 70%, preferably at least 80%, more preferably at least 90% identical to the full-length human IL-5 amino acid sequences can be employed in the present invention. In another embodiment, the IL-5 that can be used are those that are encoded by polynucleotide sequence with at least 70%, preferably 80%, more preferably at least 90% identical to the wildtype full-length human IL-5 coding sequence, these polynucleotides will hybridize under stringent conditions to the coding polynucleotide sequence of the wild-type full length human IL-5.

The terms "stringent conditions" or "stringent hybridization conditions" includes reference to conditions under which a polynucleotide will hybridize to its target sequence, to a detectably greater degree than other sequences (e.g., at least 2-fold over background). Stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides), for example, high stringency conditions include hybridization in 50% formamide, 1 M NaCl, 1% SDS at 37° C., and a wash in 0.1×SSC at 60 to 65° C. (see Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel. et al., Eds., Greene Publishing and Wiley-Interscience, New York (1995)). Amino acid and polynucleotide identity, homology and/or similarity can be determined using the ClustalW algorithm, MEGALIGN™, Lasergene, Wis.)

The various functional derivatives, variants, muteins and/or mimetics of IL-5 preferably retain at least 20%, preferably 50%, more preferably at least 75% and/or most preferably at least 90% of the biological activity of wild-type mammalian IL-5 activity—the amount of biological activity include 25%, 30%, 35%, 40%, 45%, 55%, 60%, 65%, 70%, 75%, 80%, 85%, 95%; and all values and subranges there between. Furthermore, the functional derivatives, variants, muteins and/or mimetics of IL-5 can also have 100% or more of the biological activity relative to wild-type mammalian IL-5 activity—the amount of biological activity including at least 105%, at least 110%, at least 125%, at least 150%, and at least 200%.

For practicing the present invention derivatives of IL-5, more preferably IL-5-mimetics, that retain their potential to protect neurons and that also have diminished action on eosinophiles, thereby reducing potential adverse effects, are preferred. Derivatives of IL-5, preferably IL-5-mimetics, can be tested in an in vitro neuroprotective assay. Substances demonstrating a positive neuroprotective effect in this assay can be further tested for their immune-modulatory activity.

To measure the biological activity of IL-5, several known assays can be employed singularly or in combination. Those IL-5 functions include its known immunomodulatory functions and to one or more functions relating to its role in neuroprotection. IL5 can be detected in Bioassays employing cell lines that respond to this factor (e.g., cell lines: B13; BCL1; T88-M; TALL-103; TF-1). IL5 can be detected also by sensitive immunoassays. Another assay involves the detection of eosinophilic colonies in a Colony formation assay (EDF, eosinophil differentiation factor) or the detection of eosinophil peroxidase.

These and other assays are described in (Kikuchi, et al. (1994), J Immunol Methods, 167, 289-98) (McNamee, et al. (1991), J Immunol Methods, 141, 81-8) O'Garra A and Sanderson C J Eosinophilic differentiation factor and its associated B cell growth factor activities. in: Clemens M J et al (eds) Lymphokines and Interferons. A practical Approach, pp. 323-43, IRL Press, Oxford 1987; (Schoenbeck, et al. (1991), J Immunol Methods, 137, 47-54) (Taguchi, et al. (1990), J Immunol Methods, 128, 65-73)

In other embodiments of the present invention combinations of IL-5 with other hematopoietic factors preparations to support their therapeutic actions, preferably by its neuroprotective action can be used. The effect exerted by these combinations can be cumulative or superadditive/synergistic. In one embodiment, various IL-5 and/or IL-5 derivatives are used in combination with each other. Likewise, IL-5 can be used in combination with one or more additional hematopoietic growth factors such as Erythropoietin, and derivatives thereof, which has recently been shown to mediate strong neuroprotective properties (e.g., Brines et al (2000) *Proc Natl Acad Sci USA* 97:10526-10531; Cerami et al (2002) *Nephrol Dial Transplant* 17:8-12; Siren A L, Ehrenreich H (2001) *Eur Arch Psychiatry Clin Neurosci* 251:179-184). In addition, IL-5 can be used in combination with, for example, various colony stimulating factors (such as G-CSF, GM-CSF or M-CSF), SCF (stem cell factor), SCPF (stem cell proliferation factor), various Interleukins (IL1, IL3, IL4, IL6, IL11, IL12), LIF, TGF-β, MIP-1-α, TNF-α, and also many other low molecular weight factors.

In one embodiment the biological activity of IL-5 is enhanced by fusion to another hematopoietic factor. Examples for such fusion protein were given for GCSF, GMCSF and IL-3. The enhanced activity can be measured in a biological activity assay as described above.

Also preferred are modifications or formulations of IL-5, or mimetic substances that increase its ability to cross the blood-brain barrier, or shift its distribution coefficient towards brain tissue. An example for such a modification is the addition of Protein transduction domain (PTD) or TAT sequences (Cao G. et al (2002) *J. Neurosci.* 22:5423-5431; Mi Z et al (2000) *Mol. Ther.* 2:339-347; Morris et al (2001) *Nat Biotechnol* 19:1173-1176; Park et al (2002) *J Gen Virol* 83:1173-1181). These sequences can also be used in mutated forms, and added with additional amino acids at the amino- or carboxyterminus of proteins. Also, adding bradykinin, or analogous substances to an intravenous application of any IL-5 preparation will support its delivery to the brain, or spinal cord (Emerich et al (2001) *Clin Pharmacokinet* 40:105-123; Siegal et al (2002) *Clin Pharmacokinet* 41:171-186).

In the mouse brain both IL-5 and IL-5 receptor alpha chain (IL-5 Ralpha) were expressed in vitro in astrocytes, but not in neurons. Expression of IL-5 Ralpha was highly regulated both in quantitative terms and in the number of alternatively spliced isoforms. In adulthood, no expression of IL-5 Ralpha was detected in normal mice, but all the isoforms were produced in mice with inflammatory reactions. IL-5 has a specific autocrine and/or paracrine function in astrocytes, maintaining the homogeneity of the activation state in a given astrocyte population. (Lins and Borojevic (2001), Growth Factors, 19, 145-52) (Sawada, et al. (1993), Neurosci Lett, 155, 175-8)

The inventors have also shown that IL-5R is expressed in the rat brain. In contrast to mouse, however, a predominant expression of IL-5R alpha in neurons was found (FIG. 56)

IL-5 had a neuroprotective activity in an Caspase-3/7 activity-assay in camptothecin treated rat primary cortical cultures (FIG. 46b). This shows that IL-5 has the potential to reduce cell death in neuronal cells. We also have shown that IL-5 induces Akt-Pathway in these cells, which demonstrates that a typically anti-apoptotic pathway is activated by the treatment of neuronal cells with IL-5 (FIG. 48).

Additionally we could show that IL-5 is effective on human neuroblastoma cells. Camptothecin treated SHSY5-Y cells had shown a reduced Caspase 3/7 activity when IL-5 was added. This shows the neuroprotective effect of IL-5 in rat and human cell culture (FIG. 46b).

GCSF

Granulocyte-colony stimulating factor (GCSF) is a well known growth factor. The GCSF that can be employed in the inventive methods described herein are those full length coding sequences, protein sequences, and the various functional variants, muteins, and mimetics that are known and available. In the discussion that follows these are referred to as GCSF derivatives.

The structure of both the coding DNA and protein are known as well as methods for recombinantly producing mammalian pluripotent granulocyte colony-stimulating factor (WO 87/01132; U.S. Pat. No. 4,810,643). For example, several amino acid sequences corresponding to G-CSF is shown in FIG. 10 and the Sequence Listing, i.e., SEQ ID NOS: 28, 29, 30, 31, 32, and 33.

In one embodiment, the proteins that are at least 70%, preferably at least 80%, more preferably at least 90% identical to the full-length human GCSF amino acid sequences described herein can be employed in the present invention, e.g., SEQ ID NO:28. In another embodiment, the GCSF that can be used are those that are encoded by polynucleotide sequence with at least 70%, preferably 80%, more preferably at least 90%, 95%, and 97% identity to the wildtype full-length human GCSF coding sequence, e.g., a polynucleotide encoding SEQ ID NO:28, these polynucleotides will hybridize under stringent conditions to the coding polynucleotide sequence of the wild-type full length human GCSF. The terms "stringent conditions" or "stringent hybridization conditions" includes reference to conditions under which a polynucleotide will hybridize to its target sequence, to a detectably greater degree than other sequences (e.g., at least 2-fold over background). Stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides), for example, high stringency conditions include hybridization in 50% formamide, 1 M NaCl, 1% SDS at 37° C., and a wash in 0.1×SSC at 60 to 65° C. (see Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995)). Amino acid and polynucleotide identity, homology and/or similarity can be determined using the ClustalW algorithm, MEGALIGN™, Lasergene, Wis.)

Examples of the various GCSF functional variants, muteins, and mimetics include functional fragments and variants (e.g., structurally and biologically similar to the wildtype protein and having at least one biologically equivalent domain), chemical derivatives of GCSF (e.g., containing additional chemical moieties, such as polyethyleneglycol and polyethyleneglycol derivatives thereof, and/or glycosylated forms such as Lenogastrim™), and peptidomimetics of GCSF (e.g., a low molecular weight compound that mimics a peptide in structure and/or function (see, e.g., Abell, *Advances in Amino Acid Mimetics and Peptidomimetics*, London: JAI Press (1997); Gante, *Peptidmimetica—massgeschneiderte Enzyminhibitoren Angew. Chem.* 106: 1780-1802 (1994); and Olson et al., *J. Med. Chem.* 36: 3039-3049 (1993)).

Additional examples of GCSF derivatives include a fusion protein of albumin and GCSF (Albugranin™), or other fusion modifications such as those disclosed in U.S. Pat. No. 6,261, 250); PEG-GCSF conjugates and other PEGylated forms; those described in WO 00/44785 and Viens et al., *J. of Clin. Oncology, Vl., Nr.* 1, 2002: 24-36; norleucine analogues of GCSF, those described in U.S. Pat. No. 5,599,690; GCSF mimetics, such as those described in WO 99/61445, WO 99/61446, and Tian et al., *Science*, Vol. 281, 1998:257-259; GCSF muteins, where single or multiple amino acids have been modified, deleted or inserted, as described in U.S. Pat. Nos. 5,214,132 and 5,218,092; those GCSF derivatives described in U.S. Pat. No. 6,261,550 and U.S. Pat. No. 4,810, 643; and chimeric molecules, which contain the full sequence or a portion of GCSF in combination with other sequence fragments, e.g. Leridistim—see, for example, Streeter, et al. (2001) *Exp. Hematol.*, 29, 41-50, Monahan et al. (2001) *Exp. Hematol.*, 29, 416-24, Hood, et al. (2001) *Biochemistry*, 40, 13598-606, Farese et al. (2001) *Stem Cells*, 19, 514-21, Farese, et al. (2001) *Stem Cells*, 19, 522-33, MacVittie, et al. (2000) *Blood*, 95, 837-45. Additionally, the GCSF derivatives include those with the cysteines at positions 17, 36, 42, 64, and 74 (of the 174 amino acid species (SEQ ID NO:37) or of those having 175 amino acids, the additional amino acid being an N-terminal methionine (SEQ ID NO:38)) substituted with another amino acid, (such as serine) as described in U.S. Pat. No. 6,004,548, GCSF with an alanine in the first (N-terminal) position; the modification of at least one amino group in a polypeptide having GCSF activity as described in EP 0 335 423; GCSF derivatives having an amino acid substituted or deleted in the N-terminal region of the protein as described in EP 0 272 703; derivatives of naturally occurring GCSF having at least one of the biological properties of naturally occurring GCSF and a solution stability of at least 35% at 5 mg/ml in which the derivative has at least $Cys^{17}$ of the native sequence replaced by a $Ser^{17}$ residue and $Asp^{27}$ of the native sequence replaced by a $Ser^{27}$ residue as described in EP 0 459 630; a modified DNA sequence encoding GCSF where the N-terminus is modified for enhanced expression of protein in recombinant host cells, without changing the amino acid sequence of the protein as described in EP 0 459 630; a GCSF which is modified by inactivating at least one yeast KEX2 protease processing site for increased yield in recombinant production using yeast as described in EP 0 243 153; lysine altered proteins as described in U.S. Pat. No. 4,904, 584; cysteine altered variants of proteins as described in WO/9012874 (U.S. Pat. No. 5,166,322); the addition of amino acids to either terminus of a GCSF molecule for the purpose of aiding in the folding of the molecule after prokaryotic expression as described in AU-A-10948/92; substituting the sequence Leu-Gly-His-Ser-Leu-Gly-Ile (SEQ ID NO:11) at position 50-56 of GCSF with 174 amino acids (SEQ ID NO:37), and position 53 to 59 of the GCSF with 177 amino acids (SEQ ID NO:39), or/and at least one of the four histadine residues at positions 43, 79, 156 and 170 of the mature GCSF with 174 amino acids (SEQ ID NO:37) or at positions 46, 82, 159, or 173 of the mature GCSF with 177 amino acids (SEQ ID NO:39) as described in AU-A-76380/91; and a synthetic GCSF-encoding nucleic acid sequence incorporating restriction sites to facilitate the cassette mutagenesis of selected regions and flanking restriction sites to facilitate the incorporation of the gene into a desired expression system as described in GB 2 213 821. Further examples of G-CSF analogs include SEQ ID NOS:64 and 65, and others described in U.S. Pat. No. 6,632,426. The contents of the above are incorporated herein by reference.

The various functional derivatives, variants, muteins and/or mimetics of GCSF preferably retain at least 20%, preferably 50%, more preferably at least 75% and/or most preferably at least 90% of the biological activity of wild-type mammalian GCSF activity—the amount of biological activity include 25%, 30%, 35%, 40%, 45%, 55%, 60%, 65%, 70%, 75%, 80%, 85%, 95%; and all values and subranges there between. Furthermore, the functional derivatives, variants, muteins and/or mimetics of GCSF can also have 100% or more of the biological activity relative to wild-type mammalian GCSF activity—the amount of biological activity including at least 105%, at least 110%, at least 125%, at least 150%, and at least 200%.

To measure the biological activity of GCSF, several known assays can be employed singularly or in combination. One example of determining GCSF function is illustrated in Example 1. Other methods for determining GCSF function are known and include a colony formation assay employing murine bone marrow cells; stimulation of proliferation of bone marrow cells induced by G-CSF; specific bioassays with cells lines that depend on G-CSF for growth or that respond to GCSF (e.g., AML-193; 32D; BaF3; GNFS-60; HL-60, M1; NFS-60; OCI/AML1a; and WEHI-3B). These and other assays are described in Braman et al. *Am. J. Hematology* 39: 194-201 (1992); Clogston C L et al *Anal Biochem* 202: 375-83 (1992); Hattori K et al *Blood* 75: 1228-33 (1990); Kuwabara T et al *Journal of Pharmacobiodyn* 15: 121-9 (1992); Motojima H et al *Journal of Immunological Methods* 118: 187-92 (1989); Sallerfors B and Olofsson *European Journal of Haematology* 49: 199-207 (1992); Shorter S C et al *Immunology* 75: 468-74 (1992); Tanaka H and Kaneko *Journal of Pharmacobiodyn.* 15: 359-66 (1992); Tie F et al *Journal of Immunological Methods* 149: 115-20 (1992); Watanabe M et al *Anal. Biochem.* 195: 38-44 (1991).

In one embodiment, the GCSF is modified or formulated, or is present as a GCSF mimetic that increases its ability to cross the blood-brain barrier, or shift its distribution coefficient towards brain tissue. An example of such a modification is the addition of PTD or TAT sequences (Cao et al. (2002) *J. Neurosci.* 22:5423-5431; Mi et al. (2000) *Mol. Ther.* 2:339-347; Morris et al. (2001) *Nat Biotechnol* 19:1173-1176; Park et al. (2002) *J Gen Virol* 83:1173-1181). These sequences can also be used in mutated forms, and added with additional amino acids at the amino- or carboxy-terminus of proteins. Also, adding bradykinin, or analogous substances to an intravenous application of any GCSF preparation will support its delivery to the brain, or spinal cord (Emerich et al. (2001) *Clin Pharmacokinet* 40:105-123; Siegal et al (2002) *Clin Pharmacokinet* 41:171-186).

In one embodiment the biological activity of GCSF is enhanced by fusion to another hematopoietic factor. The enhanced activity can be measured in a biological activity assay as described above. Such a preferred modification or formulation of GCSF leads to an increased antiapoptotic effect and/or an increase in neurogenesis. An example for such a modification is Myelopoietin-1, a GCSF/IL-3 fusion protein (McCubrey, et al. (2001), Leukemia, 15, 1203-16) or Progenipoietin-1 (ProGP-1) is a fusion protein that binds to the human fetal liver tyrosine kinase flt-3 and the G-CSF receptor.

GM-CSF

Granulocyte-macrophage colony stimulating factor (GMCSF) is a well known growth factor (see, e.g., FIG. 18, SEQ ID NOS:25, 26, and 27). The GMCSF that can be employed in the inventive methods described herein are those full length coding sequences, protein sequences, and the various functional variants, chimeric proteins, muteins, and mimetics that are known and available, for example PEGylated forms or albumin-coupled forms. The structure of both the coding DNA and protein are known as well as methods for recombinantly producing mammalian pluripotent granulocyte macrophage colony-stimulating factor (U.S. Pat. No. 5,641,663). The GMCSF receptor is also known and is described, for example, in U.S. Pat. No. 5,629,283.

In one embodiment, the proteins that are at least 70%, preferably at least 80%, more preferably at least 90% identical to the full-length human GMCSF amino acid sequences can be employed in the present invention. In another embodiment, the GMCSF that can be used are those that are encoded by polynucleotide sequence with at least 70%, preferably 80%, more preferably at least 90%, 95%, 97% and 98% identical to the wildtype full-length human GMCSF coding sequence, e.g., a polynucleotide which encodes SEQ ID NO:25, these polynucleotides will hybridize under stringent conditions to the coding polynucleotide sequence of the wild-type full length human GMCSF. The terms "stringent conditions" or "stringent hybridization conditions" includes reference to conditions under which a polynucleotide will hybridize to its target sequence, to a detectably greater degree than other sequences (e.g., at least 2-fold over background). Stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides), for example, high stringency conditions include hybridization in 50% formamide, 1 M NaCl, 1% SDS at 37° C., and a wash in 0.1×SSC at 60 to 65° C. (see Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., Eds., Greene Publishing and Wiley-Interscience, New York (1995)). Amino acid and polynucleotide identity, homology and/or similarity can be determined using the ClustalW algorithm, MEGALIGN™, Lasergene, Wis.)

The various functional derivatives, variants, muteins and/or mimetics of GMCSF preferably retain at least 20%, preferably 50%, more preferably at least 75% and/or most preferably at least 90% of the biological activity of wild-type mammalian GMCSF activity—the amount of biological activity include 25%, 30%, 35%, 40%, 45%, 55%, 60%, 65%, 70%, 75%, 80%, 85%, 95%; and all values and subranges there between. Furthermore, the functional derivatives, variants, muteins and/or mimetics of GMCSF can also have 100% or more of the biological activity relative to wild-type mammalian GMCSF activity—the amount of biological activity including at least 105%, at least 110%, at least 125%, at least 150%, and at least 200%.

For practicing the present invention derivatives of GMCSF, more preferably GMCSF-mimetics, that retain their potential to protect neurons and that also have diminished action on leukocytes, thereby reducing potential adverse effects, are preferred. Derivatives of GMCSF, preferably GMCSF-mimetics, can be tested in an in vitro neuroprotective assay, such as described in Example 17. Substances demonstrating a positive neuroprotective effect in this assay can be further tested for their immune-modulatory activity.

To measure the biological activity of GMCSF, several known assays can be employed singularly or in combination. Those GMCSF functions include its known immunomodulatory functions and to one or more functions relating to its role in neuroprotection. Other methods for determining GMCSF function include, for example, in a colony formation assay by the development of colonies containing macrophages, neutrophils, eosinophils, and megakaryocytes; in specific Bioassays with cell lines that depend in their growth on the presence of GM-CSF or that respond to this factor (e.g., cell lines: AML-193; B6SUt-A; BAC1.2F5; BCL1; Da; FDCP1; GF-D8; GM/SO; IC-2; MO7E; NFS-60; PT-18; TALL-103; TF-1; UT-7). These and other assays are described in Cebon J et al *Blood* 72: 1340-7 (1988); Katzen N A et al *European Cytokine Network* 3: 365-72 (1992); Lewis C E et al *Journal of Immunological Methods* 127: 51-9 (1990); Mortensen B T et al *Experimental Hematology* 21: 1366-70 (1993); Oez S et al *Experimental Hematology* 18: 1108-11 (1990); Roncaroli F et al *Journal of Immunological Methods* 158: 191-6 (1993); Sallerfors B and Olofsson *European Journal of Haematology* 49: 199-207 (1992); Zenke G et al *Journal of Immunoassay* 12: 185-206 (1991).

Also preferred are modifications or formulations of GMCSF, or mimetic substances that increase its ability to cross the blood-brain barrier, or shift its distribution coefficient towards brain tissue. An example for such a modification is the addition of Protein transduction domain (PTD) or TAT sequences (Cao G, et al (2002) *J. Neurosci.* 22:5423-5431; Mi Z et al (2000) *Mol. Ther.* 2:339-347; Morris et al (2001) *Nat Biotechnol* 19:1173-1176; Park et al (2002) *J Gen Virol* 83:1173-1181). These sequences can also be used in mutated forms, and added with additional amino acids at the amino- or carboxyterminus of proteins. Also, adding bradykinin, or analogous substances to an intravenous application of any GMCSF preparation will support its delivery to the brain, or spinal cord (Emerich et al (2001) *Clin Pharmacokinet* 40:105-123; Siegal et al (2002) *Clin Pharmacokinet* 41:171-186). Examples for different suitable forms and derivatives are sargramostim (Leukine®, Prokine®), Leucotropin® or molgramostim (Leucomax®).

GMCSFR mRNA has been detected in isolated microglia, astrocytes, oligodendrocytes and neurons (Sawada et al. (1993), *Neurosci Lett,* 160, 131-4); Baldwin, et al. (1993), *Blood,* 82, 3279-82). It has been shown that GMCSF stimulates the proliferation of astrocytes (Guillemin, et al. (1996), *Glia,* 16, 71-80). GMCSF also induces the release of interleukin 6 from microglia (Suzumura et al. (1996), *Brain Res,* 713, 192-8). Recently, a publication showed that interleukin 1 increased GMCSF protein production in the neuronal cell line NT2 (Dame et al. (2002), *Eur Cytokine Netw,* 13, 128-33). The presence of GMCSFR in the brain was shown on material from a human fetus on a systematic search for GMCSF receptor expression in the fetus (Dame, et al. (1999), *Pediatr Res,* 46, 358-66). Dame et al. conclude from their findings, that GMCSF may have a role in neural development in the fetus, and a role in immunosurveillance in the adult brain. Importantly, they do not mention any possible disease relevance, especially no involvement in neuroprotection. GMCSF augments choline acetyltransferase activity in vitro (SN6.10.2.2 cell line and cultured mouse septal neurons) and in vivo increases survival of lesioned rat cholinergic septal neurons after fimbria-formix transections (Kamegai, et al. (1990), *Brain Res*, 532, 323-5.) (Konishi, et al. (1993), *Brain Res*, 609, 29-35). Importantly, this finding only pertains to a certain subtype of neurons, and has not been generalized by the authors to other neuronal or neural cell types. They have not derived a general neuroprotective property of GMCSF from these data, nor have they mentioned any possible therapeutic applicability. GMCSF is upregulated in astrocytes upon addition of advanced glycosylation end products (AGEs) (Li, et al. (1998), *Mol Med*, 4, 46-60). GMCSF has been shown to promote microglia proliferation in vitro (Lee, et al. (1994), *Glia*, 12, 309-18). Recently, it has been found that GMCSF level were elevated in the cerebrospinal fluid (csf) of patients with Alzheimer's disease (Tarkowski, et al. (2001), *Acta Neurol Scand*, 103, 166-74). GMCSF has also been studied in the CSF of stroke patients (Tarkowski, et al. (1999), Stroke, 30, 321-7). In the latter study, the level of the FAS ligand, a proapoptotic protein, correlates positively with GMCSF levels in the cerebrospinal fluid of stroke patients at day 21-26 and later than 3 months. However, there is no conclusion drawn to any therapeutic usefulness of this finding in stroke patients, and no mentioning of any possible neuroprotective role of GMCSF. A release of GMCSF after stroke per se can have many reasons, and does not allow any functional prediction to be made. GMCSF crosses the blood-brain-barrier (McLay, et al. (1997), *Brain*, 120, 2083-91). This study has not been performed with the purpose of showing any therapeutic applicability of GMCSF to neurological diseases, and there is no contextual mentioning of a possible usefulness of GMCSF in neurodegenerative diseases or stroke.

In summary, the above mentioned references in the literature provide evidence for presence of the GMCSF receptor and ligand in the nervous system, but do not show any general neuroprotective property of GMCSF. These studies certainly do not imply use of GMCSF for the treatment of neurodegenerative and ischemic disorders such as stroke.

In one embodiment the biological activity of GMCSF is enhanced by fusion to another hematopoietic factor, e.g IL-3/GMCSF-fusion protein PIXY321, Immunex (Vadhan-Raj (1994), Stem Cells, 12, 253-61) (Anderson and Appelbaum (1994), Curr Opin Hematol, 1, 203-9) (Buescher, et al. (1993), Exp Hematol, 21, 1467-72); Promegapoietin; IL-3/thrombopoietin, Pharmacia (Farese, et al. (2001), Stem Cells, 19, 329-38). The enhanced activity can be measured in a biological activity assay as described above. Such a preferred modification or formulation of GCSF leads to an increased antiapoptotic effect and/or an increase in neurogenesis.

Other Hematopoeitic Growth Factors

In other embodiments of the present invention combination preparations that support its therapeutic actions, preferably its neuroprotective action can be used. The effect exerted by these combinations can be cumulative or superadditive/synergistic. In a one embodiment, the factors discussed above are used in combination with each other. Likewise, one or more additional hematopoietic growth factors such as Erythropoietin, and derivatives thereof, which has recently been shown to mediate strong neuroprotective properties (e.g., Brines et al (2000) *Proc Natl Acad Sci USA* 97:1.0526-10531; Cerami et al (2002) *Nephrol Dial Transplant* 17:8-12; Siren A L, Ehrenreich H (2001) *Eur Arch Psychiatry Clin Neurosci* 251:179-184). In addition, combinations of the above along with, for example, various colony stimulating factors (such as M-CSF), SCF (stem cell factor), SCPF (stem cell proliferation factor), various Interleukins (other than those delineated above, e.g., IL1, IL4, IL6, IL11, IL12), LIF, TGF-β, MIP-1-α, TNF-α, and also many other low molecular weight factors.

In another embodiment, the various hematopoietic growth factors with the exception of Erythropoetin may be used alone. In another embodiment, for example, in the context of stroke, one or more of the hematopoeitic factors can be combined with substances that have thrombolytic activities, e.g., tissue-plasminogen activator (TPA), streptokinase, urokinase, and/or Ancrod. GCSF and/or GMCSF can also be combined with either acetylsalicylic acid (Aspirin) or Heparin; with Melatonin; and/or substances that interfere with apoptotic signaling (e.g. inhibitors of caspases). Also, especially in, but not limited to, the treatment of amyotrophic lateral sclerosis (ALS) combinations of GCSF and/or GMCSF with Riluzole (Rilutek®), vitamins such as vitamin E, Q10, or antioxidative substances are possible. For treating Parkinson's disease, combinations of GCSF and/or GMCSF with known drugs used in the treatment of Parkinson's disease, such as Trihexyphenidyl, Selegiline, L-DOPA, Pergolide, and others may be employed. Other substances that may be combined with the hematopoietic growth factors, e.g., G-CSF and/or GM-CSF, include bFGF, anti-GPIIb/IIa, anti-ICAM, nitric oxide inhibitors, thrombolytic agents, rotamas inhibitors, calcineurin inhibitors, and cyclosporin. In addition, when treating neurodegenerative disorders the administration of one or more agents effecting neurotransmitter levels can also be included. Further, when treating cognitive conditions, one or more cholinergic agents, catecholamine reuptake inhibitors and the like may also be administered.

Combinations with existing antidepressants may also be used where advantageous, e.g., to treat depression in the individual. Non-limiting examples of antidepressants include SSRI's (selective serotonin reuptake inhibitors): Paxil (paroxetine); Prozac (fluoxetine); Zoloft (sertraline); Celexa (citalopram); Lexapro (escitalopram oxalate); Luvox (fluvoxamine), MOAI's (monoamine oxidase inhibitors): Nardil (phenelzine); Pamate (tranylcypromine); TCA's (tricyclic antidepressants) Adapin (doxepin); Anafranil (clomipramine); Elavil (amitriptyline); Endep (amitriptyline); Ludiomil (maprotiline); Norpramin (desipramine); Pamelor (nortryptyline); Pertofrane (desipramine); Sinequan (doxepin); Surmontil (trinmipramine); Tofranil (imipramine); Vivactil (protriptyline), or other drug types: Effexor (venlafaxine); Cymbalta (duloxetine); Desyrel (trazodone); Buspar (buspirone); Edronax, Vestra (reboxetine); Remeron (mirtazapine); Serzone (nefazodone); Wellbutrin (bupropion).

Neurological Conditions

Neurological conditions that can be treated according to the present invention can be generally classified into three classes: those disease with ischemic or hypoxic mechanisms; neurodegenerative diseases (see Adams et al, Principles of Neurology, 1997, 6$^{th}$ Ed., New York, pp 1048 ff); and neurological and psychiatric diseases associated with neural cell death. Other neurological conditions that can be treated according to the present invention also include enhancing cognitive ability and the treatment of brain tumors, such as glioblastomas, astrocytomas, meningiomas, and neurinomas.

Diseases with ischemic or hypoxic mechanisms can be further subclassified into general diseases and cerebral ischemia. Examples of such general diseases involving ischemic or hypoxic mechanisms include myocardial infarction, cardiac insufficiency, cardiac failure, congestive heart failure, myocarditis, pericarditis, perimyocarditis, coronary heart disease (stenosis of coronary arteries), angina pectoris, congenital heart disease, shock, ischemia of extremities, stenosis of renal arteries, diabetic retinopathy, thrombosis associated with malaria, artificial heart valves, anemias, hypersplenic syndrome, emphysema, lung fibrosis, and pulmonary edema. Examples of cerebral ischemia disease include stroke (as well as hemorrhagic stroke), cerebral microangiopathy (small vessel disease), intrapartal cerebral ischemia, cerebral ischemia during/after cardiac arrest or resuscitation, cerebral ischemia due to intraoperative problems, cerebral ischemia during carotid surgery, chronic cerebral ischemia due to stenosis of blood-supplying arteries to the brain, sinus thrombosis or thrombosis of cerebral veins, cerebral vessel malformations, and diabetic retinopathy.

Examples of neurodegenerative diseases include amyotrophic lateral sclerosis (ALS), Parkinson's disease, Huntington's disease, Wilson's disease, multi-system atrophy, Alzheimer's disease, Pick's disease, Lewy-body disease, Hallervorden-Spatz disease, torsion dystonia, hereditary sensorimotor neuropathies (HMSN), Gerstmann-Straussler-Schanker disease, Creutzfeld-Jakob-disease, Machado-Joseph disease, Friedreich ataxia, Non-Friedreich ataxias, Gilles de la Tourette syndrome, familial tremors, olivopontocerebellar degenerations, paraneoplastic cerebral syndromes, hereditary spastic paraplegias, hereditary optic neuropathy (Leber), retinitis pigmentosa, Stargardt disease, and Kearns-Sayre syndrome.

Examples of neurological and psychiatric diseases associated with neural cell death include septic shock, intracerebral bleeding, subarachnoidal hemorrhage, multiinfarct dementia, inflammatory diseases (such as vasculitis, multiple sclerosis, and Guillain-Barre-syndrome), neurotrauma (such as spinal cord trauma, and brain trauma), peripheral neuropathies, polyneuropathies, epilepsies, schizophrenia, depression, metabolic encephalopathies, and infections of the central nervous system (viral, bacterial, fungal).

By "treating" is meant the slowing, interrupting, arresting or stopping of the progression of the disease or condition and does not necessarily require the complete elimination of all disease symptoms and signs. "Preventing" is intended to include the prophylaxis of the neurological disease, wherein "prophylaxis" is understood to be any degree of inhibition of the time of onset or severity of signs or symptoms of the disease or condition, including, but not limited to, the complete prevention of the disease or condition.

Since strong expression of the GCSF receptor, and the GMCSF receptor on the large motor neurons in the spinal cord was found (see FIG. 4 i-l), and GCSF is effective in focal cerebral ischemia (see FIG. 1), where the same basic pathogenetic mechanisms are operative like in ALS and other neurodegenerative diseases, such as glutamate involvement, oxidative stress, and programmed cell death GCSF is especially suited for long-term therapy in a chronic condition such as ALS, since it is well-tolerated in humans when given chronically (Ozer et al. (2000), *J. Clin. Oncol.*, 18, 3558-85). Accordingly, in one embodiment of the present invention, the hematopoeitic growth factors such as GCSF and GMCSF alone, in combination with each other, and/or in combination with one or more additional factors can be used to treat ALS. In an additional embodiment, IL-3 and IL5 alone, in combination with each other, and/or in combination with one or more additional factors can be used.

The pathophysiology associated with Parkinson's disease, such as the involvement of oxidative stress and apoptosis also places Parkinson's disease amongst the other neurodegenerative disorders and stroke. GCSF is strongly neuroprotective in $H_2O_2$-invoked cell death in the cell line PC12 (FIG. 1b). PC12 cells display features of dopaminergic cells, for example presence of a functional dopamine transporter (Maruvama, et al. (2001), *Arch Toxicol*, 75, 209-13), and are used as in vitro models for important aspects of Parkinson's disease, for example toxicity by the MPTP metabolite MPP+ (Bai et al. (2002), *Neurosci Lett*, 321, 81-4). $H_2O_2$ is a noxious stimulus for PC12 cells that clearly models some aspects of Parkinson's disease in PC12 cells. For example, $H_2O_2$ is one of the intermediates of MPTP-evoked cellular events (Fabre et al 1999 *J Physiol Biochem* 55(4):325-31). There is a remarkable overlap in the cascade of cellular events and signaling mechanisms involved in MPTP- and $H_2O_2$-mediated cell death in dopaminergic neurons (Chun. H S, et al., *J Neurochem* 2001 February; 76(4):1010-21; Lai et al., *Biochem Pharmacol* 1993 Feb. 24; 45(4):927-33). $H_2O_2$ acts by producing reactive oxygen species (ROS) that lead to oxidative stress and apoptosis. Damage by oxygen radicals is one of the main pathophysiological events in Parkinson's disease (Bonnet and Houeto (1999), *Biomed Pharmacother*, 53, 117-21, Beal (2001), *Nat Rev Neurosci*, 2, 325-34), and antioxidant therapy is effective in patients (Beal (2002), *Free Radic Res*, 36, 455-60, Shults, et al. (2002), *Arch Neurol*, 59, 1541-50). Therefore, efficacy of GCSF in $H_2O_2$ evoked cell death in PC12 cells, a model for the important pathophysiological mechanisms of oxidative stress and apoptosis predicts efficacy in Parkinson's disease (PD): Surprisingly, the expression of the GCSF receptor in the area affected by Parkinson's disease, the substantia nigra (SN), in particular the substantia nigra pars compacta (SNC) (see FIG. 4 m-o) was demonstrated. Efficacy in a cellular model, in vivo localization of receptors, and overlap of pathophysiological mechanisms with cerebral ischemia (oxygen radicals/apoptosis) provides compelling evidence that GCSF and/or other growth factors, for example, GMCSF, can be used to treat Parkinson's disease. Efficacy testing in rodent models can be performed as exemplified in Example 5. Accordingly, in another embodiment of the present invention, the hematopoeitic growth factors such as GCSF and GMCSF alone, in combination with each other, and/or in combination with one or more additional factors can be used to treat Parkinson's disease. In an additional embodiment, IL3 and IL5 alone, in combination with each other, and/or in combination with one or more additional factors can be used.

Pathologically Parkinson's disease is defined as a neurodegenerative disorder characterized chiefly by depigmentation of the substantia nigra and by the presence of Lewy bodies. These criteria, however, are too restrictive and simple, and they do not take into account the heterogeneous clinical and pathologic presentation of Parkinson's disease and the overlap with other parkinsonian disorders, each with presumably distinct etiology. In the absence of a specific biologic marker for Parkinson's disease, the differentiation of Parkinson's disease from other parkinsonian disorders rests on clinicopathologic criteria. (see Table 2; (Dauer and Przedborski (2003), Neuron, 39, 889-909)

In one embodiment the neurological condition is Parkinsonism, with Parkinsonism being a Parkinsons disease, Secondary Parkinsonism, a familial neurodegenerative disease or a 'parkinsonism plus syndrome'.

Classification of Parkinsonism is shown in below

Primary (idiopathic) parkinsonism—Parkinson's disease (sporadic, familial)

Secondary (acquired, symptomatic) parkinsonism—infectious (postencephalitic, slow virus), drug-induced (dopamine antagonists and depletors), Hemiatrophy (hemiparkinsonism), Hydrocephalus (normal pressure hydrocephalus), hypoxia, infectious (postencephalistis), metabolic (parathyroid dysfunction), toxin (MPTP, CO, Mn, Hg. CS2, methanol, ethanol), Trauma (pugilistic encephalopathy), tumor, and vascular (multiinfarct state).

Heredodegenerative parkinsonism—Huntington's disease, Wilson's disease, Hallervorden-Spatz disease, Olivopontocerebellar and spinocerebeller degenerations, neuroacanthocytosis, Lubag (X-linked dystonia-parkinsonism), and mitochondrial cytopathies with stratial necrosis Multiple system degenerations (parkinsonism plus)—Cortical-basal ganglionic degeneration, Dementia syndromes (Alzheimer's diseases, diffuse Lewy body disease, frontotemporal dementia), Lytico-Bodig (Guamanian Parkinsonism-dementia-ALS), Multiple system atrophy syndromes (striatonigral degeneration, Shy-Drager syndrome, sporadic olivopontocerebellar degeneration (OPAC), motor neuron disease parkinsonism), Progressive pallidal atrophy, and progressive supranuclear palsy.

The inventors have shown, by the discussion contained herein, that GCSF and GMCSF have the ability to enhance neurogenesis, and improve behavioural outcome after an ischemic lesion. Neurogenesis is one mechanism that can lead to increased plasticity of neural networks, and can replace gradual loss of neurons. Therefore, one embodiment of the present invention is to provide enhancement, improvement or an increase in cognitive ability to an individual suffering from, displaying, and/or believed to some level of cognitive loss by administering one or more compositions as described herein to the individual in accordance with the administration discussion herein. In an alternative embodiment, cognitive enhancement may also benefit those individuals even useful under non-pathological conditions, e.g, those individuals who do not present with cognitive impairment.

Determining cognitive ability and therefore enhancement is known by one of skill in the art. Where increases or enhancement of cognitive ability are measured, they are compared before administration of the compositions of the invention and after the administration (and can also be measured during the administration in some embodiments) using the same test, e.g., with same criteria, parameters, etc.

In addition, the use of compositions according to the invention in cognition enhancement is not limited to a non-pathological decline in mental capacity, but can also be applied to boosting the normal, physiological repertoire of mental capabilities, for example memory enhancement, enhancement of fine motor coordination, and/or enhancement of logical capabilities.

Depression is characterized by sadness, loss of interest in activities, and decreased energy. Other symptoms include loss of confidence and self-esteem, inappropriate guilt, thoughts of death and suicide, diminished concentration, and disturbance of sleep and appetite. A variety of somatic symptoms may also be present. Though depressive feelings are common, especially after experiencing setbacks in life, depressive disorder is diagnosed only when the symptoms reach a threshold and last at least two weeks. Depression can vary in severity from mild to very severe.

Depression can affect individuals at any stage of the life span, although the incidence is highest in the middle ages. There is, however, an increasing recognition of depression during adolescence and young adulthood (Lewinsohn, et al. (1993), J Abnorm Psychol, 102, 110-20). Depression is essentially an episodic recurring disorder, each episode lasting usually from a few months to a few years, with a normal period in between. In about 20% of cases, however, depression follows a chronic course with no remission (Thomicroft and Sartorius (1993), Psychol Med, 23, 1023-32), especially when adequate treatment is not available. The recurrence rate for those who recover from the first episode is around 35% within 2 years and about 60% at 12 years. The recurrence rate is higher in those who are more than 45 years of age. One of the particularly tragic outcomes of a depressive disorder is suicide. Around 15-20% of depressive patients end their lives by committing suicide. Suicide remains one of the common and avoidable outcomes of depression. To summarize, depression is a common mental disorder, causing a very high level of disease burden, and is expected to show a rising trend during the coming 20 years.

Depression can harm a patient constantly (unipolar) or have a bipolar character (manic or bipolar depression). The bipolar depression is marked by extreme mood swings, from "highs" of excessive energy and elation to "lows" of utter despair and lethargy. Manic depression is often treated with Lithium, which evens out the mood swings.

The depression can be a Seasonal Affective Disorder (SAD). It is a type of depression which generally coincides with the approach of winter, starting with September and lasting until Spring brings longer days and more sunshine.

The depression can be a postnatal depression that can occurs from about 2 weeks and up to 2 years after the birth.

Attempts have been made to classify the severity of a depression, eg. (Abdel-Khalek (2003), Psychol Rep, 93, 544-60) identified the following eight basic dimensions i.e., Pessimism, Weak Concentration, Sleep Problems, Anhedonia, Fatigue, Loneliness, Low Self-esteem, and Somatic Complaints to define the profile of children's and adolescents' depression.

Depression can occur as an idiopathic disease (with no somatic disease associated with it), or it can be a psychiatric symptom of a somatic disorder, especially a number of neurodegenerative disorders. Depressive disorders (DDs) are frequent psychiatric comorbidities of neurological disorders like multiple sclerosis, stroke, dementia, migraine, Parkinson's disease, and epilepsy. The clinical manifestations of DDs in these neurological disorders are identical to those of idiopathic mood disorders. Neurodegenerative disorders often exhibit "classical" psychiatric symptoms as an initial presentation of the disease. The symptomatology of depression in the context of a neurodegenerative disorder may differ from depression alone. In the following some neurodegenerative disorders that have depression as a symptom are listed:

1. Multiple Sclerosis
2. Traumatic brain injury: Depression also affects patients with traumatic brain injury (TBI): Between 30% and 38% of patients with TBI can be classified as depressed (Seel and Kreuzer 03)
3. Stroke: Approximately 30% of stroke patients are clinically depressed. (Williams 86)
4. Dementia and Alzheimers disease
5. Migraine
6. Parkinsons disease: Depressive symptoms occur in approximately half of PD patients and are a significant cause of functional impairment for PD patients. There is accumulating evidence suggesting that depression in PD is secondary to the underlying neuroanatomical degeneration, rather than simply a reaction to the psychosocial stress and disability. The incidence of depression is correlated with changes in central serotonergic function and neurodegeneration of specific cortical and subcortical pathways. Understanding comorbid depression in PD may therefore add to the understanding of the neuroanatomical basis of melancholia.
7. Epilepsy: Epilepsy is a chronic condition that has complex effects on social, vocational, and psychological function. Several psychiatric disorders have been shown to have increased prevalence in persons with epilepsy compared to the general population. Depression appears to be the most common psychiatric comorbidity, but anxiety and other diagnoses have not been extensively investigated. In epilepsy, however, Depressive Disorders can frequently also present with clinical characteristics that differ from those of idiopathic depression and fail to meet the criteria included in the Diagnostic and Statistical Manual of Psychiatric Disorders-Fourth Edition. Several studies have found that depression or psychological distress may be the strongest predictors of health-related quality of life, even including seizure frequency and severity, employment, or driving status (Gilliam, et al. (2003), Epilepsy Behav, 4 Suppl 4, 26-30). Clinically depressed people with epilepsy reported higher levels of perceived severity and bother from seizures, as well as greater problems with overall seizure recovery than did nondepressed people experiencing similar types of seizures. The pervasive influence of depressive symptoms on reports of seizure activity suggests that people with epilepsy should be screened for depression. These data highlight the importance of detecting and treating depression among people with epilepsy (Gilliam, Hecimovic, and Sheline (2003), Epilepsy Behav, 4 Suppl 4, 26-30).

8. Huntington's disease: Huntington's disease (HD) is a neurodegenerative process that is manifest as deterioration in a person's motor control, cognition and emotional stability. Emotional instability is reflected through a variety of symptoms such as personality change, anxiety and irritability. Cognitive decline may precede motor symptoms in Huntington's disease (HD). Depression is common in HD and has also been linked to cognitive impairment. Depressed mood and estimated time to disease onset, calculated by using DNA mutation length, both were significant predictors of working memory performance. Findings are consistent with and contribute to existing research with individuals presymptomatic for HD, identifying a potentially remediable contribution to cognitive decline (i.e., depressed mood) (Nehl, et al. (2001), J Neuropsychiatry Clin Neurosci, 13, 342-6). Depression may also occur in relation to other somatic diseases not listed here.

Recently, new exciting progress has been made towards the pathogenesis of depression that implies that depression is linked to neurodegenerative events in brain structures, and to the possible failure of correct adult neurogenesis in hippocampal structures. Therefore, hematopoietic growth factor, e.g., G-CSF, GM-CSF, IL3 and/or IL5 treatment with both its anti-apoptotic actions and pro-regenerative actions (including stimulation of endogenous adult neural stem cells) as described herein may be used to treat depression.

The following describes research related to the neurodegenerative concept of depression (Reviewed by Kempermann and Kronenberg (2003), Biol Psychiatry, 54, 499-503).

The study of morphological alterations of depressive patients has revealed structural changes in the hippocampus including grey matter changes (Sheline (2000), Biol Psychiatry, 48, 791-800). Studies of early-onset recurrent depression, late life depression associated with neurologic disorders, and bipolar illness have revealed structural brain changes within a neuroanatomical circuit. This circuit has been termed the limbic-cortical-striatal-pallidal-thalamic tract and is comprised of structures which are extensively interconnected. In three-dimensional magnetic resonance imaging studies of affective illness, many of the structures that comprise this tract have been found to have volume loss or structural abnormalities. Mechanisms proposed to explain volume loss in depression include neurotoxicity caused neuronal loss, decreased neurogenesis, and loss of plasticity. These aspects can all be treated by activities of GCSF or GMCSF, Il-3 or IL-5. One favoured hypothesis is a disturbance in adult hippocampal neurogenesis (Kempermann and Kronenberg (2003), Biol Psychiatry, 54, 499-503, Jacobs, et al. (2000), Mol Psychiatry, 5, 262-9, Jacobs (2002), Brain Behav Immun, 16, 602-9). Depression and other mood disorders are therefore 'stem cell disorders'. Recent research brought up new aspects on how adult hippocampal neurogenesis is regulated. One of the factors that potently suppresses adult neurogenesis is stress, probably due to increased glucocorticoid release. (Jacobs, Praag and Gage (2000), Mol Psychiatry, 5, 262-9).

Adult hippocampal neurogenesis was first described in 1965 by Altman and Das, and underwent several rediscoveries. A broader interest in the phenomenon was first sparked in the early 1980s by reports on activity correlated neurogenesis in the brain of adult canaries. Marking proliferating cells in the brain with bromodeoxyuridine (BrdU) in combination with confocal laser scanning microscopy, instead of the more cumbersome use of tritiated thymidine and autoradiographic techniques, allowed a more straightforward quantitative approach to adult neurogenesis. A subset of the new cells survives, migrates into the granule cell layer and differentiates into neurons. They establish axonal projections to area CA3 along the mossy fiber tracts, as do all other granule cells in the granule cell layer, and become virtually indistinguishable from the surrounding older cells.

The finding that chronic antidepressive treatment alleviates the decrease in adult neurogenesis strengthens the hypothesis outlined above (Benninghoff, et al. (2002), J Neural Transm, 109, 947-62, Dremencov, et al. (2003), Prog Neuropsychopharmacol Biol Psychiatry, 27, 729-39, D'Sa and Duman (2002), Bipolar Disord, 4, 183-94, Duman, et al. (2001), J Pharmacol Exp Ther, 299, 401-7, Duman, et al. (1999), Biol Psychiatry, 46, 1181-91).

Therefore, in another embodiment of the present invention, the hematopoeitic growth factors, for example, G-CSF and GM-CSF, alone, in combination with each other, in combination with additional factors as described herein, can be used to treat depression and/or provide prophylactic depression therapy by, for example, administration to a patient predisposed to depression or expected to develop depression symptoms. In an additional embodiment, IL-3 and IL5 alone, in combination with each other, and/or in combination with one or more additional factors can be used.

In one embodiment, depression can be treated with formulations with longer plasma half-lives, such as described hereinabove, for example PEGylated forms (PEGfilgrastim), albumin-coupled forms (albugranin). Treatment will not be limited to idiopathic depression, but used also for symptomatic depressions, and depression as a co-morbidity. In another embodiment, the treatment can provide weekly subcutaneous injections and which may be combined with orally available agonists of the cognate receptors in the brain. Treatment doses can be as described hereinabove, and in one preferred embodiment, can be from 0.1 to 1000 µg/kg body weight of the factor (or combination of factors) daily. The similar neurochemical milieu around the ischemic core and the site of trauma, along with similarly altered gene transcription suggest that similar neuroprotective strategies, aimed at interference with harmful mechanisms should be effective in cerebral ischemia and traumatic brain injury. The goal of such therapy in both types of injuries is to minimize activating toxic pathways and to enhance activity of endogenous neuroprotective mechanisms as the balance between these pathways will eventually determine the fate of the tissue at risk. Indeed, most neuroprotectants found to be effective in models of experimental stroke are also effective in models of experimental traumatic brain injury (TBI).

In light of the common pathological and protective processes active in cerebral ischemia and traumatic brain injury, as well as, a common response to neuroprotective strategies indicates that GCSF therapy will be effective in traumatic brain injury. There has been one study that examined GCSF under conditions of traumatic brain injury (Heard. et al. (1998), *Crit. Care Med.*, 26, 748-54). However this study did not aim at any neuroprotective effects of GCSF (filgrastim), but merely reducing infection parameters (primary endpoints of the study: increase in absolute neutrophil count, safety of filgrastim, and frequency of nosocomial infections (pneumonia, bacteremia, and urinary tract infection)). There was no improvement of mortality in that study. In the context of clinical safety, this study demonstrated that GCSF administration is safe for TBI, confirming the safe practicability of GCSF treatment for neuroprotection according to the present invention. Accordingly, in another embodiment of the present invention, the hematopoeitic growth factors, for example GCSF and GMCSF, alone, in combination with each other, and/or in combination with one or more additional factors can be used to treat cerebral ischemia and traumatic brain injury, for example, by providing a prophylactic way of protecting neuronal cells in those patients with the injury. In an additional embodiment, IL-3 and IL5 alone, in combination with each other, and/or in combination with one or more additional factors can be used.

Since the basic pathophysiological mechanisms operative in cerebral ischemia due to cardiac failure and resuscitation are comparable to those occurring under cerebral ischemia due to occlusion of blood vessels (see Example 1), GCSF therapy will also be effective under conditions of cardiac problems for neuroprotection. Therefore, in another embodiment of the present invention, the hematopoeitic growth factors, for example, GCSF and GMCSF, alone, in combination with each other, and/or in combination with one or more additional factors can be used to treat ischemia as a result of cardiac problems/diseases and/or provide prophylactic neuroprotective therapy. In an additional embodiment, IL-3 and IL5 alone, in combination with each other, and/or in combination with one or more additional factors can be used. Therapy can be started as soon as emergency resuscitation is started. Alternatively, in patients belonging to known risk groups for cardiac problems (prior myocardial infarction, high blood cholesterol levels, high blood pressure, diabetes, smoking), a prophylactic continued therapy with the hematopoietic growth factors, for example, GCSF, can also be performed, e.g. using a slow release form of the factor(s).

Likewise, these above considerations apply to the large group of patients that undergo surgery with subsequent cerebral ischemia. In particular, cardiac surgery (Hogue et al. (1999), *Circulation,* 100, 642-7), and surgery on the large blood vessels supplying the brain (e.g. carotid endarterectomies) have a high risk of neurological complications associated with them. An objective, retrospective review of 358 carotid endarterectomies performed in the neurosurgical teaching units of the University of Toronto in the year 1982 demonstrated a perioperative stroke rate of 3.9% and a death rate of 1.5%. Most (82%) surgical neurological complications occurred after the immediate post-operative period (24 hours). This high incidence of delayed stroke suggests that most perioperative strokes are embolic rather than hemodynamic. A 5-6% combined morbidity and mortality should be expected in carotid endarterectomy (Group (1986), *Stroke,* 17, 848-52). These and other data demonstrate a clear need for a prophylactic neuroprotective therapy in these procedures. Therefore, in another embodiment of the present invention, the hematopoeitic growth factors, for example, GCSF and GMCSF, alone, in combination with each other, and/or in combination with one or more additional factors can be used to treat ischemia as a result of surgically induced cerebral ischemia and/or provide prophylactic neuroprotective therapy. In an additional embodiment, IL-3 and IL5 alone, in combination with each other, and/or in combination with one or more additional factors can be used. In one embodiment, the treatment is started in the at risk patients prior to a major surgical procedure.

In another embodiment of the present invention, the hematopoeitic growth factors, for example, such as GCSF and GMCSF, alone, in combination with each other, and/or in combination with one or more additional factors can be used to treat multiple sclerosis (MS) and/or provide prophylactic neuroprotective therapy in multiple sclerosis patients. This method is based on the presence of the GCSF receptor on oligodendrocytes, supporting a direct efficacy of GCSF on the primary target cells of the MS. In addition, the GCSF receptor is present on nerve cells and their processes, which are compromised at later stages of the disease, and could correlate with lasting disabilities (Cid, et al. (2002), *J Neurol Sci,* 193, 103-9). Indeed, recently a paradigm shift in therapeutic concepts for multiple sclerosis from immunomodulation to neuroprotection has occurred, as it appears that neurodegenerative mechanisms are most important for the disabling aspects of multiple sclerosis (Bo, et al. (2003), Mult Scler, 9, 323-31, Bjartmar, et al. (2003), J Neurol Sci, 206, 165-71, Wujek, et al. (2002), J Neuropathol Exp Neurol, 61, 23-32, Bjartmar, et al. (2001), Neurology, 57, 1248-52, Peterson, et al. (2001), Ann Neurol, 50, 389-400, Bjartmar and Trapp (2001), Curr Opin Neurol, 14, 271-8, Bjartmar, et al. (2000), Ann Neurol, 48, 893-901, Bjartmar, et al. (1999), J Neurocytol, 28, 383-95, Trapp, et al. (1999), Curr Opin Neurol, 12, 295-302, Trapp, et al. (1998), N Engl J Med, 338, 278-85, Neuhaus, et al. (2003), Trends Pharmacol Sci, 24, 131-8, Pryce, et al. (2003), Brain, 126, 2191-202, Waubant (2003), Expert Opin Emerg Drugs, 8, 145-61, Graumann, et al. (2003), Brain Pathol, 13, 554-73, Golde, et al. (2003), Eur J Neurosci, 18, 2527-37). Even areas in the brain that appear normal with regard to white matter changes show signs of neurodegeneration. Axonal pathology and neurodegeneration therefore are important therapeutic targets in Multiple Sclerosis. GCSF and GMCSF with their anti-apoptotic activity in neurons, as shown in the present invention, and their pro-regenerative potential (by enhancing neurogenesis and plasticity) supports that the compositions described herein can be used as new therapies for treating Multiple Sclerosis. In an additional embodiment, IL-3 and IL5 alone, in combination with each other, and/or in combination with one or more additional factors can be used.

Furthermore, pathophysiological mechanisms in multiple sclerosis overlap with important mechanisms in cerebral ischemia, e.g. the involvement of nitric oxide (Smith, et al. (2001), *Ann Neurol,* 49, 470-6), and involvement of glutamate excitotoxicity (Pitt, et al. (2000), *Nat Med,* 6, 67-70). In light of this information, the hematopoeitic growth factors such as GCSF and GMCSF are a novel treatment option for multiple sclerosis which while not being bound to any particular mechanism or theory protects neurons directly as opposed to common treatments which reduce inflammation. In an additional embodiment, IL-3 and IL5 alone, in combination with each other, and/or in combination with one or more additional factors can be used.

Another embodiment of the present invention relates to the neuroprotective treatment of schizophrenia. There has been surprising evidence in the recent years of progressive grey matter loss in schizophrenics. This evidence has been primarily provided by novel magnetic resonance imaging techniques. Although neurodegenerative processes in schizophrenia are not understood at the molecular level, neuroprotective treatment in schizophrenia with GCSF and/or GMCSF is a novel approach to this disease. In an additional embodiment, IL-3 and IL5 alone, in combination with each other, and/or in combination with one or more additional factors can be used.

To test the efficacy of hematopoietic growth factors, such as GCSF, in the protection of primary neurons neurons can be prepared as follows. 10-12 rat cortices can be prepared from embryos of the stage E18 (embryonic day 18). Tissue can be dissociated using trypsin [10 mg/ml]/EDTA/DNase [5 mg/ml] (Roche diagnostics, Mannheim, Germany) in HBSS (Hanks balanced salt solution, BioWithakker). The digest can be stopped using 4 parts medium (neurobasal medium+1 ml 50× B-27 supplement (Invitrogen)+0.5 mM L-glutamine+25 µM glutamate) and can be centrifuged at room temperature for 5 min at 800 g. The pellet can be dissolved in 5 ml medium and cell number determined by counting (Neubauer slide). The cells can be plated at a density of 250 000 cells per well of a 24-well-plate on cover slips which can be coated with poly-L-lysine. These neurons can then be treated with combinations of a protective stimulus (GCSF) and a noxious stimulus (glutamate, 100 µM). GCSF is applied 30 min prior to treatment of cultures with glutamate. Control groups are treated with either no GCSF (just saline) or no glutamate. After 24 h, neuronal cell death can be determined using the LDH assay (Roche Diagnostics, Mannheim, Germany), following the manufacturers recommendations. Alternatively, other noxious stimuli known for inducing cell death can be used, e.g., NMDA and glycine, 3-nitropropionic acid (3-NPA), $H_2O_2$, staurosporine, hypoxia/glucose deprivation, potassium withdrawal, MPP+, Interleukin-1beta, TNFalpha, FAS ligand or others known to be harmful to cells and neurons. Different assays can also be used for assessing cell death or relative cell survival, e.g. the cell-death ELISA (Roche Diagnostics), Annexin/propidium iodide staining followed by a laser-scanning cytometry analysis (Kamentsky (2001), *Methods Cell Biol*, 63, 51-87), Compucyte, Cambridge, Mass.), counting of cell nuclei with apoptotic features following DAPI or HOECHST33342 staining (condensation, fragmentation), counting of cells positive for activated caspase 3 after immunostaining with a cleavage-specific antibody (e.g., Promega caspase 3 antibody), or an assay for caspase3 activity in cell lysates (e.g., ApoOne Assay, Promega; Western blots, Elisas), or any other assay suited for measuring cell survival or apoptotic features. Alternatively, other cells can be used, for example differentiated PC12 cells, HN33 cells, SHSY5 cells, primary hippocampal neurons, primary motor neurons, primary sensory ganglia cells, primary mesencephalic cultures, neuronal stem cells, differentiated ES cells, or other neuron-like cells known in the art, or cells exhibiting one or more neuronal phenotypes. Times and concentrations exemplified here can also be varied, for example, GCSF can be applied concomitantly with a stimulus, or before or after the stimulus. Varying concentrations of the factor (or combination of factors) can also be used, e.g. 0.1-100 µg/ml. In principal, this assay can also be adapted for the use in brain slice cultures.

To test the effectiveness of hematopoietic growth factors, such as GCSF, in a model of brain trauma (controlled cortical impact) the following can be performed. Experimental protocols can be approved by the local ethics committee. Twenty male Wistar rats (Charles River, Germany) weighing 280 to 320 g can be randomly assigned to the following groups: A (Control group, n=10, traumatic brain injury (TBI), treatment with 2 ml saline 0.9% for 90 min beginning 30 min TBI); B (GCSF group, n=10, ischemia for 90 min, treatment with 60 µg/kg body weight of recombinant G-CSF, Neupogen®, Amgen, Europe B.V., Netherlands, soluted in 2 ml saline 0.9% for 90 min beginning 30 min TBI); C (sham-operated GCSF-treated control group, n=10, sham operation, treatment with 60 µg/kg body weight of recombinant G-CSF, Neupogen®, Amgen, Europe B.V., Netherlands, soluted in 2 ml saline 0.9% for 90 min beginning 30 min after TBI).

Animals can be anesthetized with an intraperitoneal injection of 100 mg/kg body weight ketaminehydrochloride (WDT, Garbsen, Germany). Anesthesia can be maintained with 50 mg/kg body weight, if necessary. A PE-50 polyethylene tube can be inserted into the right femoral artery for continuous monitoring of mean arterial blood pressure, blood gases, hematocrit, leukocyte count, and blood glucose levels. The right femoral vein can be cannulated by a PE-50 tube for treatment infusion. During the experiment, rectal temperature can be monitored and maintained at 37° C. by a thermostatically controlled heating pad (Föhr Medical Instruments, Germany).

For TBI the skin then can be cut around the probe and the skull exposed and cleaned. TBI can be inflicted using a weight-drop device with indirect impact, modified for compatibility with microdialysis (a weight of 150 g dropped from 40 cm onto a PVC cylinder with a Teflon point of 2.0 mm diameter). Sham operated controls can be identically prepared to rats that received TBI, without the trauma.

In all animals outcome can be measured by mortality, as well as, Neurological Severity Scores (NSS), performed daily for 1 week after traumatic brain injury by an investigator blinded to the experimental groups. Neurological function can be graded on a scale of 0 to 16 (normal score, 0; maximal deficit score, 16). NSS is a composite of motor, sensory, and reflex tests and includes the beam balance test. In the severity scores of injury, 1 score point is awarded for the inability to perform the test or for the lack of a tested reflex; thus, the higher score, the more severe is the injury.

One week after TBI, the rats can be anesthetized with ketamine 150 mg/kg body weight and decapitated. The brains can be removed, and fixed with 4% paraformaldehyde in 0.1 mol/l phosphate buffer for 24 hrs. After paraffin-embedding, 1-µm-thick sections can be cut and used for H&E staining, Nissl staining and immunohistochemical analysis.

Immunohistochemical study can be performed with antisera against myeloperoxidase (DAKO, USA), and G-CSFR (Santa Cruz Biotechnology Inc., USA). Antisera can be generated in rabbits immunized with the isolated human protein (anti-myeloperoxidase) or with a synthetic peptide mapping the carboxy terminus of G-CSFR of mouse origin, respectively. For antigen retrieval, sections provided for G-CSFR immunohistochemistry can be heated for 20 min in a 10 mM citrate buffer at 99° C. Sections can be then incubated in normal swine serum (10% in phosphate-buffered saline) for 30 min and then in the primary antisera overnight at 4° C. The primary antibodies can be diluted 1:150 (myeloperoxidase) 1:400 (G-CSFR). Immunoreactivity can be visualized by the avidin biotin complex method. (Vectastain, Vector Laboratories, USA). Sections can be developed in 0.02% diaminobenzidine (DAB) with 0.02% hydrogen peroxide. The reaction product can be intensified by the addition of 0.02% cobalt chloride and nickel ammonium sulfate. Neuronal survival after TBI can be measured by quantifying neurons under the microscope (magnification×40) in the hippocampus of G-CSF treated animals and controls. Invasion of neutrophilic granulocytes (NG) can be measured semiquantitatively on a four point scale (0=MPO negative, 1=low MPO expression, 2=moderate MPO expression, 3=strong MPO expression).

The description provided herein demonstrates that GCSF and GM-CSF as well as IL-3 and IL-5 can stimulate neuronal stem cells to differentiate into a neuronal cell type, these four cytokines are valuable in treating neurodegenerative diseases. Independent of the pathogenic mechanism treatment of a patient with neuronal damage GCSF and GMCSF induce the differentiation of stem cells in the brain into new neurons. These newborn neurons are able to take on the lost function and in the end lead to a (at least partial) recovery of the patient.

For Multiple Sclerosis it was shown that several cytokines are upregulated in the brain. (Baranzini, et al. (2000), J Immunol, 165, 6576-82) It has become evident that multiple sclerosis (MS) has significant neurodegenerative components. An increasing number of reports show neuronal and axonal damage in MS patients and experimental allergic encephalomyelitis (EAE) in an animal model of MS. The mechanisms behind this neurodegeneration are unknown, but evidence suggests immune-mediated damage. (Giuliani and Yong (2003), Int MS J, 10, 122-30). These data show that the mode of action of Hematopoietic factors is still thought to be immune-mediated.

In contrast to this, in one embodiment of the present invention a direct action of Hematopoietic factor directly on a neuron or a neuronal stem cell, with the Hematopoietic factor being G-CSF, GM-CSF, IL-3 or IL-5. The beneficial effect is given by preventing/treating/providing prophylaxis for neuronal and axonal damage and/or recover from damage by formation of new neurons.

Huntington's disease (HD) is a devastating genetic disorder. Despite the absence of effective therapy, there has been an explosion in interest for developing treatment strategies aimed at lessening or preventing the neuronal death that occurs in this disease. In large part, the renewed interest in neuroprotective strategies has been spurred by our increasing understanding of the genetic and molecular events that drive the underlying neuropathology of HD. (Emerich (2001), Expert Opin Biol Ther, 1, 467-79)

There is evidence in HD that cell death is mediated through mitochondrial pathways, and mitochondrial deficits are commonly associated with HD. Keene et al. have previously reported that treatment with tauroursodeoxycholic acid (TUDCA), a hydrophilic bile acid, prevented neuropathology and associated behavioral deficits in the 3-nitropropionic acid rat model of HD. They show that TUDCA is a nontoxic, endogenously produced hydrophilic bile acid that is neuroprotective in a transgenic mouse model of HD and, therefore, may provide a novel and effective treatment in patients with HD. (Keene, et al. (2002), Proc Natl Acad Sci USA, 99, 10671-6)

Other approaches to treat HD include novel anti-oxidants (such as BN82451 (Klivenyi, et al. (2003), J Neurochem, 86, 267-72), intracerebrally delivered neurotrophic factors (Anderson, et al. (1996), Proc Natl Acad Sci USA, 93, 7346-51); (Perez-Navarro, et al. (2000), J Neurochem, 75, 2190-9) the use of antiglutamatergic drugs ((Kieburtz (1999), J Neural Transm Suppl, 55, 97-102)) or the use of caspase inhibitors (Toulmond, et al. (2004), Br J Pharmacol, 141, 689-97)

All of these possibilities are highlighted in the context that HD is a neurodegenerative disorder in which genetic detection provides a clear and unequivocal opportunity for neuroprotection. (Emerich (2001), Expert Opin Biol Ther, 1, 467-79).

Other neurodegenerative trinucleotide disorders are also characterised by selective and symmetric loss of neurons in motor, sensory, or cognitive systems. Neuroprotective strategies are a chance for all these diseases. The neuroprotective activity of G-CSF, GM-CSF IL-3 and/or IL-5 can be used pharmacologically to treat neurodegenerative trinucleotide disorders, like HD or even prevent from developing symptoms.

Currently, glaucoma is recognised as an optic neuropathy. Selective death of retinal ganglion cells (RGC) is the hallmark of glaucoma, which is also associated with structural changes in the optic nerve head. The process of RGC death is thought to be biphasic: a primary injury responsible for initiation of damage that is followed by a slower secondary degeneration related to noxious environment surrounding the degenerating cells. For example, retinal ischaemia may establish a cascade of changes that ultimately result in cell death: hypoxia leads to excitotoxic levels of glutamate, which cause a rise in intracellular calcium, which in turn, leads to neuronal death due to apoptosis or necrosis. Neuroprotection is a process that attempts to preserve the cells that were spared during the initial insult, but are still vulnerable to damage. (Kaushik, et al. (2003), J Postgrad Med, 49, 90-5). Hematopoietic factors like G-CSF, GM-CSF, IL-5 or IL-3 have the potential to protect RGC from dying and therefore will be of great use at least in arresting the progression of glaucoma.

In one embodiment the growth factor to treat Glaucoma is a Hematopoietic factor; e.g. G-CSF, GM-CSF, IL-3 or IL-5. In another embodiment of the present invention, the hematopoeitic growth factors, for example, such as G-CSF, GM-CSF, IL-3 and IL-5 alone, in combination with each other, and/or in combination with one or more additional factors can be used to treat Glaucoma and/or provide prophylactic neuroprotective therapy.

Theories abound and numerous animal models exist for the pathophysiology of neuropathic pain. Most studies conclude that there is a primary process that causes direct damage to the axons. Thereafter, the waters get muddied. The most common postulation states that axonal damage causes local and distal inflammatory responses. These inflammatory responses lead to hyperexcitability of the nerve at its axons with increased sodium fluxes generating sensations of pain. In addition, an up-regulation of pain pathways leads to increased pain sensation at the dorsal root ganglion and at the substantia gelatinosa of the spinal cord. Until recently patients with neuropathic pain had limited effective treatment options.

Historically, treatment options were limited to effective drugs with numerous side effects (i.e. TCAs and Tegretol), or ineffective regimens (TENS units, SSRIs (i.e. Prozac, Zoloft). Based on their modest side-effect profiles and overall effectiveness, newer Anti-epileptic drugs (AEDs) have supplanted TCAs and older AEDs as the first-line agents for the treatment of neuropathic pain. (Covington (1998), Cleve Clin J Med, 65 Suppl 1, SI21-9; discussion SI45-7)

New therapies could include newer AEDs, the use of NMDA antagonists or preventative measures with intrathecal steroids, or nerve regeneration. Reversing peripheral nerve damage through nerve regeneration with nerve growth factor is one hope to treat neuropaty. (Pittenger and Vinik (2003), Exp Diabesity Res, 4, 271-85)

In one embodiment the growth factor to treat peripheral Neuropathy is a Hematopoietic factor; e.g. G-CSF, GM-CSF, IL-3 or IL-5. In another embodiment of the present invention, the hematopoeitic growth factors, for example, such as G-CSF, GM-CSF, IL-3 and IL-5 alone, in combination with each other, and/or in combination with one or more additional factors can be used to treat peripheral Neuropathy and/or provide prophylactic neuroprotective therapy in e.g. diabetic patientsor patiens with Herpes infection.

Although the causes of peripheral neuropathy are diverse, the pathophysiological mechanisms in peripheral Neuropathy often overlaps with important mechanisms in cerebral ischemia, e.g. the involvement of nitric oxide (Smith, et al. (2001), Ann Neurol, 49, 470-6), and involvement of glutamate excitotoxicity (Pitt, et al. (2000), Nat Med, 6, 67-70). In light of this information, the hematopoeitic growth factors such as G-CSF, GM-CSF, IL-3 and IL-5 are a novel treatment option for peripheral Neuropathy and inflammatory brain disorders.

Lysosomal storage diseases result from a deficiency of specific lysosomal enzymes that normally degrade glycoproteins, glycolipids or mucopolysaccharides (MPS). When not degraded, these substances accumulate in the lysosomes, eventually causing cells to fail and damage the organ in which they live.

Enzyme replacement therapy is actually the main therapy in Lysosomal storage diseases. Neural stem cells (NSCs) in the treatment of diffuse central nervous system (CNS) alterations in a murine model of mucopolysaccharidosis VII (MPS VII), a lysosomal storage disease caused by a genetic defect in the beta-glucuronidase gene. NSCs would serve as a useful gene transfer vehicle for the treatment of diffuse CNS lesions in human lysosomal storage diseases and are potentially applicable in the treatment of patients suffering from neurological disorders. (Meng, et al. (2003), J Neurosci Res, 74, 266-77)

Early transplantation is the goal so that enzyme replacement may occur before extensive central nervous system injury becomes evident (Malatack, et al. (2003), Pediatr Neurol, 29, 391-403). Hematopoietic factors could be supportive by providing neuroprotection to the neural cells involved. Additionally, by the induction of neurogenesis it might help a patient to recover at least partly.

In one embodiment the growth factor to treat a neurological and/or psychiatric conditions is a Hematopoietic factor; e.g. G-CSF, GM-CSF, IL-3 or IL-5. In another embodiment of the present invention, the hematopoeitic growth factors, for example, such as G-CSF, GM-CSF, IL-3 and IL-5 alone, in combination with each other, and/or in combination with one or more additional factors can be used to treat neurological and/or psychiatric conditions.

In one embodiment a Hematopoietic factor is given in combination to an enzyme replacement therapy, e.g. stem cell transplantation or vector mediated gene transfer.

Spinal cord injury (SCI) will permanently handicap about 1 in 1,000 individuals over the course of their lifetime. Much effort has been devoted to understanding the complex cellular changes that develop after injury, and to inventing ways to overcome the poor capacity of the adult spinal cord for spontaneous regeneration. Programmed cell death within the damaged tissue is one of these changes. Some cells undergo apoptosis shortly after SCI. Like in other models of neurodegenerative diseases, such as stroke, some cells undergo apoptosis shortly after the injury. Hematopoietic factors like GCSF, GMCSF, IL-3 or IL-5 can be beneficial to prevent cells from dying after SCI. Application of the hematopoietic factor can be locally or systemically.

On the other hand first experiments of transplanting stem cells are promising in being beneficial for recovery from SCI (Gorio, et al. (2004), Neuroscience, 125, 179-89). Hematopoietic factors can be useful by treating a stem cell previous to transplantation into the lesion side to force the development towards a neuronal phenotype.

To test the efficacy of a hematopoietic factor in a model of Spinal cord injury the cytokine can be assayed as follows: SCI can be performed in female wild-type or gld mice on a C57BL/6 background, all matched for age (mean, 75 d old) and weight (mean, 24 g). After a laminectomy on the vertebral level Th8/9, the dorsal spinal cord is symmetrically lesioned with fine iridectomy scissors. Mice are postoperatively treated once with GCSF by intravenious injection and treated with gentamycin (5 ml/kg at 0.2 mg/ml) once a day for 7 d. Their bladders were emptied manually once a day until restoration of autonomic bladder function. The overall locomotor performance of the animals was assessed one to four weeks after the injury using the BBB locomotor, the grid-walk test and the swimming score.

Likewise the test substance can be GMCSF, IL-3 or IL-5. The application of the test substance can be done by single or repetitive depositioning at the lesion site, constant injection by a operatively attached pump, subcutaneous injection, oral administration or as suppositories. Other locomotor performance assays, like open-field or locomotor activity, rotarod performance, etc. can be useful as a readout, too.

Also cells can be transplanted into the side of injury, whereby the cell can be a stem cell after treatment with a hematopoietic factor or a cell that expresses and releases a hematopoietic factor.

To test the efficacy of hematopoietic growth factors, such as GCSF, GM-CSF, IL-3 or IL-5, in the protection of human e.g. neuroblastoma cells (SHSY5-Y) can be prepared as described herein.

Another way to test the efficacy of hematopoietic growth factors, such as GCSF, GM-CSF, IL-3 or IL-5, in the protection of neuronal or neuronal like cells (E.g. primary neuronal cells, primary neuronal cultured cells, SHSY5-Y, PC-12, etc) can be done by FACS analysis. Cells can be prepared as follows: 200,000 primary neuronal cells are seeded into a Poly-L-Lysin coated 24-well plate. After 2 weeks of culture cells are treated with 0.5 µM Staurosporin and GCSF. After 16 h of incubation the cells are harvested with Trypsin and a single cell suspension can be stained with AnnexinV-FITC and PI (e.g. bdbioscience). Cells can be analysed by flow cytometry (e.g. FACSCalibur (Becton-Dickinson)) whereby AnnexinV detects early and PI late apoptotic cells. Likewise cells can be treated with another stressor like NOR3, Camptothecin, $H_2O_2$, fas-ligand, etc. Another modification of the assay would be to exchange the hematopoietic factor (e.g. GMCSF, IL-3 or IL-5 instead of GCSF) or to use combinations thereof. Likewise derivatives can be tested for efficacy in neuroprotection. Also the detection method can be changed to another Apoptosis-marker e.g. a TUNEL-staining can be performed or a marker-protein of Apoptosis can be detected by a fluorescent labelled commercially available antibody (e.g. activated Caspase-3, cleaved PARP, etc).

Statistical Analysis

Values are displayed as means±SD. After acquiring all the data, the randomization code can be broken. ANOVA and subsequent post hoc Fisher protected least significant difference test can be used to determine the statistical significance of differences in continuous variables such as physiological parameters. The t-test can be used for comparison of neuronal damage and immunohistochemical data. The Mann-Whitney U test can be performed for nonparametric data such as the mortality rate and MPO immunohistochemistry. A p value <0.05 is considered statistically significant.

Based on the effect of hematopoietic factors, such as GMCSF, GCSF, IL-3 and IL-5, and the effects of agonizing the cognate receptors on neuronal cells, another embodiment of the present invention is to treat brain tumors or other neurological cancers by antagonizing the GMCSF and/or GCSF receptors on the cancerous cells.

Neuronal Stem Cells

Recently, the importance of forming new nerve cells (neurogenesis) for treating neurological disease has been recognized. Unlike many other tissues, the mature brain has limited regenerative capacity, and its unusual degree of cellular specialization restricts the extent to which residual healthy tissue can assume the function of damaged brain. However, cerebral neurons are derived from precursor cells that persist in the adult brain, so stimulation of endogenous neural precursors in the adult brain could have therapeutic potential.

Neurogenesis occurs in discrete regions of the adult brain, including the rostral subventricular zone (SVZ) of the lateral ventricles and the subgranular zone (SGZ) of the dentate gyrus (DG). Neurogenesis occurs in the adult animal especially after a particular neurological paradigm (e.g. cerebral ischemia (Jin et al. (2001), Proc. Natl. Acad. Sci. USA, 98, 4710-5, Jiang, et al. (2001), Stroke, 32, 1201-7, Kee, et al. (2001), Exp. Brain. Res., 136, 313-20, Perfilieva, et al. (2001), J. Cereb. Blood Flow Metab., 21, 211-7)). Neurogenesis has also been demonstrated in humans (Eriksson, et al. (1998), Nat Med, 4, 1313-7), and indeed leads to functional neurons (van Praag, et al. (2002), Nature, 415, 1030-4). In particular, the subgranular zone of the dentate gyrus, and the hilus has the potential to generate new neurons during adult life (Gage, et al. (1998), J Neurobiol, 36, 249-66). It is striking that the GCSF Receptor is expressed in this area (FIG. 4 a,d). Together with the surprising data demonstrating improvement of functional outcome after GCSF treatment (FIG. 8), and the fact that GCSF is a stem cell factor in another system (hematopoesis), it is expected that GCSF exerts part of its actions, especially the long-term effects observed (FIG. 8) via its stimulating function on adult stem cells at least in the dentate gyrus.

Figure 12:
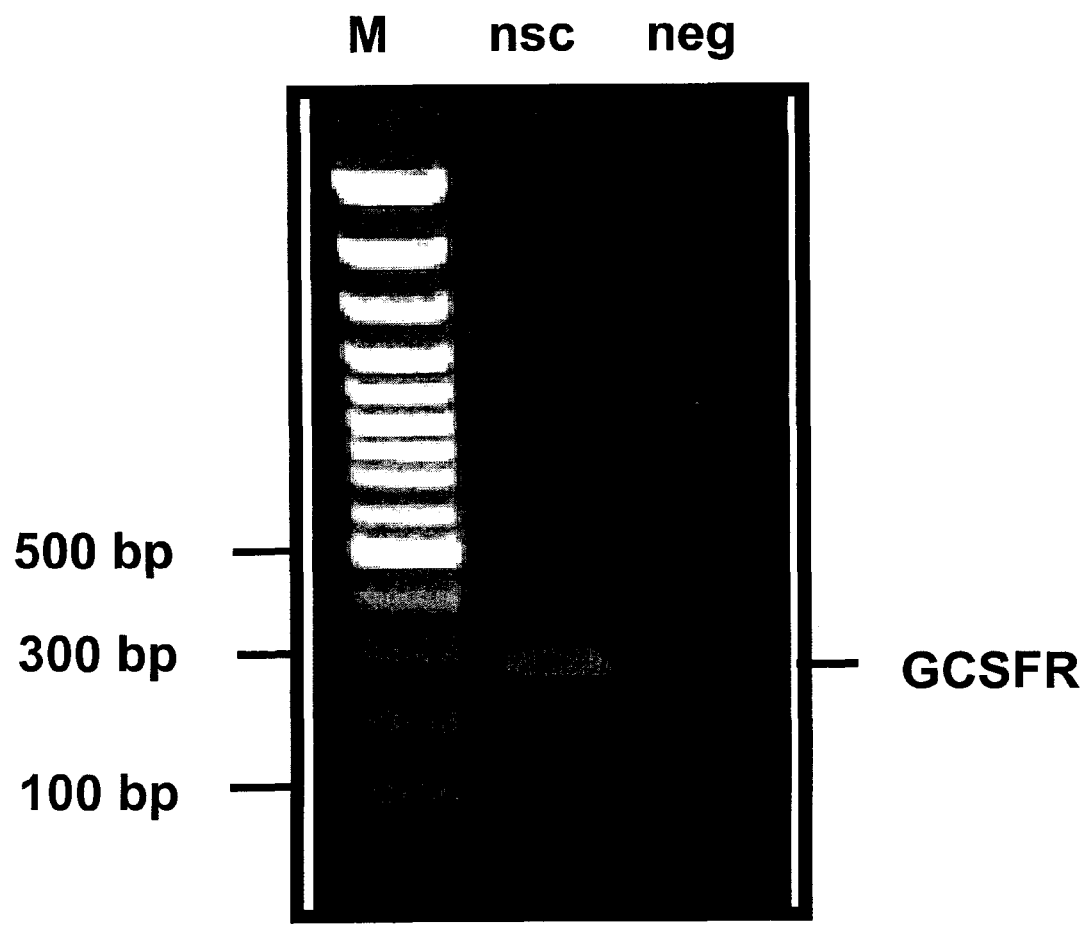
FIG. 12 demonstrates the presence of the GCSF receptor on adult neuronal stem cells (nsc) by RT-PCR (reverse transcription PCR). Shown is an agarose gel. Lane 1: size marker.

This is confirmed in the present application by demonstrating the presence of the GCSF receptor on adult neuronal stem cells, isolated from the hippocampal region encompassing the dentate gyrus from rat (FIGS. 12 and 13). The importance in neurogenesis provides another reason for the applicability and usefulness of GCSF treatment in all facets of neurodegenerative disease, and all conditions where neurons die. In contrast to acting on endogenous stem cells in the brain for the treatment of neurological conditions, GCSF can be applied to in vitro manipulations of stem cells, for example differentiation and proliferation. Stem cell therapy in humans is presently being explored for a number of diseases, in particular Parkinson's disease and stroke. It is desirable to differentiate stem cells in culture to particular types of neural cells, e.g., dopaminergic cells for the treatment of Parkinson's disease. Differentiated, or otherwise adapted cells to the new environment, are then administered via different routes to the organism. In Parkinson's disease, for example, stem cells have been injected directly into the brain to substitute for the loss of dopaminergic neurons in the substantia nigra ("replacement therapy") (Arenas (2002), Brain Res. Bull, 57, 795-808, Barker (2002), Mov. Disord., 17, 233-41).

Therefore, one embodiment of the present invention is to stimulate the growth and differentiation of neuronal stem cells or precondition neuronal stem cells prior to implantation into a mammal using the hematopoietic growth factors and derivatives thereof. A further embodiment of this method is to utilize these neuronal stem cells in methods for treating neurological disease as described herein, preferably in methods which provide a neuroprotective effect when the neuronal stem cells are administered to the individual.

In one embodiment, the stem cells can be administered intravenously or intra-arterially. It has been shown, for example, in cerebral ischemia or traumatic brain injury, that bone marrow stromal cells injected i.v. find their way to target areas in the brain (Mahmood, et al. (2001), Neurosurgery, 49, 1196-203; discussion 1203-4, Lu, et al. (2001), J Neurotrauma, 18, 813-9, Lu, et al. (2002), Cell Transplant, 11, 275-81, Li et al. (2002), Neurology, 59, 514-23). Stem cells may thus be treated by GCSF or GMCSF, or other hematopoetic factors in vitro, and then injected via different routes to patients with any of the diseases described herein.

In one embodiment of the present invention, the stem cells that are transplanted are genetically engineered to express factors that are secreted, and enhance the survival of neighboring cells, or lead to increase proliferation and/or differentiation of adult endogenous stem cells. For example, stem cells may be engineered to stably express GCSF, GMCSF, and/or one or more additional hematopoietic factors such as IL3 and/or IL5; and then be delivered to the central nervous system to constantly secrete GCSF or GMCSF, or other hematopoetic factors to the local environment. Stem cells can be treated with GCSF, GMCSF, and/or other hematopoetic factor receptor agonists. Stem cells that can be used include immortalized stem cells (e.g., oncogene immortalized), neurospheres, and embryonic stem cell (ES)-derived neural cells (Gottlieb (2002), Annu Rev Neurosci, 25, 381-407), but can also include cells like bone marrow stromal cells, or umbilical cord cells (Lu, et al (2002), Cell Transplant, 11, 275-81, Li et al (2002), Neurology, 59, 514-23). Transplantation of stem cells of variable types is a therapeutic possibility in a variety of neurological diseases, including Parkinsons disease (Isacson (2002), Brain Res Bull, 57, 839-46) and stroke (Kondziolka, et al. (2002), J Clin Neurosci, 9, 225-30).

The stem cells, e.g., human neuronal stem cells, can be treated with factors to condition them prior to transplantation. One example of those conditioning factors is growth factors. One example of conditioning is differentiating them in the direction of desired cells, e.g. neurons. (Svendsen, et al. (1999), Brain Pathol, 9, 499-513). The presence of the GCSF receptor on stem cells indicates the importance of agonists for this receptor for conditioning these cells. Adult neuronal stem cells can be treated with different concentrations of GCSF, or other GCSF receptor agonists, and assayed for increased differentiation potential by a quantitative PCR approach, e.g., by quantifying the ratio of neuronal markers (Map2, NSE (neuron-specific enolase), neurofilament, NeuN) compared to markers of neuronal stem cells (nestin). An increased ratio after treatment signals an increased differentiation of stem cells towards the neuronal lineage. A suited concentration and time window can be used to treat stem cells prior to transplantation for neurological disease.

In another embodiment of the invention, GCSF, GMCSF, derivatives thereof as well as GCSF and GMCSF receptor agonists can be used to facilitate culturing of neural cell, such as, for example, neural stem cells. In this method, the GCSF, GMCSF, derivatives thereof as well as GCSF and GMCSF receptor agonists can be added to the media and premixed before adding to the cells or can be added into the media in which the cells are being cultured. In another embodiment of this method, the neural cells are transfected with a polynucleotide which encoded GCSF, GMCSF, and derivatives thereof, which when transfected express the respective factors in the cell.

In the present application we additionally demonstrate that GCSF and GMCSF trigger the differentiation of a neuronal stem cell towards a neuronal phenotype of the cells. The importance in neurogenesis provides another reason for the applicability and usefulness of GCSF and/or GMCSF treatment in all facets of neurodegenerative disease, and all conditions where neurons die. In contrast to acting on endogenous stem cells in the brain for the treatment of neurological conditions, GCSF and GMCSF can be applied to in vitro manipulations of stem cells, for example differentiation and proliferation.

To test the efficacy of a hematopoietic factor or combinations thereof in triggering neurogenesis stem cells can be prepared as follows: Adult neural stem cells are generated and cultured. The cells are plated in 15 $cm^2$ culture flasks at a density of 4 million cells and are treated once with 100 ng/ml G-CSF. 4 days after stimulation the cells are harvested for the antibody staining and the FACS-analysis. A single cell suspension is made by triturating the neurospheres, and then the cells are pelleted by centrifugation. After resuspension in 1× phosphate-buffered saline (PBS), the cells are fixed by adding the same volume of 2% Paraformaldehyde (PFA). The cells are incubated for 15 min on ice, washed once with 1×PBS and then permeabilised by resuspension in 0.2% tween20 solved in 1×PBS. After an incubation on ice for 15 min, fetal calf serum (FCS) is added in a 1:50 dilution for blocking. As primary antibody an anti-MAP2 antibody can be used and added at a dilution 1:100. The cells are incubated for 2 hrs on ice and washed three times with 0.1% tween20 in 1×PBS. Following an incubation for 30 min on ice with a FITC-conjugated secondary antibody, the cells are washed again three times with 0.1% tween20 in 1×PBS and are finally resuspended in 1×PBS for FACS analysis. Flow cytometry of cells can be performed on a FACSCalibur (Becton-Dickinson). The cells can be analyzed by light forward and right-angle (side) scatter, and for FITC fluorescence through an adequate filter system. The number of FITC, e.g. MAP2, positive cells gives the number of stem cells that have developed a neuronal like phenotype.

Likewise cells can be stimulated with another hematopoietic factor, like GMCSF, IL-3 or IL-5 or combinations thereof.

IL-3 and IL-5 have the potential to induce neurogenesis in stem cells, too. The described methods to treat stem cells with a hematopoietic factor hold true for IL-3 and IL-5, also.
Administration/Formulation/Dosage G-CSF, GM-CSF, IL-3, IL-5 and the other factors, derivatives, genes, and combinations thereof, may be administered in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The composition may be in the form of a liquid, slurry, or sterile solid which can be dissolved in a sterile injectable medium before use. The parenteral administration is preferably intravenously. This injection can be via a syringe or comparable means. This may contain a pharmaceutically acceptable carrier. Alternatively, the compositions, e.g. containing G-CSF, may be administered via a mucosal route, in a suitable dose, and in a liquid form. For oral administration, the compositions, e.g., containing G-CSF, can be administered in liquid, or solid form with a suitable carrier.

The mammal to be treated can be, for example, a guinea pig, dog, cat, rat, mouse, horse, cow, sheep, monkey or chimpanzee. In one embodiment, the mammal is a human. Likewise, in one embodiment the hematopoietic factors, such as GCSF IL-3, IL-5 and GMCSF used for therapy or prophylaxis is a human factor or derived from a human source.

A therapeutically effective amount of the hematopoeitic factors for use in the methods of treating neurological disease when the factors are used either singularly or in combination should be used in an amount that results in a neuroprotective effect. Such an amount can range from about 100 ng to about 10 mg/kg body weight per factor or as a combination and can be determined based on age, race, sex, and other factors based on the individual patient. For example, an amount of GCSF for use in the present methods would be from about 5 to about 60 µg/kg and for GMCSF from about 5 to about 750 µg/kg body weight. Likewise, IL-3, or IL-3 mimetics, IL-5, or IL-5-mimetics can be administered in the given doses and formulations as described for G-CSF and GM-CSF, for example, a therapeutically effective amount of IL-3 or IL-5 can be from about 1 to about 1000 µg/kg body weight. When the factors are administered in combination, they may be premixed prior to administration, administered simultaneously, or administered singly in series.

In certain embodiments of treating neurological conditions as described herein, higher doses of G-CSF, GM-CSF, IL-3, IL-5 and/or the other factors described herein can be especially useful, for example, at least 1 mg, at least 2 mg, or at least 3 mg may be used, a range from about 1 to 3 mg is preferable. These higher doses cannot be conveniently achieved for adult patients by using the currently available packaging units. Therefore, in one embodiment, the present invention provides packages, especially for doses in the range of 20 to 250 µg/kg body weight, which may be administered, e.g., intravenously, or subcutaneously, for the purpose of neuroprotection according to the description herein. Examples of the packaged units useful for delivery of the high dosage compositions include, for example, single use vials and prefilled syringes containing 0.75 to 25 mg G-CSF, GM-CSF, IL-3, IL-5 and/or the other factors described herein at a fill volume of 1.0 ml or 2.0 ml. In a preferred embodiment, the packaged units would also contain instructions, on a label or separate printed material, for the delivery of the composition(s) contained therein.

Preferred are also prefilled syringes for G-CSF, GM-CSF, IL-3, IL-5 and/or the other factors described herein administration calibrated with kg/bdy weight scales that allow the exact and fast dosage for each individual patient according to the patient's body weight. These packaging units are very useful under emergency settings, for example in the case of stroke, where patients have to be treated very quickly after injury. Accordingly, another embodiment of the present invention is to provide neuroprotection, for example, in a patient who has suffered a stroke or other neurotraumatic event, by administration of one or more composition as described herein a short time after the injury has occurred. In an alternative embodiment, the compositions described herein, such as the prefilled syringes, may also be administered/used anytime after the injury not specifically limited to only a short time after the injury.

As used in the context of this embodiment, "a short time after injury" means within about 10 minutes, 15 minutes, 20 minutes, 25 minutes, 30 minutes or even up to about 1 hour after the occurrence of the injury or the event causing the injury. The compositions may be administered by a medical professional or in some instances a non-medical professional who has access to a packaging unit containing the appropriate dosages of factor(s). In the case of a medical professional, such as an ambulance technician, nurse, doctor, etc, the administration may be performed at the location where the patient has suffered a neurotrauma, e.g., such as stroke, in an ambulance or other vehicle while being transported to the hospital (or other medical facility), or in the hospital, such as in the emergency room. Without being limited to theory, the administration of one or more hematopoietic factors, such as G-CSF, GM-CSF, IL-3, IL-5 and/or the other factors described herein containing compositions, within a short time after injury, a greater neuroprotective effect may be achieved.

In another embodiment, the present invention also provides a device especially suited for slow release and constant long-term application that may be an implanted mini-pump, preferably implanted sub-cutaneously (for example, as described in Edith Mathiowitz; (Ed.), Encyclopedia of Controlled Drug Delivery, John Wiley & Sons vol. 2, pp. 896-920, 1999). Such pumps are known to be useful in insulin therapy. Examples of such pumps include those manufactured/distributed by Animas, Dana Diabecare, Deltec Cozm, Disetronic Switzerland, Medtronic, and Nipro Amigo as well as those described, for example, in U.S. Pat. Nos. 5,474,552; 6,558,345; 6,122,536; 5,492,534; and 6551276, the relevant contents of which are incorporated herein by reference.

The present invention also provides a device that measures endogenous serum-levels of G-CSF, GM-CSF, IL-3, IL-5 and/or the other factors described herein and upon this basis, taking into account age and body weight, calculates and injects the appropriate amount of drug (for example, as described in Renard E., Curr Opin Pharmacol. 2002 December; 2(6):708-16). This can be done on a chronic basis, for example by using the above described mini-pump, or on an acute basis. An example of such a device is produced by the company Medtronic minimet (Medtronic MiniMed, 18000 Devonshire Street, Northridge, Calif. 91325-1219) for insulin therapy. A way of measuring the G-CSF, GM-CSF, IL-3, IL-5 and/or the other factors described herein serum level may be accomplished using protein chips or arrays, for example, as described in U.S. Pat. Nos. 6,630,358; 6,537,749; and 6,475,809, the relevant disclosures of which are incorporated herein by reference.

The above embodiments of drug delivery using pumps and/or coupled with serum level detection of G-CSF, GM-CSF, IL-3, IL-5 and/or the other factors described herein can be especially useful for the treatment of chronic neurodegenerative diseases, for example, Parkinson's disease, amyotrophic lateral sclerosis (ALS), dementia, and others.

The route of administration can include the typical routes including, for example, orally, subcutaneously, transdermally, intradermally, rectally, vaginally, intramuscularly, intravenously, intraarterially, by direct injection to the brain, and parenterally. In addition, in some circumstances, pulmonary administration may be useful, e.g., pulmonary sprays and other respirable forms.

In addition to pulmonary sprays, intranasal (IN) delivery (for example by nasal sprays) is a preferred application mode of delivering the compositions of the present invention for neurological/psychiatric conditions. Intranasal delivery is well suited to serve as application mode of proteins and peptides, and is very convenient to use, especially for long-term treatments. Examples for the use of intranasal delivery (nasal sprays) for applying peptides or proteins to the brain can be found in: (Lyritis and Trovas (2002), Bone, 30, 71S-74S, Dhillo and Bloom (2001), Curr Opin Pharmacol, 1, 651-5, Thorne and Frey (2001), Clin Pharmacokinet, 40, 907-46, Tirucherai, et al. (2001), Expert Opin Biol Ther, 1, 49-66, Jin, et al. (2003), Ann Neurol, 53, 405-9, Lernere, et al. (2002), Neurobiol Aging, 23, 991-1000, Lawrence (2002), Lancet, 359, 1674, Liu, et al. (2001), Neurosci Lett, 308, 91-4). For intranasal application, G-CSF, GM-CSF, IL-3, IL-5 and/or other compositions as described herein can be combined with solvents, detergents and substances that increase penetration of the nasal epithelium or delivery into blood vessels, such as drugs that widen nasal blood vessel, increase perfusion, etcetera.

Based on the mode of administration, and under consideration of the relevant pharmacokinetics involved, the dose may be further modified, e.g., for a direct injection into the brain the dose would be lower, and the amount would be specified in absolute doses, based on local availability of G-CSF, GM-CSF, IL-3, IL-5 and/or other compositions as described herein (e.g., 5 µg total dose). Preferably, G-CSF, GM-CSF, IL-3, IL-5 and/or other compositions as described herein are administered intravenously, subcutaneously, or by direct intracerebral injection, which may be performed with an osmotic pump.

In another embodiment, G-CSF, GM-CSF, IL-3, IL-5 and/or other compositions as described herein can be provided to the individual by administrating one or more nucleic acids that encodes these factors. The coding sequence nucleic acid is preferably administered in the form of a recombinant vector, such as a viral vector. The selection of a suitable vector and expression control sequences as well as vector construction is known. Examples, of viral vectors include an adenovirus (Acsadi et al., *Hum. Gene Ther.* 7(2): 129-140 (1996); Quantin et al., *PNAS USA* 89(7): 2581-2584 (1992); and Rapot et al., *Nature* 361 (6413): 647-650 (1993)), an adeno-associated viral vector (Rabinowitz et al., *Curr. Opin. Biotechnol.* 9(5): 470-475 (1998)), a retroviral vector (Federico, *Curr. Opin. Biotechnol.* 10(5): 448-453 (1999)), a Herpes simplex viral vector (Latchman, *Gene* 264(1): 1-9 (2001)), a lentiviral vector, a Sindbis viral vector, or a Semliki forest viral vector. Suitable vectors are also liposomes containing proteins that will attach to neural cells, e.g., virus epitopes, and contain either nucleic acid encoding G-CSF, GM-CSF, IL-3, IL-5 and/or other factors as described herein, or protein, or oligonucleotides. An example of such a transfer system is the HVJ-liposome (Kaneda, et al. (2002), *Mol Ther,* 6, 219-26. Kaneda (1999), *Mol Membr Biol,* 16, 119-22). Preferably, the isolated and purified nucleic acid encoding and expressing the protein or polypeptide is operably linked to a promoter that is suitable for expression in neural cells. These and other suitable vectors are reviewed in Kay et al., *Nature Medicine* 7: 33-40 (2001); Somia et al., *Nature Reviews* 1: 91-99 (2000); and van Deutekom et al., *Neuromuscular Disorders* 8: 135-148 (1998).

Suitable promoters for operable linkage to the isolated and purified nucleic acid are known in the art. Preferably, the isolated and purified nucleic acid encoding the polypeptide is operably linked to a promoter selected from the group consisting of the muscle creatine kinase (MCK) promoter (Javnes et al., *Mol. Cell. Biol.* 6: 2855-2864 (1986)), the cytomegalovirus (CMV) promoter, a tetracycline/doxycycline-regulatable promoter (Gossen et al., *PNAS USA* 89: 5547-5551 (1992)).

Generally, to ensure effective transfer of the vectors of the present invention, about 1 to about 5,000 copies of the vector are employed per cell to be contacted, based on an approximate number of cells to be contacted in view of the given route of administration, and it is even more preferred that about 3 to about 300 pfu enter each cell. These viral quantities can be varied according to the need and use whether in vitro or in vivo. The actual dose and schedule can also vary depending on whether the composition is administered in combination with other compositions, e.g., pharmaceutical compositions, or depending on individual differences in pharmacokinetics, drug disposition, and metabolism. Similarly, amounts can vary in in vitro applications depending on the particular type of cell or the means by which the vector is transferred.

The above-described proteins or derivatives thereof, substances or nucleic acids can be formulated for medical purposes according to standard procedures available in the art, e.g., a pharmaceutically acceptable carrier (or excipient) can be added. A carrier or excipient can be a solid, semi-solid or liquid material which can serve as a vehicle or medium for the active ingredient. The proper form and mode of administration can be selected depending on the particular characteristics of the product selected, the disease, or condition to be treated, the stage of the disease or condition, and other relevant circumstances (*Remington's Pharmaceutical Sciences*, Mack Publishing Co. (1990)). The proportion and nature of the pharmaceutically acceptable carrier or excipient are determined by the solubility and chemical properties of the substance selected the chosen route of administration, and standard pharmaceutical practice. The pharmaceutical preparation may be adapted for oral, parenteral or topical use and may be administered to the patient in the form of tablets, capsules, suppositories, solution, suspensions, or the like. The growth factors, derivatives thereof, a nucleic acid coding sequence thereof of the present invention, while products themselves, can be formulated and administered as pharmaceutically acceptable salts, such as acid addition salts or base addition salts, for purposes of stability, convenience of crystallization, increased solubility, and the like.

For some neurological diseases, especially in ischemic diseases it is crucial for an effective therapy not to delay the onset of the therapy. In a preferred embodiment, the present invention relates to a method, wherein G-CSF, GM-CSF, IL-3, IL-5 and/or other compositions as described herein or a substance activating STAT proteins or an agonist to the GCSF, GMCSF, IL-3, and/or IL-5 receptors is administered within 24, preferably within 10, most preferably within 3 to 6 hours after the occlusion of a blood vessel, or the onset of neurological symptoms, or anotherwise detected onset of an ischemic event. As G-CSF, GM-CSF, IL-3, IL-5 and/or other compositions as described herein also have beneficial effects for long-term functional improvement, treatment begins at considerable time after the ischemic insult is also possible (e.g., 1 day to 7 days after the insult). Treatment may be continued for several days and weeks after the ischemic event, as a means to improve functional recovery of the patient in analogy to the functional improvement seen in our long-term cortical infarct model (see FIG. 8). Treatment may consist of several doses per day (e.g. short i.v. infusions) to reach steady-state trough levels of G-CSF, GM-CSF, IL-3, IL-5 and/or other compositions as described herein or related factors. Treatment may also include continuous slow infusion of the described substances (e.g., by a perfusor unit) to guarantee steady serum levels.

In the case of chronic neurodegenerative processes, such as Parkinson's disease, or amyotrophic lateral sclerosis, treatment will more likely consist in one daily dose of G-CSF, GM-CSF, IL-3, IL-5 and/or other compositions as described hereinor related factors, or preferably use slow-release formulations, or more stable derivatives of G-CSF, GM-CSF, IL-3, IL-5 and/or other compositions as described hereinor related factors.

Screening for Neuroprotective Substances which Bind to a GCSF, IL-3, IL-50R GM-CSF Receptor on Neural Cells For practicing the present invention, derivatives of GCSF, GMCSF (e.g., GCSF- or GMCSF-mimetics), and/or other hemotopoietic factors that retain their potential to protect neurons and that also have diminished action on leukocytes, thereby reducing potential adverse effects, are preferred. Therefore, one embodiment of the present invention is to screen for compounds that bind to the GCSF or GM-CSF receptor on neural cells and which stimulate the neuroprotective effect observed with GM-CSF or GCSF as described in this application.

Derivatives of GCSF, e.g., GCSF-mimetics, can be tested in an in vitro neuroprotective assay such as exemplified in Example 10. This neuroprotective assay can be varied without changing the basic principle of the test by adapting for, for example, (i) other damaging stimuli like Interleukin-1, oxygen deprivation, A4 peptides, FAS ligand, or (ii) other cells, e.g. neuronal-like cells like SH-SY5Y cells, or PC12 cells, or (iii) other readouts for cell-viability or cell-death such as e.g. DNA-fragmentation, nuclear condensation, activity of co-transfected beta-galactosidase, detection of a fluorigenic substrate of caspases etc. All these numerous adaptations are known and may also be used in high-throughput systems. High throughput screening technology is commonly used to define the rapid processing of cells on a large scale. Substances demonstrating a positive neuroprotective effect in this assay can be further tested for their granulopoetic activity as, for example, described in Tian et al., *Science* 281, 257-259. Selection of GCSF derivatives is preferably based on the comparison of these two specific effects elicited by the test substances with those effects elicited by known forms of GCSF. Likewise, derivatives of GMCSF, e.g., GMCSF-mimetics can be tested in an in vitro neuroprotective assay as described for GCSF.

Further neuroprotective substances can be obtained by measuring the presence of activated transcription factors such as STAT-proteins, including STAT-3 and STAT-5 in neuronal or neuron-like cells (for example, PC12, SH-SY5Y, hNT, NT2, hn33) after exposure of these cells to a test substance. Therefore, in another embodiment of the present invention, the ability of a particular substance or compound to act as an agonist to the GCSF or GMCSF receptor can be assessed by the activation of the STAT proteins, e.g., STAT3 and/or STAT5, in neuron-like cells as described herein and using conventional gene expression assays, such as quantitative PCR by LightCycler™ or Taqman™ analysis.

Activated STAT proteins are phosphorylated (pSTAT) and can be detected by a commercially available pSTAT-specific antibody (Santa Cruz Biotechnology) in Western Blot or in immunohistochemical studies, or ELISAs.

Alternatively, STAT activity can be measured using a reporter construct which includes a STAT-responsive promoter element (for example, a multimerized STAT-binding element, such as a multimerized STAT-3 or STAT-5-binding element) linked to a reporter gene, such as luciferase, SEAP (secreted alkaline phosphatase), chloramphenicol transferase (CAT), green fluorescent protein (GFP), or other common gene expression reporters. After transfecting cells with reporter construct, the cell is contacted with the test substance and the amount of the reporter expression can be identified. This method of measuring STAT activity can be adapted to a high-throughput format.

A typical reporter assay can be conducted using, for example, commercially available assay systems (Mercury Pathway Profiling System from Clontech; Path Detect-System from Stratagene). An example of a protocol that can be performed is as follows.

Cells are cultured in a multiwell plate, e.g. 20,000 cells per well in a 96 well plate. Two days after seeding the cells culture medium is exchanged to an serum-free medium (40 µl per well) and cells can be transfected with a reporter plasmid, encoding the STAT-binding element and the reporter protein (STAT-3_firefly-luciferase plasmid; 50 ng/well), and a transfection control plasmid (renilla-luciferase expression plasmid; 10-20 ng/well) under optimized conditions referring to each cell type (for example: PC-12 cells can be transfected by lipofection using LIPOFECTAMINE2000™, Invitrogen, as recommended). 48-72 h after transfection the assay can be run. Cells are stimulated with the testing substance in multiple concentrations which should cover a broad range of concentrations. Multiple assaying time points starting within 5 minutes of stimulation should be chosen. When using a Luciferase assay, the readout can be assessed in a Luminometer, plate format (Berthold, Germany), measuring stepwise the activity of renilla and firefly luciferase. The detection of the two luciferase-activities is done by the use of commercially available detection kits (Dual luciferase reporter assay kit, Promega; Luciferase reporter assay kit, Clonetech). Values of firefly luciferase are then normalized to renilla luciferase values and relative induction of reporter gene can be calculated.

In an alternative example of a screening method, the agonist activity on the GCSF or GMCSF receptor on neuronal cells can be utilized and measured. For example, the homodimerization upon ligand binding can be assayed by using fluorescence resonance transfer energy measurements (FRET, or BRET (bioluminescence resonance energy transfer) (Siegel R M et al *Sci STKE* (2000) 2000 (38):L1; Xu Y et al *Proc Natl Acad Sci USA* (1999) 96(1):151-6), or reporter systems for dimerization events, e.g. the double switch system (DE 10211063.8), the beta-gal reporter system (Rossi F et al *Proc Natl Acad Sci USA* (1997) 94 (16):8405-10), or the split-ubiquitin system (WO 954/29195, U.S. Pat. No. 5,585, 245, or Johnsson, N. and Varshavsky, *Proc Natl Acad Sci USA* (1994) 91 (22):10340-4).

In an additional alternative to screening for neuroprotective substances which bind to GCSF and GMSCF on neuronal cells, inducing the brain-endogenous levels of GCSF and/or GMCSF is provided in the present invention. As described herein and demonstrated in the following examples, GCSF as well as GMCSF were surprisingly discovered as brain-endogenous ligands. These ligands were induced by several ischemic conditions of the brain. Therefore, they act as part of a brain-endogenous neuroprotective system. In the same sense as exogenously added GCSF or GMCSF that cross the blood-brain barrier are beneficial for a wide range of conditions where neuroprotection is a valid therapeutic principle, drugs that increase the brain-endogenous levels of GCSF/GMCSF can be beneficial for these conditions.

A screening system to identify such substances can be setup in the basic way of adding substances (for example from a large small molecule library) to cells in culture, for example, neuronal cells, either primary cells or neuron-like immortalized cells such as PC12 cells, SHSY5-cells, and others, and measuring levels of GCSF and GMCSF.

Measuring the levels of GCSF/GMCSF can be performed by assaying the proteins themselves (by Western blotting, ELISA, RIA, and other techniques known to one skilled in the art), by assaying the mRNA encoding these proteins (such as quantitative PCR, Northern blotting, RNAse protection assay, RNA dot-blotting, and other techniques known to one skilled in the art), or by assaying the activity of the regulatory elements of the genes for GCSF/GMCSF. Preferably, the activity of regulatory elements can be assessed by reporter constructs consisting of DNA segments from the promoter, enhancer, and/or intronic elements coupled to cDNAs encoding reporters (such as luciferase, beta-galactosidase, green fluorescent protein, or other reporting genes that can be easily assayed). These reporter constructs can be transfected into cells, either stably, or transiently.

The cells may be kept under physiological conditions, or additionally exposed to noxious stimuli (such as hypoxia/glucose deprivation, NO donors, glutamate excess and others) to observe effects of concomitant addition of the respective substances to test.

Identified substances can be further validated by giving the substance to an animal, and measuring content of GCSF/GMCSF in the brain (e.g. by quantitative PCR).

In another embodiment, increasing the expression levels of the receptors for GCSF and GMCSF can be useful for increasing the responsiveness of the cells to the ligands. Therefore, the screening assays outlined above can also be adaptred to screen for increases in receptor expression.

Derivatives of GCSF, e.g., GCSF-micmetics can be tested in an in vitro assay as described in Example 23. This neuroprotective assay is one preferred variation of the given neuroprotective assay given in Example 10 with the cell type being primary cortical cells or SHSY5-Y cells and the damaging stimulus being Camptothecin. The detection of cell death is done by a fluorogenic substrate of caspases.

In addition to JAK/STAT-Pathway the PI3K/Akt pathway and ERK-pathway are activated by GCSF (see FIG. 43). Additionally neuroprotective substances can be obtained by measuring the activation of one of the three pathways activated by GCSF. Activated proteins of these pathways can be detected by commercially available antibodies (e.g., cell signalling) that detect their phosphorylation status in Western Blot, or in immunohistochemical studies, or in ELISA (see, e.g., Example 21).

A selection of derivatives can be based on the comparison of the two species elicited by the test substances with those effects elicited by known forms of GCSF. Thereby a comparison of the amount of phosphorylation or the time pattern of activation can be done.

The different time pattern of activation of any of the pathways can be used to identify substances of long lasting or transient activation. This can be useful in selection of a substance or a combination of substances for optimized effect with respect to the neurological condition that is treated.

Alternatively the activated Pathway can be detected by a downstream transcription factor (TF) that is activated (e.g. p53, FKHR/AFX for PI3K/Akt-Pathway or Stat1/3 or Creb for ERK-Pathway). TF activity can be measured by using a reporter construct that includes the TF responsive element linked to a reporter gene, such as luciferase, SEAP (secreted alkaline phosphatese), chloramphenicol acetyltransferase (CAT), green fluorescent protein (GFP), or common gene expression reporters. After transfecting the cells with the reporter construct, the cell is contacted with the test substance and the amount of reporter expression can be identified.

Furthermore pathway activation can be detected by a commercially available Kinase activity assay. (MAP Kinase (ERK1/2) Activity Assay Kit; Chemikon; Kinase-Glo™ Luminescent Kinase Assay; Promega). Such an assay can be used to identify derivatives of GCSF or combinations of GCSF with other hematopoietic factors that have a higher activity.

Likewise, derivatives of GMCSF or IL-3 or IL-5, e.g., GM-CSF or IL-3 or IL-5-mimetics can be tested in an in vitro neuroprotective assay as described for G-CSF. Likewise, combinations or fusion proteins of CGSF, GMCSF, IL-3 or IL-5 or derivatives thereof can be tested in an in vitro neuroprotective assay as described for GCSF.

Also, the efficacy derivatives of GMCSF or IL-3 or IL-5, e.g., GM-CSF or IL-3 or IL-5-mimetics in protecting a neuronal cell from dying can be assayed in an FACS analysis as described above. Likewise the derivative can be a fusion protein of GCSF, GMCSF, IL-3 or IL-5 with another Hematopoietic factor.

Having generally described this invention, a further understanding can be obtained by reference to certain specific examples which are provided herein for purposes of illustration only and are not intended to be limiting unless otherwise specified.

EXAMPLES

The experiments underlying the present invention demonstrate that GCSF is neuroprotective in vitro, and that GCSF displays significant infarct reducing effects after transient focal cerebral ischemia. Neurons in the periphery of the infarction but also on the contralateral side exhibited specific binding of anti GCSFR-antibody, indicative for a GCSF receptor. The presence of GCSFR on neurons is novel and was verified by Western blot, RT-PCR, and a detailed immunohistochemistry in the brain, and by PCR and immunocytochemistry in cultured primary neurons. Furthermore, STAT3 activation as judged by nuclear translocation of STAT3 was significantly increased in neurons of the penumbra of GCSF treated animals compared to controls suggesting a GCSFR/STAT mediated mechanism of action. In the in vivo ischemic experiment (middle cerebral artery occlusion, MCAO) there was no effect on cerebral blood flow as measured by laser Doppler flowmetry (ldf) when comparing both groups. There were no significant differences in physiological parameters and weight decline between both groups during the MCAO experiment. Mortality rate was significantly improved in animals treated with GCSF compared to controls in the MCAO experiment. Neutrophilic blood count (NGC) was significantly increased after 24 hours in GCSF treated animals compared to controls. Myeloperoxidase (MPO)-staining as a measure of invading neutrophilic granulocytes (NGs) into the ischemic hemisphere was not significantly different between GCSF treated animals and controls.

The dose of the i.v. delivered GCSF (60 µg/kg/body weight) used in the experiments was comparable to the doses used for other experimental conditions. It had been tested for safety in an earlier pilot project before and consequently no significant side effects were observed. This dose (60 µg/kg/body weight) is six times higher than the approved dose for the treatment of human myelodysblastic and other diseases, and has shown no appreciable side effects in the rat model.

An infarct reducing effect of 50% achieved with GCSF is comparable with that of other growth factors such as bFGF, or IGF after systemic application (Fisher M. et al., *J. Cereb. Blood Flow Metab.*, 1995; 15:953-9; Schäbitz W R, et al., *Stroke* 2001; 32:1226-33). It seems that glucose deprivation and excitotoxicity with subsequent $Ca^{2+}$ overload of cells as well as apoptosis, reactive oxygen species, and decreased energy reserve in the face of increased requirements (e.g., from spreading depression) are the main causes of neuronal cell death following ischemia (Lee J M, et al., *Nature* 1999; 399(Suppl):A7-14). As demonstrated in the examples, GCSF protects in vitro neuronal-like cells (NGF-differentiated PC12 cells) against $H_2O_2$ induced cell death. $H_2O_2$ elicits oxidative stress by the production of reactive oxygen species (ROS), which invokes cell death. $H_2O_2$-mediated cellular stress in mammalian cells is well-characterized in terms of cellular phenotype, dosage, time-course and signaling pathways involved. The wide-spread usage of $H_2O_2$ in a multitude of studies supports apoptotic mechanisms as effects of $H_2O_2$ in cells (see for example *FASEB J.* 2002 January; 16(1):111-3; *J Cell Biochem* 2001; 82(3):437-44). For example, roles of the pro-apoptotic Kinase ASK1 and the FasLigand have been convincingly demonstrated in $H_2O_2$-mediated cell-death (Tobiume K, *EMBO Rep* 2001 March; 2(3):222-8; Kwon, D., *J Neuroimmunol.* 2001 Feb. 1; 113(1):1-9; Facchinetti. F., *J Neurosci Res.* 2002 Jul. 15; 69(2):178-88). Therefore, it is likely that GCSF interferes with apoptotic mechanisms invoked in cerebral ischemia. GCSF's action is probably mediated by binding to the high-affinity receptor GCSFR. Interaction with this receptor activates the Janus family kinases (JAKs) and STATs (Darnell J E Jr., *Science* 1997; 277:1630-5). JAK are non-receptor-type tyrosine protein kinases that become activated upon ligand-induced receptor dimerization. GCSF induced activation of JAKs phosphorylate STATs on a conserved tyrosine residue, which induces STAT dimerization (Quelle F W, et al., *Mol. Cell. Biol.* 1994; 14:4335-41). Furthermore, STATs translocate to the nucleus and subsequently regulate gene expression (Shuai K, et al., *Nature* 1993; 366:580-3; Shuai K., *Oncogene* 2000; 19:2638-44). STAT3 is the principal STAT protein activated by GCSFR (Shuai K., *Oncogene* 2000; 19:2638-44). STAT3 mediates antiapoptotic function by activating bcl-2 and induces proliferation and differentiation of granulocytes by upregulating the c-myc gene (Fukada T, *Immunity* 1996; 5:449-60; Shimozaki K, *J. Biol. Chem.* 1997; 272:25184-9). As shown here by using immunohistochemistry, RT-PCR, and Western-Blot GCSFR exists not only on hematopoetic cells but also on neurons, glial cells, neuronal-like cells, and neuronal stem cells. Furthermore, GCSF induced STAT3 upregulation in neurons of the penumbra may mediate antiapoptotic effects such as bcl-2 upregulation as shown for BDNF or bFGF, (Schäbitz W R, et al., *Stroke* 2001; 32:1226-33) and provide trophic support of neurons to survive. Dense nuclear labeling of STAT3 in the penumbra of the infarction could reflect membrane receptor-mediated translocation of STAT3 from the cytoplasm to the nucleus which was already shown for activated microglia after cerebral ischemia (Planas A M. et al., *Eur. J. Neurosci.* 1996; 8:2612-8). GCSF is known to stimulate release, enhancement of effector function, and extension of lifetime by delaying apoptotic cell death of neutrophilic granulocytes (NGCs), the body's first line of defense against all kinds of infections (Hartung T., *Curr Opin Hematol* 1998; 5:221-5). Neutrophils could occlude microvessels, subsequent invasion of leukocytes triggers the release of proteolytic enzymes, oxygen free radicals, interleukines, and TNF-α-effects known to deteriorate infarct size and outcome after cerebral ischemia (Del Zoppo G J, *Stroke* 1991; 22:1276-83; Jean W C, et al., *Neurosurgery* 1998; 43:1382-96; Matsuo Y. et al., *Brain Res.* 1994; 656:344-52). In contrast, GCSF has significant anti-inflammatory effects: GCSF reduces in models of peripheral infections TNF-α; IL-1β, IL-2, IL-6 and IL-8 and elevates IL-1 receptor-antagonists (Gorgen I, et al., *J Immunol* 1992; 149:918-24; Heard S O, et al., *Crit. Care Med.* 1999; 27:1019-21; Heard S O, et al., *Crit. Care Med.* 1998; 26:748-54; Hebert J C. et al., *Arch. Surg.* 1990; 125:1075-8; Lundblad R, et al., *Crit. Care Med.* 1996; 24:820-6; Squadrito F, et al., *Br J Pharmacol* 1997; 120:333-9). GCSF decreased TNF-α release in vitro and in vivo in healthy volunteers and elevated levels of antagonists for TNF, IL-6, IL-8, and IL-1β (Hartung T. *Curr Opin Hematol* 1998; 5:221-5; Gorgen I. et al., *J. Immunol.* 1992; 149:918-24; Heard S O, et al., *Crit. Care Med* 1999; 27:1019-21). Moreover, reduced neutrophil infiltration in lung and ileum was observed in a model of splanchnic ischemia and reperfusion 15 minutes after administration of GCSF and reperfusion of the small bowel (Squadrito F. et al., *Br J Pharmacol* 1997; 120:333-9). Consistent with these findings an increase of neutrophil infiltration into the ischemic hemisphere was not found although total neutrophilic granulocytes (NGCs) increased after GCSF treatment.

Another possible mechanism of action of growth factors in particular bFGF includes effects on cerebral blood flow. bFGF treatment dilates collaterals in the peri-ischemic zone even at doses not promoting systemic hypotension, thus increasing the blood flow to the penumbral regions (Tanaka R, et al., Stroke 1995; 26:2154-8; discussion 2158-9). However, as shown here, GCSF treatment did not reduce systemic blood pressure or change cerebral blood flow compared with the control group as measured by LDF.

In the photothrombotic bengal rose model, postischemic intravenous GCSF treatment clearly improved sensory motor functional outcome six weeks after photothrombotic stroke, further supporting the hypothesis that growth factors induce recovery and regeneration after traumatic brain lesions in vivo. Two other compounds, basic fibroblast growth factor (bFGF) and osteogenic protein-1 (OP-1) were reported before to improve sensorimotor function and to induce neuronal sprouting after focal cerebral ischemia (Kawamata et al Proc Natl Acad Sci USA 1997; 94:8179-84; Kawamata et al Neuroreport 1998; 9:1441-5; Ren et al Neuropharmacology 2000; 39:860-5). In most of these studies growth factors were administered into the cerebral ventricles which is clinically not relevant. Only Ramirez et al. (Ramirez, et al. (1999), Neuroreport, 10, 1201-4.) reported that intravenous administration of bFGF supports lesion-induced hippocampal sprouting, but the authors did not study functional outcome measures. The results presented here indicate that a clinically relevant dose protocol of GCSF administration induces functional recovery after cerebral ischemia. The capacity for enhancement of plasticity is clearly not limited to ischemic brain damage, but also relevant for neurodegenerative diseases such as Parkinson's disease and amyotrophic lateral sclerosis (ALS), the trinucleotide repeat diseases, cerebral ischemias due to resuscitation or intrapartal problems, probably also to dementias such as Alzheimer's disease, and to the neurodegenerative aspects of schizophrenia.

The results also show the similarities in the mode of action of GCSF, GMCSF, IL-3 and IL-5 and support their beneficial activity in the case of neuronal damage.

Overview of the Methods for the Experiments on Cerebral Ischemia

Ischemia was induced by using the suture occlusion model of the middle cerebral artery (90 min) in the rat. 30 min after induction of ischemia, animals (n=12 per group) received 60 µg/kg body weight of GCSF intravenously for 90 min or vehicle. Infarct volume was calculated based on TTC (2,3,5-triphenyltetrazolium chloride)-staining 24 hours after ischemia. Expression of the GCSFR was studied by immunohistochemistry, verified by RT-PCR and immunoblotting. Expression of STAT3 was studied by immunohistochemistry. Efficacy of GCSF in functional recovery was studied in the Bengal rose photothrombotic model.

Statistical Analyses

The values presented in this study are means±SD. After acquiring all the data, the randomization code was broken. ANOVA and subsequent post hoc Fisher protected least significant difference test or Bonferroni correction were used to determine the statistical significance of differences for in vitro data and physiological parameters, or functional outcome in test batteries. The t-test was used for comparison of postmortem infarct volumes, MPO, and STAT3 immunohistochemistry. The Chi-Square test was performed for mortality data. A p value <0.05 was considered statistically significant.

Results

GCSF reduced infarct volume to $131.96 \text{ mm}^3 \pm 112.7 \text{ mm}^3$ vs $279.9 \text{ mm}^3 \pm 91.56 \text{ mm}^3$ ($p<0.05$) in the control group. Immunohistochemistry, Western blotting, and RT-PCR revealed the existence of GCSF receptors in neurons and glial cells. GCSF significantly activated STAT3 in the periphery of the infarction compared to controls ($p<0.05$). GCSF is effective in improving functional recovery after ischemia in the model of Bengal rose photothrombosis.

It has therefore been demonstrated that GCSF has a significant neuroprotective effect in cell culture and after focal cerebral ischemia. This effect seems to be mediated by interaction with GCSFR and activation of STAT3.

Example 1

Focal Cerebral Ischemia

Procedure for Inducing Focal Cerebral Ischemia (MCAO, Middle Cerebral Artery Occlusion)

Experimental protocols were approved by the local ethics committee. Twenty-four male Wistar rats (Charles River, Germany) weighing 280 to 320 g were randomly assigned to the following groups: A (Control group, n=12, ischemia for 90 min, treatment with 2 ml saline 0.9% for 90 min beginning 30 min after vessel occlusion); B (GCSF group, n=12, ischemia for 90 min, treatment with 60 µg/kg body weight of recombinant human GCSF, Neupogen®, Amngen, Europe B. V., Netherlands, soluted in 2 ml saline 0.9% for 90 min beginning 30 min after vessel occlusion. Alternatively, any GCSF or derivative or formulation of other source (another manufacturer (e.g. Lenogastrim™ by Roche or Granocyte™ by Chugai or Albugranin™ by HGS or Neulasta™ by Roche/Amgen) can be used here.

Animals then were anesthetized with an intraperitoneal injection of 100 mg/kg body weight ketamine hydrochloride (WDT, Garbsen, Germany). Anesthesia was maintained with 50 mg/kg body weight if necessary. A PE-50 polyethylene tube was inserted into the right femoral artery for continuous monitoring of mean arterial blood pressure, blood gases, hematocrit, leukocyte count, and blood glucose levels. The right femoral vein was cannulated by a PE-50 tube for treatment infusion. During the experiment rectal temperature was monitored and maintained at 37° C. by a thermostatically controlled heating pad (Föhr Medical Instruments, Germany). Transient focal cerebral ischemia was induced by using the suture occlusion model as described in detail by Zea Longa et al. (Stroke 1989; 20:84-91). Briefly, the right common carotid artery and the right external carotid artery were exposed through a midline neck incision. A 4-0 monofilament nylon suture (Ethicon, Germany) coated with silicon (Bayer, Germany) was inserted through an arteriectomy in the common carotid artery, gently advanced into the internal carotid artery and positioned approximately 17 mm from the carotid bifurcation. Using this technique, the tip of the suture occludes unilaterally the proximal anterior cerebral artery, the origins of the MCA and the posterior communicating artery. A large infarct in the territory of the MCA is typically produced. Reperfusion was performed by withdrawal of the occluder filament 90 minutes after vessel occlusion. Sham-operated animals underwent the same experimental procedures as described above but the nylon filament was not advanced beyond the common carotid artery, so that no infarction occurred. After surgery, the catheters were removed, and the animals were allowed to recover from the anesthesia and given food and water ad libitum.

Measurement of Regional Cerebral Blood Flow

Laser-Doppler flowmetry (LDF) (Periflux 4001 Master, Perimed AB, Sweden) was used to monitor cerebral blood flow (CBF) before, during and after occlusion of the MCA. After placing the animal into a stereotactic frame, the animal's skull was exposed and a hole of 1.5 mm in diameter was drilled under the microscope on the right side 4 mm lateral and 2 mm caudal to the bregma. The dura was left intact and the LDF probe (1.4 mm in diameter) was placed into the burr hole. The area selected for CBF monitoring corresponded to the ischemic penumbra of the MCA occlusion model in rats.

Infarct Volume Calculation 24 hours after MCA occlusion, the rats were anesthetized with ketamine 150 mg/kg body weight and decapitated. The brains were dissected and cut into 5 coronal slices of 2 mm thickness, incubated in a 2% solution of 2,3,5-triphenyltetrazolium chloride (TTC) at 37° C. for 30 min and fixed by immersion in a 10% buffered formalin solution. TTC-stained sections were photographed using a charge coupled device camera (EDH-1000HR Computer Camera, Electrim Corporation, Princetown, N.J., USA). A blinded investigator measured the infarct sizes with a computerized image analyzer (Bio Scan Optimas, Edmonds, Wash.). To compensate for the effect of brain edema the corrected infarct volume was calculated as previously described in detail: Corrected infarct area equals left hemisphere area minus (right hemisphere area minus infarct area) (Schäbitz W R, et al., Stroke 2001; 32: 1226-33). Infarct volumes were expressed as a percentage of the contralateral hemisphere.

Ischemia Experiment

Figure 1:
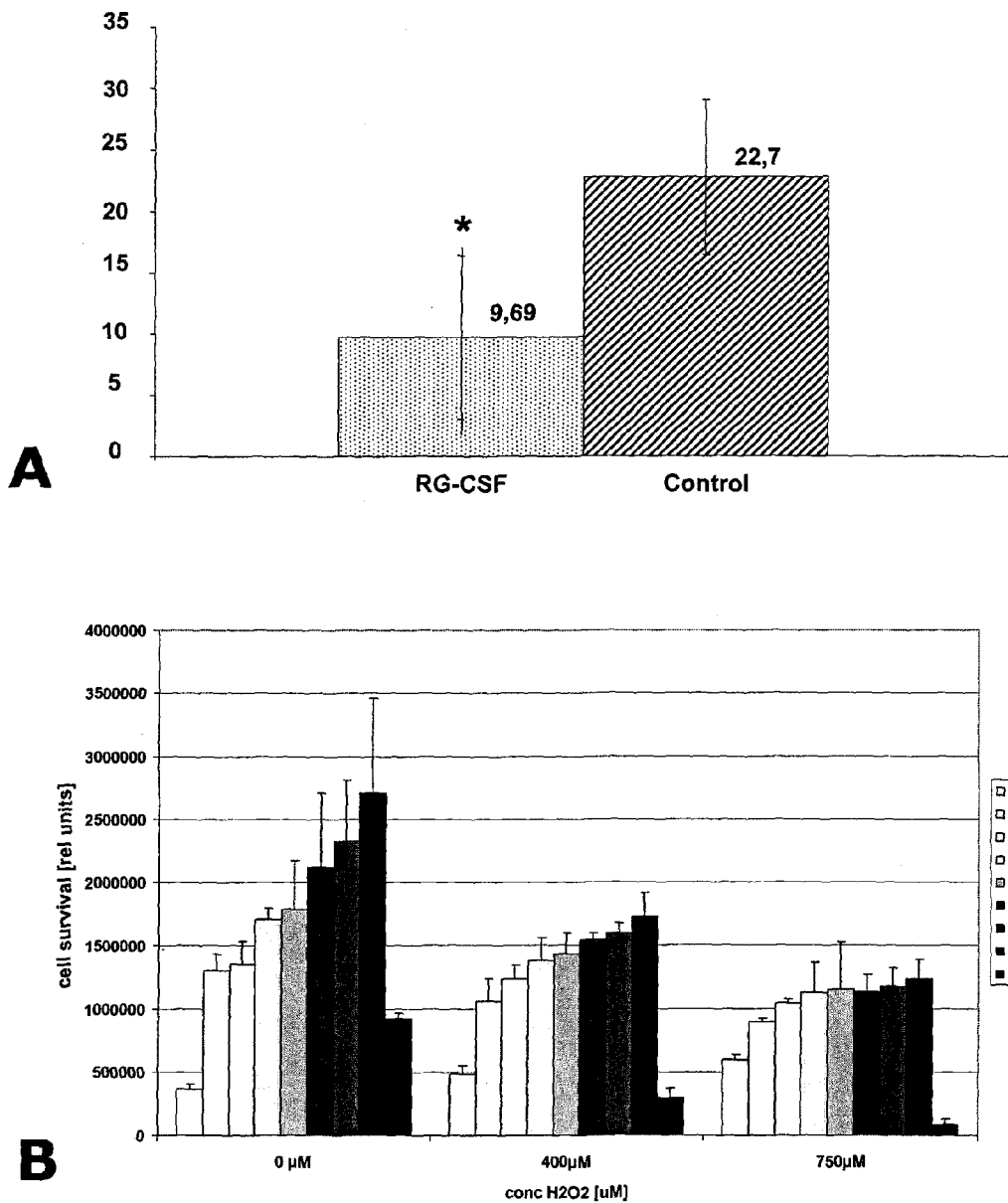
FIG. 1 demonstrates effective neuroprotection by GCSF in vivo and in vitro. A. The extent of neuroprotection of GCSF after focal cerebral ischemia (filament model; middle cerebral artery occlusion, MCAO) as measured by TTC-staining. The values of the y-axis relate to percent of infarction of the total hemisphere (data are mean±SD; T-test; $p<0.05$). B. Cell survival assay in NGF-treated PC12 cells under increasing oxidative stress by $H_2O_2$ (O uM, 400 uM, 750 uM). GCSF treatment produces dramatic increases in cell survival. In comparison, cell survival after treatment of the cells with Erythropoetin (EPO), a known neuroprotective substance, is given. Y-axis: Relative (Rel.) cell survival (light units of luciferase activity).

GCSF achieved a potent neuroprotective effect after focal cerebral ischemia. Mean infarct volume in intraperitoneal GCSF treated animals was 131.96 mm$^3$±112.7 mm$^3$ versus 278.9 mm$^3$±91.56 mm$^3$ in the control group or 9.96±8.31% (n=12) versus 22.7±6.69% of the total hemisphere (p<0.05; FIG. 1).

GCSF treatment significantly reduced mortality: Four animals in the control group and one in the GCSF-treated group died within the 24-hour reperfusion period (p<0.05). No statistical differences were observed between the control and GCSF-treated group for rectal temperature, pH, pCO$_2$, pO$_2$, hematocrit (hct), blood glucose, heart rate, mean arterial pressure, and body weight for all animals (Table 1). Leukocyte count in the peripheral blood was significantly increased 24 hours after ischemia in GCSF treated animals compared to controls (p<0.05, Table 1).

Example 2

Immunohistochemistry in the Context of Focal Cerebral Ischemia

Immunohistochemical Methods Used

For morphological analysis of STAT3 activation (FIG. 6) and GCSFR distribution in infarcted brains, and counts of neutrophilic granulocytes, a 2-mm-thick brain slice of GCSF-treated animals and controls was immersion fixed in 4% paraformaldehyde in 0.1 mol/l phosphate buffer for 24 hrs (n=5 per group). After paraffin-embedding, 1-μm-thick sections were cut and used for H&E staining, Nissl staining and immunohistochemical analysis.

Immunohistochemical studies were performed with antisera against myeloperoxidase (DAKO, Carpinteria, Calif., USA), glial fibrillary acidic protein (GFAP) (DAKO, Carpinteria, Calif., USA), GCSFR (Santa Cruz Biotechnology Inc., Santa Cruz, Calif., USA) and STAT3 (Santa Cruz Biotechnology Inc., Santa Cruz, Calif., USA). For antigen retrieval, sections provided for GCSFR and STAT3 immunohistochemistry were heated for 20 min in a 10 mM citrate buffer at 99° C. Sections were then incubated in normal swine serum (10% in phosphate-buffered saline) for 30 min and then in the primary antisera overnight at 4° C. The primary antibodies were diluted 1:150 (myeloperoxidase), 1:400 (GFAP), 1:400 (GCSFR) and 1:100 (STAT3), respectively. Immunoreactivity was visualized by the avidin biotin complex method (Vectastain, Vector Laboratories, USA). Sections were developed in 0.02% diaminobenzidine (DAB) with 0.02% hydrogen peroxide. The reaction product was intensified by the addition of 0.02% cobalt chloride and nickel ammonium sulfate. In a subset of control slides preabsorption of the GCSFR antiserum with the respective peptide did not produce immunostaining (not shown). When omitting the primary antisera, no immunostaining was produced either (not shown).

Invasion of neutrophilic granulocytes (NG) was quantitatively measured by counting NGs per infarcted hemisphere. STAT3 protein expression was quantified in 2 overlapping fields rostro-caudal in the vincinity of the infarction of the parietal cortex and the corresponding contralateral side (magnification×400). To this end, neurons with nuclear translocation were counted, given as percent of STAT3 positive neurons from all neurons.

TABLE 1

| Time | Group (n = 1) | rectal Temp | pH | pCO2 (mm Hg) | pO2 (mm Hg) | Hct (%) | Gluc (mg/dL) | MABP (mm Hg) | HR (Beats/min) | Leukocytes (×10$^9$/L) | Body Weight (g) |
|---|---|---|---|---|---|---|---|---|---|---|---|
| Pre-ischemia | Control | 37 ± 0.2 | 7.38 ± 0.03 | 39 ± 7 | 89 ± 7 | 47.4 ± 3.6 | 263 ± 25 | 98 ± 12 | 358 ± 13 | 1.9 ± 0.3 | 314 ± 25 |
| | rGCSF | 37 ± 0.3 | 7.35 ± 0.02 | 38 ± 5 | 91 ± 7 | 46 ± 0.9 | 251 ± 31 | 102 ± 15 | 350 ± 24 | 1.8 ± 0.4 | 318 ± 29 |
| 1 h | Control | 37 ± 0.1 | 7.38 ± 0.02 | 41 ± 6 | 88 ± 5 | 45.3 ± 0.8 | 160 ± 13 | 112 ± 21 | 384 ± 16 | 6.5 ± 0.6 | |
| | rGCSF | 37 ± 0.2 | 7.37 ± 0.03 | 39 ± 4 | 89 ± 8 | 44.3 ± 0.7 | 172 ± 17 | 109 ± 19 | 371 ± 27 | 6.8 ± 0.3 | |
| 2 h | Control | 37 ± 0.3 | 7.39 ± 0.03 | 37 ± 3 | 87 ± 8 | 44.6 ± 0.8 | 149 ± 12 | 101 ± 14 | 368 ± 13 | 8.2 ± 0.4 | |
| | rGCSF | 37 ± 0.2 | 7.4 ± 0.04 | 39 ± 6 | 89 ± 5 | 44.2 ± 0.4 | 152 ± 14 | 99 ± 8 | 372 ± 9 | 8.5 ± 0.3 | |
| 3 h | Control | 37 ± 0.2 | 7.38 ± 0.02 | 38 ± 5 | 91 ± 5 | 43.3 ± 0.9 | 133 ± 7 | 102 ± 16 | 366 ± 17 | 9.7 ± 0.8 | |
| | rGCSF | 37 ± 0.1 | 7.37 ± 0.03 | 37 ± 4 | 94 ± 10 | 43.1 ± 1.2 | 141 ± 10 | 99 ± 12 | 384 ± 13 | 10.6 ± 0.5 | |
| 4 h | Control | 37 ± 0.2 | 7.36 ± 0.02 | 37 ± 6 | 87 ± 5 | 42.1 ± 0.9 | 168 ± 13 | 113 ± 24 | 373 ± 21 | 13.2 ± 0.6 | |
| | rGCSF | 37 ± 0.3 | 7.38 ± 0.03 | 39 ± 7 | 89 ± 9 | 42.8 ± 1.1 | 174 ± 16 | 120 ± 17 | 361 ± 12 | 13.7 ± 0.6 | |
| 24 h | Control | 37 ± 0.2 | 7.37 ± 0.03 | 38 ± 4 | 86 ± 6 | 46.7 ± 1.5 | 198 ± 13 | 115 ± 17 | 365 ± 10 | *3.8 ± 0.8 | 285 ± 24 |
| | rGCSF | 37 ± 0.2 | 7.37 ± 0.04 | 41 ± 5 | 87 ± 8 | 47 ± 0.5 | 204 ± 16 | 117 ± 21 | 359 ± 15 | 9.7 ± 0.4 | 293 ± 16 |

Table 1 lists physiological parameters of GCSF treated animals and controls. Values are given as mean ± SD (p < 0.05; ANOVA; F-test).
LDF-monitoring revealed no statistical differences between the two treatment groups (data not shown).

Results of the Immunohistochemical Experiments in Focal Cerebral Ischemia

Myeloperoxidase (MPO) staining detected no neutrophilic granulocytes (NGs) in the non-ischemic hemispheres of both groups. MPO staining was not significantly different between GCSF treated animals and controls based on quantified MPO positive cells in the ischemic hemisphere (14±17.6 versus 14.3±12.5, n.s.).

GFAP immunoreactivity (IR) was present in scattered astrocytic processes throughout the cortex, striatum and white matter of the non-infarcted hemisphere. No difference in the pattern and intensity of GFAP staining was detectable in the cortical peri-infarct zone both in untreated and GCSF treated rats. In particular, GFAP IR was not increased in the cortical penumbra, neither in the placebo group, nor in the GCSF group (not shown). Within the infarct core, scattered GFAP immunoreactive astrocytes were detectable (not shown).

Immunohistochemically, staining for GCSFR was detectable in scattered cortical neurons and neurites (not shown) both in untreated and GCSF treated animals. Glial cells were also stained with the GCSF-R antibody (not shown). In the infarct core, no GCSF-R immunreactive cells were seen. No difference in the pattern and intensity of GCSF-R IR was evident between the two experimental groups.

Figure 6:
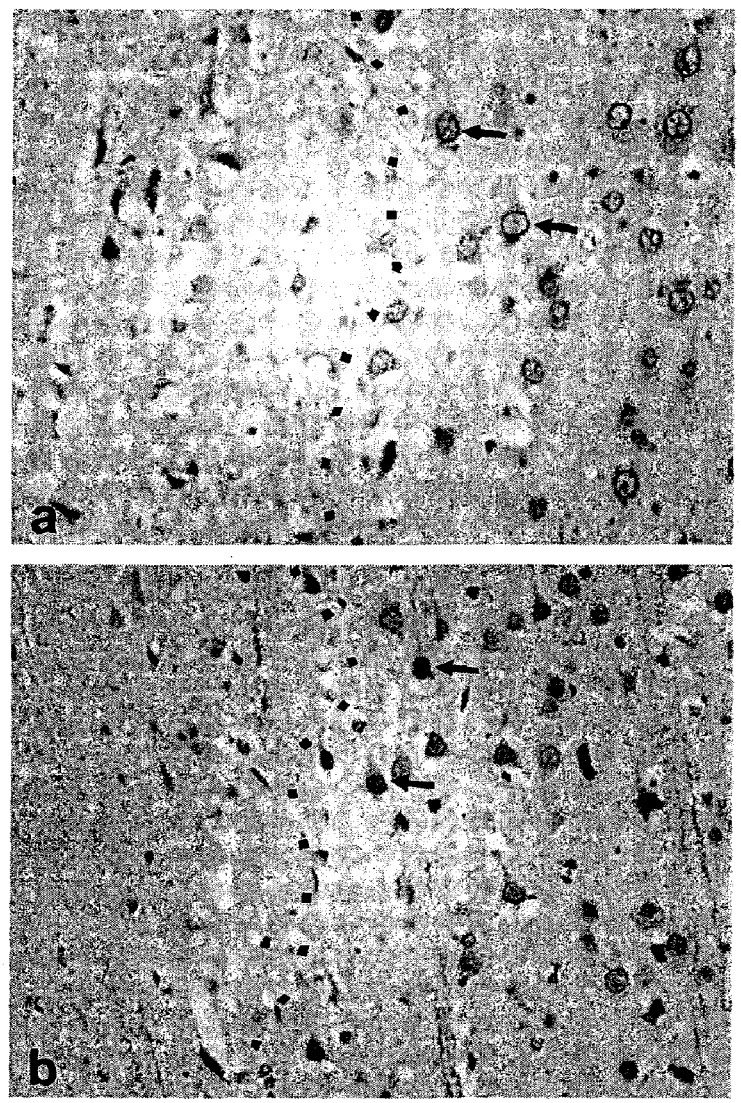
FIGS. 6 and 7 show the immunohistochemical results obtained with an antibody against STAT3.
Figure 7:
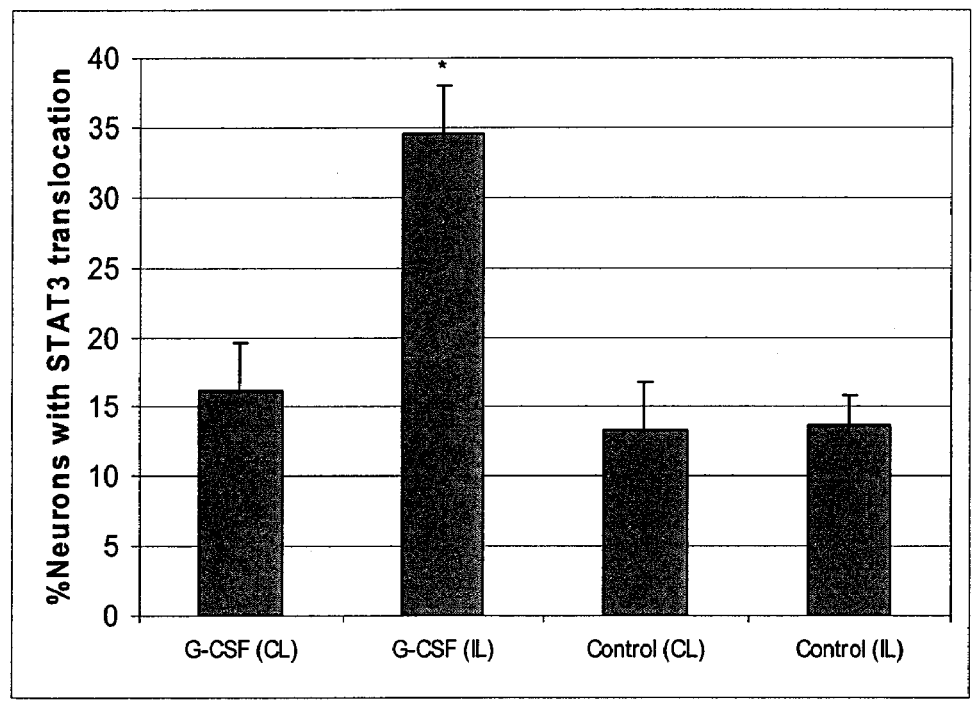

STAT3 IR was seen in scattered nuclei of neurons and glial cells within the uninfarcted hemisphere of both placebo and GCSF treated rats. Some cytoplasmic staining was also present in a few scattered neurons. STAT3 protein expression was significantly increased after GCSF treatment in the penumbra of the infarction compared to untreated controls (34.4±7.05 versus 13.7±4.4; $p<0.0003$) (FIG. 6, 7). No difference occurred on the contralateral side (16.2±6.9 versus 13.3±6.9; n.s.).

Example 3

Western Blots and PCR in the Context of Focal Cerebral Ischemia

Figure 3:
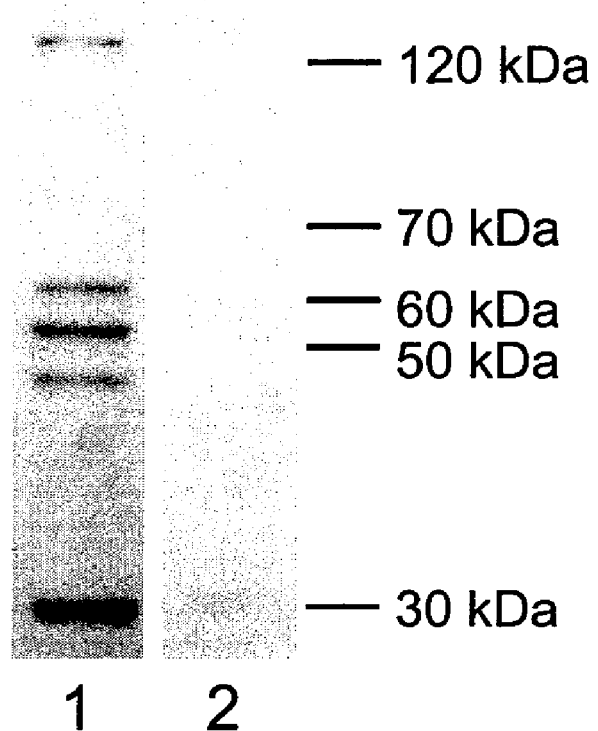
FIG. 3 Representative immunoblots of GCSF-R. Using the GCSF-R antiserum a band at about 130 kDa is detectable in tissue of the rat cortex (lane 1). Additional bands of lower molecular weight most probably reflect break down products. After preabsorption of the antiserum with the respective peptide, no bands are yet detectable (lane 2).
Figure 5:
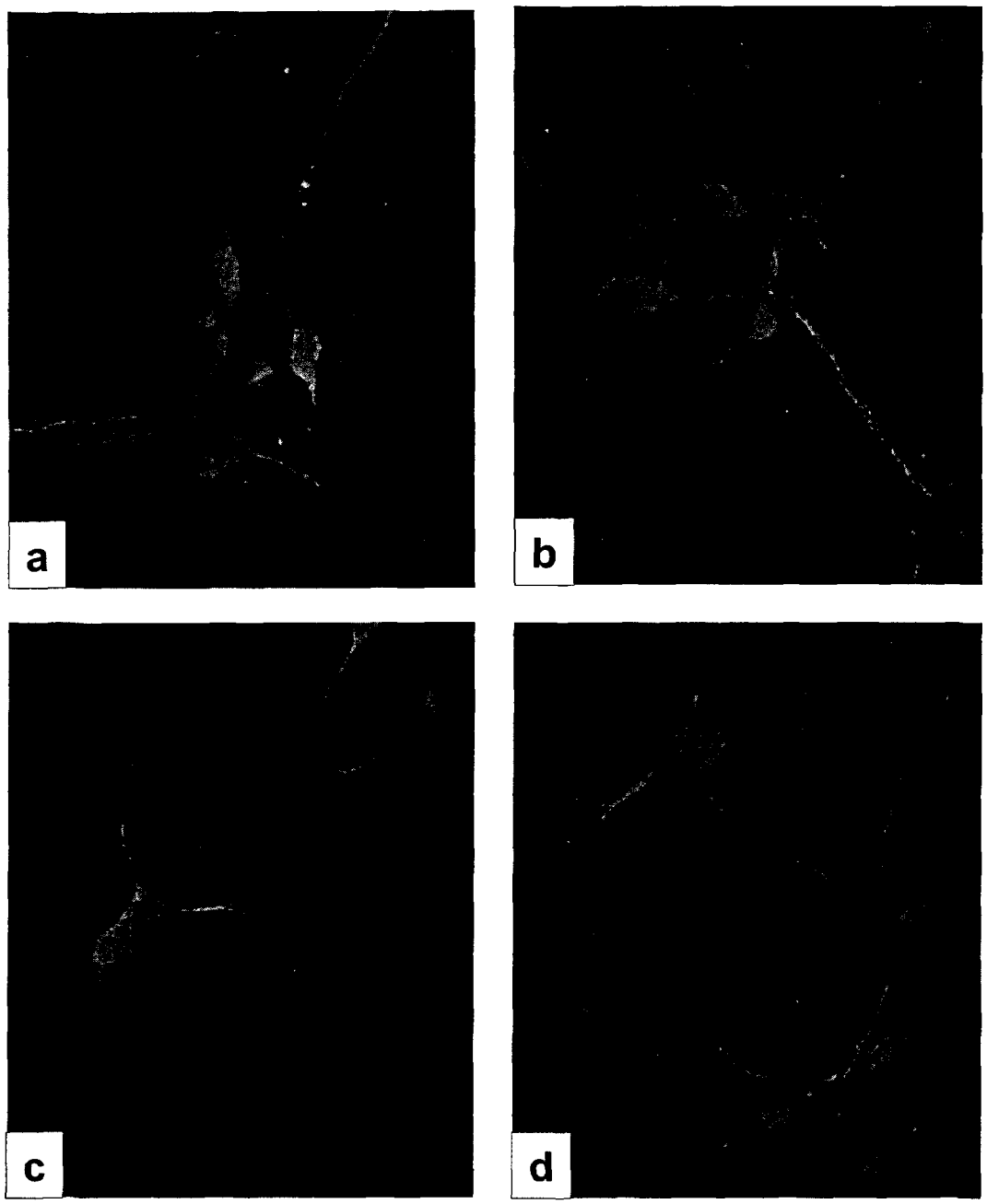
FIG. 5 shows a staining for the GCSFR on cortical (a, b) and hippocampal cultured neurons (c, d). The receptor is both present on the somata and processes of the neurons. Not all neurons on the slide were labelled. Preincubation of the antibody with the respective peptide, or omission of the primary antibody did not result in specific staining (not shown).

Western Blots (FIG. 3)

For immunoblotting, brain tissue (transient ischemia of 2 hours) was lysed in 20 volumes (w/v) of homogenization buffer (320 mM sucrose, 0.1 mM phenylmethylsulfonyl fluoride, and 2 µg/ml Pepstatin) at 4° C. Homogenates were centrifuged at 9,200 G for 15 min at 4° C. After resuspending pellets in 1/10 of the homogenization volume, aliquots for protein determination (Bio-Rad protein-assay, Munich, Germany) were separated and samples were rapidly frozen in nitric oxide and stored at −70° C. Per lane 15 µg protein were loaded on a 8% SDS polyacrylamide gel containing 4 M urea and electrophoresed under standard conditions. Proteins were electrophoretically transferred to Immobilon-P™ membranes (Millipore Corp., Eschborn, Germany) by semi-dry blotting. After blocking in 3% nonfat dry milk in TBST (20 mM Tris base, pH 7.6, 137 mM NaCl and 0.05% Tween-20) for 1 hour at room temperature (RT), membranes were incubated with the primary GCSFR antibody (1:500) overnight at 4° C. After washing in TBST the membranes were incubated for 1 hour at RT with 1:2,000 dilutions of the appropriate horseradish peroxidase-conjugated secondary antibody. Immunoreactive bands were visualized in the linear range with enhanced chemoluminescence (Amersham Intl., Braunschweig, Germany).

In immunoblotting experiments with cortical extracts (FIG. 3), the GCSF-R antiserum detected a protein band of approximately 130 kD, consistent with the deduced molecular weight (Fukunaga R. et al., *J Biol Chem* 1990; 265:14008-15). In addition, a few bands of lower molecular weight were seen, probably reflecting breakdown products. After preabsorption of the GCSFR antiserum with the respective peptide the bands disappeared (FIG. 3).

PCR for the GCSF Receptor in Brain (FIG. 2A)

After rats were deeply anesthetized and perfused transcardially, brains were rapidly dissected. RNA was extracted from brains by the RNA-clean kit (AGS, Heidelberg, Germany), according to the manufacturer's instructions. A total of 10 µg RNA was reverse transcribed with MMLV reverse transcriptase and random hexamers. For PCR, the following primers from exons 5 and 7 of the murine GCSFR were used: sense, 5'-CCC CTC AAA CCT ATC CTG CCT C-3' (SEQ ID NO:5); and antisense, 5'-TCC AGG CAG AGA TCA GCG AAT G-3' (SEQ ID NO:6). (Ashihara E, et al., *J Cell Physiol* 1997; 171:343-56). PCR was performed according to the following protocol: 3 min 94° C., 1 min 94° C., 1 min 58° C., and 1 min 72° C. (40 cycles). The product was analyzed on a 2% agarose gel.

Figure 2:
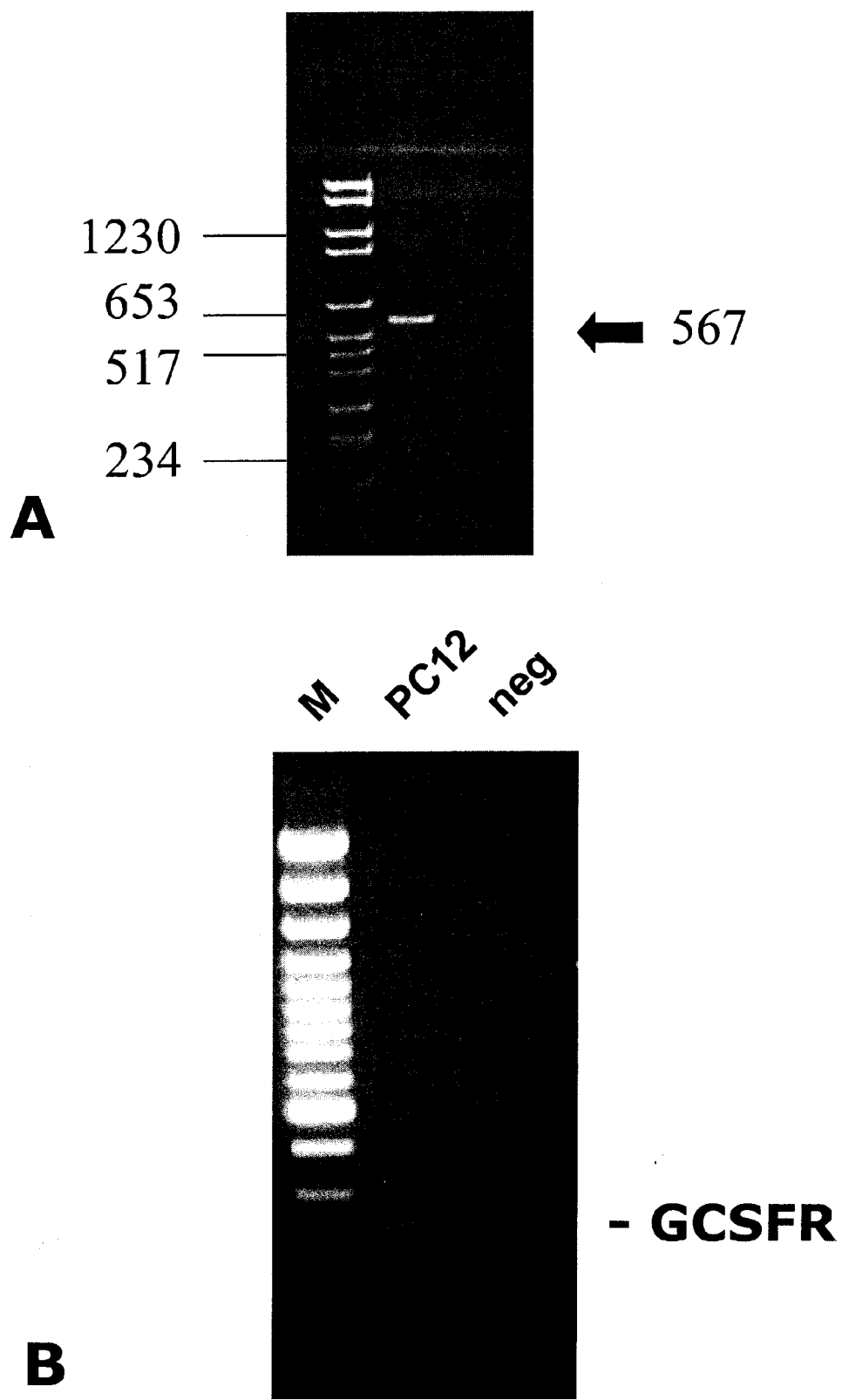
FIG. 2A shows a RT-PCR specific for the mouse GCSFR. GCSF-R RNA was detected in the brain tissue with the expected size of 567 bp. The identity was verified by sequencing the PCR product.

Using a RT-PCR specific for the mouse GCSFR, GCSF-R mRNA was detected in the brain tissue (FIG. 2A). The PCR product had the expected size of 567 bp. The identity was verified by sequencing the PCR product (FIG. 2).

Example 4

GCSF Efficacy in ALS Models

Survival Test in ALS Mouse Models

Previous experiments have demonstrated that SOD1 mouse models of ALS are predictive of the success of therapy in humans (Cleveland and Rothstein (2001), *Nat Rev Neurosci,* 2, 806-19). Primary endpoints in such analyses are both onset of motor signs, and mortality. For example, the onset of motor signs can be defined as the first day that a mouse can not remain on the rotarod for 7 min at a speed of 20 rpm (Li et al (2000), *Science,* 288, 335-9). Mortality is scored as the day of death, or the day where deficits are so severe that the mouse has to be sacrificed (e.g. apathy and unability to right itself). Additional parameters are determined by the measurement of motor strength by grip strength tests, counts of motor neurons in the spinal cord, nerve thickness (e.g. sciatic nerve, phrenic nerve), and the presence of apoptotic stainings in spinal cord motor neurons. GCSF can be infused via an osmotic pump into the cerebral ventricles at a pre-determined dose, e.g. at 60 ug/kg body weight/day. Alternatively, GCSF is given via i.v. or i.p. injection at a dose of 60 ug/kg body weight per day, or higher doses. Alternatively, a slow-release form of GCSF is administered, such as a PEG formulation (see above), or an albumin formulation (see above), or other slow-release formulations. Alternatively, any GCSF or derivative or formulation of other source (another manufacturer (e.g. LENOGASTRIM™ from Roche, GRANOCYTE™ from Chugai Pharma, Co. Ltd., ALBUGRANIN™ from Human Genome Sciences, or NEULASTA™ from Roche/Amgen) is used. Treatment is started at day 60 in the late presymptomatic stage of the SOD1 G93A mutant. In nontreated familial ALS mice, motor impairments appear at 12-14 weeks of age, whereas paralysis is not observed before 20 weeks of age. Life expectancy is 140-170 days. Effective treatment should prolong life as compared to the control group by more than 15% (Cleveland and Rothstein (2001), *Nat. Rev. Neurosci.,* 2, 806-19). As a control group for treatment, both vehicle and zVADfmk (a potent caspase inhibitor that has shown efficacy in this model) treated animals will be used. Each group comprises 10 animals each.

Example 5

GCSF Efficacy in Parkinson Models

There are various rodent models of Parkinson's disease available, that are suitable for efficacy studies of GCSF (Grunblatt, et al. (2000), *J Neurol,* 247 Suppl 2, II95-102). One well-characterized model is the use of 1-methyl-4-phenyl-1,2,3,6-tetrahydropyridine (MPTP). 4 doses of MPTP-HCl (15 mg/kg per dose) can be given to eight-week-old male mice (n=20) via i.p. injection at 2 hr intervals. Sham-treated animals receive saline. 20 animals receive both the MPTP treatment, and a daily dose of GCSF (i.v., 60 ug/kg bodyweight) seven days after the last MPTP treatment mice are sacrificed. Until that time, mice are analyzed both for motor parameters (rotarod performance, free locomotion). The brains of 10 mice each are processed for immunohistochemistry to assay the total number of neurons in the substantia nigra that are positive for tyrosine hydroxylase or the dopamine transporter (using commercially available antibodies), the number of apoptosis-positive neurons (TUNEL staining, caspase-3 staining). Remaining dopaminergic neurons after MPTP treatment are compared to those receiving MPTP plus GCSF, and to the sham group.

The remaining 10 animals in each group will be perfused transcardially with saline, sacrificed, and the striatum dissected out. The striatum will be homogenized on ice, and the dopamine content measured by HPLC with electrochemical detection. Comparison of the three groups will provide a good measure of dopamine depletion due to loss of cells in the substantia nigra.

This experiment can also be performed using different dosing schemes for MPTP (i.e. 40 mg/kg body weight once; 30 mg/kg body weight twice, etc.).

Example 6

GCSF Improves Sensory-Motor Function after Photothrombotic Cerebral Ischemia (FIG. 8)

Experimental Groups

Experimental protocols were approved by the local ethics committee. Male Wistar rats (Charles River, Germany) weighing 280 to 320 g were randomly assigned to the following groups: A (Control group, n=6), ischemia, treatment with 0.5 ml saline 0.9% as i.v. bolus infusion beginning 1 h after ischemia); B (GCSF group, n=6), ischemia, treatment with 5 µg GCSF (Amgen) soluted in 0.5 ml saline 0.9% as i.v. bolus beginning 1 h after ischemia. Alternatively, any GCSF or derivative or formulation of other source (another manufacturer (e.g. Lenogastrim™ by Roche or Granocyte™ by Chugai or Albugranin™ by HGS or Neulasta™ by Roche/Amgen) can be used here. Repetitive i.v. bolus infusions via the tail vene followed at day 1 to 5. C (sham operated group, n=6), sham operation, no ischemia, treatment with 0.5 ml saline 0.9% as i.v. bolus infusion beginning 1 h after ischemia.

Focal Cerebral Ischemia by Photothrombosis

Animals were anesthetized with an intramuscular injection of 100 mg/kg body weight ketaminehydrochloride (WDT, Garbsen, Germany). Anesthesia was maintained with 50 mg/kg body weight if necessary. A PE-50 polyethylene tube was inserted into the right femoral artery for continuous monitoring of mean arterial blood pressure, and blood gases. The right femoral vein was cannulated by a PE-50 tube for treatment infusion. During the experiment rectal temperature was monitored and maintained at 37° C. by a thermostatically controlled heating pad (Föhr Medical Intruments, Germany).

Photothrombotic ischemia was induced in the right rat parietal cortex according to the method of Watson et al. (Watson B D, Dietrich W D, Busto R, Wachtel M S, Ginsberg M D. Induction of reproducible brain infarction by photochemically initiated thrombosis. *Ann Neurol.* 1985; 17:497-504). Animals were anesthetized with ketaminehydrochloride and placed in a stereotaxic frame, and the scalp was incised for exposure of the skull surface. For illumination, a fiber-optic bundle with a 1.5-mm aperture was placed stereotaxically onto the skull 4 mm posterior to the bregma and 4 mm lateral from the midline. The skull was illuminated with a cold, white light beam (150 W) for 20 minutes. During the first 2 minutes of illumination, the dye rose bengal (0.133 mL/kg body wt, 10 mg/mL saline) was injected intravenously. Sham-operated animals underwent the same experimental procedures as described above without infusion of rose bengal and illumination. After surgery, the catheters were removed, and the animals were allowed to recover from the anesthesia and given food and water ad libitum.

Behavioural Testing

In all animals a battery of behavioral tests was performed before ischemia and at baseline, 2, 3, 4, 5, and 6 weeks after ischemia by an investigator who was blinded to the experimental groups. For the rotarod test, rats were placed on an accelerating rotarod cylinder, and the time the animals remained on the rotarod was measured (Hamm et al, *J Neurotrauma* 1994 April; 11(2):187-96, Chen J, Li Y, Wang L, Zhang Z, Lu D, Lu M, Chopp M. Therapeutic Benefit of Intravenous Administration of Bone Marrow Stromal Cells After Cerebral Ischemia in Rats. Stroke. 2001; 32:1005). The speed was slowly increased from 4 to 40 rpm within 5 minutes. The trial ended if the animal fell off the rungs or gripped the device and spun around for 2 consecutive revolutions without attempting to walk on the rungs. An arbitrary limit of time was set for the rats at 500 seconds on the rotarod cylinder in training as well as in testing procedures. The animals were trained 3 days before ischemia. The mean duration (in seconds) on the device was recorded with 3 rotarod measurements 1 day before surgery. Motor test data are presented as percentage of mean duration (3 trials) on the rotarod compared with the internal baseline control (before surgery).

For the adhesive-removal test, somatosensory deficit was measured both before and after ischemia (Schallert T, Kozlowski D A, Humm J L, Cocke R R. Use-dependent structural events in recovery of function. Adv Neurol. 1997; 73:229-238; Chen J, Li Y, Wang L, Zhang Z, Lu D, Lu M, Chopp M. Therapeutic Benefit of Intravenous Administration of Bone Marrow Stromal Cells After Cerebral Ischemia in Rats. Stroke. 2001; 32:1005). All rats were familiarized with the testing environment. In the initial test, 2 small pieces of adhesive-backed paper dots (of equal size, 113.1 mm$^2$) were used as bilateral tactile stimuli occupying the distal-radial region on the wrist of each forelimb. The rat was then returned to its cage. The time to remove each stimulus from forelimbs was recorded on 5 trials per day for each forepaw. Individual trials were separated by at least 5 minutes. Before surgery, the animals were trained for 3 days. Once the rats were able to remove the dots within 10 seconds, they were subjected to ischemia.

Neurological Severity Scores (NSS) were modified according to Chen J, Li Y, Wang L, Zhang Z, Lu D, Lu M, Chopp M. Therapeutic Benefit of Intravenous Administration of Bone Marrow Stromal Cells After Cerebral Ischemia in Rats. Stroke. 2001; 32:1005., and Schallert T, Kozlowski D A, Humm J L, Cocke R R. Use-dependent structural events in recovery of function. Adv Neurol. 1997; 73:229-238. Neurological function was graded on a scale of 0 to 16 (normal score, 0; maximal deficit score, 16). NSS is a composite of motor, sensory, reflex, and balance tests (Chen J, Li Y, Wang L, Zhang Z, Lu D, Lu M, Chopp M. Therapeutic Benefit of Intravenous Administration of Bone Marrow Stromal Cells After Cerebral Ischemia in Rats. Stroke. 2001; 32:1005., Germano A F, Dixon C E, d'Avella D, Hayes R L, Tomasello F. Behavioral deficits following experimental subarachnoid hemorrhage in the rat. J. Neurotrauma. 1994; 11:345-353). In the severity scores of injury, 1 score point is awarded for the inability to perform the test or for the lack of a tested reflex; thus, the higher score, the more severe is the injury.

Results

No statistical differences were observed between the groups for rectal temperature, pH, $pCO_2$, $PO_2$, hematocrit (hct), blood glucose, heart rate, mean arterial pressure, body weight, and mortality for all animals (data not shown).

Functional recovery in GCSF treated animals was remarkably better over time compared with all other groups. GCSF treated animals had significantly lower NSS scores including Beam-Balance during the experiment compared to the control group ($p<0.001$, FIG. 8 b), and resulted in significantly better rotarod performance compared to controls ($P<0.05$, FIG. 8 a). Sensorimotor function as measured by adhesive tape removal was also better in GCSF treated animals on the contralateral forepaw over time compared to controls as well as on the ipsilateral forepaw at week 6 (see FIG. 8 c,d).

Example 7

GCSF Receptor is Upregulated in the Photothrombotic Model of Cerebral Ischemia

Figure 9A:
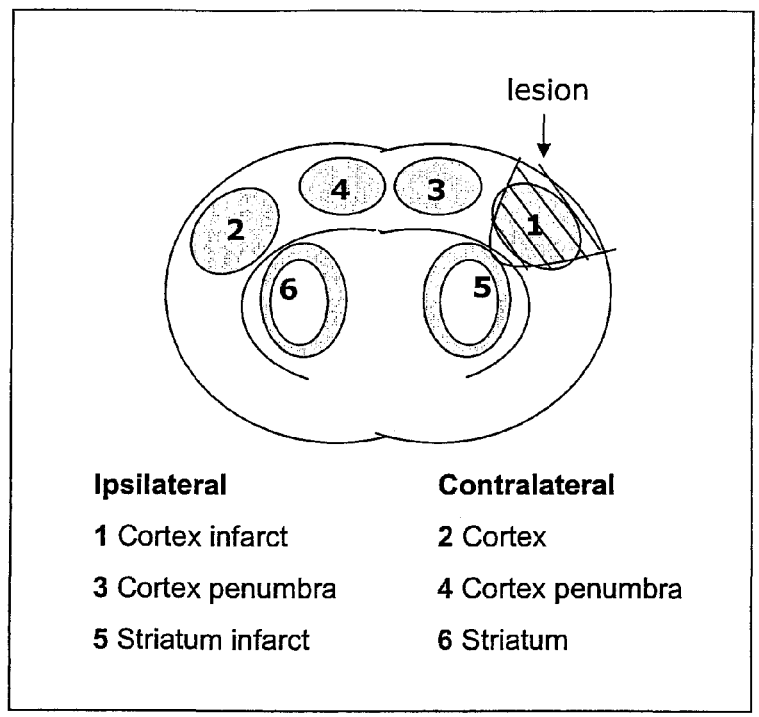
FIG. 9 shows the upregulation of the GCSF-Receptor in the bengal-rose model 48 h after induction of photothrombosis on the contralateral side to the ischemia. A, scheme of a coronal section of a rat brain, tissue samples 3 and 4 were used for the quantification of the GCSF receptor mRNA compared to the same tissue samples from sham-operated rats. B, quantification of GCSF receptor mRNA in the cortical penumbral samples (samples 3 and 4 from A). An initial upregulation at 6 h after ischemia induction on the ipsilateral side is followed by an upregulation on the contralateral side at 48 h after the infarct. This contralateral upregulation was also seen with the GMCSF receptor (see below).
Figure 9B:
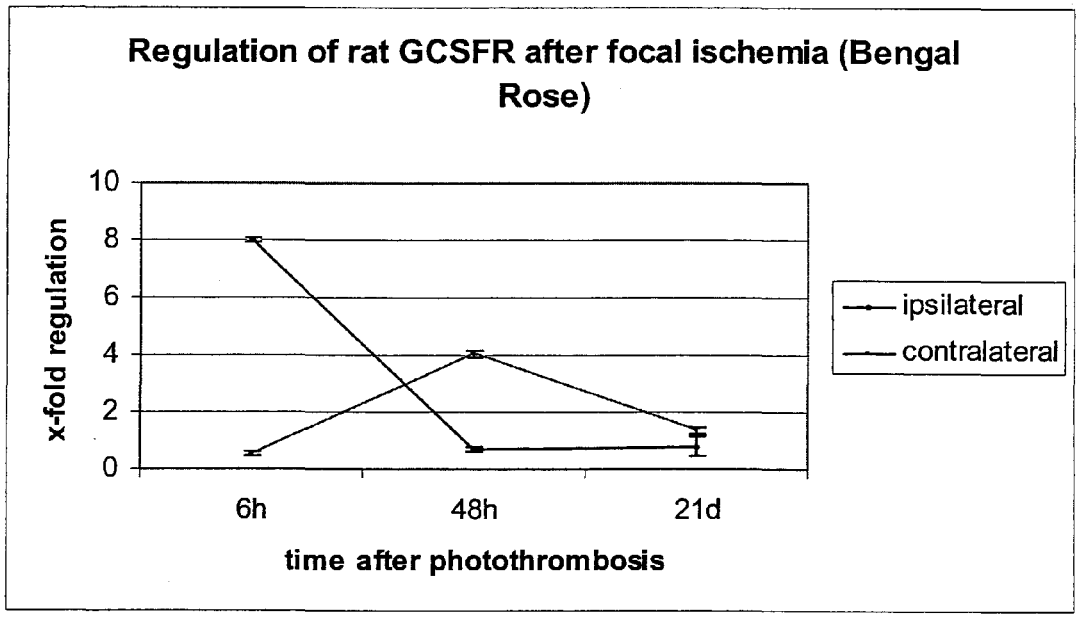

RNA was isolated according to standard protocols (Chomczynski and Sacchi (1987), *Anal. Biochem.*, 162, 156-159), followed by Qiagen RNeasy™ mini kit purification from rat cortical penumbral samples, ipsi- and contralateral to the lesion side (see FIG. 9a for localization of the tissue samples; here: 3 vs. 4). cDNA was synthesized from 1 μg total RNA using oligodT primers, superscript II reverse transcriptase (Gibco) using standard conditions. Quantitative PCR was performed using the Lightcycler® system (Roche Diagnostics, Mannheim, Germany) with SYBR-green staining of DNA doublestrands. Cycling conditions were as follows: 5 min 95° C., 5 sec 95° C., 7 sec 66° C., 30 sec 72° C.; 9 sec 84° C. for 55 cycles. Melting curves were done with the following parameters: 95° C. cooling to 50° C.; ramping to 99° C. at 0.2° C./sec. The following primer pairs were used: "rat GCSFR-frag-32s" CCATTGTCCATCTTGGGGATC (SEQ ID NO:7), and "rat GCSFR-frag-265as" CCTGGAAGCTGT-TGTTCCATG (SEQ ID NO:8). The Lightcycler® PCR was performed using the SYBR green master mix, following the manufacturer's recommendations (Roche Diagnostics). Specificity of product was ensured by melting point analysis and agarose gel electrophoresis. cDNA content of samples was normalized to the expression level of Cyclophilin (primers: "cyc5" ACCCCACCGTGTTCTTCGAC (SEQ ID NO:9); "acyc300" CATTTGCCATGGACAAGATG (SEQ ID NO:10)). Relative regulation levels were derived after normalization to cyclophilin, and comparison to the sham-operated animals. FIG. 9 b shows upregulation of the GCSFR after 48 h on the contralateral side, error bars indicate standard deviations, these are calculated from 3-fold serially diluted cDNA-samples, and reflect reliability of measurements.

Example 8

GCSF Receptor is Present on Neuronal Cells in Primary Cultures: Immunocytochemistry Preparation of Neurons 10-12 Cortices were prepared from embryos of the stage E18 (embryonal day 18). Tissue was dissociated using trypsin [10 mg/ml]/EDTA/DNase [5 mg/ml] (Roche Diagnostics) in HBSS (Hanks balanced salt solution, BioWithakker). The digest was stopped using 4 parts medium (neurobasalmedium+1 ml 50× B-27 supplement (Invitrogen)+0.5 mM L-glutamin+25CM glutamate) and centrifuged at room temperature for 5 min at 800 g. The pellet was dissolved in 5 ml medium and cell number determined by counting (Neubauer slide). The cells were plated at a density of 250 000 cells per well of a 24-well-plate on cover slips which were coated with poly-L-lysine.

Immunocytochemistry 14 days after preparation neurons were washed with PBS (Gibco) (37° C.) and fixed with 2% paraformaldehyde for 10 min on ice. Then, cells were washed with PBS (4° C.) and stored at 4° C. Cells were incubated for 10 min in 50 mM glycine in PBS, and then washed with PBS. Cells were permeabilised on ice using 0.2% TritonX-100 (Sigma) in PBS, and incubated with blocking solution (0.2% Triton-X100, 4% normal goat serum (NGS) (Jackson Immunoresearch Laboratories) in PBS) at room temperature. The primary antibody (rabbit-anti-GCSF-Rezeptor-antibody directed against the C-terminus of mouse GCSFR, M-20; sc-694; SantaCruz Biotechnology, Inc.) was used in a dilution of 1:800 (in 0.1% Triton-X100/2% NGS), and incubated overnight at 4° C. Cells were then washed with 1% NGS/PBS, and incubated for 30 min with the secondary antibody (anti-rabbit-FITC, 1:400; dianova) at room temperature. Cells were then washed briefly in 1% NGS/PBS, and stained with Hoechst 33342 (Molecular Probes) (1:10000 in PBS) for counterstaining the nuclei. Finally, cover slips were washed briefly twice in 1% NGS/PBS, twice in PBS, and once for 10 min in 10 mM Tris/HCl, pH 7,6. The cover slips were embedded using Aquamount (Polyscience).

Pictures were taken digitally with an Olympus IX81 microscope, and the "Analysis" software package (Soft Imaging Systems, Stuttgart, Germany).

Example 9

GCSF Receptor is Present on Neuronal Stem Cells: PCR and Immunocytochemistry (FIG. 12,13); GCSF Receptor is Present on PC12 Cells: PCR (FIG. 2B)

Generation of Neural Stem Cells

Neural stem cells were isolated from the brain areas with known spontaneous neurogenesis, i.e., hippocampus, olfactory bulb, and subventricular zone, of 4-6 week old male Wistar rats as described. (Ray J et al (1993), *Proc Natl Acad Sci USA* 90: 3602-6). Protocols are concordant with the policy on the use of animals, as endorsed by the National Research Council of the U.S.A., and fulfill the requirements of German law. Briefly, animals were anesthesized with 1% (v/v) isoflurane, 70% N2O, 29% oxygen and sacrificed by decapitation. The brains were removed and washed in 50 mL ice-cold Dulbecco's Phosphate Buffered Saline (DPBS) supplemented with 4.5 g/L glucose (DPBS/Glc). Hippocampus, olfactory bulb, and subventricular zone from 6 animals were dissected, washed in 10 mL DPBS/Glc and centrifuged for 5 min at 1600×g at 4° C. After removal of the supernatant, the tissue was homogenized with scissors and scalpels. The tissue pieces were washed with DPBS/Glc medium for 5 min at 800 g, and the three pellets were resuspended in 0.01% (w/v) papain, 0.1% (w/v) dispase II (neutral protease), 0.01% (w/v) DNase I, and 12.4 mM manganese sulfate in Hank's Balanced Salt Solution (HBSS). The tissue was triturated with plastic pipet tips and incubated for 40 min at room temperature, but every 10 min the solution was mixed well. The suspension was centrifuged at 800×g for 5 min at 4° C. and pellets were washed three times in 10 mL DMEM-Ham's F-12 medium supplemented with 2 mM L-glutamine, 100 units/mL penicillin and 100 units/mL strepotomycin. Then, the cell pellets were resuspended in 1 mL Neurobasal medium supplemented with B27 (Invitrogen, Carlsbad, Calif., USA), 2 mM L-glutamine, 100 units/mL penicillin and 100 units/mL strepotomycin, 20 ng/mL EGF, 20 ng/mL FGF-2, and 21 g/mL heparin. Cells were plated under sterile conditions in 6-well dishes in a concentration of 25,000-100,000 cells/mL. The dishes were incubated at 37° C. in 5% $CO_2$. Cell culture media were changed once a week, where about two thirds of the media were replaced. (Ray J et al (1993), *Proc Natl Acad Sci USA* 90: 3602-6.)

RT-PCR Protocol:

RNA was isolated according to standard protocols from hippocampal stem cells (FIG. 12) that were propagated 3 weeks in culture after thawing them from frozen stocks, following the manufacturer's recommendations (RNeasy kit, Qiagen). cDNA was synthesized using oligodT primers, Superscript II reverse transcriptase (Gibco) using standard conditions. Polymerase chain reaction (PCR) was performed with the following cycling conditions: 3 min 94°, 30 sec 94°, 30 sec 60°, 1 min 72°; for 32 cycles, using the primer pairs "rat GCSFR-frag-8s" GCGGGCAAATCAGGATCTCAC (SEQ ID NO:2), and "rat GCSFR-frag-287 as" CGAAGCT-CAGCTTGATCCAGG (SEQ ID NO:3). The primers were derived from a fragment of rat GCSFR identified from rat genomic databases by TBLASTX searches (see FIG. 11). Reaction conditions: 2 mM $MgCl_2$, 200 uM dNTP, 200 nM each primer, 1 unit Taq Polymerase (Invitrogen)/25 μl. The PCR product was resolved on a 1.5% agarose gel. The specific PCR product length was 279 bp, with the following sequence (SEQ ID NO:4) (primer sequences are underlined):

<u>gcgggcaaatcaggatctcac</u>cccccattgtccatcttggggatcctgtc ctggcctcctgcaccatcagcccaaactgcagcaaactggaccgacagcc aaagatcctatggagactgcaagatgaaccaaaccagcctggggacagac agcatcacctgcctgacgggtcccaggagtccatcatcactctgcctcat ctgaactacactcaggccttcctcttctgcttggtgccatggaacaacag cttccaggt<u>cctggatcaagctgagcttcg</u>.

For PCR on PC12 cells (FIG. 2B), the above protocol was followed.

Immunocytochemistry of Neurospheres:

Neurospheres consisting of the neural stem cells were pipetted onto the glass slide, coverslip was put onto the cells, and the slide was put at −80° C. for at least 30 min. The coverslip was removed, and put into 4% PFA (paraformaldehyde) in 0.1 M Phosphatpuffer, pH 7.4 immediately. Cells were fixed for 20 min. Cells were washed 3×5 min in PBS (pH 7.4) with 1% FCS and 0.02% $NaN_3$. Cells were permeabilised for 10 min in PBS containing 0.5% TX-100. Antigens were blocked for 60 min in PBS (pH 7.4) containing 1% FCS and 0.02% $NaN_3$. Cells were stained for 12 min with the nuclear dye DAPI at a concentration of 0.001 mg/ml in PBS. Cells were then washed 2×5 min with PBS (pH 7.4) containing 1% FCS and 0.02% $NaN_3$. The first antibody was applied for 2 h diluted in PBS (pH 7.4) containing 1% FCS and 0.02% $NaN_3$, at concentrations of: anti-G-GSF 1:1000, anti-G-CSF-R 1:1000, anti-GM-CSF-R 1:1000 (Santa Cruz), respectively. Cells were washed for 3×5 min with PBS (pH 7.4) containing 1% FCS and 0.02% $NaN_3$. The second antibody (goat anti-rabbit IgG-FITC, (DAKO)) was then applied for 60 min in PBS (pH 7.4) containing 1% FCS and 0.02% $NaN_3$, at a concentration of 1:30. Cells were washed for 3×5 min in PBS (pH 7.4) containing 1% FCS and 0.02% $NaN_3$. Cells were finally mounted with Aquamount and coverslips.

Example 10

GMCSFR Alpha is Upregulated in the Photothrombotic Model of Cerebral Ischemia (Discovery by RMDD)

Experimental protocols were approved by the local ethics committee. Male Wistar rats (Charles River, Germany) weighing 280 to 320 g were assigned to the following treatments: a) ischemia for various timepoints (6 h, 48 h, and 21d); b) sham operation, no ischemia, for accordant timepoints (6 h, 48 h, and 21d), with n=2 for each timepoint and treatment.

Focal Cerebral Ischemia by Photothrombosis

Animals were anesthetized with an intramuscular injection of 100 mg/kg body weight ketaminehydrochloride (WDT, Garbsen, Germany). Anesthesia was maintained with 50 mg/kg body weight if necessary. A PE-50 polyethylene tube was inserted into the right femoral artery for continuous monitoring of mean arterial blood pressure, and blood gases. The right femoral vein was cannulated by a PE-50 tube for treatment infusion. During the experiment rectal temperature was monitored and maintained at 37° C. by a thermostatically controlled heating pad (Föhr Medical Intruments, Germany).

Photothrombotic ischemia was induced in the right rat parietal cortex according to the method of Watson B D, Dietrich W D, Busto R, Wachtel M S, Ginsberg M D. Induction of reproducible brain infarction by photochemically initiated thrombosis. Ann Neurol. 1985; 17:497-504. Animals were anesthetized with ketaminehydrochloride and placed in a stereotaxic frame, and the scalp was incised for exposure of the skull surface. For illumination, a fiber-optic bundle with a 1.5-mm aperture was placed stereotaxically onto the skull 4 mm posterior to the bregma and 4 mm lateral from the midline. The skull was illuminated with a cold, white light beam (150 W) for 20 minutes. During the first 2 minutes of illumination, the dye rose bengal-(0.133 mL/kg body wt, 10 mg/mL saline) was injected intravenously. Sham-operated animals underwent the same experimental procedures as described above without infusion of rose bengal and illumination. After surgery, the catheters were removed, and the animals were allowed to recover from the anesthesia and given food and water ad libitum. Animals were killed according to the various timepoints (6 h, 48 h, and 21d after ischemia and sham operation, respectively) and the preparation of the penumbral cortex both ipsi- and contralateral is known to those skilled in the art.

RNA Isolation and RMDD

RNA was isolated according to standard protocols (Chomczynski and Sacchi (*Anal Biochem* (1987), 162, 156-9), followed by Qiagen RNeasy mini kit purification) from rat cortical penumbral samples, ipsi- and contralateral to the lesion side (see FIG. 13a for localization of the tissue samples; here: 3 vs. 4). cDNA synthesis was performed from 1 μg total RNA according to the RMDD (restriction mediated differential display)-protocol as described in EP 0 743 367 A2 and U.S. Pat. No. 5,876,932. Following first strand and second strand synthesis, and MboI digestion an adaptor ligation was done. Two PCR reactions with subsets of primer combinations were performed. Subsequently the PCR reactions were loaded on a denaturing gel and blotted on a nylon membrane (GATC Biotech AG, Konstanz, Germany). Biotin-labeled bands were visualised with a common streptavidin-peroxidase reaction. PCR samples from the cortical penumbra were loaded on the gel in the following order: ipsilateral: naive (untreated), sham 6 h, sham 48 h, sham 21d, and 6 h, 48 h and 21d photothrombosis; contralateral: sham 6 h, sham 48 h, sham 21d, and 6 h, 48 h and 21d photothrombosis. Bands having different intensity in the ipsi- and contralateral region were cut out of the nylon membrane and reamplification of the according PCR product was performed. Amplified products were cloned in the pCR-BluntII-TOPO vector (Invitrogen GmbH, Karlsruhe, Germany) and sequenced with T7 and M13rev primers (ABI 3700). Obtained sequences were compared with the EMBL-database. A sequence upregulated after 48 h both in ipsi- and contralateral cortical penumbra was identified (FIG. 14). The identified EST-sequence was extended with BLASTN-searches in EST-databases and a mouse homologous sequence coding for the mouse GM-CSFR alpha was identified in EST- and genomic databases (ensembl; www.ensembl.org) by using screening programs (BLAST, TBLASTN (Altschul, et al. (1997), Nucleic Acids Res, 25, 3389-402)).

Screens were performed in rat cDNA libraries with the PCR cloning method of Shepard ((1997) *Nucleic Acids Res* 25:3183-3185) to confirm the obtained rat sequence. This method is based on hybridization of cDNA molecules derived from a plasmid library to a biotin-coupled oligonucleotide sequence. Following plasmid extraction with streptavidin-coupled magnetic beads the result was ensured by diagnostic PCR and two fold replication of the steps following retransformation of the obtained plasmids until recovering the single clone. The following primer combinations were used:

```
5'block-2.clb4-4-4:
                                     (SEQ ID NO: 12)
CGGGATCCGGGACCGCGTATCTGATGACGAGCGTGTCAA 25bio-2.clb4-4-4:
                                     (SEQ ID NO: 13)
CTCGGAGACGCTGAGGAAGGACCTG 3'block-2.clb4-4-4:
                                     (SEQ ID NO: 14)
CTGCGGCCCTAGACCACGCCCACCGCTCCCCGTGACGTCG
```

(The ORF was determined for the single clone and the sequence is shown as SEQ ID NO:40, the corresponding amino acid sequence is shown as SEQ ID NO:41).

Example 11

GMCSF Receptor Alpha is Upregulated in the Photothrombotic Model of Cerebral Ischemia (Verification by Quantitative PCR)

RNA was isolated according to standard protocols (Chomczynski and Sacchi (Anal Biochem (1987), 162, 156-9), followed by Qiagen RNeasy mini kit purification), from rat cortical penumbral samples, ipsi- and contralateral to the lesion side (see FIG. 13a for localization of the tissue samples; here: 3 vs. 4). cDNA was synthesized from 1 µg total RNA using oligodT primers, Superscript II reverse transcriptase (Gibco) using standard conditions. Quantitative PCR was performed using the Lightcycler system (Roche Diagnostics, Mannheim, Germany) with SYBR-green staining of DNA doublestrands. Cycling conditions were as follows: 5 min 95° C., 5 sec 95° C., 7 sec 62° C., 30 sec 72° C.; 9 sec 80° C. for 50 cycles. Melting curves were done with the following parameters: 95° C. cooling to 50° C.; ramping to 99° C. at 0.2° C./sec. The following primer pairs were used: "rat BR4-4s96" ACGTCGTTGGCTCAGTTATGTC (SEQ ID NO:15), and "rat BR4-4 as272" ATTTATGTCA-GAGATGGAGGATGG (SEQ ID NO:16). The Lightcycler™ PCR was performed using the SYBR green master mix, following the manufacturer's recommendations (Roche diagnostics). Specificity of product was ensured by melting point analysis and agarose gel electrophoresis. cDNA content of samples was normalized to the expression level of Cyclophilin (primers: "cyc5" ACCCCACCGTGTTCTTCGAC (SEQ ID NO:17); "acyc300" CATTTGCCATGGACAA-GATG (SEQ ID NO:18)). Relative regulation levels were derived after normalization to cyclophilin, and comparison to the sham-operated animals. FIG. 14 *a* shows upregulation of the GMCSFR alpha after 48 h on the ipsi- and contralateral side. There is no significant regulation detectable 21d after induction of photothrombosis (FIG. 14 *b*). Error bars indicate standard deviations, these are calculated from 3-fold serially diluted cDNA-samples, and reflect reliability of measurements.

Example 12

GMCSF-Receptor Alpha is Present on Neuronal Cells in Primary Cortical Cultures: Preparation of Neurons 10-12 Cortices were prepared from embryos of the stage E18 (embryonal day 18). Tissue was dissociated using trypsin [10 mg/ml]/EDTA/DNase [5 mg/ml] (Roche diagnostics) in HBSS (Hanks balanced salt solution, BioWithakker). The digest was stopped using 4 parts medium (neurobasalmedium+1 ml 50× B-27 supplement (Invitrogen)+0.5 mM L-glutamin+25 µM glutamate) and centrifuged at room temperature for 5 min at 800×g. The pellet was dissolved in 5 ml medium and cell number determined by counting (Neubauer slide). The cells were plated at a density of 250 000 cells per well of a 24-well-plate on cover slips which were coated with poly-L-lysine.

Immunocytochemistry 1 week after preparation neurons were washed with PBS (Gibco) (37° C.) and fixed with 2% paraformaldehyde for 10 min on ice. Then, cells were washed with PBS (4° C.) and then incubated for 10 min in 50 mM glycine in PBS, then washed with PBS. Cells were permeabilized on ice using 0.2% TritonX-100 (Sigma) in PBS, and incubated with blocking solution (0.2% Triton-X100, 4% normal goat serum (NGS) (Jackson Immunoresearch Laboratories) in PBS) at room temperature. The primary antibody (rabbit-anti-GM-CSF-Receptor-antibody directed against the C-terminus of mouse GMCSFR, M-20; sc-691; SantaCruz) was used in a dilution of 1:300 (in 0.1% Triton-X100/2% NGS), and incubated overnight at 4° C. Cells were then washed with 1% NGS/PBS, and incubated for 30 min with the secondary antibody (anti-rabbit-FITC, 1:400; dianova) at room temperature. Cells were then washed briefly in 1% NGS/PBS, and stained with Hoechst 33342 (Molecular Probes) (1:10.000 in PBS) for counterstaining the nuclei. Finally, cover slips were washed briefly twice in 1% NGS/PBS, twice in PBS, and once for 10 min in 10 mM Tris/HCl, pH 7.6. The cover slips were embedded using Aquamount (Polyscience).

Pictures were taken digitally with an Olympus IX81 microscope, and the "Analysis" software package (Soft Imaging Systems, Stuttgart, Germany).

Example 13

GMCSF Receptor is Present on Neural Stem Cells: Generation of Neural Stem Cells (FIG. 13)

Neural stem cells were isolated from the brain areas with known spontaneous neurogenesis, i.e. hippocampus, olfactory bulb, and subventricular zone, of 4-6 week old male Wistar rats as described (Ray J et al (1993) Proc Natl Acad Sci USA 90: 3602-6). Protocols are concordant with the policy on the use of animals, as endorsed by the National Research Council of the U.S.A., and fullfill the requirements of German law. Briefly, animals were anesthesized with 1% (v/v) isoflurane, 70% N20, 29% oxygen and sacrificed by decapitation. The brains were removed and washed in 50 mL ice-cold Dulbecco's Phosphate Buffered Saline (DPBS) supplemented with 4.5 g/L glucose (DPBS/Glc). Hippocampus, olfactory bulb, and subventricular zone from 6 animals were dissected, washed in 10 mL DPBS/Glc and centrifuged for 5 min at 1600×g at 4° C. After removal of the supernatant, the tissue was homogenized with scissors and scalpels. The tissue pieces were washed with DPBS/Glc medium for 5 min at 800 g, and the three pellets were resuspended in 0.01% (w/v) papain, 0.1% (w/v) dispase II (neutral protease), 0.01% (w/v) DNase I, and 12.4 mM manganese sulfate in Hank's Balanced Salt Solution (HBSS). The tissue was triturated with plastic pipet tips and incubated for 40 min at room temperature, but every 10 min the solution was mixed well. The suspension was centrifuged at 800×g for 5 min at 4° C. and pellets were washed three times in 10 mL DMEM-Ham's F-12 medium supplemented with 2 mM L-glutamine, 100 units/mL penicillin and 100 units/mL strepotomycin. Then, the cell pellets were resuspended in 1 mL Neurobasal medium supplemented with B27 (Invitrogen, Carlsbad, Calif., USA), 2 mM L-glutamine, 100 units/mL penicillin and 100 units/mL strepotomycin, 20 ng/mL EGF, 20 ng/mL FGF-2, and 2 μg/mL heparin. Cells were plated under sterile conditions in 6-well dishes in a concentration of 25,000-100,000 cells/mL. The dishes were incubated at 37° C. in 5% CO2. Cell culture media were changed once a week, where about two thirds of the media were replaced. (Ray J et al (1993) *Proc Natl Acad Sci USA* 90: 3602-6.)

RT-PCR Protocol

RNA was isolated according to standard protocols from hippocampal stem cells that were propagated 3 weeks in culture after thawing them from frozen stocks, following the manufacturers recommendations (RNeasy kit, Qiagen). cDNA was synthesized using oligodT primers, superscript II reverse transcriptase (Gibco) using standard conditions. Polymerase chain reaction (PCR) was performed with the following cycling conditions: 3 min 94°, 30 sec 94°, 30 sec 60°, 1 min 72°; for 32 cycles, using the primer pairs "rat BR4-4s96" ACGTCGTTGGCTCAGTTATGTC (SEQ ID NO:19), and "rat BR4-4 as272" ATTTATGTCAGAGATG-GAGGATGG (SEQ ID NO:20). Reaction conditions: 2 mM MgCl2, 200 uM dNTP, 200 nM each primer, 1 unit Taq Polymerase (Invitrogen)/25 μl. PCR was resolved on a 1.5% agarose gel. The specific PCR product length was 176 bp with the following sequence (primer sequences are underlined):

(SEQ ID NO: 21)
<u>ACGTCGTTGGCTCAGTTATGTC</u>AGACAGGAAATCTCACCATCCCACAATG

ATTGACAGCTCTCACAGGGAATCCCGCCTCCGCTGGGACCAATTGACATC

ACGGACAGGAATACCCGCCCCTGTGGCCCTGATGGGCAGGTCCTGCCTGG

CTC<u>CCATCCTCCATCTCTGACATAAAT</u>

Example 14

Assay for Determining the Serum Half-Life and Passage of GCSF/GM-CSF Through the Blood Brain Barrier It is desirable to know whether GCSF and GMCSF pass the blood-brain barrier. GCSF/GM-CSF are biotinylated to make use of the highly sensitive avidin-biotin-interaction for detection of the chemokines in brain tissue. G-CSF (Neupogen, Amgen) was biotinylated using Biotin-XX-SE (Molecular Probes B 1606). G-CSF was diluted into 20 mM sodium carbonate buffer pH 8 with 250 mM sorbitol and 0.004% Tween-80 and Biotin-XX-SE added. After 1 h at room temperature, Tris-buffer pH 8 was added to 50 mM concentration to quench unreacted labeling reagent. The sample was spun 30 min at 45000 rpm in a TLA 110 rotor (Beckman Instruments) to remove aggregates.

7.5 μg biotinylated G-CSF was injected into mice intraperitoneally at time zero (in 200 μl 20 mM sodium carbonate buffer pH 8 with 250 mM sorbitol and 0.004% Tween-80). Mice were anesthesized with chloralhydrate at times indicated and blood samples (approx 200 μl) were taken from the right heart chamber. EDTA was added to 5 mM and the sample centrifuged for 10 min at 1000 g to obtain serum. 4× sample buffer was added to serum, proteins denatured by heating to 95° C. for 5 min and 20 μl applied to a minigel. Proteins were transfered to nitrocellulose, blocked and incubated with Streptavidin-HRP (Amersham) in TBST. After washing, signals were detected using Pierce Supersignal chemiluminiscence reagent.

For Elisa analysis serum samples were diluted 1:20 in assay buffer and the assay performed according to the manufacturer's instructions (IBL, Hamburg, Germany).

This assay can be adapted accordingly to cerebrospinal fluid (csf) or brain homogenate to determine the transition of GCSF across the blood-brain-barrier.

Example 15

Assay for Neuroprotective Action of GCSF, GMCSF (FIG. 1b)

The neuroprotective action of GCSF/GMCSF was determined in vitro on NGF-treated PC12 cells. PC12 cells were seeded into 96 well plates coated with poly-1-lysine (0.01% final concentration) at a density of 40.000 cells/well. Cells were kept in DMEM medium containing 1000 mg glucose/l and 10% HS (horse serum) 5% FCS (fetal calf serum), 1% Penicillin/Streptomycin. Cells were then transfected with pSV40-RL (encoding the renilla luciferase gene) using the Lipofectamine-2000® transfection agent (Gibco BRL) (0.2 ug DNA/well), following the manufacturers recommendations. Immediately after transfection, NGF (nerve growth factor) was added at a concentration of 40 ng/ml to induce differentiation of PC12 cells. At 24 h after treatment, PC12 cells develop a neuron-like morphology with extended processes. Cells were then treated with $H_2O_2$ at varying concentrations (FIG. 1b), and GCSF at varying concentrations (1-100 ng/ml). EPO was added as a positive control for a substance with known neuroprotective potency in vitro (Cerami, et al. (2002), Nephrol Dial Transplant, 17, 8-12., Kawakami, et al. (2001), J Biol Chem, 276, 39469-75., Sinor and Greenberg (2000), Neurosci Lett, 290, 213-5., Chong, et al. (2002), J Cereb Blood Flow Metab, 22, 503-14.) at concentrations of 0.01 U/ml to 1 U/ml. After 24 h, medium supernatant was discarded, and cells were lysed using the passive lysis buffer (Promega). Renilla luciferase activity was then recorded in a luminometer (Mithras, Berthold), and readings expressed as relative light units. This assay measures cell survival as the amount luciferase detectable. Therefore, the higher the relative light units, the more cells have survived. In this assay, GCSF showed a dose-dependent neuroprotection of PC12 cells, that was more potent than Erythropoetin.

Example 16

GCSF Receptor is Expressed in Various Brain Regions Important for Neurological Diseases (FIG. 4); GMCSF is Expressed in Various Important Brain Regions (FIG. 19)

To systematically assess the distribution of the GCSF receptor in the normal mouse brain, C57/bl6 mice (2-3 months old) were anesthesized using an i.p. injection of Rompun® and Ketanest®. Mice were then transcardially perfused with 20 ml hanks balanced salt solution (HBSS), followed by 20 ml of 4% paraformaldehyde (PFA) in PBS (pH 7.4). The brain was dissected out, and stored overnight in 2% PFA solution. Paraffin-embedded tissues were sectioned (2 μm), mounted on pre-treated slides (DAKO, Glostrup, Denmark), air-dried overnight and subsequently deparaffinized. After microwave treatment (citrate buffer; 500 W, 10 min), the anti-GCSFR antibody (1:400) was applied and tissues were incubated for 1 h at room temperature in a moist chamber. Antibody labeling was visualized using the routine ABC technique and DAB as a chromogen following manufacturers recommendations (DAKO, Glostrup, Denmark). Negative controls included similarly processed sections in which the primary antibody had been totally omitted as well as sections where the appropriate normal serum was used (Dianova, Hamburg, Germany). Localization of GCSF-R was seen in the hippocampus (FIG. 4a-d) with predominant staining of neurons in the CA3 area (FIG. 4 a,b), with a sharp boundary between the CA3 and CA2 region (FIG. 4 c, arrow). GCSF-R is distributed over the soma, as well as processes of neurons (FIG. 4 b, arrow). The receptor is present in the hilus and the basal cell layers of the dentate gyrus (FIG. 4 d, arrow). GCSF-Receptor was also detected in cortical areas: piriform cortex (FIG. 4 e), and perirhinal cortex (f) as examples. In the cerebellum, Purkinje cells were labeled (FIG. 4 g, arrow). Also, some of the large mitral cells in the olfactory bulb are GCSF-R positive (FIG. 4 h, arrow). Strong staining is exhibited by the anterior columns in the spinal cord (FIG. 4 i,j), and higher magnification identifies the large motoneurons as GCSF-R positive (FIG. 4 k,l). Note that the neuronal processes are strongly labeled. In the midbrain, neurons in the substantia nigra show GCSF-R positivity (FIG. 4 m,n,o). Apart from neurons, oligodendrocytes in white matter tracts are stained, for example, in the anterior commissure (FIG. 4, p, arrow).

The same example applies for the localization of the GMC-SFR (FIG. 19). Here, staining was seen in the hippocampus, in the cortex, in the cerebellum, and in the choroid plexus. Midbrain and spinal cord were not examined so far.

Example 17

Assay for Neuroprotective Action of GCSF, GMCSF (FIG. 1b, FIG. 23)

The neuroprotective action of GCSF/GMCSF was determined in vitro on NGF-treated PC12 cells. PC12 cells were seeded into 96 well plates coated with poly-1-lysine (0.01% final concentration) at a density of 40,000 cells/well. Cells were kept in DMEM medium containing 1000 mg glucose/l and 10% HS (horse serum) 5% FCS (fetal calf serum), 1% Penicillin/Streptomycin. Cells were then transfected with pSV40-RL (encoding the renilla luciferase gene) using the Lipofectamine-2000® transfection agent (Gibco BRL) (0.2 ug DNA/well), following the manufacturers recommendations. Immediately after transfection, NGF (nerve growth factor) was added at a concentration of 40 ng/ml to induce differentiation of PC12 cells. At 24 h after treatment, PC12 cells develop a neuron-like morphology with extended processes. Cells were then treated with $H_2O_2$ at varying concentrations (FIG. 1b, FIG. 23), and GCSF and GMCSF at varying concentrations (1-100 ng/ml). EPO was added as a positive control for a substance with known neuroprotective potency in vitro (Cerami, et al. (2002), Nephrol Dial Transplant, 17, 8-12., Kawakami, et al. (2001), J Biol Chem, 276, 39469-75., Sinor and Greenberg (2000), Neurosci Lett, 290, 213-5., Chong, et al. (2002), J Cereb Blood Flow Metab, 22, 503-14.) at concentrations of 0.01 U/ml to 1 U/ml (FIG. 1b), or 0.5 U/ml (FIG. 23). After 24 h, medium supernatant was discarded, and cells were lysed using the passive lysis buffer (Promega). Renilla luciferase activity was then recorded in a luminometer (Mithras, Berthold), and readings expressed as relative light units. This assay measures cell survival as the amount luciferase detectable. Therefore, the higher the relative light units, the more cells have survived. In this assay, GCSF as well as GMCSF showed a dose-dependent neuroprotection of PC12 cells that was more potent than Erythropoetin.

Example 18

Thrombembolic Cerebral Ischemia

Experimental protocols will be approved by the local ethics committee. Forty male Wistar rats (Charles River, Germany) weighing 280 to 320 g will be randomly assigned to the following groups: A) early thrombolysis with 10 mg rt-PA/kg body weight for 1 hour, 1 hour after thrombembolic vessel occlusion; B late thrombolysis with 10 mg rt-PA/kg body weight for 1 hour, 3 hour after thrombembolic vessel occlusion; C) no thrombolysis, but treatment with 60 μg/kg body weight of recombinant G-CSF (Neupogen®, Amgen, Europe B.V., Netherlands) in 2 ml saline 0.9% for 90 min beginning 30 min after thrombembolic ischemia; D) treatment with 60 μg/kg body weight of recombinant G-CSF (Neupogen®, Amgen, Europe B.V., Netherlands) in 2 ml saline 0.9% for 90 min beginning 30 min after thrombembolic ischemia combined with late thrombolysis with 10 mg rt-PA/kg body weight for 1 hour, 3 hour after thrombembolic vessel occlusion.

Animals will be anesthetized with an intraperitoneal injection of 100 mg/kg body weight ketaminehydrochloride (WDT, Garbsen, Germany). Anesthesia will be maintained with 50 mg/kg body weight, if necessary. A PE-50 polyethylene tube will be inserted into the right femoral artery for continuous monitoring of mean arterial blood pressure, blood gases, hematocrit, leukocyte count and blood glucose levels. The right femoral vein will be cannulated by a PE-50 tube for treatment infusion. During the experiment rectal temperature will be monitored and maintained at 37° C. by a thermostatically controlled heating pad (Föhr Medical Intruments, Germany).

Thromboembolic stroke will be induced according to the modified method described by Busch et al (*Brain Res* 1997 Dec. 5; 778(1):16-24). Briefly, the right common carotid (CCA), internal carotid (ICA) and external carotid arteries (ECA) will be exposed through a midline incision of the neck. Further dissection identified the origin of the pterygopalatine artery (PPA). The ECA and the PPA will be permanently ligated by a 6-0 silk suture. The CCA will be only temporarily ligated for the time of embolization. A catheter will be inserted into the ECA proximal to its ligation and 12 red blood clots (each 0.35 mm in diameter and 3 mm in length) were injected, resulting in embolization of the right middle cerebral artery (MCA).

Infarct evolution will be monitored by MR-imaging at 1, 2, 4, and 24 hours by using diffusion-, perfusion-, and T2-weighted imaging. In all animals, outcome will be measured by mortality as well as neurological outcome based on a five point scale 24 hours after ischemia. 24 hours after ischemia, the rats will be anesthetized with ketamine 150 mg/kg body weight and decapitated. The brains will be removed, and fixed with 4% paraformaldehyde in 0.1 mol/l phosphate buffer for 24 hrs. After paraffin-embedding, 1-μm-thick sections will becut and used for TTC, H&E, and Nissl staining and immuno-histochemical analysis.

Statistical Analysis

The values will be means±SD. After acquiring all the data, the randomization code will be broken. ANOVA and subsequent post hoc Fisher protected least significant difference test will be used to determine the statistical significance of differences in continuous variables such as physiological parameters, and infarct volume. The Mann-Whitney U test will be performed for nonparametric data such as the mortality rate. A p value <0.05 will be considered statistically significant.

Example 19

G-CSF is Effective when Given at an Extended Time Window in Middle Cerebral Artery Occlusion (MCAO), a Rodent Stroke Model FIG. 24 shows the effect of intravenously applied G-CSF on infarct volume in the rat MCAO model when applied 120 min after onset of ischemia. The experiment was conducted as described in Example 1, with the exception that anesthesia was induced by inhalation anesthesia (1% halothane, 30% $O_2$, and 70% $N_2O$). Also here, a dose of 60 μg G-CSF (Neupogen®, AMGEN)/kg bodyweight of the rat was used. A significant protection was seen when comparing infarct volumes by TTC-staining (see FIG. 25). The operations were performed by another set of investigators as those in example 1, demonstrating efficacy in another laboratory setup. This example further demonstrates the usefulness of G-CSF as a treatment for stroke and other ischemic disorders of the nervous system.

Example 20

Colocalisation of GCSF and its Receptor in the Brain

Immunohistochemical Methods Used

Sections of paraffin-embedded tissues (2 μm) were deparaffinated by treating them 2×5 min with Xylol, 2×2 min 100% ethanol, and then with descending concentrations of ethanol from 96% up to 70%. Finally the sections are washed with distilled water and microwaved (citrate buffer at 600 W for 15 min). Afterwards, sections were washed with distilled water and antigens were blocked 3×5 min in 1×TBS (pH 7.4) containing 0.2% BSA. The GCSF-receptor antiserum (SC694; Santa Cruz Biotechnology, Santa Cruz, Calif., USA; 1:100) diluted in 1×TBS (pH 7.4) containing 0.2% BSA was incubated at room temperature for 1 h in a humid chamber. Sections were then washed 3×2 min with 1×TBS (pH 7.4) containing 0.2% BSA. The second antibody (goat anti-rabbit Fab-FITC, dianova, 1:50) was then applied over night at 4° C. in 1×TBS (pH 7.4) containing 0.2% BSA. After washing the sections 3×2 min with 0.2% BSA in 1×TBS (pH 7.4), the GCSF antiserum (SC13102; Santa Cruz Biotechnology, Santa Cruz, Calif., USA) diluted 1:100 in 0.2% BSA in 1×TBS (pH 7.4) was applied for 1 h at room temperature. The sections were washed 3× as described before and incubated for 30 min with biotinylated goat anti-rabbit IgG (Vector Laboratories, USA) diluted 1:200 in 1×TBS (pH 7.4) containing 0.2% BSA. Again after washing the sections, TRITC-conjugated streptavidin (dianova; 1:200) was applied for 1.5 h at room temperature. Then, the sections were washed 3×2 min with 1×TBS and stained for 10 min with the nuclear dye DAPI diluted 1:10 000 in 1×TBS. Finally the sections were washed 3×2 min with 1×TBS and mounted with mounting medium for fluorescence (Vectashield, Vector Laboratories, USA). Pictures were taken digitally with an Olympus IX81 microscope, and the "Analysis" software package (Soft Imaging Systems, Stuttgart, Germany).

All double-fluorescence experiments were controlled by parallel single-staining, which were checked for absence of any fluorescence carry-over in the second channel. As a second control, all double-fluorescence staining were done with switched chromophores for the secondary antibody.

Results

The GCSF receptor (FIG. 25 *a, d, g*) shows a co-localization with its ligand (FIG. 25 *b, e, h*) both in the hippocampus (FIG. 25 *a-c* dentate gyrus, d-f hilus) and the cortex (FIG. 25 *g-i*). The surprising finding that the same neurons express both the receptor and the ligand, suggest an autocrine signaling mechanism of GCSF, which supports a novel endogenous neuroprotective system of the nervous system.

Example 21

Colocalisation of the GCSF Receptor and the GMCSF Receptor in the Brain

Immunohistochemical Methods

Immunohistochemistry was performed as described in example 20. After incubating the sections with the GCSFk antiserum and goat anti-rabbit Fab-FITC, the sections were washed 3×2 min with 0.2% BSA in 1×TBS (pH 7.4). Afterwards, the GMCSFR antiserum (SC690; Santa Cruz Biotechnology, Santa Cruz, Calif., USA; 1:100) was applied for 1 h at room temperature. The following procedure including incubation with biotinylated goat anti-rabbit IgG (Vector Laboratories, USA) and TRITC-conjugated streptavidin (dianova; 1:200) was done as described for GCSF detection in example 2.

All double-fluorescence experiments were controlled by parallel single-stainings, which were checked for absence of any fluorescence carry-over in the second channel. As a second control, all double-fluorescence stainings were done with switched chromophores for the secondary antibody.

Results

The GCSF receptor (FIG. 26 a, d, g) and the GMCSF receptor (FIG. 26 b, e, h) are expressed on the same neurons in both the hippocampus and the cortex (FIG. 26 c, f, i). FIG. 26 shows coexpression of both receptors on neurons in the dentate gyrus (a-c) and the hilus (d-f) of the hippocampus as well as in the cortex (g-i). This finding further illustrates the claim that GCSF and GMCSF could be used in conjunction to treat neurological conditions, and that the neuroprotective properties of hematopoietic factors could be enhanced by combined application.

Example 22

GCSF Acts Anti-Apoptotically by Activating stat3 in Neurons

Results

Primary cultured neurons are a tool to dissect mechanisms of action. We therefore checked whether the G-CSF receptor would be expressed on hippocampal or cortical neurons after 21 days in culture. Indeed, we confirmed expression by PCR (previous examples) and immuno-cytochemistry, both on cortical as well as most hippocampal neurons. One of the most important mechanisms in stroke pathophysiology is delayed neuronal cell death (Choi (1996), Curr Opin Neurobiol, 6, 667-72, Schneider, et al. (1999), Nat Med, 5, 554-9, Mattson (2000), Nat Rev Mol Cell Biol, 1, 120-9). We therefore hypothesized that G-CSF might be interfering with apoptotic cascades in neurons. In primary neuronal cultures that were found to express the G-CSF receptor, exposure to nitric oxide, a relevant event during cerebral ischemia, leads to dose-dependent increase in programmed cell death as evidenced by PARP-cleavage (not shown). Treatment with 50 ng/ml G-CSF drastically reduced apoptotic cell death after NOR3 treatment, as exemplified in FIG. 27. In cells of the hematopoietic lineage, the GM-CSF receptor transmits its anti-apoptotic signal via the Janus kinase 2 (JAK2) and signal transducer and transactivator (stat) proteins (Jak-stat pathway) (e.g. (Epling-Bumette, et al. (2001), J Immunol, 166, 7486-95, Sakamoto, et al. (2003), Int J Hematol, 77, 60-70)). While we could not detect activation by phosphorylation of stati or stat5 (FIG. 27, part III), stat3 was strongly phosphorylated by the addition of G-CSF in a time-dependent manner typical (FIG. 27, part IV) of the JAK-stat kinetics in other cell types (FIG. 27, part V; taken and adapted from: Kuroki, M. & O'Flaherty, J. T. Extracellular signal-regulated protein kinase (ERK)-dependent and ERK-independent pathways target STAT3 on serine-727 in human neutrophils stimulated by chemotactic factors and cytokines. *Biochem J* 341 (Pt 3), 691-6 (1999)). The stat3 tyr705 phosphorylation evoked by the addition of G-CSF to the culture medium was specifically mediated via the G-CSF receptor/JAK2 pathway, as blocking of the JAK2/stat3 connection by the inhibitor AG490 led to drastically reduced signals in the presence of G-CSF (Figure X). Stat3 activation leads to induction of anti-apoptotic proteins of the bcl family (Yoshida, et al. (2002), J Exp Med, 196, 641-53, Sakai and Kraft (1997), J Biol Chem, 272, 12350-8, Nielsen, et al. (1999), Leukemia, 13, 735-8). Addition of G-CSF to neuronal cultures led to a time-dependent increase of both Bcl-Xl and Bcl-2, potent anti-apoptotic proteins in neurons, and during cerebral ischemia (FIG. 27, part VI). Interestingly, a recent report suggests stat3 as an essential survival protein for motoneurons after nerve injury (Schweizer, et al. (2002), J Cell Biol, 156, 287-97). G-CSF therefore seems to act differently from the proposed anti-apoptotic mechanism of EPO involving stat5 and NF-kB activation (Digicaylioglu and Lipton (2001), Nature, 412, 641-7).

Methods

Primary cortical neurons from rats were generated as follows: Ten to 12 cortices were dissected from rat embryos E18. The tissue was dissociated using 10 mg/ml trypsin, 5 mg/ml EDTA/DNase (Roche diagnostics, Mannheim, Germany) in HBSS (BioWhitakker, Taufkirchen, Germany). The digestion was stopped using four parts neurobasal medium containing 1×B-27 supplement (Invitrogen, Karlsruhe, Germany). After centrifugation, the pellet was dissolved in 5 ml medium and cells were plated at a density of 250,000 cells per well of a 24-well-plate on glass cover slips coated with poly-L-lysine. The medium typically contains: 50 ml neurobasal medium (life technologies, Karlsruhe, Germany), 1 ml supplement B 27 (Life technologies), 5 µl bFGF (Sigma, 19 µg was dissolved in 100 µl 10 mM Tris/HCl pH 7), and 50 µl Penicillin/Streptomycin (Life technologies).

Detection of STAT1, pSTAT1, STAT5, pSTAT5, GCSFR, PARP, cleaved PARP, caspase3, cleaved caspase3, Bcl2, and Bcl x1 was done by Western blotting. In brief, neurons were treated for 24 h with 150 mM NOR-3 (Sigma-Aldrich, Seelze, Germany), and 50 ng/ml G-CSF (Neupogen, Amgen, Thousand Oaks, Calif., USA) as indicated. The cells were scraped off the plate, spun down at 800 rpm for 5 min, and washed in ice-cold PBS containing 2.5 mg/ml pepstatin (Sigma-Aldrich, Seelze, Germany) and aprotinin (1:1000, Sigma-Aldrich). Pellets were resuspended in 100 µl benzonase solution (containing 10 µl 10×PBS, 79.5 µl $H_2O$, 10 µl 10% SDS, 0.5 µl 100 mM $MgCl_2$, 0.1 µl Aprotinin, 0.1 µl Leupeptin, 0.1 µl Pepstatin, 0.1 µl PMSF, 0.1 µl benzonase (Roche Diagnostics, Mannheim, Germany)) was added. After solubilization, 1 volume PBS was added and the protein concentration determined (BCA-Test, Pierce, Rockford, Ill., USA). After denaturing at 95° C. for 5 min, 100 µg was run on 8%-12% SDS-polyacrylamide gels. Proteins were transferred to nitrocellulose membranes (Protan BA79, Schleicher & Schuell, Dassel, Germany) using a semi-dry-blotting chamber (Whatman Biometra, Göttingen, Germany). Blots were blocked with 5% milk powder in PBS/0.02% Tween 20, washed three times with PBS/0.02% Tween 20, and incubated overnight at 4° C. with the respective primary antibody (anti-cleaved-PARP-antibody, Cell Signaling, 1:1000; anti PARP, Cell Signaling, 1:1000; anti cleaved caspase 3, Cell Signaling, 1:200; anti caspase3, Cell Signaling, 1:200; anti Bcl2, BD Transduction Laboratories, 1:500; anti Bcl X1, BD Transduction Laboratories, 1:500; anti pSTAT3tyr, Cell Signaling, 1:500; anti STAT3, Cell Signaling, 1:500; anti GCSFR, Santa Cruz, 1:200; anti pSTAT5, Cell signaling, 1:500; anti stat5, Cell signaling, 1:200; anti pSTAT1, Cell signaling, 1:500). After washing, the blots were incubated with the respective secondary antibody (anti-rabbit, or anti-mouse-antiserum HRP-coupled, Dianova, Hamburg, Germany 1:4000) for 1 h at room temperature. Signals were detected using the supersignal chemiluminescence system (Pierce, Rockford, USA) and exposed to Hyperfilm-ECL (Amersham Pharmacia Biotech, Piscataway, N.J., USA). PARP cleavage was quantified on scanned autoradiographs using Windows ImageJ v1.29 (http://rsb.info.nih.gov/ij/index.html).

Example 23

GCSF and its Receptor are Induced by Cerebral Ischemia MCAO Model of Cerebral Ischemia Procedure for inducing focal cerebral ischemia (MCAO, middle cerebral artery occlusion) was performed as described in example 1.

Global Ischemia Model

The experimental procedures on animals randomized for ischemia/reperfusion were performed as previously described in details (Brambrink, et al. (2000), J Cereb Blood Flow Metab, 20, 1425-36). In brief, the rats were anesthetized (chloral hydrate), orally intubated and mechanically ventilated ($Pa_{CO2}$ at 35-40 mmHg, $Pa_{CO2}$ at 95-110 mmHg throughout the experiment). Both common carotid arteries (CCA) were exposed and the left side was catheterized with polyethylene tubing (PE-50) for blood sampling and continuous monitoring of MABP (Sirecust 310, Siemens, Danvers, Mass., USA). On the right side a nylon thread was looped loosely around the CCA to be used later to induce transient cerebral ischemia. The head of the animal was fixed in a stereotaxic frame for EEG and CBF measurements (for details see (Brambrink, Schneider, Noga, Astheimer, Gotz, Komer, Heimann, Welschof and Kempski (2000), J Cereb Blood Flow Metab, 20, 1425-36)). The calvarium was exposed by a median incision and two depressions designed to hold chlorinated silver pin EEG electrodes were made (high speed dental drill, positioned over the left somatosensory cortex and frontal sinus according to the Praxinos and Watson (1986) brain atlas). Over the right hemisphere about 24 $mm^2$ of the skull bone was removed leaving a thin bone lamina (1.3-5.3 mm lateral to the right and 1.5-7.5 mm occipital from the bregma). A laser Doppler-flow probe (wavelength: 780 µm, BPM 403A, TSI Inc., St. Paul, Minn., USA) controlled with a computer driven micromanipulator was employed to determine regional cerebral blood flow (rCBF) at 30 locations, using the "scanning technique" (Soehle, et al. (2000), Acta Neurochir Suppl, 76, 181-4)). On the contralateral side (3.3-5.3 mm lateral to the left and 5.0-7.0 mm occipital of the bregma) a smaller (4 $mm^2$) window was established to measure local cerebral blood flow (1CBF), using a stationary laser Doppler-flow probe (wavelength: 780 µm, BPM 2, Vasamedices Inc., St. Paul, Minn., USA). Temperature probes were placed as described previously ((Brambrink, et al. (1999), J Neurosci Methods, 92, 111-22)) in the right temporal muscle, in the left auricular tube, and at 6 cm depth in the rectum. Core temperature (thermostatically controlled heating blanket) and temporal muscle temperature (near infarcted heat radiator) were controlled to 37.5±0.1° C. throughout the experimental procedures. The lower body section of the animal was placed in an air-tight chamber. This allows to establish hypobaric pressures by an electronically regulated vacuum pump, thereby reducing arterial blood pressure of the animal (venous pooling) in a controlled fashion ("hypobaric hypotension"). After a 30-minutes post surgical stabilization period, transient global cerebral ischemia was initiated by pulling the nylon thread attached to a defined weight around the right carotid artery to occlude the vessel (arterial pressure was measured by a catheter placed in the left carotid artery); MABP was simultaneously reduced to 35 mm Hg, using the hypobaric hypotension technique. Brain ischemia was confirmed by continuous lCBF, rCBF, and EEG measurements. After 15 minutes of global cerebral ischemia, the thread was cut and vacuum was terminated to allow reperfusion. After 90 minutes of recovery the CCA catheter was removed, incisions were closed, and the animals were weaned from the ventilator. On extubation (around 110 minutes of reperfusion) and in the presence of stabile vital signs, the rats were returned to their cage and a heating blanket was used to prevent heat loss.

Quantitative PCR

RNA was isolated according to standard protocols ((Chomczynski and Sacchi (1987), Anal Biochem, 162, 156-9), followed by Qiagen Rneasy™ mini kit purification. Tissue samples were taken from total rat brain after global cerebral ischemia, and ipsi- and contralateral to the lesion side at various timepoints after focal cerebral ischemia, respectively. cDNA was synthesized from 10 µg total RNA using oligodT primers, superscript II reverse transcriptase (Gibco) using standard conditions. Quantitative PCR was performed using the Lightcycler® system (Roche Diagnostics, Mannheim, Germany) with SYBR-green staining of DNA doublestrands. Cycling conditions were as follows: GCSFR: 5 min 95° C., 5 sec 95° C., 10 sec 66° C., 30 sec 72° C.; 10 sec 84° C. for 50 cycles; GCSF: 5 min 95° C., 5 sec 95° C., 10 sec 64° C., 30 sec 72° C.; 10 sec 88° C. for 50 cycles. Melting curves were done with the following parameters: 95° C. cooling to 50° C.; ramping to 99° C. at 0.2° C./sec. The following primer pairs were used: "rat GCSFR-frag-32s" CCA TTG TCC ATC TTG GGG ATC (SEQ ID NO:42), "rat GCSFR-frag-265 as" CCT GGA AGC TGT TGT TCC ATG (SEQ ID NO:43), "rat GCSF-345s" CAC AGC GGG CTC TTC CTC TAC CAA (SEQ ID NO:44), and "rat GCSF-862 as" AGC AGC GGC AGG AAT CAA TAC TCG (SEQ ID NO:45). The Lightcycler® PCR was performed using the SYBR green master mix, following the manufacturer's recommendations (Roche Diagnostics). Specificity of products was ensured by melting point analysis and agarose gel electrophoresis. cDNA content of samples was normalized to the expression level of Cyclophilin (primers: "cyc5" ACC CCA CCG TGT TCT TCG AC (SEQ ID NO:46); "acyc300" CATTTGCCATGGACAA-GATG (SEQ ID NO:47)). Relative regulation levels derived from normalization to cyclophilin, and comparison to the sham-operated animals. Error bars indicate standard deviations, these are calculated from 3-fold serially diluted cDNA-samples, and reflect reliability of measurements.

FIG. 28 (part I and II) A shows a very strong upregulation of GCSF 2 h and 6 h after focal ischemia on the ipsi- and contralateral side, whereas the receptor is moderately regulated (FIG. 28 B) after 6 h.

An induced expression of GCSF is not specific to the MCAO model, but could also be seen albeit to a lesser degree in global ischemia (FIG. 28 C). This finding supports the hypothesis that G-CSF indeed is a brain-endogenous neuroprotective ligand, and that treatment with GCSF or GMCSF utilizes an endogenous principle of neuroprotection.

Example 24

GCSF and its Receptor are Upregulated in the Penumbral Zone of a Cortical Infarct Methods The ischemic model of photothrombotic cortical ischemia was conducted as described in above examples.

Immunohistochemistry: Sections of paraffin-embedded tissues (2 µm) were deparaffinated and microwaved (citrate buffer at 500 W for 10 min). Afterwards, sections were incubated at room temperature with GCSF or GCSF-receptor antiserum (SC13102 or SC694; Santa Cruz Biotechnology, Santa Cruz, Calif., USA; 1:500) for 1 h in a humid chamber. Staining was visualized using the ABC technique with DAB as chromogen (DAKO, Glostrup, Denmark). Negative controls were done by omitting the primary antiserum.

Results 6 h following induction of photothrombotic ischemia, there was clear evidence for enhanced staining of neurons in the surrounding area of the primary ischemic lesion ("penumbra"), as shown by arrows in FIG. 29, both for the receptor and the lignad. This finding underlines the principle that we have uncovered a novel endogenous neuroprotective system of the nervous system. It also underlines that the primary mechanism of action of GCSF in the penumbral zone is indeed most likely antiapoptotic.

Example 25

Colocalisation of the GCSFR and Doublecortin in the Hippocampus

Immunohistochemical Methods Used

The experiment was performed as described in example 21. Instead of the GCSF antiserum, a guinea-pig anti-doublecortin (DCX) polyclonal antibody (Chemicon International, Germany) diluted 1:200 in 0.2% BSA in 1×TBS (pH 7.4) was applied. After washing the sections 3×2 min with 0.2% BSA in 1×TBS (pH 7.4), they were incubated for 30 min with biotinylated goat anti-guinea-pig IgG (Vector Laboratories, USA) diluted 1:200 in 1×TBS (pH 7.4) containing 0.2% BSA. Again after washing the sections, TRITC-conjugated streptavidin (dianova; 1:200) was applied for 1.5 h at room temperature following the protocol described in example 21.

Results

FIG. 30 shows the expression of GCSF receptors (a, d, g) and doublecortin (b, e, h) on neurons in the dentate gyrus (a-f) and the hilus (g-i) of the hippocampus. The overlap of the expression of both the G-CSF receptor and the early neuronal marker doublecortin (Jin, et al. (2001), Proc Natl Acad Sci USA, 98, 4710-5) (FIG. 30 c, f, i) implicate a functional role of G-CSF at an early stage of neuronal differentiation.

Example 26

GCSF Induces Neuronal Differentiation of Adult Neural Stem Cells

Generation of Neural Stem Cells (NSCs)

Generation of adult neural stem cells from rat was performed as described in example 9.

39 DIV cultured neurospheres derived from the subventricular zone (SVZ) were stimulated once with the following GCSF-concentrations: 10 ng/ml, 100 ng/ml and 500 ng/ml, respectively. 4 days after addition of recombinant human GCSF (Neupogen Amgen, Europe B.V., Netherlands) cells were harvested and RNA was isolated. Untreated cells served as control.

Quantitative PCR

RNA of GCSF-treated and untreated neurospheres of the SVZ was isolated using the Qiagen RNeasy mini kit following the manufacturers protocol. cDNA was synthesized from 2 μg total RNA using oligodT primers, superscript II reverse transcriptase (Gibco) using standard conditions. Quantitative PCR was performed using the Lightcycler system (Roche Diagnostics, Mannheim, Germany) with SYBR-green staining of DNA doublestrands. Cycling conditions were as follows:

Nestin and NSE (neuron specific enolase): 3 min 95° C., 5 sec 95° C., 10 sec 58° C., 30 sec 72° C.; 10 sec 81° C. for 50 cycles; beta III-tubulin: 3 min 95° C., 5 sec 95° C., 10 sec 65° C., 30 sec 72° C.; 10 sec 87° C. for 50 cycles; PLP: 3 min 95° C., 5 sec 95° C., 10 sec 62° C., 30 sec 72° C.; 10 sec 84° C. for 50 cycles; GFAP: 3 min 95° C., 5 sec 95° C., 10 sec 60° C., 30 sec 72° C.; 10 sec 81° C. for 50 cycles. Melting curves were determined using the following parameters: 95° C. cooling to 50° C.; ramping to 99° C. at 0.2° C./sec. The following primer pairs were used: "rat nestin-plus" AGG AAG AAG CTG CAG CAG AG (SEQ ID NO:48), "rat nestin-minus" TTC ACC TGC TTG GGC TCT AT (SEQ ID NO:49), "rat NSE-plus" GGC AAG GAT GCC ACT AAT GT (SEQ ID NO:50), "rat NSE-minus" AGG GTC AGC AGG AGAC TTG A (SEQ ID NO:51), "rat beta III-tub-716s" CCA CCT ACG GGG ACC TCA ACC AC (SEQ ID NO:52), "rat beta III-tub-1022 as" GAC ATG CGC CCA CGG AAG ACG (SEQ ID NO:53), "rat PLP-518s" TCA TTC TTT GGA GCG GGT GTG (SEQ ID NO:54), "rat PLP-927 as" TAA GGA CGG CAA AGT TGT AAG TGG (SEQ ID NO:55), "rat GFAP3'-1123s" CCT TTC TTA TGC ATG TAC GGA G (SEQ ID NO:56), "rat GFAP3'-1245 as" GTA CAC TAA TAC GAA GGC ACT C (SEQ ID NO:57). The Lightcycler PCR was performed using the SYBR green master mix, following the manufacturer's recommendations (Roche diagnostics). Specificity of product was ensured by melting point analysis and agarose gel electrophoresis. cDNA content of samples was normalized to the expression level of Cyclophilin (primers: "cyc5" ACC CCA CCG TGT TCT TCG AC (SEQ ID NO:58), "acyc300" CAT TTG CCA TGG ACA AGA TG (SEQ ID NO:59)). Relative regulation levels derived from normalization to cyclophilin, and comparison to the untreated cells. FIG. 31 shows a strong and concentration dependent upregulation of the neuronal markers NSE and beta III-tubulin-4-d after GCSF treatment. PLP and GFAP are moderately regulated in dependency of the GCSF-concentration. Error bars indicate standard deviations, calculated from 3-fold serially diluted cDNA-samples, and reflect reliability of measurements.

Example 27

Colocalisation of GMCSF and its Receptor in the Brain

Immunohistochemical Methods Used

Sections of paraffin-embedded tissues (2 μm) were deparaffinated by treating them 2×5 min with Xylol, 2×2 min 100% ethanol, and then with descending concentrations of ethanol from 96% up to 70%. Finally the sections are washed with destined water and microwaved (citrate buffer at 600 W for 15 min). Afterwards, sections were washed with destined water and antigens were blocked 3×5 min in 1×TBS (pH 7.4) containing 0.2% BSA. The GMCSF receptor antiserum (SC690; Santa Cruz Biotechnology, Santa Cruz, Calif., USA; 1:100) diluted in 1×TBS (pH 7.4) containing 0.2% BSA was incubated at Room temperature for 1 h in a humid chamber. Sections were then washed 3×2 min with 1×TBS (pH 7.4) containing 0.2% BSA. The second antibody (goat anti-rabbit Fab-FITC, dianova, 1:50) was then applied over night at 4° C. in 1×TBS (pH 7.4) containing 0.2% BSA. After washing the sections 3×2 min with 0.2% BSA in 1×TBS (pH 7.4), the GMCSF antiserum (SC 13101; Santa Cruz Biotechnology, Santa Cruz, Calif., USA) diluted 1:100 in 0.2% BSA in 1×TBS (pH 7.4) was applied for 1 h at room temperature. The sections were washed 3× as described before and incubated for 30 min with biotinylated goat anti-rabbit IgG (Vector Laboratories, USA) diluted 1:200 in 1×TBS (pH 7.4) containing 0.2% BSA. Again after washing the sections, TRITC-conjugated streptavidin (dianova; 1:200) was applied for 1.5 h at room temperature. Then, the sections were washed 3×2 min with 1×TBS and stained for 10 min with the nuclear dye DAPI diluted 1:10 000 in 1×TBS. Finally the sections were washed 3×2 min with 1×TBS and mounted with mounting medium for fluorescence (Vectashield, Vector Laboratories, USA). Pictures were taken digitally with an Olympus IX81 microscope, and the "Analysis" software package (Soft Imaging Systems, Stuttgart, Germany).

All double-fluorescence experiments were controlled by parallel single-stainings, which were checked for absence of any fluorescence carry-over in the second channel. As a second control, all double-fluorescence stainings were done with switched chromophores for the secondary antibody.
Results The GMCSF receptor (FIG. 32 a, d, g) and GMCSF (FIG. 32 b, e, h) are colocalised on neurons in the dentate gyrus (FIG. 32 a-c), the hilus (FIG. 32 d-f), and the cortex (FIG. 32 g-i). These data support the notion that GMCSF is an autocrine ligand.

Example 28

GCSF and its Receptor are Upregulated by Cerebral Ischemia

MCAO Model of Cerebral Ischemia

Procedure for inducing focal cerebral ischemia (MCAO, middle cerebral artery occlusion) was performed as described in example 1.
Global Ischemia Model Surgical preparations and transient global cerebral ischemia were performed as described before.
Quantitative PCR RNA isolation and cDNA synthesis were done following the protocol described before. Cycling conditions were as follows: GCSFR: 5 min 95° C., 5 sec 95° C., 10 sec 62° C., 30 sec 72° C.; 10 sec 80° C. for 50 cycles; GCSF: 5 min 95° C., 5 sec 95° C., 10 sec 60° C., 30 sec 72° C.; 10 sec 80° C. for 50 cycles. Melting curves were done with the following parameters: 95° C. cooling to 50° C.; ramping to 99° C. at 0.2° C./sec. The following primer pairs were used: rat GCSFR "BR4-4s96" ACG TCG TTG GCT CAG TTA TGT C (SEQ ID NO:60), "BR4-4as272" ATT TAT GTC AGA GAT GGA GGA TGG (SEQ ID NO:61), "rat GCSF-723s" GGA GCT CTA AGC TTC TAG ATC (SEQ ID NO:62), and "rat GCSF-908 as" GGC TCA ATG TGA TTT CTT GGG (SEQ ID NO:63). The Lightcycler® PCR was performed using the SYBR green master mix, following the manufacturer's recommendations (Roche Diagnostics). By melting point analysis and agarose gel electrophoresis the specificity of products was ensured. cDNA content of samples was normalized to the expression level of Cyclophilin (primers: "cyc5" ACC CCA CCG TGT TCT TCG AC (SEQ ID NO:58); "acyc300" CATTTGCCATGGACAAGATG (SEQ ID NO:59)). Relative regulation levels derived from normalization to cyclophilin, and comparison to the sham-operated animals. Error bars indicate standard deviations, these are calculated from 3-fold serially diluted cDNA-samples, and reflect reliability of measurements.

A very strong upregulation of GCSF 2 h and 6 h after focal ischemia on the ipsi- and contralateral side is shown in FIG. 33 A. An induction of GCSF can be shown in global ischemia as well albeit to a lesser extend (FIG. 33 B). Even the GCSF receptor is slightly upregulated 6 h after global ischemia (FIG. 33 C). These data support the hypothesis that GCSF is part of an endogenous neuroprotective mechanism.

Example 29

Colocalised Expression of the GCSFR and Doublecortin in the Hippocampus

Immunohistochemical Methods Used

The experiment was performed as described before. Instead of the GMCSF antiserum, a guinea-pig anti-doublecortin (DCX) polyclonal antibody (Chemicon International, Germany) diluted 1:200 in 0.2% BSA in 1×TBS (pH 7.4) was applied. After washing the sections 3×2 min with 0.2% BSA in 1×TBS (pH 7.4), they were incubated for 30 min with biotinylated goat anti-guinea-pig IgG (Vector Laboratories, USA) diluted 1:200 in 1×TBS (pH 7.4) containing 0.2% BSA. After again washing the sections, TRITC-conjugated streptavidin (dianova; 1:200) was applied for 1.5 h at room temperature following the protocol described before.
Results FIG. 34 shows the expression of the GMCSF receptor (a, d, g) and doublecortin (b, e, h) on neurons in the dentate gyrus (a-c) and the hilus (d-i) of the hippocampus. The overlap of the expression of both the G-CSF receptor and the early neuronal marker doublecortin (Jin, Minami, Lan, Mao, Batteur, Simon and Greenberg (2001), Proc Natl Acad Sci USA, 98, 4710-5) (FIG. 34 c, f, i) implicate a functional role of GMCSF at an early stage of neuronal differentiation, and underline the applicability of GMCSF to all neurodegenerative diseases, where influencing neurogenesis may be a therapeutic target, such as stroke, Parkinson's disease, ALS, and many others.

Example 30

GMCSF Induces Neuronal Differentiation of Adult Neural Stem Cells

Generation of Neural Stem Cells

Generation of adult neural stem cells from rat was performed as described in example 9. Cells were passaged every two to three weeks by centrifugating the cells for 5 min at 800×g, removing the supernatant, and washing them once with 1×PBS. After resuspension in 1 ml Accutase (Sigma) and incubation for 15 min at 37° C. the cells were counted and plated at a density of 1.5-2.0×10$^5$ cells per well in a 6 well plate. Neural stem cells derived from the hippocampus were stimulated after the 4$^{th}$ passage with 10 ng/ml GMCSF (Leukine®, Berlex, Schering AG Germany), and after 3 days they were harvested for RNA isolation. Untreated cells served as a control.
Quantitative PCR RNA of the GMCSF-treated and untreated neurospheres of the SVZ was isolated using the Qiagen RNeasy mini kit following the manufacturers recommendations. cDNA was synthesized from 5 µg total RNA using oligodT primers, superscript II reverse transcriptase (Gibco) using standard conditions. Quantitative PCR was performed using the Lightcycler system (Roche Diagnostics, Mannheim, Germany) with SYBR-green staining of DNA doublestrands. The performance of the Lightcycler PCR, the cycling conditions and primer pairs used for beta III-tubulin, NSE, PLP, and GFAP are described before. Relative regulation levels derived from normalization to cyclophilin, and comparison to the untreated cells. In FIG. 35 A the differentiation potential of neural stem cells and the specific marker expressions of differentiated cells are illustrated schematically. Treatment of neural stem cells with 10 ng/ml GMCSF results in a significantly induced expression of beta III-tubulin (n=3; $p<0.05$, two-tailed t-test) and to a lesser extend of NSE, a marker for mature neurons (FIG. 35 B). There was no change observed in the expression level of PLP and GFAP. This example underlines the applicability of GMCSF to modulation of neurogenesis. This is useful for both in vitro generation of differentiating neurons, as well as influencing endogenous stem cells, and applicable to a wide range of human diseases, particularly neurodegenerative diseases.

Example 31

G-CSF Passes the Blood-Brain-Barrier (BBB)

The most data available in the literature contain information about serum levels of G-CSF and related cytokines. One important parameter for the effective use of G-CSF in the therapy of neurological disorders however, is the passage of the protein through the blood-brain-barrier (BBB). This question is of special interest because it is known that many proteinacious drugs cannot cross this natural border between blood and neurons. On the other hand, it was shown for several proteins, including hematopetic factors like Erythropoietin and also granulocyte-macrophage colony stimulating factor (GM-CSF) that they can pass the BBB and get effective on neurons in the CNS (McLay, et al. (1997), Brain, 120, 2083-91., Brines, et al. (2000), Proc Natl Acad Sci USA, 97, 10526-31).

To prove that G-CSF can pass the blood-brain barrier, we tested the appearance of injected G-CSF in rat brain. Therefore we applied an extremely sensitive iodinination assay. G-CSF and BSA as a control were radiolabelled with $^{131}$I (Amersham Biosciences, Freiburg Germany) by the Iodogen (Sigma, Taufkirchen, Germany) method and purified on Sephadex G-25 (Amersham Biosciences, Freiburg Germany) columns. The purified proteins coeluted with the unlabeled standard compounds as a single peak of correct molecular weight when analyzed by size exclusion chromatography. The radiolabeled proteins were injected via the tail vein of female Sprague-Dawley rats (250-300 g). For competitive uptake studies the cold proteins were mixed with the labelled compound and coinjected. Shortly before dissection rats were anaesthetized with Rompun/Ketanest and perfused with 100 ml of saline via the inferior abdominal aorta (at 1, 4 and 24 hours after injection) to remove the blood. The whole brain and blood were dissected, blotted dry and weighed. Blood was centrifuged to obtain the serum. The radioactivity was measured with a γ-counter (LB 951 G, Berthold, Germany) along with a sample of the injectate to calculate % ID/g of the tissues. The results showed that G-CSF was present in the brain and compared to albumin the passage of the blood brain barrier was increased by a factor of 4-5 over the time. Samples, that were taken 24 h after injection of radiolabeled G-CSF show an increased level compared to 1 and 4 h (FIG. 36). These observations shows that G-CSF injected intravenously in the blood crosses the BBB and can principally activate specific receptors on CNS-neurons.

The amount of radiolabeled G-CSF in serum and brain was measured and the ratio of brain/serum was plotted against the time. As a control bovine serum albumin was used. To avoid blood contamination of brain tissue the rats were perfused with 100 ml of saline prior to dissection.

Example 32

GM-CSF Passes the Blood-Brain-Barrier (BBB)

To show that GM-CSF can cross the blood-brain-barrier we injected rats with iodinated GM-CSF as described in Example 31 for G-CSF. The experiment gave similar results, a comparison of GM-CSF and Albumin presence in rat brain after intravenous administration show that GM-CSF levels (ratio brain vs. serum) are 3-4 fold higher than albumin. The data demonstrate that GM-CSF can cross the blood-brain-barrier (FIG. 37).

FIG. 37 The amount of radiolabeled GM-CSF in serum and brain was measured and the ratio of brain/serum was plotted against the time. As a control bovine serum albumin was used. To avoid blood contamination of brain tissue the rats were perfused with 100 ml of saline prior to dissection.

Example 33

GCSF for the Treatment of Amyotrophic Lateral Sclerosis (ALS)

The idea that G-CSF and GM-CSF is beneficial for the treatment of ALS originated from two directions: First, both receptor and ligand for both GCSF and GMCSF are expressed in the large motoneurons in the anterior horn of the spinal cord. Second, the prove that G-CSF partly acts by counteracting apoptotic cascades is very attractive in light of the evidence for apoptotic mechanisms operative in ALS (Li, et al. (2000), Science, 288, 335-9). The most commonly used mouse model for ALS is transgenic mice carrying mutations in the SOD1 gene that have been shown to be responsible for familial human ALS. The most frequently used of those is the SOD1 (G93A) transgenic line. Typically, these mice have a reduced life span, and show progressing signs of motor weakness, that can be easily accessed by behavioural tests (e.g. grip strength test, rotarod tests). A number of tests for therapeutic efficacy have been conducted in these mice, and shown life-prolonging activity for substances such as Riluzole, Minocycline, Carnitine, and others. These mice are thought to have clinically predictive relevance, as Riluzole, the only approved drug in human, has protective effects in these mice, whereas BDNF, which failed in a human trial, has not. Therefore we have tested if G-CSF prolongs life expectancy, or functional outcome in the SOD1-transgenic mouse model of ALS. SOD1 and wildtype mice were injected subcutaneously with 10 μg/KG BW G-CSF or vehicle starting from postnatal day 60 and monitored over the time. The results indicated a clear trend for longer life expectancy in the G-CSF treated group (FIG. 38 A), as well as improvement of motor function (grip strength test (FIG. 38 B)), that reached significance at several measurement points over time. Moreover, there was a trend for increased weight in the treated group.

FIG. 38 A: SOD1-tg mice were injected with 10 μg/KG BW starting from postnatal day 60. There is a clear trend for prolonged life expectancy in the G-CSF treated SOD1-tg mice (closed line vs. dashed line). At several points this difference reached significance.

FIG. 38 B: SOD1-tg mice were injected with 10 μg/KG BW starting from postnatal day 60. The grip strength assay shows a improvement for motor strength in the G-CSF treated SOD1-tg mice (open squares vs. open triangles). At several points this difference reached significance.

Example 34

Efficacy of GCSF in Rodent Models of Parkinson's Disease (PD)

MPTP Model:

The best-characterized model of Parkinson's Disease (PD) has been developed by using the neurotoxin 1-methyl-4-phenyl-1,2,3,6-tetrahydropyridine (MPTP). To study the efficacy of GCSF in the Parkinson model, we administrated MPTP in eight-week-old male mice. Each group of mice (n=15) was given a repeated i.p. injection of MPTP-HCl or saline (once daily for 5 consecutive days at a concentration of 30 mg/kg, 5 ml/kg) and a repeated s.c. (once daily, for 22 consecutive days) administration of buffer, GCSF (0.03 mg/kg/; 5 ml/kg) or minocycline (45 mg/kg; 5 ml/kg). While the first application of GCSF was performed immediately after MPTP (or saline for group 0), minocycline was administered 30 minutes thereafter, because of possible interactions of both compounds. All animals of each group were sacrificed at day 22. Until that time, mice were analyzed both for locomotor activity (accelerating RotaRod) and body weight was determined daily. Furthermore each brain is subjected to a HPLC analysis with electrochemical detection for measuring the concentration of dopamine, 3,4-Dihydroxyphenylacetic acid (DOPAC) and the Homovanilic acid (HVA) in the striatum and nucleus accumbens.

However, the most important and direct parameter for the action of a neuroprotective drug in that model is the number of surviving neurons after that toxin. Therefore, tyrosine hydroxylase (TH) immunohistochemistry and stereological quantitation of TH-positive neurons were performed with midbrain sections of each animal (Triarhou, et al. (1988), J Neurocytol, 17, 221-32).

Results indicated a trend for a gain of body weight for the GCSF treated group (data not shown). Moreover an improvement of locomotor activity is observed after the testing in accelerating Rotarod (data not shown). A recent study with MPTP induced Parkinson in mice shown that minocycline prevents nigrostriatal dopaminergic neurodegeneration in these animals (Du, et al. (2001), Proc Natl Acad Sci USA, 98, 14669-74). In our study we selected minocycline as neuroprotective compound reference for validating our data. Subacute treatment with MPTP over 5 consecutive days significantly decreased tyrosine hydrolase (TH)-positive neurons within the substantia nigra pars compacta (FIG. 39 A). A treatment with GCSF and minocycline shown nearly the same efficient counteracting this reduction of nigral level of TH-positive neurons (FIG. 39 B). Furthermore GCSF and minocycline shown nearly the same therapeutic efficacy when striatal levels of dopamine (FIG. 39 B), and its metabolites were taken in consideration.

Example 35

GMCSF Efficacy in a Model for Parkinson's Disease

MPTP Model

As described for GCSF the efficacy of GMCSF in the Parkinson model is ascertained in the following study (see previous example).

Each group of mice (n=15) was given a repeated i.p. injection of MPTP-HCl or saline (once daily for 5 consecutive days at a concentration of 30 mg/kg, 5 ml/kg) and a repeated s.c. (once daily, for 22 consecutive days) administration of buffer, GMCSF (0.03 mg/kg/; 5 ml/kg) or minocycline (45 mg/kg; 5 ml/kg). While the first application of GCSF was performed immediately after MPTP (or saline for group 0), minocycline was administered 30 minutes thereafter, because of possible interaction of both compounds. All animals of each group are sacrificed at day 22.

An improvement of the gain of body weight and an amelioration of the locomotor activity with the accelerating rotarod have been observed after application of GMCSF, similar to the results scored by GCSF (data not shown). The therapeutic efficacy of GMCSF is therefore better compared to GCSF when the nigral levels of TH-positive neurons is taking in consideration (FIG. 39 B). The reduction of striatal dopamine levels and its metabolites can be counteract after administration of GMCSF comparable to GCSF (data not shown).

Example 36

Efficacy of GCSF and GMCSF in the 6-Hydroxydopamine (6OHDA) Model for Parkinson's Disease in Rats As exemplified above, GCSF as well as GMCSF had strong neuroprotective properties in the MPTP model in mice. This is a very strong proof for the applicability to human Parkinson's disease, as MPTP is a toxin that was discovered due to its ability to cause PD in humans.

One additional model for studying efficacy of the hematopoeitic factors for Parkinson's disease is the 6-OHDA model. This model is based upon the injection of 6OHDA directly into the substantia nigra or into the striatum. The drug selectively accumulates in dopaminergic neurons and leads to the apoptosis of these cells. In rats, 6OHDA is an effective neurotoxin that has been predominantly used to produce unilateral lesions. The extent of dopamine depletion can be assessed by examining rotational behaviour in response to amphetamine or apomorphine (Ungerstedt 1971). The easily and good quantifiable motor deficit constitutes a major advantage of this model. Additionally to the behaviour parameter the striatal level of tyrosine hydroxylase (TH) positive neurons after immunohistochemistry and the level of dopamine and its metabolites after a HPLC analysis can also been determined. The 6OHDA can be used to ascertain the efficacy of GCSF and GMCSF in a PD rat model. Adult Sprague-Dawley rats (body weight 250 g) are unilateral lesioned after one stereotaxic injection of 8 µg in 2 µl 6OHDA in the substantia nigra or in the striatum. Different doses of GCSF (0.03 mg/kg; 0.1 mg/kg, or others) can be administrated subcutaneously daily immediately after the lesioning for 2 weeks. Other groups of treated animals receive a single dose of intrastriatal or intranigral GCSF, or GMCSF (300 µg/kg) immediately after the injection of 6OHDA. As for the MPTP model study minocycline can be used as a neuroprotective reference compound (45 mg/kg once daily s.c.). Sham animals and lesioned animals treated with buffer are used as control groups. Two weeks after lesioning animals are subjected to rotational behaviour testing. Rats are injected s.c. with apomorphine, placed in a bowl cage and the number of contralateral rotations over a 1 h period are recorded. Numbers of rotations for each animal group are compared using standard statistical tests. After the behavioural testing, animals are killed and the brains are processed to for immunochemistry to assay the total number of TH-positive neurons and for HPLC for determining the level of dopamine.

Example 37

GMCSF Acts Anti-Apoptotically in Neurons by Activating stat3 Pathways

As already exemplified above (Example 22), GCSF had potent activities by inhibiting apoptosis in primary neurons. We suspected that GMCSF might also have a strong anti-apoptotic mechanism-of-action. Therefore, the same type of experiment as exemplified in example 22 was conducted for GMCSF. Here, the concentration applied to the neurons was 50 ng GMCSF (Leukine, Immunex)/ml medium.

FIG. 40, part I shows that GMCSF inhibits PARP cleavage, that is specifically occurring as a sign of apoptosis. Cell death was induced in primary neurons by using the NO-donor NOR-3.

FIG. 40, part II shows that GMCSF does not lead to increased phosphorylation of STAT1 ("pSTAT1") or STAT5 ("pSTAT5"), although the proteins themselves are expressed in neurons.

FIG. 40, part III A shows that GMCSF leads to a time-dependent activation of STAT3, that is maximal at 5 min following the GMCSF stimulus. At 60 min, the level of pSTAT3 drops below the initial level, a response kinetic known from cells of the hematopoeitic system. B, quantification of three independent experiments. C. Activation of STAT3 by phosphorylation can be inhibited by the JAK2 inhibitor AG490. 5 min after giving GMCSF the levels of pSTAT3 are quite different in presenc eof the inhibitor.

FIG. 40, part IV shows that GMCSF strongly induces the expression of the stat3 target genes Bcl2, and BclXl. These genes are known as being antiapoptotic.

This experiment demonstrates that 1.) GMCSF acts anti-apoptotically on neurons 2.) this is mediated by the stat3 pathway. Therefore this also demonstrates the possibility to use the stat3 system in neurons as a screening tool for finding novel neuroprotective drugs, including novel mimetics of gcsf or gmcsf.

Example 38

GMCSF Reduces Infarct Volume in Rodent Stroke Models

We conducted experiments with GMCSF in the most accepted model for stroke in the rat, the middle cerebral artery occlusion model (MCAO).

In principle, the experiment was conducted as exemplified in example 1 and 19. In brief, male Wistar rats were anesthesized using inhalation anesthesia (halothane/$N_2O/O_2$). The carotid artery was exposed, and a coated nylon filament inserted into the common carotid artery, and advanced until it blocked blood flow to the MCA. Correct positioning of the filament was monitored by Laser Doppler flowmetry. After 90 min occlusion, the filament was withdrawn allowing reperfusion. GMCSF (Leukine, Imunex) was applied at a dose of 250 µg/kg body weight to the rats via an intravenous catheter (femoral vein) over a period of app. 20 min by an infusion pump at either 30 min or 3 h following onset of ischemia. Infarct volumes were determined 24 h later with the standard method of TTC-staining, and a computer-based volumetry.

FIG. 41 demonstrates that there is a significant reduction of infarct volume in the GMCSF-treated animals, both at the early (FIG. 41, part I), and at the late time window of 3 h (FIG. 41, part II).

This exemplifies the applicability to GMCSF to neurodegenerative disorders in general, and to stroke treatment in particular.

Example 39

IL-5 is Upregulated in the MCAO Model of Focal Ischemia

RNA was isolated according to standard protocols (Chomczynski and Sacchi (1987), Anal Biochem, 162, 156-9) followed by Qiagen RNeasy™ mini kit purification from rat cortical penumbral samples, ipsi- and contralateral to the lesion side (see FIG. 9a for localization of the tissue samples; here: 3 vs. 4). cDNA was synthesized from 1 µg total RNA using oligodT primers, superscript II reverse transcriptase (Gibco) using standard conditions. Quantitative PCR was performed using the Lightcycler® system (Roche Diagnostics, Mannheim, Germany) with SYBR-green staining of DNA doublestrands. Cycling conditions were as follows: 5 min 95° C., 5 sec 95° C., 7 sec 62° C., 30 sec 72° C.; 9 sec 83° C. for 50 cycles. Melting curves were done with the following parameters: 95° C. cooling to 50° C.; ramping to 99° C. at 0.2° C./sec. The following primer pairs were used: "rat IL-5-38s" GCTGTGTCTGGGCCATTGCTAT (SEQ ID NO:66), and "rat IL-5-318 as" CTCTTCGCCACACTTCTCTTTTG (SEQ ID NO:67). The Lightcycler® PCR was performed using the SYBR green master mix, following the manufacturer's recommendations (Roche Diagnostics). Specificity of product was ensured by melting point analysis and agarose gel electrophoresis. cDNA content of samples was normalized to the expression level of Cyclophilin (primers: "cyc5" ACCCCACCGTGTTCTTCGAC (SEQ ID NO:9); "acyc300" CATTTGCCATGGACAAGATG (SEQ ID. NO: 10)). Relative regulation levels were derived after normalization to cyclophilin, and comparison to the sham-operated animals. FIG. 42 shows upregulation of IL-5 after 2 h and 6 h on the ipsilateral side, and a slight upregulation after 6 h on the contralateral side, error bars indicate standard deviations, these are calculated from 3-fold serially diluted cDNA-samples, and reflect reliability of measurements.

Example 40

G-CSF, GM-CSF, IL-3 and IL-5 Induce Antiapoptotic Pathways in Neuronal Cell Cultures Cortices were dissected from rat embryos E18. The tissue was dissociated using 10 mg/ml trypsin, 5 mg/ml EDTA/DNase (Roche diagnostics) in HBSS. The digestion was stopped using four parts neurobasal medium containing 1× B-27 supplement (Invitrogen), 0.5 mM L-glutamine, and 25 µM glutamate. After centrifugation, the pellet was dissolved in 5 ml medium and cells were plated at a density of 2mio cells on 6 cm dishes coated with poly-L-lysine.

For Pathway mapping culture medium was removed after 21 days in culture and fresh medium containing 50 ng/ml G-CSF or 20 ng/ml GM-CSF. In the case of IL3 and IL-5 3 ml culture medium was removed and fresh medium was added containing IL-3 or IL-5 to reach a final concentration of 10 ng/ml each. Cells were harvested at different timepoints after onset of Cytokine treatment, stating with 5 min after onset (see below and Figures).

For Western blots cells were harvested and cells were lysed in SDS-Benzonase-Buffer (1% SDS, 5 mM $MgCl_2$, PBS, Inhibitors 1:1000: Aprotinin, Leupeptin, Pepstatin, PMSF, ALLN, ALLM, Benzonase 1:100). Blots containing 100 µg of neuronal protein per sample were loaded on a SDS polyacrylamide gel containing 4 M urea and electrophoresed under standard conditions. Proteins were electrophoretically transferred to Immobilon-P™ membranes (Millipore Corp., Eschborn, Germany) by semi-dry blotting. The membranes were blocked in 3% nonfat dry milk in TBST (20 mM Tris base, pH 7.6, 137 mM NaCl and 0.05% Tween-20) for 1 hour at room temperature (RT).

For Detection blots were incubated for 1 h at room temperature with the respective primary (all antibodies from Cell Signalling Technology) and secondary antibodies (Dianova). Signals were detected using the supersignal chemiluminescence system (Pierce).

G-CSF

Another potent anti-apoptotic transduction pathway that can be activated by a number of growth factor receptors is the PI3K/Akt pathway (Dudek, et al. (1997), Science, 275, 661-5). Akt is activated via PI3-kinase and the kinase PDK, and active Akt can be determined by the level of Ser$^{473}$ phosphorylation. In untreated cells, there was only a faint band visible corresponding to phosphorylated Akt (FIG. 43A, first lane). 5 min after addition of 20 ng/ml G-CSF there was a massive increase in phosphorylated Akt, that appeared stable for at least 1 h after G-CSF addition (FIG. 43A). Overall levels of Akt remained constant (FIG. 43A, second row). Parallel to the induction of Akt, we observed an even stronger phosphorylation of the upstream kinase PDK1, that appeared as two bands with a slight size difference (FIG. 43B). Interestingly, the activation of both PDK and Akt appeared bi-phasic with a temporary decrease of the signal at 15 min. The phosphorylation of Akt 5 min after G-CSF addition could be completely blocked by the PI3-kinase inhibitor LY294002 (FIG. 43C). Thus, Akt is a prominent signal induced by G-CSF in neurons, and appears activated via the known PI3-kinase—PDK pathway.

Finally, we determined activation levels of the Erk family of kinases, that also have a protective function in neurons (Anderson and Tolkovsky (1999), J Neurosci, 19, 664-73). While Erk1/2 was only transiently activated (FIG. 43D), Erk5 had a stronger and longer-lasting activation (FIG. 43D, lower rows). Interestingly, a recent report connects Erk5 activation to survival signals elicited by trk receptors (Watson, et al. (2001), J Biol Chem, 276, 3536-42).

Together, G-CSF leads to the induction of three anti-apoptotic pathways in neurons.

GM-CSF

GM-CSF led to a massive increase in phosphorylated Akt, that appeared stable for at least 1 h after GM-CSF addition (FIG. 44A), too. Parallel to the induction of Akt, we observed an even stronger phosphorylation of the upstream kinase PDK1 (FIG. 44A). The phosphorylation of Akt 5 min after GM-CSF addition could be completely blocked by the PI3-kinase inhibitor LY294002 (FIG. 44A). Thus, Akt is a prominent signal induced by GM-CSF in neurons, and is activated via its cognate PI3-kinase—PDK pathway originating at the GM-CSF receptor. A third pathway that may originate at cytokine receptors is the Raf-Erk pathway. Erk 1/2 was shown to promote neuronal survival (Anderson and Tolkovsky (1999), J Neurosci, 19, 664-73, Xia, et al. (1995), Science, 270, 1326-31), and mediates BDNF's protective action in ischemic models (Han and Holtzman (2000), J Neurosci, 20, 5775-81). Indeed, GM-CSF also induced rapid but transient activation of Erk 1/2 by phosphorylation (FIG. 44B). Surprisingly, we also detected activation of the newly discovered Erk 5, that appeared stronger and lasted for at least 1 h after GM-CSF addition (FIG. 44B). Erk 5 has also been implied in mediating neuronal survival signals (Watson, et al. (2001), Nat Neurosci, 4, 981-8).

Together, GM-CSF leads to the induction of at least three major independent survival pathways in neurons.

IL-3

Also IL-3 led to a massive increase in phosphorylated Akt, that was detected at 5 min and 1 h after IL-3 addition (FIG. 47). Thus, Akt is a prominent signal induced by IL-3 in neurons, and is activated via its cognate PI3-kinase—PDK pathway originating at the IL-3 receptor. As for GCSF and GMCSF we also could show that PDK is phosphorylated by IL-3 stimulation of neuronal cells. (FIG. 47) The phosphorylation could be detected 5 min and 1 h after onset of IL-3 stimulation.

IL-5

IL-5 led to a massive increase in phosphorylated Akt and PDK, as described for IL-3, that was detected at 5 min and 1 h after IL-5 addition (FIG. 47). Thus, Akt and PDK are a prominent signal induced by IL-5 in neurons, and is activated via its cognate PI3-kinase—PDK pathway originating at the IL-5 receptor.

Example 41

GM-CSF is Upregulated after Cell Death In Vitro

Primary cortical neurons from rats were generated as described in example 12. Two weeks after preparation, neurons were treated with various concentrations of $H_2O_2$ (0 µM, 300 µM, 450 µM, 600 µM and 900 µM) for 6 h. Medium was withdrawn, and the cells were scraped off the plate by adding Lysisbuffer and following the manufacturer's recommendations for the RNA-preparation by Qiagen RNeasy mini kit. In principle, the Light-Cycler measurements were performed as described in example 23. The PCR was performed using "rat GM-CSF-94s" CTGGAGAACGAAAAGAACGAAGAC (SEQ ID NO:93) and "rat GM-CSF-359 as" TCAAAAGG-GATATCAAACAGAAAG (SEQ ID NO:94), and the following cycling conditions were used: 10 min 95° C., 10 sec 95° C., 10 sec 63° C., 30 sec 72° C.; 10 sec 86° C. for 50 cycles.

Results

With increasing concentrations of $H_2O_2$, the expression of GM-CSF increases as well up to 4-fold in comparison to untreated neurons (FIG. 45). This concentration-dependent induction of GM-CSF after stimulation of cell death confirms the suggestion that GM-CSF might act as an endogenous neuroprotective factor after brain damage.

Example 42

IL-3 and IL-5 Protect Cells from Camptothecin Induced Dying in Rat Primary Cortical Cell Culture and Human Neuroblastoma Cells (SHSY5-Y)

SHSY5-Y cells were cultured in DMEM (high glucose; 4500 mg/ml)+20% FCS+1% Penicillin/Streptomycin. For Caspase3/7 activity assay 45000 cells/well were seeded into a 96 well plate. One day after plating culture medium was adjusted to 90 µl/well and 10 µl of camptothecin was added or cells were left untreated. Then 10 µl of diluted Cytokine was added to Capmtothecin treated cells to reach final concentrations of 0, 1, 10, 20, 50 or 10 ng/ml. After 16 h of incubation at 37° C., 5% $CO_2$ Caspase 3 and 7-activity was measured (Caspase3/7 activity assay, Promega; following the instructions) with a plate reader (Berthold).

Cortical cultures were prepared as described above. 30000 cells/well were seeded in a 96 well plate and cultured for 2 weeks. Then culture medium was adjusted to 90 µl/well and 10 µl of Camptothecin was added or cells were left untreated. Then 101 of diluted Cytokine was added to Camptothecin treated cells to reach final concentrations of 0, 1, 10, 20, 50 or 100 ng/ml. After 16 h of incubation at 37° C., 5% $CO_2$ Caspase 3 and 7-activity was measured (Caspase3/7 activity assay, Promega; following the instructions) with a plate reader (Berthold).

The results show that the Cytokines have their highest anti-apoptotic activity at different concentrations (FIG. 46).

IL-3 has its highest anti-apoptotic activity at a concentration of 1-20 ng/ml on neuronal cultures and was most protective at 1 ng/mlon SHSY5-Y cells (FIG. 46a).

IL-5 was most protective at 1 ng/ml on both rat neuronal cells and human SHSY5-Y (FIG. 46b).

Example 43

G-CSF is Protective in Cortical Ischemia

Ischemic Model

Distal MCA/CCA occlusion model. Transient left common carotid/MCA (CCA/MCA) occlusion was achieved as described previously. Briefly, animals fasted overnight were anesthetized with chloral hydrate (0.45 g/kg IP). The right femoral vein and artery were cannulated for arterial blood pressure recording and drug administration. Core body temperature was maintained at 36.5±0.5° C. during ischemia and the first hour of reperfusion through the use of a feed-forward temperature controller. The ipsilateral CCA was isolated and tagged through a ventral, cervical midline incision. A 0.005-inch-diameter stainless steel wire (Small Parts Inc) was placed underneath the left MCA rostral to the rhinal fissure, proximal to the major bifurcation of the MCA, and distal to the lenticulostriate arteries. The artery was then lifted, and the wire was rotated clockwise to ensure occlusion. The CCA was next occluded with an atraumatic aneurysm clip. Cerebral perfusion at the cortical surface, 3 mm distal to the locus of the MCA occlusion, was measured with a laser-Doppler flowmeter (LDF) (model BPM2, Vesamedic). Only those animals that displayed a cerebral perfusion of 10% to 15% of the initial value on the LDF scale (expressing relative values of cerebral perfusion) were included in the study. 50 µg/kg G-CSF was infused i.v. over 20 min starting 60 min after induction of ischemia. After 180 minutes of MCA/CCA occlusion, reperfusion was established by reversing the occlusion procedure. After 72 hours of reperfusion, animals were reanesthetized and transcardially perfused with 50 mL of saline. Perfused isolated brains were transferred into ice-cold PBS for sectioning. Infarct volumes were determined by TTC staining. All procedures were in compliance with National Institutes of Health guidelines for the humane care of animals and were approved by the institutional animal welfare committee.

Example 44

G-CSF Induces Neurogenesis in Adult Neural Stem Cells

Generation of Neural Stem Cells (NSCs)

Generation of adult neural stem cells from rat was performed as described in example 9. For transfection of neural stem cells with the luciferase reporter, they were passaged once a week and luciferase-experiments were performed after 14 weeks in vitro.

For the differentiation experiment, the cells were plated in 15 cm² culture flasks at a density of 4 million cells and were treated once with 100 ng/ml G-CSF (Neupogen™, Amgen, Europe B.V., Netherlands) (n=6). The control cells were left untreated (n=4) and 4d after stimulation the cells were harvested for the antibody staining and the FACS-analysis.

Luciferase Assay

The effects of G-CSF treatment on adult neural stem cells in vitro were further examined by a reporter strategy using luciferase under control of an adequate β-III-tubulin promoter fragment. The class III β-tubulin gene promoter (fragment −450-+54) (described previously) was amplified by using genomic DNA as a template for PCR, and then the fragment was inserted into the Mlu I/Xho I site of the pGL3-Basic firefly luciferase reporter vector (Promega). The pRL SV40 vector (Promega) served as an internal control vector. For DNA transfection, the cells were dissociated and plated on poly-L-ornithin/laminin-coated 96-well plates at a density of 35 000 cells/well. After 24 hrs cultivation, cells were washed once with 1× Dulbecco's phosphate-buffered saline (DPBS, Gibco). Cotransfection with the pGL3-p-βIII-tubulin vector (150 ng/well) and the pRL SV40 vector (100 ng/well) was carried out according to the Lipofectamine method (Invitrogen). The pGL3-basic firefly luciferase reporter vector served as negative control, and as positive control the cells were cotransfected with pCMV-luciferase. The DNA-Lipofectamine 2000 complexes were added to each well after removing the DPBS, without adding Neurobasal medium. Following the incubation of transfected cells for 24 hrs, Opti-MEM was removed and cells were stimulated with various concentrations of G-CSF (Neupogen®, Amgen, Europe B.V., Netherlands) in Neurobasal medium (5 ng/ml, 10 ng/ml, 100 ng/ml) for 48 hrs. As a control for in vitro differentiation, stem cells were treated by adding 5% fetal calf serum (FCS) to the medium and withdrawing mitogens. Then the cells were harvested to prepare the cellular extracts for luciferase assay following the directions of Promega. As the cells were cotransfected with the firefly and the Renilla luciferase, the Dual-Luciferase Reporter Assay System (Promega) was used and the ratio of luminescence signals from the reaction mediated by firefly luciferase to those from the reaction mediated by Renilla luciferase were measured with a luminometer (Berthold Technologies, Mithras LB 940).

As shown in FIG. 50, the luciferase activity increased dose-dependently in a range of 5 to 100 ng/ml. Interestingly, 100 ng/ml had a stronger differentiation-inducing effect compared to the standard differentiation procedure of omitting bFGF and EGF from the medium, and adding FCS.

FACS Analysis

A single cell suspension was made by triturating the neurospheres in 1 ml plastic pipettes, and then the cells were pelleted by centrifugation. After resuspension in 1× phosphate-buffered saline (PBS), the cells were fixed by adding the same volume of 2% Paraformaldehyde (PFA) in 1×PBS resulting in a final concentration of 1% PFA. The cells were incubated for 15 min on ice, washed once with 1×PBS and then permeabilised by resuspension in 0.2% tween20 solved in 1×PBS. After an incubation on ice for 15 min, fetal calf serum (FCS) was added in a 1:50 dilution for blocking. As primary antibody served a monoclonal mouse anti-rat MAP2 antibody (Sigma) added at a dilution 1:100. The cells were incubated for 2 hrs on ice and washed three times with 0.1% tween20 in 1×PBS. Following an incubation for 30 min on ice with a donkey anti-mouse FITC-conjugated secondary antibody (Dianova), the cells were washed again three times with 0.1% tween20 in 1×PBS and were finally resuspended in 1×PBS for FACS analysis. Flow cytometry of cells was performed on a FACSCalibur (Becton-Dickinson). The cells were analyzed by light forward and right-angle (side) scatter, and for FITC fluorescence through an adequate filter system.

After treatment of adult neural stem cells for 4d with G-CSF, the percentage of cells expressing the neuronal marker MAP-2 increased from 32.8±6.4 to 65.0±3.3% ($p<0.005$; N=4 and 6, respectively) (FIG. 45). Taken together, G-CSF induces differentiation of neural stem cells towards a neuronal phenotype as shown before in example 26.

Example 45

GM-CSF Induces Neurogenesis in Adult Neural Stem Cells

Generation of Neural Stem Cells (NSCs)

Generation of adult neural stem cells from rat was performed as described in example 9. For transfection of neural stem cells with the luciferase reporter, they were passaged once a week and luciferase-experiments were performed after 14 weeks in vitro.

For the differentiation experiment, the cells were plated in 15 cm² culture flasks at a density of 4 million cells and were treated once with 10 ng/ml GM-CSF (Leukine®, Berlex, Schering AG Germany) (n=3). The control cells were left untreated (n=3) and 4d after stimulation the cells were harvested for the antibody staining and the FACS-analysis.

Luciferase Assay

To examine the effects of GM-CSF treatment on adult neural stem cells in vitro, a reporter strategy using luciferase under control of a β-III-tubulin promoter fragment was used as described in example 44. Neural stem cells were stimulated with various concentrations of GM-CSF (Leukine®, Berlex, Schering AG Germany) in Neurobasal medium (0.5 ng/ml, 5 ng/ml, 10 ng/ml) for 48 hrs. In FIG. 51, a concentration-dependent increase in luciferase-activity is shown after GM-CSF treatment of the neural stem cells. With a concentration of 10 ng/ml GM-CSF, the same differentiation-inducing effect can be achieved as with omitting bFGF and EGF and adding FCS which is known as standard differentiation protocol.

FACS Analysis

The antibody staining for the neuronal marker MAP2 was performed as described in example 44. The counts of MAP2-positive cells increases from 28.36±2.26% in untreated to 56.86±8.36 in GM-CSF treated stem cells ($p<0.03$; N=3) as shown in FIG. 52. Thus, GM-CSF induces significantly neurogenesis in adult neural stem cells.

Example 46

GM-CSF and its Receptor are Expressed in Human Brain

Immunohistochemical Methods

Sections of paraffin-embedded tissues (2 µm) were deparaffinated by treating them 2×5 min with Xylol, 2×2 min 100% ethanol, and then with descending concentrations of ethanol from 96% up to 70%. Finally the sections are washed with distilled water and microwaved (citrate buffer at 600 W for 15 min). Afterwards, sections were washed with distilled water and antigens were blocked 3×5 min in 1×TBS (pH 7.4) containing 0.2% BSA. The GM-CSF antiserum (SC13101; Santa Cruz Biotechnology, Santa Cruz, Calif., USA; 1:100) diluted in 1×TBS (pH 7.4) containing 0.2% BSA was incubated at room temperature for 1 h in a humid chamber. Sections were then washed 3×2 min with 1×TBS (pH 7.4) containing 0.2% BSA. The biotinylated secondary antibody (goat anti-rabbit, Vector Laboratories, 1:200) was then applied for 30 min in 1×TBS (pH 7.4) containing 0.2% BSA. Following washing the sections 3×2 min with 1×TBS (pH 7.4) containing 0.2% BSA, the sections were incubated for 1 h at room temperature with a saturating amount of TRITC-conjugated Streptavidin (Dianova 1:200). Again after washing 3×2 min with 1×TBS (pH 7.4) containing 0.2% BSA, the GM-CSF receptor alpha antiserum (Chemicon, 1:100) was applied. After 1 h, the sections were washed 3×2 min with 1×TBS (pH 7.4) containing 0.2% BSA. As described above, the detection was performed by applying a biotinylated secondary antibody (goat anti-mouse, Vector Laboratories, 1:200), and afterwards the sections were incubated with Cy5-conjugated Streptavidin (Dianova 1:200). After washing the sections 3×2 min with 1×TBS, they were stained for 10 min with the nuclear dye DAPI diluted 1:10 000 in 1×TBS. Finally the sections were washed 3×2 min with 1×TBS and mounted with mounting medium for fluorescence (Vectashield, Vector Laboratories, USA). Pictures were taken digitally with an Olympus IX81 microscope, and the "Analysis" software package (Soft Imaging Systems, Stuttgart, Germany).

All double-fluorescence experiments were controlled by parallel single-staining, which were checked for absence of any fluorescence carry-over in the second channel.

Results

In the human frontal cortex the GM-CSF receptor alpha (FIG. 53 a, d) was expressed on the same neurons as GM-CSF (FIG. 53 b, e) as shown in FIG. 53 c, f, where the two stainings are merged. Thus, the expression of GM-CSF and its receptor is not restricted to mouse and rat brain, but can also be found in human brain.

Example 47

The G-CSF Receptor is Expressed in Human Brain

Immunohistochemical Methods

The sections of paraffin-embedded tissues (2 µm) were treated as described in example 46. Briefly, after deparaffinisation and microwaving in citrate buffer, the sections were blocked with 1×TBS (pH 7.4) containing 0.2% BSA. After washing, the G-CSF receptor antiserum (SC694; Santa Cruz Biotechnology, Santa Cruz, Calif., USA; 1:100) was applied for 1 h in a humid chamber. Following incubation with a biotinylated secondary antibody (goat anti-rabbit, Vector Laboratories, 1:200) and detection with Cy5-conjugated Streptavidin (Dianova 1:200), nuclei were stained for 10 min with DAPI diluted 1:10 000 in 1×TBS. Finally the sections were mounted and pictures were taken digitally with an Olympus IX81 microscope, and the "Analysis" software package (Soft Imaging Systems, Stuttgart, Germany).

Results

As shown in example 46 for the GM-CSF receptor alpha, the G-CSF receptor was expressed in the frontal cortex of human brain (FIG. 54).

Example 48

G-CSF is Upregulated after Cell Death In Vitro

Primary cortical neurons from rats were generated as described in example 12. Two weeks after preparation, neurons were treated with various concentrations of $H_2O_2$ (0M, 300 µM, 450 µM, 600 µM and 900 µM) for 6 h. Medium was withdrawn, and the cells were scraped off the plate by adding Lysisbuffer and following the manufacturer's recommendations for the RNA-preparation by Qiagen RNeasy mini kit. The Light-Cycler measurements on G-CSF were performed as described in example 23.

Results

As cell death arises with increasing concentrations of $H_2O_2$, the expression of G-CSF was increased as well (FIG. 55). These results confirm the suggestion that G-CSF might act as an endogenous neuroprotective factor after brain damage.

Example 49

Expression of the IL-5 Receptor in Rat Brain

To systematically assess the distribution of the IL-5 receptor in the normal rat brain, sections of paraffin-embedded tissues (2 µm) were deparaffinated and microwaved (citrate buffer at 500 W for 10 min). Afterwards, sections were incubated at room temperature with IL-5 receptor alpha antiserum (AF553; R&D Systems; 1:100) for 1 h in a humid chamber.

Staining was visualized using the ABC technique with DAB as chromogen (DAKO, Glostrup, Denmark). Negative controls were done by omitting the primary antiserum.

Results

The expression of the IL-5 receptor alpha was detected in the frontal Cortex (FIG. 56 *a*), in the dentate gyrus (FIG. 56 *b*), in the mitral cells of the olfactory bulb (FIG. 56 c), and in Purkinje cells of the cerebellum (FIG. 56 *d*).

Example 50

Neuroprotective Effect of G-CSF on Human Cells

In this example we tested the neuroprotective potential of G-CSF and GM-CSF on cells of human origin. Therefore we used the human neuroblastoma cell line SHSY5Y. To model oxidative stress the cells were treated with NO-donor NOR3 in the presence or absence of G-CSF/GM-CSF and elevated caspase 3/7 activity was used as a measure for damage. Cells were seeded in 96 well plates ($5 \times 10^4$ cells/well) for 2 days. To induce oxidative stress the cells were treated with 150 µM Nor3 for 5 h with or without G-CSF (50 µg/ml). Caspase 3/7 activity was then determined by Caspase-Glow Assay (Promega) according to the manufacturer's protocol and luminescence detected with a plate reader (Berthold). FIG. 57 shows that G-CSF [60 ng/ml] and GM-CSF [20 ng/ml] both reduce the NOR3 evoked Caspase activity in human neuroblastoma cells. This underlines the neuroprotective efficacy of both cytokines and shows that human neuronal cells are susceptible to them.

Example 60

Human and Rodent GM-CSF are Neuroprotective on Rat Primary Neurons

Testing for different efficacy of G-CSF from human and rodent GM-CSF origin. We compared the neuroprotective activity of recombinant mouse GM-CSF and recombinant human G-CSF on primary neurons prepared from fetal rats. To induce apotosis in neuron preparations we treated the cells with the topoisomerase inhibitor Camptothecin [20 µM] for 5 h before measuring Caspase activity. FIG. 58 shows the result of the experiment, addition of GM-CSF [20 ng/ml] significantly reduced Camptothecin induced caspase 3/7 activity as measured by luminescence increase with the CaspaseGlow assay (Promega). We could not observe any significant difference between treatment with mouse and human G-CSF, this indicates that G-CSF different species can activate the G-CSF-receptor on rat neurons.

All of the references cited herein, including patents, patent applications, and publications, are hereby incorporated in their entireties by reference.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of reducing infarct size caused by cerebral ischemia during an operative procedure in a mammal, comprising administering to the mammal in need thereof before the operative procedure, a hematopoietic factor selected from the group consisting of mammalian granulocyte-colony stimulating factor (G-CSF), human G-CSF, a protein having at least 90% homology to SEQ ID NO: 37, a protein having at least 90% homology to SEQ ID NO: 38, a protein having at least 90% homology to SEQ ID NO: 39 to a second PEG-modified G-CSF or a combination thereof in an amount sufficient to reduce infarct size caused by cerebral ischemia during an operative procedure.

2. The method of claim 1, wherein the operative procedure is carotid surgery.

3. The method of claim 1, comprising administering mammalian G-CSF.

4. The method of claim 1, comprising administering human G-CSF.

5. The method of claim 1, comprising administering a protein having at least 90% homology to SEQ ID NO:37.

6. The method of claim 1, comprising administering a protein having at least 90% homology to SEQ ID NO:38.

7. The method of claim 1, comprising administering a protein having at least 90% homology to SEQ ID NO:39.

8. The method of claim 1, comprising administering PEG-modified G-CSF.

* * * * *